US008962329B2

(12) United States Patent
Liu et al.

(10) Patent No.: US 8,962,329 B2
(45) Date of Patent: Feb. 24, 2015

(54) GENE CLUSTER

(75) Inventors: Wen Liu, Shanghai (CN); Nan Jiang, Shanghai (CN); Xudong Qu, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 559 days.

(21) Appl. No.: 13/119,868

(22) PCT Filed: Sep. 24, 2009

(86) PCT No.: PCT/CN2009/074178

§ 371 (c)(1), (2), (4) Date: Jun. 9, 2011

(87) PCT Pub. No.: WO2010/034243

PCT Pub. Date: Apr. 1, 2010

(65) Prior Publication Data

US 2011/0229941 A1 Sep. 22, 2011

(30) Foreign Application Priority Data

Sep. 24, 2008 (CN) .......................... 2008 1 0200388

(51) Int. Cl.

| | |
|---|---|
| ***C12N 15/00*** | (2006.01) |
| ***C12N 1/20*** | (2006.01) |
| ***C12N 9/00*** | (2006.01) |
| ***C07H 21/04*** | (2006.01) |
| ***C12P 17/00*** | (2006.01) |
| ***A61K 31/35*** | (2006.01) |
| ***A61K 31/5025*** | (2006.01) |
| ***C07D 491/10*** | (2006.01) |
| ***C07K 14/36*** | (2006.01) |
| ***C12N 15/52*** | (2006.01) |
| ***C12P 17/18*** | (2006.01) |

(52) U.S. Cl.

CPC ................. *C12P 17/00* (2013.01); *A61K 31/35* (2013.01); *A61K 31/5025* (2013.01); *C07D 491/10* (2013.01); *C07K 14/36* (2013.01); *C12N 15/52* (2013.01); *C12P 17/188* (2013.01)

USPC ..... 435/440; 435/183; 435/252.3; 435/320.1; 536/23.2

(58) Field of Classification Search

CPC ................................ C12N 15/52; C12N 15/67

See application file for complete search history.

(56) References Cited

U.S. PATENT DOCUMENTS 7,312,048 B2 * 12/2007 Khosla et al. ................... 435/41

FOREIGN PATENT DOCUMENTS

| | | | |
|---|---|---|---|
| CN | 1193979 | A | 9/1998 |
| CN | 101242842 | A | 8/2008 |
| WO | 00/00620 | | 1/2000 |
| WO | 98/07743 | | 7/2011 |

OTHER PUBLICATIONS

Branden et al. Introduction to Protein Structure, Garland Publishing Inc., New York, p. 247, 1991.*

Schmoll, T., et al. "Complete genetic organization and functional aspects of the *Escherichia coli* S fimbrial adhesin determinant nucleotide sequence of the genes sfa B, C, D, E, F." Microbial Pathogenesis. 1990;9:331-343.

Wu, K., et al. "The FK520 gene cluster *Streptomyces hygroscopicus* var. *ascomyceticus* (ATCC 14891) contains genes for biosynthesis of unusual polyketide extender units." Gene. 2000;251:81-90.

Aparicio, J.F., et al. "Organization of the biosynthetic gene cluster for rapamycin in *Streptomyces hygroscopicus*: analysis of the enzymatic domains in the modular polyketide synthase." Gene. 1996;169:9-16.

Sanglier, J.J., et al. "Sanglifehrins A, B, C and D, novel cyclophilin-binding compounds isolated from *Streptomyces* sp. A92-308110. I. Taxonomy, fermentation, isolation and biological activity." J Antibiot (Tokyo). May 1999;52 (5):466-73.

Gregory, M., et al. "Mutasynthesis of rapamycin analogues through the manipulation of a gene governing starter unit biosynthesis." Angew Chem Int Ed Engl. Jul. 25, 2005;44(30): 4757-60.

Kennedy, J. "Mutasynthesis, chemobiosynthesis, and back to semi-synthesis: combining synthetic chemistry and biosynthetic engineering for diversifying natural products." Nat Prod Rep. Feb. 2008;25(1):25-34. doi: 10.1039/b707678a. Epub Sep. 4, 2007.

* cited by examiner

*Primary Examiner* — Yong Pak

(74) *Attorney, Agent, or Firm* — Robert C. Netter, Jr.; Kathleen D. Rigaut; Dann, Dorfman, Herrell & Skillman

(57) ABSTRACT

Novel isolated DNA sequences which comprise all or part of a gene cluster encoding sanglifehrin synthase, processing and regulatory genes involved in the biosynthesis of a mixed non-ribosomal peptide/polyketide compound, or mutants having altered biosynthetic capability, polypeptides or mutants thereof encoded by DNA or the mutants, vectors containing the DNA or the mutants thereof, host cells transformed with the DNA, the mutants thereof, or the vector, and a method for producing sanglifehrin compounds. Compounds with cyclophilin inhibition activity used as immunosuppressants, antivirals or cardiac protection agents.

9 Claims, 13 Drawing Sheets

Sanglifehrin A

Sanglifehrin B C35/C36

Sanglifehrin E C38/C42

Sanglifehrin C

Sanglifehrin D C35/36

A WT B Standard C Mutant

Sanglifehrin T
*Streptomyces flaveolus* mv. *tsekangenesis*

Sanglifehrin H
*Streptomyces flaveolus* mv. hasangensis

SEQUENCE LISTING

```
<160> NUMBER OF SEQ ID NOS: 67

<210> SEQ ID NO 1
<211> LENGTH: 118372
<212> TYPE: DNA
<213> ORGANISM: Streptomyces flaveolus (Streptomyces sp.(DSM 9954))

<400> SEQUENCE: 1

agcacgcgga gaacgcccgc ctgcgggcgg cggggagagc cgttccggtc caactccccg      60

gcggtgtgcg ggcgtgggcg attccgcacc acgaggacct gcgccgagtg ctgacggatc     120

ccagggtcgc caagggaatc acgcactggg aggcagcggc ccgcggcgaa gtgccggacg     180

ggtggccgtt gatgggcttc gtcgcgaccg acagcgtcat caattcgcac ggcgcggatc     240

accggcggct gcgcggactg gtcgaccagg cactgacccc ggaacgggtg gaggccatgc     300

gcccgggggt ggaacgcctc gtcgacgggc tcctcgacca gctcgccaca cggccggaag     360

accggccggt ggatctccgc aaggctttcg cctaccccat ccccaccacc gtcatctcgg     420

acctgctggg gatcccgcag cgcaagcggc gtctgctgca cgtgctcacc ggcatgcaga     480

cccgtacgaa caactccccc gaacaggtcc aggagatcga cggacggatc gaagcgctgc     540

tccgggagat cgtcgccgaa cgtcgcgacg tcccccggga cgacctcatc agcgtcctgc     600

tcacggcacg ccaggacgga gacgaccggc tcaccgacag cgaactgcac ggcatgatcc     660

tgctgatgtt cttcgccggc caccagagcg tcatcaacgt actcgtcaac gcctgccacg     720
```

```
cgctgctcac ccaccccgag caactggcct ccgcccgcgc cggggaggtc ccgtggagtg    780
cggtggtcga ggagacgatg cgctggaacg gcgcggtgaa ccagttcccg atgcgctacc    840
cgaccgagga cgtcgtcatc gccggccaga cgatccaccg gggagaagcc atcctcgcgt    900
ccttcggctc ggcgggccgg gacccggcgc accacgggcc ggacgcggac ctcttcgacg    960
tccgccggcg gcaggccggc cacctcggct tcgggcacgg cccgcacttc tgtatcggga   1020
cacacctggc ccgtctccag ctggagacgg cactggccgg attcttcacc cggttccccg   1080
acgtgcggct ggccccgtcc gacacgtgga ccgtgcggcc cgtgccctcg ttcgtcagca   1140
acagcatcga ggcgctgccc gtactcctcg gccctgccgc ggagtacggg cggctctgac   1200
gtcgcggcac gcacgtgtta cggagccgag ccccacacaa cgcgcggcaa ggtgctcgcc   1260
gacggcctgc gcagaccgac agagaggacg ccctccgtgc cccgcacacc catcgccctg   1320
ctggcaccca ccaccgcagt ctcccccgcc gaaaggctca ccgtccccgc cttcggcgac   1380
gtcaccgtgg accggccggc acacgccgac tggcaccgct acctgcacga gttcgaaccg   1440
tcatccgagc tcgcggcggt gtggatcggg gcggacgccg agccgctgcc cgccgtccgg   1500
gcgctgcggt cgcactcgaa gttcaaccgg acccgggtgt acgtcgtcgg gcccgatacg   1560
gcgggcccgg ttcccggctg ggcggaagca ctggacgtcg aggacatcgt ccggcccgcc   1620
gcggtggcgc ccgaagggtt caccacctcg gtcgaactgg ccctgcgggc gcaccgcgcg   1680
ctgatgacgg acgacctcta caccgactac tacctcgaca tgaccttcaa caagatcttc   1740
gactggttcg agacgacgcg ctgggactgg accgaggtgg acctggaccg catcgagcac   1800
ggcatgctcg acgaacggac cgtggacttc ctcaccgagg cggccgtcat cgagttcggc   1860
accctacccg gcgctcacaa cttcctgcgg gaatggcagg acgaggtcag cttctcctcc   1920
tgggcactgc aatggggtgc ggaggaatcc cggcactcac tggtccaggc ccgctacctg   1980
gaccggatcg gggtctcact ccgttcgaag cacgcgctct acaaacgaga gccgtatccg   2040
cagggcgacg tgcgctccgc caccctcatg atgaacgtga tctcggagtc acgcgcgtcc   2100
gccctctaca aggcgctcgc cgcccatgtg tcggagccgg tgatccgcag aatctggcgg   2160
ctcctggccc gcgacgaggc ccggcactgc cgtgcgttct ccgtcttcat gcgggaactg   2220
tgcgacagcg atccggccca tcaggccgcc gcgctgcgca tggcctacat ctggctcgcg   2280
gaccgtagca acggcgtcaa gcacccggcg ggcatgttct acccgcattc cacatccacg   2340
gccggcatcc gccgtatcga gaccatccag cacgactcgg tggacgccgc ggacgccaag   2400
gtgatgtcga tcgtccggct cctggcggac gacgactcgt tggagacccc gcgggacatc   2460
aaagccaagc tgcgcgccct ggcccgccgg cccggcgctc gctgaccgtc agtcccggcg   2520
tccgcctccc gccgcgcccc gacgcgccgg cctcacagaa caggacaaca ccacgccatg   2580
tcacaggcga gtgtcaccga catcgaacag accgtccgcc gatccgtcgc cgagcaactg   2640
cgcatcggtg tcgaggaggt gggcgtggac accgatctgc gctccttgcc gcgcttcgac   2700
tcgatccacg cgctccagat cgtgctggag atcgagcagc actacgacat cgaggtggag   2760
gaccgcatcg tcttcgagac gagcaccgtg cgggagttcg cggccgcgat caccaaggtg   2820
atcgcggagg ccggcacgga accgctgtcg tgaccctgtt cgccgcgctc ggccgcgtcg   2880
ccgcacaagg ctccggacgg ggcatgcacg tgctgcgccg gggccaggac ggcgacgcgc   2940
tgtcctacag cgacctcttc gccgaggccg ggcgggtggc cgcggggctg ctgtcgcgcg   3000
gggtgcgacc cggcgagcgg gtcgccctcg tcctgccgac gtcggtggac ttcgcgcgcg   3060
```

-continued

```
ccttcttcgg cgtgctggcg gcgggcgcgg tcgcggtgcc gctgcccggt cccgcgccct   3120
tcgggtcgtc cgacgcctat ctccggcgca cctccgcggc cctgcgccgc tctcgggtac   3180
ggaccgtgct gacggctccg gccatgcgcc cgctgctcgg tcctggactg tccgacggcg   3240
cccgcccggt cgacgtactc ctggtgccgg aggtggccga gccgtccgcg gcccacgtcg   3300
cgcgggcggc gtcggacccg gccgtcgttc agtacacgtc gggcacgagc agcgaaccgc   3360
ggggcgtcgt gctcagccac ggcaacgtgg cggccggggt ggcggccatc gcccatggca   3420
cacggctcgc caggaccgac gtcggctgca cctggctgcc cctcttccac gacatgggcc   3480
tgatcggttc cttcttgaca ccgctgctgc acgacgtcga catccatctg ctgacaccgg   3540
aggactacct gcgcagtccg ggtgactgga tccgggccat ggggcggctg gggcgacct    3600
tcaccatggc tcctgactcc ggctaccgct acgtcctgag gcgcgacgcg gcgccgccgg   3660
ccggcctcga tctctcccgc tggcgcatcg cggtgaacgg cgccgagccg gtcgaccggc   3720
ggcttcagga cgccttcgcc gagcgtttcg cgcccgccgg actgtccgag aacgtcttcc   3780
tgccggccta cggactggcg gaggcgaccc tggcggtcgc cttccctccc ctcggccgcc   3840
cggccaaggt gctgcgtgcc gaccgggacg aactgaaccg gggccgttac gtaccggtgc   3900
cgtccggcgc cgggccgtgt cgcgaactgg tcagtgtggg aacgccggtg cggcgtaccg   3960
aggtccggct caccaccgcg agcggcgcac cggccgtgcc cggcacggtc ggcgccgtcg   4020
aggtccgggg ggcgtccgtc acgagcaccg ggtacgaccg ccacccccgaa gagagccgtc  4080
gcgtcctcct tccgggcggc tggttggcga ccggtgacct gggcctgtgg cacgacggcg   4140
agctgtacat cgtgggccgc acgaaagagg tgatcatcgt cttcggcgcg aaccactggg   4200
cgagcgacat cgaggcggtc gtgcgggaca cacccggcct cctcgtccac ggcgtcctgg   4260
ccgagcagat ctggagcgac gagggaggcc gcctcgggct cgtcgtcgag acgacgcggc   4320
acgacgaggc gagccgtcgt gccacgacgc aacacatccg cgcacgtgtg gtggccgagc   4380
tgggcatcac acccgacacg atcgagttcg tgcggcgcgg cgggatcgca cgcacctcca   4440
gcggcaaggc tctgcgccgc ccgccgcctt cggacacgta catgtcccgc tccggtgcgt   4500
gacatacccg gaacaccgga ccacaccgca cggccgctac agggcactca gtgctccaga   4560
caccgcggag ccccctggcc acctgccgtg gggaactccc cgcacgaccg gccctggagg   4620
cctcgcatgg cgcacgacgc atacctgctc ggttactccg atagcgagca ccaaaggctg   4680
acccttcaga acgaggcgat ctcgccgttc accgaacgca ccctgcggtc ggccggagta   4740
cgtccgggga tgagcgtcct cgacatcggt gccggactgg gatacgtctc tctgctggcc   4800
gcccaactgg tcgggcccgg cggacacgtc gtgggaatcg agcgcgaccc cggaaccgtc   4860
cacaaggcgc ggatcctggc acaggaggcg gggctcgcgg actcggtgcg gtacgaagcc   4920
gcggacctgg ccgacttcac ctggccgatg aagttcgacg tcctggtcgg caggtacatc   4980
ctgatgtacc tgcccgatcc cgcatccgca ctgcgccgtc tgacgtccct gctgaaaccg   5040
gacgggatcg tcgtcatgca cgagatggac ttcaccaaca cgtcgccgtc acgtccgccg   5100
ctgccggagt gggacgagta ctacgcgctg tggcccggcc ccttcctggc ggccggcgcc   5160
gtccccgact tcggcccccg cctcacccgg acgttcctcg acgccggcct ccggcagccg   5220
gaagtggcca cctggacgcc ggtcgcgggc cgctcgggag atcccgcggt cctcaactgg   5280
ctcagcacca cctgccgcga gatcgcgacg ccgctgcgca acgccggcgt cacggtgccg   5340
gaccacctcc gctttgacga cgccctgcca cagcgactcc gggacctcgt cctgtcccgc   5400
agagcgcagg tcgacgggcc gacgcagttc ggtgcccacg ctcggctgag accacaggcg   5460
```

tccaacgcgt caggccgcga cggcgggatg cgctgagagg cagggaacac accgtgcgcg 5520
ctacgtgacg aacatccggc agccggtctg tccgccaaag ccggtctgtc cgccgaagcc 5580
gggcagcccg aacagcgtgc agaccgaaca gcgggccgcc ttccgggcgg tggaaaaagc 5640
ccgctcgccc gacccggccg ccacccgatg ggtcgtctcc cacggccgtc ggcggcaggg 5700
gagacagaca ccccgcggcg tttccgaccg aacaggagta atcgaccatg tccggcactt 5760
tcgatcacca cagggtcggc cccctgccgc ccttcctggc agcgccatca agtgaggccg 5820
tcaaacgggt gcggatgccc actggtgatc acatgtggct ggtcaccgac tacgccgtgg 5880
ggcgcgccgc gctcgccgac acacgtctca gcagagctgc ggccacccac cccgatgctc 5940
cgaaatgggg atccgtcgac ctctcaccca actcgatcat gagtctggac ggtgcggacc 6000
acgcccggct gcgccgggtc gccggagcag cgttcaccag cgcccgagtc accgcacagg 6060
cagcggtgat cgaggaggcc gccgacgcac tgctggatcg gctacaggtt gcggggccag 6120
gcgccgacct ggtcagcggt tatgcttcgc cccttcccat ggtcgcgttg agctcactgc 6180
tcggcgtgcc ggcggcggag cggcccgttt tcgacgccgc cgtgactgcg ctgttcgaca 6240
tgacgcctca gggaacccgc agaagaggcc gccatatcct gactcttatc aagtacatgt 6300
cctcactgat cgaaagaaag agggatgcgc ccgggcagga tctcctgagc gcgctggtgc 6360
gggttgagca gtcgggtgag atatcccgca tcgagttgat caacctcgga ctggcacttc 6420
tcatggccgg ttacgagacc accgcccatc aattgagcct tgccatactc gaactgctca 6480
ccggtgacgc gctcgacggg caatccgtgg aggatctggt tgaggagctg ctccgcaaga 6540
cgccgtccac acctatcagt tttccccgag tggccatcga ggaccttgtc ctgggcggga 6600
cgacggtgcg ccaaggagag gccgtcatcg tctcgttgct gcacggcaat catgacgccg 6660
aagtattttg cacatcgggt gcgaagagca gcgcccgccg gcctgcacac ctcacattcg 6720
gacacggcgc ccaccggtgc atgggcgcgc cactggttct tctccagatg aagatcgcgc 6780
tgacccgctt gtggcagcgc ttccccggcc tgcgactcgc accgggggac gaggccctcg 6840
tatggcggga gggcctcgcg acgcgcggtg tgtcaaggct ggtcgtcgag tggtaaccga 6900
cacgttcggc gtccacacag gctcggctgc tcgctcgggg tcgcggcgtc gttctcctga 6960
tcggtgtacg cgctgttccg gggaggagcg ggcgagcctg gcatgcgggc gatctttcct 7020
tggtcaccgg tgagagtgaa cctgtggagg tcggcgactc cagcgcggct gcggatacgt 7080
gcgtcagtgg cccctgtccc accactccgt cgttccgcgt cgttccgccc acccgctaca 7140
tgatcacctc cgatgatccc gctacccggt gcaccagcgt cttccatcca gggcacgagc 7200
acgtagattc gaacacccct ccgtgccgat atgatgccgc ttcggtcgtc cgacggaggc 7260
caggctcgtc acctgcgcct ggggcgcttc cacgactgcg ctccgcggcg gtgcgtgtgc 7320
cgtggaagag ccggtgcgcg ggaatcgcgc ccgcggacgg tgtcccggga aagaagcgag 7380
gtatggcagt gatctgcgtc ggcggcatga tcgggatcgg gaagacaagc gtggccgagc 7440
tgatcgccaa agagctgggg agcatggtct tctacgagag cgtggaggac aacccgatcc 7500
tgccgctctt ctacaccgcc ggtcctgagg agatagcggc gaagcgctat cccttccttc 7560
tccagctcta cttcttgcag acgcgattcg ccgcgatcaa ggaggcgtac aaacaggacg 7620
acaacgtcct cgaccggtcg atctacgagg actggtactt cgccaaagtc aatcacgacc 7680
tcggcaggat cagttccctg gagatgcagg tgtacgaggg gttgctcgcg gagatgatgc 7740
gtgagatcga cggcctgccc tatcgcaagg cacccgatct catggtgtat ctcagagcgg 7800

-continued

```
acttcgagac ggtgctgcgc cgcatcggac tgcgggggcg tgacttcgag caggaccaaa   7860
gtctcgtcga gtactaccgg acgctttggg ccgggtacga cgactgggtg cacgagcact   7920
attccgccag cgatgtcctc gtgatcgaca tgaaccgcac cgacgtggtg aacagccccg   7980
acgacgcgaa gcgtgtcgtc cgggaggtcg cggacgccct tgccgtggcg aaagtccggc   8040
gcatctgacg ctgcgcggcg atcggtcgcc gaggcggcgc ggcatgcgca gcacggctca   8100
gccgtccgga gacctcgtcg gcacggcagc ggagcagcgt gccgtgaaag ccgccgcatc   8160
caggatcggg ggagcggcgg tcagcgtctt ccgaagtggg acgggtggca caatgaccgc   8220
tgacttggcc gacagcgacc cgaggaaacc ggcgtgaatc cgacgcggca gcgcgactgg   8280
gcctgcccgt caagatggcg ccgcggctgc tcgcgggcaa ctcggcgccc gcgctcatcg   8340
ggtcggctgg gcaactgctg aggtcccggg ccggtctggg acaccgctca ccgagctgac   8400
acgggggatg aagatgaagt cgagcaccgc cgcggccgcg cgtccggcga cggggccgag   8460
catcccctgt ccgggcatcg tgacggtcca ggtggtgtct tcggccagga ccgtttccag   8520
ctcgggtata tgcaactcgt ccaaggcgtg ggcgtagttc gccaccgcct gctggagttt   8580
cggcgatcac gaggccaccg tcagcacgat cttgccttgg atgtggccct gcgcggctcg   8640
cgtgtgtgcg ctgaccgctt cggacagcgg gtaggtgctg tccaccccga cccggagtgt   8700
gccctcgtcg aacaggcgcc cgatctcggc gagctggggg ccgtgggaac gtacctgaat   8760
gttcgagacg gtgatgtcca gactcgccgt ctcttccggg tcgtactcgg cgaagaacac   8820
cgggagcagg gtgccgccgc gcttgagtac ggtcaggaag cgtgagccgt ccgggccgcc   8880
gacggtgtcg atcaccaggt cgacaccgct gaccacgtcc gcggcctgcg tcgtggtgta   8940
gtcgatgaac tcatcggcac cgagctcgcg caggaaccgc tcgtgccgac ttgaggccac   9000
cgcgatgacg tgtgccccct tccatttcgc caattgcacc gcgaaatggc ccactccacc   9060
ggcggccccg ttgaccagca cggtcatccc cggcgtgatc ggcaccggct ggtgcacctg   9120
gccggtgaaa ggagacggca cctcgtggcc gaggtcgacc aggtactgcc aggccgtgag   9180
cacggccatc ggcgccccgg ccgcctgcac gtggtcgata ccggccggct tgtgagccag   9240
gtcagaagcc ggcgcggcca cgtactgggc gtacgtccgg ccgtcgaatc cggggaaccg   9300
cagcatgccg aagacctcgt cgccgacgcc gaaccccggc acgtccggag cgaccgcctg   9360
gaccacgccc gacatgtccg ttccggggat cagagggaac tccagcgccg gcctcatccc   9420
ggccggcatg accttcatcc cttcacgcag gtaccagtcc ggcgggttga tgcccgccgc   9480
gtgcacccgg acgagcacct cgcccgggcc gatctcggga gccggcacct cgtcgtaccg   9540
cagaacttcc ggcccacccg cttcgtggat ctggatcgcc ttcatcgcgc ctgtcgcttt   9600
ctcggggaaa cgttgctcct tcagtcaaag cccgggacgg catggccgtc caagaccggt   9660
tcggcaatct gaccattccg aaacggcatg acgcgtaccc tgcgagggtg aacgatctcg   9720
ggcaggacct ggaactgcgg ctggtgcgct acttcaccgt ggtggcggcg caccagcact   9780
tcggccgggc cgccgccgac ctgcacgtag cccagccggc gctgagccgt cagatccaac   9840
ggctcgagaa atatctcggc acacgactgc tggaccgcac cccccagggc acccggctca   9900
ctccggccgg ccggacgttc ctcccccggg cccaggccct gctgcgggcc gcccgccagg   9960
ccgagctggc cgtgcgtgaa caagcccgga ccgaacgaat cgccatcggc tacgtcgaag  10020
acctggtgat cactgccgcc gtgcgggaac tgcgccgccg ttaccccgac gccgagatcg  10080
ccacccggca tctgcactgc cgcgacgtcg gggcactgtc cgacaggcgc gtcgacgccc  10140
tgatcgcgcg ggccccgctg ccgctcgtcg ccgacgacgt gttcaccacc ccgctgtacg  10200
```

aggagccccg gatgctcgtg gtcccgcgcg gccatcctct ggccgaccgc gcgtcggtga 10260
ccgcggaaga actggccggc gaagaggcgg cgccgtgtgc gttcgagacc gcaggctggg 10320
cttcctacca gttcctcggg accggcgtgc cgccgatcga gagctacgag gacaagctcg 10380
aactcgtcgc gagcggcagg gccatcgccg tgctaccggt cggcgatcgg cgcagctcac 10440
tgcgtcccga cctcgtcacc gtcccggtcg agggcgctcc ccccagccgg gtcgtcctgg 10500
tcagccgcaa gggcgacccg aatccgatga tcaggaattt ccggctggct gccaaggccg 10560
tcctgaccgc cccggcatcc tgagcgggac caggccgggc gatggccagg ccgacgagcc 10620
gggcggcgcg tggcggttca caacggccac caccgatccg gagcaccttg acgggccgtg 10680
atgctggggc ctctccggga gcgggcgacc tgctcgtgcg gcagtactgc gagcgcagcg 10740
aggactcgcc ctggggggcg ggggagtggc ggaacagcgc gcagtgggaa cgtggcggca 10800
cgaggtcgcc caccgggccg gcgagcgacc gcgtggccca gaggttcggg ctcgccgttg 10860
gcgccgccgt gatgcaggcg ggagattctc gggatgggcc cgcccggtcc ggtagcgcgc 10920
gagtgtcgcg ggacgactga cacggcccca cagaatcggg catcctggga aaatgtctga 10980
cgtgccttgc tccgcttgca gcggatccgg agtcactgag cacaccgagc actctgtcga 11040
agtcgataag gacgggaacc agaagcccgt cgcccgtagc tggaccggct cctgcaatac 11100
ctgccacggc agcggcctca gctgacgaag gggaagcgcc ttgcgatcaa tctatctgtg 11160
cgtcggctgc gcagcgatct acctgccgcc cgagcatccg acggtcggac ggccggtatc 11220
gtcggcgcac tgctcacggc ccgactgccg ggccgcagtg cgccaggccg tcaggatgtc 11280
cggactgccc gaggagaaga tcggagagct ggcccgtcgt gccgccggca tcgacggcga 11340
acctcgccgg ccgagcctcc gcttccgacc cgcacgcggg cgccgagcaa ccgccgctcc 11400
gggcggcggg cgcggcaagc tgcggtagct gtccgatgta gagaagtgac cccgctttcc 11460
tgaacctcat caaccagcgc actgggaagc ggcgatgcgc ttcgtcttcg gtggtctgcg 11520
ctcggtcggc tcgtcgtggg ctttgaggcc tggtgcacgg tggaggtgcg aggtcacctt 11580
ttcgaggatc tcgctgtgcg gaaccttgga ctccggaatc gtctgtatcc gtgcgttcgg 11640
ccgggtgcgg atgcggcgat gaggagaggg gcgagacgat gggtgaaggt gagagggaga 11700
cgtggacgac ggaggagttc gggtcgtccc acgtgggtgc ggtcggggtg ttgctggccg 11760
atggcaccgt cccggatcct gtgctcttcc tcagctcttc cggagcggag gccaggtggc 11820
tatcggagcg gagcgtctac gacggccggc ctcatggcgg accgcgggcg gcagcgttgc 11880
gcgcggtgtg ctcgtgcgga tgggcgggac ccggccgcgc tctcgactgg aacgagagcg 11940
acgaggaaga gggcgaggac ccgagggagg ccgccgaagc cgcatcgccc gcgtccttgc 12000
ggtactcgtt cccccacgcg agcgacaccc gggcagcatg ggccagcgcc cacggcgtgt 12060
acttcccgga cgggctccga agccacgacg actccaacga acaggctgcc ggcacccgcg 12120
cgaacagcgg aagcagcgca ctgggccgat gcctccacac ccgcgctaca tcatccccat 12180
cccgtaccgc ccgaccccct gatggccacg tcgtgcactc cagggatctc gtgtccaccc 12240
ctctgcgctg tcctgctcat tgcagcccgt ccaggggacc ggcaccgatg ccccccgacc 12300
gcaatgccct ctgcgggcaa ccgccgcgct ccccgtaggg gtcaatggcg cgcccttgcc 12360
gccacacccc taatcagaca catgtgtcaa ctgctcatcc gcccactcgg cgaaggtggt 12420
gagcgggatg cccaacttcc gggcgaatgt gggccgggcg ggctggagga ccacgttgtt 12480
ccactcgtgt ccggctcccc acttcggcat gcccgcggca agggcctctt ccacgctcag 12540

-continued

```
ggagggcgcg gtcacgggca cgccccaggc ggcggacaag gtctgcgcga tctgctccat  12600
cgtgcgaagg tcaccagcca gttccagttc cacctggtgg aaccggtcgg ggtctcggag  12660
ggcgtgtgcc gcggccgtgc cgatgtcccg cacggccacc aaggccagtt cggtgtccgg  12720
cttcagtacc gtcagcagtc cgccgcgggg ccccttgggt gccagcaggg gcaggttctc  12780
catgaagaag gcgggcttga tcaccgtcca gcgggcgaaa cccgcaccac gcaccgcctc  12840
catgatcgcc tgcttggtgt ggaagtactc cgccatcgcc gcccagcggc cctcggccca  12900
gccggcgacc cgggtgtgtt caccgactcc actggtcgag gactgtacga actgccgtac  12960
tccccctatc ttcgccgcgt ccaccaggtt ggtggcctgg gcgagttcgc tcgcgaagtc  13020
cacgctggtc tcggtcatgg gcggcatctg caccgagaac accgcgcgga ccccctcgac  13080
cgccgggtcg agggaggccc ggtcggaaag atccgcgcgt accagttccg cgcccagcgc  13140
ctcgatcgcc cgggcggact tcgacgaggg atcgcgtacg agcgcacgta cgggcacctt  13200
ggcggccaaa agcgcgcgag ccgtggcccc gccttgctgg ccggtggcgc cggtgaccag  13260
gacggtatcg ctgctgctgg gcatggtgct gctcctcaag ggccggagag acaaaaacggc  13320
ggggcccgcc gtttcgtgtg ccgctaagat atggcggggc ccgccactta gcaacgagga  13380
gaccatgact ggccagcgct cggacgcccg acgcaactat cagcgcatcc tcgccgtcgc  13440
cgaagccgaa gtcgccgcgc acggcgccga ggcatcccag gagcagatcg cccgcatcgc  13500
aggcgtcggt tcggcgaccg tgcgccgtca cttccccacc cgccgggcgc tcctcgaagc  13560
cgtcttccag gagcgcattg cgggcctgtg cgagcgcgcc catcggctga gtgcgtccga  13620
ggacggccgc accgcactgc tggagtggtt ccacgccttc gtccgctacg ccgtctcagc  13680
ccgcggattc gcccatatcc tcagctacga gccgcccacc gaagaaccct ccccgaagag  13740
ctgcgggggc gtaatcgaag cagccgcaac tcccttgctc cagcgggcca tccgcgacaa  13800
ggcggttgca ccgcacgtca cctttcacga cctgctgacc ctcgccgtcg gcatcgccct  13860
ggccaccgag caccacacag accccgacac ccaggccgac cgcctcttcc gcctcgccgt  13920
ggaagggctc agccctcagc cgggcccagc cggggagccc gggaactccg gctcgtcggc  13980
gccggtgaca ggaagtccgc cgaatgagca cgcgtgagaa gtgggatgcc tcctcggtga  14040
caaccgaact gcctcggcac gccctcctcg ccagctcatc cggcgtcgcc gtgagaacgt  14100
cctgagcttc ggcttatcca taacaccgag ggccgtcccc gggtccccag caccctgtga  14160
ggcagctggg gatccggagg aatggacccg cctgacctct ggtggacgcc ttccgagggg  14220
cgacctgagg gactgagggc ggatgacctg tgacagcgaa ccttgatcga gcgccatcga  14280
aggttgacca gtcaccgaat ccgccgtcga ccggatcggc cgacggatcg gatgccgggt  14340
gggtcggtcg gaggaaacgg gacctttgac ccgtgtggag tgttccggag cggatatccg  14400
tatgtcgccg gtcgtccgcg cggagcgacc ggcgggcagc cccggcggag cctcgtcggg  14460
ccttcctcgg caccacctac agcaaaggac gcacaccgtg ggcatcatcg cctggattct  14520
catcggcctc atcgcgggcg ccatcgccaa ggcactcatg cccggcaagg acccgggcgg  14580
ctgcctcgtc acgatgctca tcggcatcgt cggcggtctg ctcggcggct ggctcggcaa  14640
ggtgatcttc ggcgtgcact ccatcaacgg cttcttccac ctctcgacat ggatcgccgc  14700
ggtcgtcggc tcggtgatcg tgctcctgct gtaccgcctc ttcaccggac agcgttcgcg  14760
ctgaccgcga ccggcgatcc acgtctgtcc gtagccggcg tcgagccctg aaccgactgt  14820
gctgcgggcg ggcactgcgc ccctgagctg cggcggtccg tctttgctgt caagaactgc  14880
attcggtcca ccttcgaggc cagtccgctg tcacaggtca gcgggccagc tccgaattgg  14940
```

-continued

```
tgtcacgatc accgaacgtc acaatctggt tgtcacgggc tctgtcgcgc ccgccgccga  15000
acgggtgaca gtagccgctg ctgctggggg cgagctgtcc ggcctgtcct gtgggatcgg  15060
tgtgggaggc ggcgaatcgg cgttttggga cgccttgtgc gggatgccgc gcgtcgtgca  15120
gcgggcggtg ctggattctc tgctcgtcgg gccgcctggt ggagctggac cggctgcgcc  15180
gcggaccggt acgggtgacg gggcggcgca gagtggtcgc ggtacggggc ggacgacaag  15240
gtgtcgttgc cgcgccggca ctcggactct cgcagcctca caacgctgct ggccgcggcg  15300
gtgtacctca cgtcgcgggc ggtggacgac gcgctggatc tgctgaaggt cctgatcgcg  15360
acgaagcttg cagaccggct gcacatcctg gacggcggtg ctggacgcca cattcgaaaa  15420
gcgcctgctc aatacccgcc cccaacggag acgaggttga acgacaagct cagggcgtct  15480
gagtacttcg gttgagtagt tctgcccatg tgaggggcag ggccgtcgag acaggctgtg  15540
tacacaacgc cgcggtgcgc agagcgctcg gcgaagagac cagtagcggt catctatgag  15600
gggatacttc atgtccaagc gccttgtcgt ctcgtcgctc gccgtggccg cagccgtcgt  15660
tgccggcacc gtggtgttcg tctcctcggc cgacgccgct gtgccggcca agccggagat  15720
ctcaaaggcc accgcccact acaccagtac ggccggtggg agcgcctcgc tcaccttcag  15780
cgccaccgtg gccgacaact ccggaatcaa gagcctgcgg gtgctcgcct ggccggcgag  15840
ttcgggcctt gcgcccacgg cgggcgagat gcgggatgtc gaggaagcca cgtgcaaggc  15900
gacttccgcg acggcctcgg tgtgcaccta caccgtgaag agctcggcca aggaagccgc  15960
cgcgttgccc aagggcgtct ggcacgtatc cgtgctggcc accgccaagg accacgacac  16020
gaccttcgcg ccccaaggcg ccacgttcac cgtcaagcac tgacggctcc gccccgccgg  16080
aatgatgatc gcggcccgcg cgccgggcgg accgtatcgc gacctccatt ggacccgttg  16140
aaccgcacga cgcggtgaac tccgcccacc ctgccccagg gcggacggag ttcacctggg  16200
ggcgacgccg cgcatctgac gcgcgctgcc acgatgccgc accactccgc gcgcgggcgg  16260
atgcaggcga agtgactccc agctcgacgc gctcgccaaa cacggcatct cgcgcgacta  16320
catcttcggc gagaagatca gcacccgggc gcggggcagc ccgaagttcc gggaggaggc  16380
gctgagggcg gcgcgggagg tcaaggcgca cgccccacac tgccgtgtca tcttcacggt  16440
gtacgagcgg aagcggctcg gtcgcaacgc cgccgaactc accgccctcg ccgaccacct  16500
caccgcccac ggcttggtcc tggagatatt cgccgggccc tgtcgaagga ctcccggagc  16560
cgtggaaccc ggcgcccacc cgacgcgaca gcccgacgcg gcagttgggg cgctcccgcg  16620
cggcctgccc ggacaccgaa acgcccggca ccacaagcga aagagcgtcc gtcggcaagc  16680
tgacgggtcc tcatgaagga tttaggccag tgatttggga cacacccgaa cgcgccggcc  16740
ggatctgagg aatcgcctag ggcccgctcc tatcgggaac ttgaagccgc cctgccgagc  16800
caacgcttga ctccggttcc ggcggtgcgg atgacgataa tttccggtga gtctgcccaa  16860
aagggtacat agcgggcgca tagaaaactc ttgcgagtgc tgcgggtggc ttgtagggtc  16920
ctaatgaatc ggctggacaa gggaaggttg atgcgggcgt ccgaaccaaa atagcttcgg  16980
acagcaactg ctgccttctg tcgatggaag taggggaag ttcgtggaaa tcggctcggg  17040
cgcgcccgaa ttaaccgcgt cgtcggtgta tcagcagcgg cgtgaccaaa tcgccgcaag  17100
cgctgccgcc tatgtgcccg gcgagcccat tccagaggtc gagtacacgg acgccgagca  17160
cgctctgtgg cgcctggttt ccaagcggct cgcggaccgg caccggcaca tggcggcgcc  17220
ggagttcgtc gaggcggcgg agcggctcga ggtgggcggc gacggcgtcc cgcagttgcg  17280
```

tgaagtgtcc gaccggctcg accagctgac cggattccgc ctacgccccg cgtccggcgt 17340
ggttcccttc gccctgttct gcggctctct ggccgacggg tacttccact ccacccagta 17400
cctccgcgac agcgcgacac ccttctactc gacggaaccg gacatcctgc acgaggtcat 17460
cgggcacggc agcgccctgg ccgacgaccg gttcgccaac ctgtaccgcc tggccggcga 17520
ggccgtgcgc agggtggagt ccgaggacgc cgtccagttc gtcgccaaga ccttctggtt 17580
cacgctcgaa tgcggcctgc tggacgccgc cgacgggccc cgggcctacg gcgccagcgt 17640
cgtctcctcc tacggcgagc tggagcactt ccgttccgcg gagatccggc cgctggacat 17700
cgccgacatg gcccacgtcg actacgacat aacccagtac cagaccacct tttacagcgc 17760
gcgttccctc acgcatctgg aggacgtcgc aggtgaattc tgggcgtcct gcgacgatac 17820
atccattgaa aaactaatgg cggttgatat atgacccggc tcgcagagca atcatccact 17880
gcgcagcaga gcccggaatc agaagtactg gacgtcaccg gaatcggatt cggtgccgcg 17940
aatctcgccc tggcggtggc gctccatgaa tccgaagccg ccgggaaggc ccttttcctg 18000
gagaagcaga aggaattcgg ctggcatcgg gggatgctcc tggggggctc ctcgctccag 18060
gtgtcctttc tcaaggacat cgccacgatg cgcaatccca ccagtgattt cggattcctg 18120
tcctatctcc aggagaagga ccggctggtc gacttcatca accagcacac cctgctgccc 18180
tcccggatcg agtaccacga ctacctccag tgggccgccg accggctgaa ccacctggtc 18240
gagtacggcg tggaggccac cggtgtgcgg ccggtgaccg aagccggtga ggtcgtcgcg 18300
ctcgacgtgc tcgccgggga ccgggtggtc gcccggacca gaaacctcgt cctcgcctcc 18360
ggcctgcgcc cccggctgcc cgagggcgcg gagaccggcg aacgcgtctg gcacagctcc 18420
cagttgctgc accggctgcc cgcgttcgac gaacgcccgc cccgccgggc cgtcgtggtc 18480
ggcgccggcc agagcgcggc cgaggtcgcc gcgcacctca tggaccgcta cccgcaggcc 18540
gaggtgtgcg cggtgttcgc ccgctacggc tacagcgtcg ccgactccag cccgttcgcc 18600
aaccgcgtct tcgacccggc cgccgtggac gacttctact tcgccccgcc cgaggtcaag 18660
caggccatca tgcgctacca cggcggcacc aactacgccg tcgtcgacga ggacgtcctc 18720
cagggcctct accgccgcca gtacgagcag aaggtgtccg gcgccccgcg gctgcgggtg 18780
atgaacgcct cccgcctggt gtccgtcgaa ccgcgccagg aatccgccgc cgtacgcgtg 18840
gagttcctgc ccacgggcga acacaccgac ctggacgccg acctggtcgt gtacgccacc 18900
gggtacgact ccaccgaccc ggccgaactg ctcggcggcg tctccggcgc cctccgccgg 18960
gacgaggcgg gggagttgct gatcggccgc gactaccggc tcggcaccac cggggatttc 19020
cggtgcggca tctacgtcca gggcgccacc gaggcgaccc acggcatcgc ctccaccctg 19080
ctgtccatgg tggcggtccg cgcgggcgag atcgcccggt cgatcaccgg cggccggtgc 19140
gacccggacc gctccaccgg aagcaaggca gcagcgggga acaggggctg aagtgtacga 19200
acgtccgctg taccgggagg attgcgacgg cgtcgtcctg gcgtttctgc gacacaaccc 19260
actggcaatg gtcgtcacct cgcacgacga cgtcccggtg gccacccacg cgccggtgct 19320
gttccggcac ggacccgacg gcgccgacgc cgaggccgtc gccgcgggca ccgtcccgct 19380
cgccggctcc accctgatcg gccacatgaa cgtcgagaac ccgcagtggc gccggatgcg 19440
ctccggcgac cgggcgctca tcgtcttcca gggcccgcac ggctatgtct cgccgacggt 19500
ctacggggtc acgcccgcgg cccccacctg ggacttcatc gccgtccacg tgaacggcac 19560
agtggagccc accgccgacc ccgccgccgt gctggacatc gtctccgaca ccgcccggcg 19620
gctggagtcc ggcttcgggc gcggctggga ccaggagtcc tccctcgact acttccgcca 19680
gatcgcgccc ggcgtgggcg ccttcaccct gcgggtcgat tccgtgcaga cgatgttcaa 19740
gctcagccag gagaagcccg ccccgatgcg gcggcgcgtg gtcgagcagt tcgaagcaag 19800
cgagtccggc acccaccgcg ccctggccag cgtgatgcgc gaccgcggac tcaccgaagc 19860
cgacgaggag cgggagacag ccggatgacg caggggagct cgcgacggcc gggactggac 19920
tcggcactca accggctccg ggagcgcacg gcgaggaccg gcacgacacc cgcgggcatc 19980
agccgggtcc cccgcgaccg gccgctggag ctgtcgttcg cccagcagcg gctgtggttc 20040
ctcgaccggc tgatgccgga cagcgccttc tacaacttcg gcaccgccgt gcgcgtccgc 20100
ggcccgctcg gcgccggcct gctggcccgg gcgctgagct gtgtcgtcgc ccggcacgag 20160
accctgcgca ccgtcttcgc cgaccacgag ggcgtggccg gcgccgtcgt cctgccgccg 20220
gagccggtgc ccgttcccgt gaccgacgcc gtggacgagg ccgacgccga gcggctggcc 20280
ggcgaggagg ccgcgcgccc cttcgacctc accaagggcc ccctgctccg cgcccgcctg 20340
ctgcggctcg ccgacgacga ccacgtcctg ctgctgacgg tgcatcacat cgccaccgac 20400
ggctggtcgc acggcctgct gtgggccgag ctgaccgcgg cctacaccgc cctggccgac 20460
ggccggcagc ccgcgctgcc ggaactgccg gtgcagtacg ccgacttcgc cgcctggcag 20520
cgccgtaccc tgtcgcccgc cgtgctggag cggcggctgg cgtactggca ggaccggctg 20580
gccggcctgc ccccgctgga cctgccgctc gaccggcccc gcccggccgt cgcctccgcc 20640
gagggcggcg tcgtcacctg gcggctgccg gcggacgccg tcgccgccgc ccgggccgtc 20700
gccgcacggc agggcgcgac cctgcacatg accctgctgg ccgcgttcag cgcggtcctc 20760
gggcggcacg cccgcaccga ggacgtcgcc gtcgcccagc cggtcgccgg ccggcccctg 20820
gccgaggtcg agcaactcat cggattcttc gtcaacaccg tcgtcacccg caccgacctc 20880
ggcggcgacc ccaccttcgc ggaactcgtc gaacgcgtcc gcgccgcctc ggtggacgag 20940
atggcgcacc aggacgtgcc gttcgagtac ctggtggagc ggctggtccc cgagcgcgac 21000
ctgtcccgca acccgctcgc ccaggtcgtc ttccagtacg tgccccggcc cgccgcgcgc 21060
cccgcgccgt tccccggcac caccgccgaa cccttcgcgg gcgaccgcgc cttcacccgc 21120
atggacctgg aggtctacct cggcgaggac gccgagggcg gcgtcgaggg actgatcaac 21180
tacagccgcg ccctgttcga ccgggagacc gtcgagcggc tggcccgcca cctgacggcc 21240
ctgctgcgcg ccgcctgcgc cgagcccgac cggccgctgt cccggctgac gatgaccgac 21300
gcgggcgagg acgcggccct ggaccgggcc gcccggggca ccggcgtacc gctgcccgag 21360
gcctcgctgc ccgagctgtt cgccgcccag gccgcccgca ccccggacgc cgtcgccgtg 21420
gccgacggga cggaacacct cacctacgcc cagctggacc gcgccgccaa ccggctcgcc 21480
catgtcctgg ccggccacgg agccggaccc gagagcgtcg tcgcgctggc gacggaacgt 21540
tccgcccacc tggtcgtcgc cgtgctcgcg gtcctcaagg ccggcggcgc ctacctgccg 21600
ctcgacgccc gcaacccggc cgcccggacc cgcgccgtcc tcgccgacac cggtgccgcg 21660
ctgctgctga ccgacggcgg tcccgcaccc gccggcaccg agcacctgcc ggccgtagac 21720
ctgcgcgccg tccccggcac agcccccgac acggctttgc cgaacaccgt cggcccggac 21780
ggcctcgcgt acgtgatgtc cacctccggt tccaccggca cgcccaaggc cgtcgccacg 21840
acccaccgcg ccgtggccgc cctcgccctc caccggcgct ggtccggcgg cgcccacgaa 21900
cgggtcctgc tgcactcccc gcaggcgttc gacgcctcca cctacgaact gtggtccccg 21960
ctgctgtccg gccgccgcgt cgtggtggcc ccgcccggcg ccctcggacc cgccgccctc 22020
gcccgtgtcg tcgccgacca gggcgtcacc gcgctgtggc tgacctccgg cctcttcgac 22080
ctcgtggtcg aggaggacgt cacctgcctg gccggcgtcc gcgaactcgt cgtcggcggc 22140
gacaccgtgt ccccggcgac cgtggcccgc gtgcgcggcg cccacccgga cctgacggtc 22200
gtcaacggct acggccccac cgagaccacc accttcgcca ccctccaccc gatcgcgccg 22260
gccgacccgg cccccggcgg ccgggtgccc atcggcagcc ccctggacaa cacccgcgcc 22320
cacgtcctcg acgaccggct gcggcccgtc ccgttcggcg tgcccggcga actgtacgtc 22380
ggcggcccgc gcctggcccg cggctacgcc ggccggccgg cggccaccgc cgagcgcttc 22440
ctgcccgacc cgtccggacc ggcgggcagc cgcatgtacc gcaccggcga cgtggtgcgc 22500
cgccgccccg acggcgtcct ggagttcctc ggccgcgccg acgaccaggc gaagctgcgc 22560
ggcctccggg tcgagcccgg cgaggtcgag gccgtcctgg ccgcccaccc cgccgtcgcg 22620
cacgccgccg tcgtggtgcg cggtgacggc ccggccggca agcggctcgt cgcccacgtc 22680
gtcccgcgcg ccggccgcac caccgacacc gccgccctgc gcgcccacgc cgcggcggcc 22740
ctgcccgact acctggtgcc ctcggccttc gtcctcgccg acgcgctgcc gctgaccgcc 22800
accggcaagg tcgaccgcgc cgcgctgccc gccccggcgg agacggcgga cgccggcctg 22860
gccgccccgc gcaccgacgc cgagcgggcg ctgtgcgaga tcttcgccga gctgctcgac 22920
gccgacgcgt tcggcgccga ggacgacttc ttcgtacgcg gcggccactc gctgctcgcc 22980
acccgcctcg tcgcccgaat cgcccgcgcc ttcggcaccg aggtcccgct gcgcgaggtg 23040
ttcgagcacc gcaccccgcg agccctggcc tcggtggtcg ccggcgccgc gctcccggcc 23100
gacccggcgc cgccgctggt gcccgcggac cgcgaccggc tgctgccgct gtccttcgcc 23160
cagcagcgga tgtggttcct ggaccagctc gcccccggca gcgcctcgta cacctccggc 23220
ggagccctgc gcgtgcgcgg accgctggac cccgagcggc tggccggcgc cctgtcggcg 23280
gtcgtcgccc ggcacgagac cctgcgcacc accttcacgg tcgccgacgg cgtgcccgcc 23340
gcggtcatcg gcgccgccgc cccggtcgcc ccgcggatcg tcgacgtacc cgacgccgac 23400
gcggcacgcg ccgcggcctc cgccgagctg tccaccgggt tcgacctgac gcggggcccg 23460
ctgctgcgcg ccacgctgct ccggctcgcc cccgacgacc acgtcctcgt cgtcgccgtg 23520
caccacatcg cgaccgacgg ctggtcccag gccctgctgt gggccgagat cgccgccgcg 23580
tacgacggcg ccccgctgcc cgaactgccc gtccagtacg gcgaccacgc cgtatggcag 23640
cggtcctggc tgaccggcga ggtgctggag cgccgggccg gctactggac cggccggctg 23700
gccggcctcg ccccgctgga actgccgctg gacaaggccc ggcccgccgt cgccaccggg 23760
cgggcgggca ccctgccctg gcagctgccc gccgagctga tccgggacgc ccgggccgtc 23820
gccgcccgcg agggagccac gctctacatg gtgctcctgg ccgcgttcac cctcgtcctg 23880
tcccggtacg cccgcaccga ggacatcgcc gtgggctcgc cgacggccgg ccggacccgc 23940
gccgagaccg aggcgctgat cggcttcttc gtcaacgtcg tcgccgtccg caccgacctg 24000
tccggcgacc cgaccttccg ggaactcctg ggccgggtac gggagtcggt ggtcggcgcc 24060
gtcgagcacc aggacgtccc cttcgagcac ctggtggaac ggctgcgccc cgagcgcgac 24120
ctgtcccgca acccgctcgt gcaggtggcg ttccagctgc tcgccgacgc gccccggcgg 24180
ccctggtggc agggcgcccg ggccgagccg ttcgacatcg accacgcgta cacccggatg 24240
gacctggagg tgcacgccgt cgagaccggc gacgaggtcg gcgcgaccgt cctgtacgcg 24300
gccgacctgt tcgacgccga caccgtccgc cagctgatgc accacgtgtc ggtggtcctc 24360
ggcgaggtgc tcgccgaccc cgaccggccg gtctccgcgg cgaccatgct cgacgagacc 24420

-continued

```
gaccggcacc gcaccctggt cgcctggaac gacacggccg caccgctgcc ggacggctgc  24480
gtgccccggc tctacgccga gcaggccgcc cgcacccccg acgccgtcgc cctgatctgc  24540
ggcgacgagc gggtcaccta cgccgaactg gaccggcggg ccaaccgctt cgcccacctc  24600
ctgctggccc acggcgtcgg cgccgacgaa ccggtcggcg tcgccaccgg acgctccacc  24660
ggcatggtgg ccgccgtgct cggcgtgctc aaggcgggcg ccgcctacgt gccgctcgac  24720
ccgcgcaacc ccccgggccg caccgagcgc atcgtggcca cctcggggct gcgcgtcgtc  24780
atcgccgacc gcccggtgcc cggcaccgac ggcatcaccg tcctcgacgt caccgacccg  24840
ggccccgggc ccgacaccga ccccggtatc gacccgcacc ccgacaccac ggcgtacgtc  24900
atctacacct ccgggtccag cggcgagccc aagggcgtgg ccgtgaccca ccgcaacgtc  24960
gtcgtgctgg ccgccgaccg ccgctggagc aacggcaacc acgaacgggt gctgctgcac  25020
tatccgctgg ccaccgacat ctccacctac gagctgtggc cgttcctgct gaccggcaag  25080
cagatcgtcg tcgccaccga cgagcacgtc gaaccgcaca ccttcgaccg gctcatccgc  25140
gagcacggcg tcaccgcgat gtgcctgccc gcacccctgt tcagcctcct ggccgaggag  25200
tgcatggagt gcttcggcgg gctgcgcgag gtgctcaccg gcggcgaggc cgtgtccggc  25260
gagaccgtcg cccaggtgat ggccgcccac ccgcacctga ccgtggccga cgcctacggc  25320
ccgaccgagg cgaccgcgtt caccacgctg ttcccgatgg aacccggctt ccggctcgcc  25380
ggctcccggg tgcccatcgg cgcgccgatc gacaacaccc gggtgtacgt cctcgacgac  25440
accctccgcc cggcgccgct gggcgtggcg ggcgaactgg tcatcggcgg gccccgggtg  25500
gcgcgcggct acctgggccg gcccgacctg accgccgaga agttcgtgcc ggacccgtgg  25560
ggcgggccgg gcgagcggat gtaccgtacg ggcgacgtcg tacggtggct gcccggcggc  25620
gcgctggagt tcctcggccg cgccgacgtc caggtcaaga tccgcggctt ccgggtggag  25680
cccggcgagg tcgaggccgc gctgctgcgg cacccggcgg tctcgcaggt caccgtcgcc  25740
gtgcgcgagg acatcccggg cgacaagcgc ctggtcgcct atgtggtgct ggagccggag  25800
gccggcgcga gcgtgctgcc cgccctgcgc gcccacgccg cgggctccgt acccgactac  25860
atggtgccgt cggcgttcgt cgcgctcgac gcgttcccgc tgtccaccac cggcaagatc  25920
gaccgccggg ccctgcccgc gcccgacacc cgctcggtcg ccgagagcgg gtacgtcccg  25980
cccgcgaccg aggcggagcg ggtgctgtgc gagatcttcg ccgaggtgct ggacgtccac  26040
ccggtgggcg ccgacgacga cttcttcgcc ctgggcgggc actcgctgct ggccacccgc  26100
gccatcgccc ggatccgcgc ccgcttcggg cccgacgtgc cgctccaggc ggtgttcgaa  26160
cggcgctccc cgcgccggct ggccgagacc ctcggcgagc ccggcacggc cacggacgtc  26220
atccggccgg cccgccggga cggcgccgcg cttccgctgt cgtcctccca gcggcgcctg  26280
tggttcctgg accggctcac cccggacagc ggcttctgga acgtggcgat gggcgtacgc  26340
gcccacggcc cgctcgacgt cgacgccctc ggccgggcac tgtccctggt ggtctcccgc  26400
cacgaggcgc tgcgcaccgt cttcgccgcc gacgccggcg agcctatggc cgtcgtacgg  26460
cccgcgaccc cgctccgcct ggaggtcacg gacgtcgccg acgaggccga ggtacgcgcc  26520
ctggccgagg cggacgccgc gcgccccttc gacctggccc ggggaccgct gctgcgcgcc  26580
cgcgtgctgc gcctcgcggc cgaggaccac gccgtcctga tcaccgcgca ccacgcggtc  26640
acggacggct ggtcgcacgc cgtgttctgg ggcgagctgg ccgaggccta ccgcgccgaa  26700
ctgtccggcg accccgccga actgcccgaa ctgcctgtcc agtacggcga cttcgccgtc  26760
```

-continued

```
tggcagcagg gccggctcac cggcgccgaa ctggagcggt acctcaccta ctggcgggcg  26820
cggctcgccg ggctgcgccc cctggaactt cccctggacc ggccccgccc cgcggtcgcc  26880
ggctcggcgg gcgcctccca gccgtgggaa ctgcccgagg acctggtccg ggccgcgcgc  26940
gcgttcggcg acaccgaggg cgccaccctc tacatgacgc tgctgaccgc cttcaccgtg  27000
gtcctggcac ggttcgccgg caccgaggac gtcgccgtcg gcgcccccgt ggcaggccgt  27060
acccgccccg aggtggagcg gctgatcggc ttcttcgtca acatgctggt gctgcgcacc  27120
gacgtctccg gcgacccgac cttccgcgac ctgctgggcc gggtgcgcga gacggtggtg  27180
ggcgccatgg accaccagga cctgcccttc gagcacctgg tggagaccct ggcacccgag  27240
cgggacctgt cccgcaaccc gctggtccag gtggtcttcc agctgatgcg ggcgcccggg  27300
gacaagggcg accgcctcgg cgccgcccgc ctggaaccgc tgctggacga gcacgccttc  27360
acccgcgtcg acctcgaagt gcacctcacc gaggacggcg accgggtgcg cggcaccgtg  27420
ctgcactcca ccgcgctgtt cgaggcggac acggtccgcc gcctgctgca tcaccacacg  27480
gtgctgctgc gcgccgccct cgccgacccg gacgcgccgc tgtccgcgct ctcgctgctg  27540
gacgacgacg accggcgcct gctgctggag cggtggaacg acaccgccct cccgtaccgg  27600
gacgtcccgc tcgtggagct gttcgccgag caggtcgccc gcacccccgg cgcccgcgcc  27660
gtggagtgcg aggacgacgt cctcacctac gccgcgctgg accacgaggc cgagcggatc  27720
gccgccgggc tgcgggccca gggcgtgggg ccggacgacc tcgtcggcct ctgcctggag  27780
cgcggcaccg tgcagatggc cgctctgatc ggcatcctca aggccggcgc cgcctatgtg  27840
ccgatcgacc cgagccaccc ccgggaccgg atccggctca tcgtcgacga cgcccggatg  27900
accgtcgccg tcaccgaccg ggctcacgcg gacgtcttcg ccgagggcac cgccctcgtc  27960
ctcgtggacg ccccggccgg gcaggagccg cccgcggcaa cggccgccgg acgacccggc  28020
cccgactccc tcgcctacgt cgtctacacc tccggctcca ccggcgtgcc caagggcatc  28080
gccatgcccg cccggtgtgt ggtcaacatg ctcgcctggc agaagaagac ggtaccgggc  28140
ggacccggca cgcgcaccgc ccagttcacc gccctcacct tcgacgtgca tgtgcaggag  28200
gtgctctccg cgctcctgta cggcgagacg ctggtcatcc ccaccgagga gacccgccgc  28260
gacccggccc gcttcgcccg ctggctcgac gaacgggccg tcgagcagat attcgtgccc  28320
aacctgatga tccgcgcgct cgccgaggag gccggcgccg gccgggcccg gctcacctcg  28380
ctgcggcaca tctcccaggc gggcgagccg ctgtcgctgg acaccgtgct gcgcgagttc  28440
tgcgccgccc ggccccgtct gcgtctgcac aaccactacg gctccaccga gatccaggtc  28500
gtcacctcct tcaccctgcc cgctgacgtc gccgactggc cccggaccgc acacctgggc  28560
gagccggtcg acaactcccg cgcctacgtc ctggacgacc ggctgcggcc ggtccccgtg  28620
ggcgtggccg gcgaactctg cttcgccggc cccggactcg cccgcggcta cgtcggcaag  28680
ccggaactga cggcgcagaa gttcgtgccc gacccgttcg gcccgcccgg ctcccgcctc  28740
taccgcaccg gggacctggg ccgctggcgg cccgacggca gcctggaata cctgggccgg  28800
ctcgaccacc aggtcaagat ccggggcttc cgggtggagc tgggcgaggt cgaggccgtc  28860
ctgctgcgcc accccgaggt cacccgcgcc gtcatcgtcg cccgcgagga cgcccccggc  28920
gtcaagcggc tcgtcggcta cgtcgtgccc gtccccggta ccgacggagg gctgccggcc  28980
cggctgcgcg cccacctggc cgacgccgta ccggactaca tggtgccgtc ggcgctcgtc  29040
gcgctggacg cgttcccgct gaccaccacc ggcaagatcg accgggccgc gctgcccgcc  29100
ccggacctgc gcaccacgct cgacaccggc ttcaccgcac cccgtaccgg tgcggagcag  29160
```

acgctgtgcg aggtgttcgc cgaggtgctg gagaccggcg gggtcggcat cgacgacgac 29220
ttcttcgcgc tcggcgggca ctcgctggtc gcggcccgca cggtcgcccg gatccgcgag 29280
gcgctgggcg ccgaggtgtc cctgcgggag ctgttccagc accgcacccc gcgcgccctc 29340
gccgaggtcg tcgccgtggc cccgcgcacg gccgtaccgc ccctggtgcc ggtgtcccgg 29400
caggagcccc tgccgctgtc gctgggccag ctgcggctgt ggcggctgca cgaggccgac 29460
cccggcgacc cggtctggac gatcccgctg gccgtgcgga tcaccggcga actggacgcg 29520
gacctgctgg gccgcgccct gaccgaggtc gtgcgccggc acgaggcgct gcgcacggtc 29580
ttcgtgcccg gcgacgagcc ggcgtcggtg atcctgcccg ccacggacat cgtgctggac 29640
ccggtggacg tggccgacga gaccgccgcc cgcgccctgg ccgacgaggc agcggcccgg 29700
ccgttcgacc tcgtccgggg accggtgctg cggcccgcac tgctgcggat cgccccccgac 29760 gaccacgtcc tgctgctgac ggtgcaccac atcgccaccg acggctggtc ccagggcgtg 29820
ctctggaccg aactgtccgg cgcctacgcg gcactacgag agaaccgtcc ggccgagctg 29880
cccgaactgc ccgtccagta cggcgacttc gccttctggc agcggtcctg gctgaccgga 29940
gccgcgctcg acgcccagct cggccactgg cgccgccggc tggacggcct gcggcccctc 30000
gccctgccgg gcgtcccggc cgacgcggcc cacgacgcca ccggcgtgct gaccgagtgg 30060
cggctgcccg ccggcctggt cgccaccgcc cgccgggtcg gcgccgagca cgacgccacc 30120
ctctacatga ccctgctggc cgcgttcacg gccacgctcg cccgctgggc gggcacggac 30180
gacctcgccg tcggctcccc ggtggcgggc cgcacccggg ccgaggtcga ggggctgatc 30240
ggcttcttcg ccaacttcgt gcccctgcgc gtcgacctca gcggcgaccc gtccttcgcc 30300
ggcctgctgg agcgggtccg ggacaccgcc ctcgacgcct acgcccacca ggccctgccc 30360
tgggaacgcg tcgtcgaagg cctcggcctg gaccccgaac agccgctggt cgacgtcgtg 30420
ttccagctcg tcaacgtcga actcggcgaa ctcggcctgc ctggcgcccg cgtcgagcag 30480
ttcacgggcc aacaggcgta cgcccgctgg cacctcgagg tgcacctggt cgaggacccc 30540
gacggcggcc tcaccggaca cgtcgtacac cgcgccgccg ccctcggccg acgcgtcgtg 30600
gacggcctgc tggccggcac cgccgcgctg ctacaggccg cactcgccga acccggcctg 30660
cccgtctccg cactgcacgc accggacccg ctggaggga ccacccatga ctgagccgct 30720
gaccgacccg aaggctgctc agccgcccgc gctcgcgcac cggctcgccg gtctgcccga 30780
acccgagcgc cggcgcgtcg tcctggacct ggtccggaca caggtcgcgg aggtgctcga 30840
cctcggcacc gccgccgacg taccgccgga ccgggcgatc cgggaactcg gactgcgctc 30900
gctgaccgcc gtacaactgc tgctgcggct cagccgcggc accggcgtga agctgcccac 30960
caccgccatc tacgaccacc ccaccgcccg cgccctggcg gacgtcctgg tcgacgccgc 31020
ctccggccgg cacgtccggc tcgccgagga cgacgagccc gtacagcgcg cggccgacga 31080
cgacccggtc gccgtggtcg gcatggcctg ccgcttcccg ggcggtgtga ccaccccccga 31140 cgagctgtgg cggctcgtgc tggaggagcg cgacgccatc acgccgttcc ccgccgaccg 31200
cggctgggac ctcgccgccc tcgccgaccc ggacggcccc tcggccagcc gcacccggca 31260
cggcggattc ctcgacgacg tcgccctgtt cgacgccggc ttcttcggca tcagcccgcg 31320
cgaggcccag ctgatggacc cccagcagcg gctgctgctg gagaccagct gggaggcgct 31380
ggagcgggcc ggcgtcgcac ccggctcgtg gcggggcgga cgcgtcggcg tgttcgtcgg 31440
cgccaacgcc cagtcctact cctcgctgct cgccggcatc ccggaaggcg gcgacgggca 31500

-continued

```
cgccctgacc ggccgcctgg ccagcgtggt ggccggccgc atctcctacg tcctcggcct  31560
ggaaggcccc gccttcacgg tggacaccgc ctgctcgtcc tccctcgtcg ccctgcacca  31620
ggcggtgcgg tcgctgcgct cgggcgagag caccctcgcg ctggccggcg gtgtgaccgt  31680
catgccgacg ccggagctgt tcgtcgactt caccaagcag ggcggcctgt ccgaggacgg  31740
tcgctgccgc tcgtacgcca aggccgccga cggactcggc tggtccgagg gcgtcggcat  31800
gctcctgctg gagcggctct ccgacgcccg gcgaaacggc cacccggtgc tcgccctgct  31860
gcccggcacc gccgtcaacc aggacggcgc ctccaacggc ctcaccgcgc cgagcggcgc  31920
cgcccagcag cgcgtggtcc ggcaggcact ggccgacgcc ggactgcgtc ccgccgacgt  31980
ggacgccgtg gagggccacg gcaccggcac cgccctgggc gaccccatcg aggcccaggc  32040
actcctctcc tcctacggcc aggaccgcga ccggccgctg tggctgggct cgctgaagtc  32100
caacctcggc cacgcccagg ccgccgccgg cgtcggcgga gtgatcaaga cggtgctcgc  32160
gctccggcac ggactgctcc cgaagacgct gcacgtcgac gagcccaccc cgcacgtgga  32220
ctgggtgtcc ggcgacgtac ggctgctgac cgaggcccgc ccgtggcccc ggggcgagcg  32280
tccccgccgg gccggcgtgt cctcgttcgg cgtcagcggc accaacgccc atgtgatcgt  32340
ggcggaggcg cccgaacccg aggaagcgac ggcgccgccg gccggtgcgc tccccgtgcc  32400
ctggcagctg tccgcgcgca ccgaggccgc gctgctcgaa caggccgccc ggctgcgcga  32460
gttcgtcgcc gccgaccccg gcctcgagcc cgcctccgtc gggttcaccc tggccacccg  32520
ccgcaccgcg ttcgagcacc gcgccgccgt cgtgggccgg gaccgcgccg aactgctcgc  32580
cgcgctcgac gtgctcgccg cgggcggcgc cgacccggcc gtcgtccgcg gcaccgccgg  32640
agccgacggc agcgtcgtct tcgtcttcgc cggccagggc ggacagtggc tcggcatggg  32700
cgtggaactg ctcgacaccc acccggtgtt cgccgcgcgc atggccgagt gcgagcgcgc  32760
cctcgccccc tacctggact ggtcggtcgt ggacgtgctg cgcggagccg aggacgcgcc  32820
gccgctcagc cgcgtcgacg tggtgcagcc ggtgctgttc gcgctcatgg tctcgctggc  32880
cgcggtgtgg cgctcccacg gcgtcgtgcc ggcggccgtg gtcggccact cccagggcga  32940
gatcgccgcc gcctgcgtcg ccggcgccct caccctggac gacgccgcga agaccgtcgc  33000
gctgcgcgcc aaggccgtcg ccgacctgcc cggccgctgc ggcatggcct tcgtcgccgc  33060
ccccgcggcg aacgtcgagc ggatgctgga gcgctggccc ggccggctcg gcatcgccgc  33120
tgccaacagc ccccgctcgc tggtcgtcgc gggcgaccgc gatgccctgg aggagctgct  33180
cgacctctgc gacgacgagg ggctgcgcgc cggccgcgtc gccgccgact acgcctcgca  33240
ctccccgcag gtggaggccg tacggcagcg gctgctcgcc gacctcaagg gcatccgccc  33300
ccgggacggc gacgtgcccc tctactccac cgtcaccgcc gactggatcg acggcagcga  33360
actgggcgcc cgctactggt accgcaacct gcgcgagccc gtgctcttcc agaacgcgat  33420
cagcgatctg ctcgccgccg gccaccacgg cttcgtggag atcagcccgc accccgtgct  33480
cacggtcgcc atgcagcaga ccgccgaggc ggcgggcacc gaactgcggg tcgccgccac  33540
cctgcgccgc gacgagagcg accggctgcg cctgaccacc gcactggccg aggtggccgc  33600
cgacggcgtg ccggtcgact ggcgcccccct gttcgacgcc accggcgccc gcccggtcga  33660
actgcccgcc taccccttcc agcgcgagcg ctactggctc accccccagg ccgccgccgg  33720
cgacctgacc gccgtcggcc tcaccgccgg agggcatccg ctgctcgccg ccgaggccga  33780
actccccgac gaggacggcc tgctcctcac cggccggatc agccccgaga cgcacccctg  33840
gctgaccgag cacaccgtgc tgggcaccgc cctgctgccc ggcaccgccg tcctggagat  33900
```

ggtggcccac gccggccacc ggctcgaccg cgcccagatc gaggagctga ccctggccgc 33960
gcccatcggc gtccccgccg acggcctgac cctgcgcgtc accgtgcacg gcgccgacgg 34020
gtccggccgc cgcacggtcg ccgtccactc ccactccggc gacggctgga cccggcacgc 34080
cacgggcgtc ctggcaccgg ccgagccggc cgagccggcg gagcccgaga ccggcgcgtg 34140
gcccccggcg ggcgctgagc cggtcccggt ggacggcgtg tacgaccgtt tcgccgcccg 34200
cggctacggc tacgggcccg ccttccaggg cctgcgcgcc ctgtggcgcc gggacaccga 34260
ggtctacgcc gaggtcgaac tccccgacac cgtcgacacc gccggccatc tcgtgcaccc 34320
ggcgctgctc gacgccgtca cccaggccgt gcccgccgcc gagcccgagg acgcgccgct 34380
gctgctgccg ttcacctgga ccggcgtgac cgtgcacccc ggcccggccc gggtcctgcg 34440
ggtgcgcgcc gcccgggaga gcgccgacac gctgagcctc accgcgaccg accgcgaggg 34500
ccggcccgtc gtggagctgg ccgcgctgcg gctgcggccc gcgtcggccg ggcagctccg 34560
cgccgtggcc gccgccggca cgcgcgacgc gctgttccgc gtgacctggc agacccccga 34620
cgccgagaca cccgccgccg cgcgctgcgc cgtcctgggc gacggaccgg aaggcctcgc 34680
cgcgcccctg agcaccgccc tcgccgacat cgacgccggc gcggtggacc tcgtcctcgc 34740
tcccgtcagc acaggagccg atgtggtcgc cgccgcccac cgggccaccg cccaggtgct 34800
ggaactgctg cacgagtggc tcgccgacga ccggttcggg caggcccggc tcgcgatcgt 34860
cacccggcac gccgtcgccg cccggcccgg cgaggaaccc gacccggccg ccgccgcggt 34920
ctggggcctg gtgcgctccg cgcagaccga gcaccccgac cggttcctgc tcgtcgacac 34980
cgacggcaca cccgcctccc tggacgctgt gccggccgtc ggcgacgagc cgcagaccgc 35040
gctccgcgac ggcgaacgcc tcgtcgcccg gctcacccgg gccgctgaga ccgcgctgcg 35100
cccgcccgtc ggcgccgacg cctggcgcgt cgacgtggtc cggcccggca gcatcgacgg 35160
cgtcgacgcc gtcgccgctc ccgacgccac cgcccccctg gcacccggcc aggtccgcat 35220
cgccgtccgc gcggcgggcc tgaacttccg cgacgtgctg tgcgcgctcg acatgtaccc 35280
ggacgaggtc gacgcgatcg gctccgaggc cgcgggcacc gtggtcgcgg tcgccccgga 35340
cgtcaccgac ctcgccgtcg gcgaccgagt cctcggcatg gtgccgggcg gcttcggcac 35400
cctcgccgtg gtggaccggc ggctcgtggt gcccgttccc gccggctggt cctgggtccg 35460
cgccgcggcc ctgccgtccg tgttcgccac cgcctggttc gcgctgcgcg atgtggccgg 35520
ggtgcgggcg ggggagcggg tgctggtgca cgcggcggcc ggtggtgtgg gcatggccgc 35580
ggtgcgggtg gcgcggctgc tgggcgccga ggtgtatgcg acggcgagtc ccggcaagca 35640
cgaggtgctg cgggcggccg gtctggacga ggcgcgtgtg gcgtcgtcgc gggatacgga 35700
gttcgcgcag cggttcccgg agatggacgt cgtgctgaac tccctcacgg gtgagttcgt 35760
ggacgcgtcg ctgcgactgc tccgtcccgg cggacggttc gtggaactcg gcaagaccga 35820
ccgccgcgac cccgccggcc tgcccggtgt cgactacctc ccgttcgacc tgctgctgga 35880
cgccggcccc gaccgcgtcc agagcctgct gaccgaggtc gtcgcccacg ccgaggcggg 35940
cgagctgacc gggctgccca cccggacctg gcccctcgcc gacgcgcgca ccgcgttccg 36000
gttcatggcc caggcccggc acaccggcaa gatcgtgctc accgtcgccc cgtacgccga 36060
cggcaccgtc ctgatcaccg gcgccggcgt gctcggcggc atgctcgccc ggcatctggt 36120
gtccgaacac ggcgcccgtg acctggtgct ggccagccgg cgcggcgccg ccgcccccgg 36180
cagcgcggac ctggtcgccg aactggccgc ggcgggcgcc accgtccgct tcgagacctg 36240

-continued

```
cgacgtcacc gaccgcgccg ccctcgacgc gctgctcgcc aagctgaccg ccgaggcccc  36300
gctgaccgcg gtggtgcaca ccgcgggcgc cctcgacgac ggcgtgctga ccgaactcgg  36360
cgccggccgg ctgccgggcg tactgcgccc gaaggccgac gccgcctggc acctgcacga  36420
actcaccgag gacaaggacc tgtccgcctt cgtgctgttc tcctccgcgg cggccaccct  36480
cggcaccccc gcgcaggcca actacgccgc cgccaacgcc ttcctcgacg cgctcgccga  36540
acggcgccgc gccgccggcc tgcccggcac cgccgcggcc tggggcctgt gggccgacgc  36600
caccggcctc acccggcacc tggacgccgc cgacgtcgcc cgcgccggcc gcaaccgcat  36660
cgtgccgatg gccgccgccg aaggactggc cctgttcgac acggccaccg ccaccggcga  36720
cgccgtgacc gtcaccgcgc gcctggacct cgccaccgcc tccgccgcgc ccaccccgcc  36780
gctgctgcgc ggcctggtcg ccaccccggc cggcccggcc gccgcccgcc cggtgcccgg  36840
tgcggcggcc ctggtggcgc ggatcaccgg gctgcccgcg cccgagcgcg cccccgccct  36900
gctcgacgtc gtccgcggcc aggtcgccga cgtcctggga caccggggac gcgacgcggt  36960
ggcacccgac cgcggcttca aggaactggg cttcgactcg ctgaccgccg tggaactgcg  37020
caaccgcctc ggcaccgcca ccggcctgcg actgcccacc accatcgtgt tcgaccaccc  37080
gaacccggcc gcgctcgccg accacctcct cgacgcgctc ctgccgagcg agtccggcga  37140
ggcgagcgcc gaccggatca tcgccgaact ggcccgcgtg gagagcgcgc tcggcgcact  37200
gccggccgac ggcaccgacc gcgcccgggt ggcggcgcac ctgcgggacc tcgcggcccg  37260
ctgggacgcc ggcacgaccg acggcacacc cgagcgggcc gctctggacg gcgtcaccgc  37320
cgacgaactc ttcgacctga tcgaccgggg cgtctcgtga cccgcgccga acgaaccgca  37380
cgggggtgca ccgatggctg acgaggccaa actgctcgac tacctcaagc aggtcacggg  37440
cgatctccag gtcgcccggc gccggctgcg cgaggccgag gcccgcgacc gcgaaccgat  37500
cgcgatcgtg ggcatggcct gccgctaccc cggcggcgtg acctcgcccg aggacctgtg  37560
gcggctggtg accgatggga ccgacgcggt ctcggcgttc cccgccgacc gcggctggga  37620
catggcctcg gtctacgacc cggaccccga ccggcccgga acctcctacg cccgcgaagg  37680
cggattcctc gacggcgccg cggacttcga cgccggcttc ttcggcatca gcccgcgcga  37740
ggcgctggcc atggacccgc agcagcggct ggtgctggag acctcatggg aggccctgga  37800
gcgggctggc atcgacccgg ccggcctgcg ctccaccgcc accggcgtgt tcgtcggctt  37860
cagcagcgag gactactccg acatcaccgg cccggtggcc accgagctgg aggggtacgt  37920
cgtcaccggc acctcgccca gcgtgctctc cggccgggtc gcctacaccc tcggcctgga  37980
gggccccgcc ctctccgtgg acaccgcctg ctcctcgtcc ctggtcgccc tgcacctcgc  38040
ggtccgctcg ctgcgcgccg gggagtgcac gctggcgctc accggcgggg cgaccgtgct  38100
gtccacgccc ggcgtgttca ccgagtacag ccggcagcgg gccctcgcgg ccgacggccg  38160
ctgcaaggcg ttcgccgcgg cggccgacgg gttcggcttc gccgagggcg cgggcatgct  38220
cgtcctggaa cggctctcgg acgcccgccg caacggccac cccgtgctgg ccgtggtccg  38280
cggcaccgcc atcaaccagg acggcgcgag cagcggactc accgccccca acggactcgc  38340
ccagcagcgc gtgatccgcc aggcgctggc cgacgcccgc ctggccgcga gccaggtcga  38400
cgccgtggag gcgcacggta cgggcacccg gctgggcgac ccgatcgagg cgcaggccct  38460
cctcgccacc tacggccagg agcgggacga gccgctgtgg ctcggttcgg tgaagtccaa  38520
catcgggcac acgcaggccg ccgccggtgt ggccggtgtg atcaagatgg tgcaggccat  38580
gcgccacggc acgctgccgc gcacgctcca cgtggacgag gcgtcaccgc acgtcgactg  38640
```

gaccgccggc gccgtggaac tgctcaccga ggagcgggac tggccgggcg gggagcagcc 38700
gcgccgcgcg ggcgtgtcgt cgttcggcgt gtccggcacc aacgcccacg ccatcctgga 38760
gcaggcaccc gcccggcccg agcccaccga cgaggccacg gaccgcaccc tgccggtcgt 38820
cccgtggacg ctgtcctccc ggacggcggc cggactgcgc gcccaggccg aacgcctcct 38880
cgcccaccgg cccgcgcacg acgccgcccc ccacgacgtg gccctcgccc tcgccaccac 38940
ccgtacggcc ttcgaacacc gcgtggtcgt cctcggcgcg gaccacgaca ccctgctcgc 39000
cggcctgacc gccgtggcgg aaggcgccga gtcggccgac gtggtgcgcg gccgcgccgt 39060
cggcgacggc cgcgccgtct tcgtgttccc gggtcagggg gcgcagtggg tggggatggc 39120
ggtggatctg ctggattcgt cgccggtgtt cgcggggcgg atggctgagt gtgcggtggc 39180
gttggagccg ttcgtgggct ggtcgttgcg tggtgtgctg ggtgatccgg tggcgttgga 39240
gcgggtggat gtcgttcagc cggtgttgtg ggcggtgatg gtgtcgttgg cggaggtgtg 39300
gcgttcgtac ggtgtcgtgc cgtcggctgt ggtcggtcat tcgcaggggg agatcgcggc 39360
tgcttgtgtg gcgggtgtgt tgtcgctggc ggacggcgcc cgggtcgtcg ccctgcgcag 39420
cagggctttg acggcgctgg cgggcagtgg ggggatggtg tcggtcgctg ccgggccgtc 39480
cggtgtcgag gagctgttgg tgggctgggc gggccggttg gcggtggctg cggtcaacgg 39540
tcctgagtcg gtcgtcgtcg cgggtgaggg ggtggcgctg gaggagttcc tggctcattg 39600
cgggggtcgg ggggtgcggg cccggcgtat cgctgtcgac tatgcctcgc attcggtgct 39660
ggtggagccg gtgcgtgagg ctctgctggc tgatctggag ggcgtgcggc cgggtgaggg 39720
cacggttccg ctgttctcca ccgtgacggg ggagtgggcg gacggcacgg cgctggacgc 39780
cggctactgg taccgcaacc tgcgcgaacc cgtccgctac gccgacgccg tcgccgccct 39840
gctcgcccag ggccaccggg gcttcatcga ggtcagtccg caccccgtac tgaccgtcgg 39900
cacccaggag accgtcgagc gcacggagac cggagccgcg gtcgtcggca ccctccagcg 39960
cgaccgggcc ggcctgccga ccctgctgac caacctggcc gaggcgcaca cgcacggcgt 40020
gcgcatcgac tggaccgcct tcttccgggg caccggagcc cacccggccg acctgccgac 40080
gtacgccttc cagcgcgacc ggtactggcc gcccgtggac gcagcggccc gcccgctgcc 40140
cccggccgcc acccccgtcg cgctccccgc gcagcggacc gccgacgagg gcacgccctg 40200
gcgcgacgag ctggccgggc tgacccccgc cgaacgccgg caccgcgtca tggacctggt 40260
acggctgcgg accgccgccg tgctcggcca cgccgacccc gccgcgatcg aaccgcaccg 40320
cggtttcgcc gccctcggct tcgactccct cgcctccctg cggctgcgca ccgcgctgac 40380
cgaggcgacc ggcctgacgc tggccagcag cgtcgtcttc gaccacccga acccggccgc 40440
cctcaccgac catctgctca cccggctcga cggcgcgccc gtcccggccc gccccgccgt 40500
ccgcgccacc ccggccgacg agccgctggc cgtggtcggc atggcctgcc gcttccccgg 40560
cggagtggcc tcgcccgacg acctgtggca gctcctcgcc gaaggccgtg acgtcatcgg 40620
cgacttcccc gccgaccgcg gctgggacct cgacggcctc tacgaccccg acccggaccg 40680
ggccggacac acctacctgc gccagggcgg cttcctgaac gacgccgccg gcttcgacgc 40740
cgacttcttc ggcatcagcc cgcgcgaggc gctggcgatg gacccgcagc agcggctgtt 40800
cctcgaagtc gcctgggagg cgttcgagca cgccggcgtc gatccgcacg gcctgcgcgg 40860
cagcgccacc ggcgtcttcg cgggcgtcac cgaccagcgc tacgactcac ggcacggcgc 40920
ggtcgccggc gtggacgagg ggctgctcgg caccgggaac tacgccagcg tgctctccgg 40980
ccgggtggcc tacaccctcg gcctggaagg cccggccgtc agcgtggaca ccgcctgctc 41040
gtcctcgctc gtcgccctgc acctggccgg ccagtccctg cgcagcggcg aatgctcgct 41100
ggccctcgcc ggcggcgtga tggtcatgtc gaccccgcgt gccttcgtgg agttctcccg 41160
gcagcgcggc ctcgcccccg acggccgctg caaggcgttc gccgccgccg cggacggcat 41220
cggctggtcc gagggcgcgg gcgtggtcgt gctggagcgg ctgtccgacg cccgccgcaa 41280
cggccacccc gtgctggccg tggtccgcgg ctcggcgatc aaccaggacg gcgcctcctc 41340
cgggctcacc gcccccaacg gctccgccca gcagcgggtc atccgctccg cgctggccgc 41400
cgccggcctc accgccgccg acgtcgacgt cgtggaggca cacggcaccg gcaccaccct 41460
cggcgacccc atcgaggcca acgccctgct ggccacctac ggccaggacc gcgcacagcc 41520
gctgcggctg ggctcgctga agtccaacat cggccacacc ggccccgcgg cgggcgtggc 41580
cggcgtgatc aagacggtgc tcgcgctgcg cgccggcgaa gtgccccgca ccctgcacgt 41640
ggacgccccc tcaccgcaca tcgactgggc ctccggctcc gtcgaactcg tcaccggcgc 41700
cgccgtctgg cccccgaccg accggccgcg ccgcgcgggc gtgtcgtcgt tcggcgccag 41760
cggcaccaac gcccacctca tcctggagga ggccccggcg gaaccggccg cgcccgcgcg 41820
cggcgccgcg ccgcgctggg tgccgtggct gctctccgcc cgctcccagg ccgccctcgc 41880
cgagcaggcc acccggctcg ccgcccacct cgacacccac cccggcctgg acccggtgga 41940
cctctcctgg tcccttgccg cgtcgcgggc gttgttgccg catcgtgcgg tggtggtggc 42000
cgctgatgtg gccggtgcgc gggcttctct ggcggcgttg gccgcggggg agccggtgga 42060
gggtgtggtg tcgggtgttg ccgggttgcc gggtgagggc cgggtggtgt tcgtgttccc 42120
gggtcagggg gcgcagtggg tggggatggc ggtggatctg ctggattcgt cgccggtgtt 42180
cgcggggcgg atggctgagt gtgcggtggc gttggagccg ttcgtgggct ggtcgttgcg 42240
tggtgtgctg ggtgatccgg tggcgttgga gcgggtggat gtcgttcagc cggtgttgtg 42300
ggcggtgatg gtgtcgttgg cggaggtgtg gcgttcgtac ggtgtcgtgc cgtcggctgt 42360
ggtcggtcat tcgcaggggg agatcgcggc tgcttgtgtg gcgggtgtgc tgtcgctggc 42420
ggacggcgcc cggatcgtcg ccctgcggtc gcggctcatc gccgagcggc tggccgggcg 42480
cggcggcatg gtctccgtcg ccctgcccga ggccaccgtc acacggcggc tcgcaccgtg 42540
gtccggacgc gtttgcgtcg ccgccctcaa cggcccgtcg tcggtggtcc tcagcggcga 42600
ccccgatgcg ctggacgagg tgatggccgc ctggtcggcc gacggggtac gactgcgccg 42660
catcgcggtc gactacgcct cccactcggc ccatgtcgag tccctcgaag ccgagttgcg 42720
cgccgcgctc gccgaactgc ggcccggtga ggccggcatc gccttccact ccaccctgct 42780
gggcggcccc ctcggcgaga cacggctcga cgccggctac tggtaccgca acctgcggga 42840
gcccgtacgg ttcgagcccg tggtgcgcgg cctgctcgac tccggccacg ccgtgttcgt 42900
ggagatcagc ccgcacccgg tgctgacggc cgccgtgcag gagacggcgg aggccaccga 42960
gcggaccgcc gtcgtcgtcg gcaccctccg ccgcgacgag gacggcccgc gccgcctcct 43020
cacctcgctc gccgaggccg ccgtccacgg cgtgtccgtc gactggacgg tgggctgccc 43080
cgacggacgc cacgtcgacc tgcccaccta cgccttccag cgccgccgct tctggcccag 43140
cggcccggtc gcctccgacg ccgccggcct gggcctgacc ggcgccgggc acccgctgct 43200
cggcgccgtc accccgctcg ccggatccgg cggacaggtg ttcaccgggc gcgtgccggc 43260
cggcaccgag ctgccggccg gcgccgtact cgacctggcc ctgcacgcgg ccgacggcag 43320
gacgctcggc gaactgaccg aggaggcacc gctcgacacc gtcggcgaag cccgccgcct 43380

-continued ccaggtcacc ctgggcgcgg agaacgagga cggcgcccgc ccggtcgccg tccactcccg 43440
ccccgccgac gccgacgacg accagccctg gacccggcac gcgaccggcg tcctcctccc 43500
gcacaccggc accgccccgg ccgccgcgcc aggggacccg gacaccgacg tgaccgtcga 43560
gctgaccgac gtgaccgttg agctgaccga cgagaccgcc ggcggctggg gcgtacaccc 43620
cgccctgctc accgacgccc tcgcggccgt acaccccggc ctggtccccg gcgcctggca 43680
cggcgtcacc ctgcacgccg tgggcgccac ccggctgcgg gtacgcctgc accccgcggg 43740
cgagcacacg gtcaccctgc acgccaccga cgacagcgga gccgccgtgc tcaccgtcga 43800
cgcggtgacc ctgcgcccgc cggccacggc cggccccggc cgcgaccacg agctgtaccg 43860
ggtcgagtgg acgcccgtgc cgctgcccgc ggccgacgtc gacggcatcg ccgtgctcgg 43920
cggccttccg ctgcccggat acccctcctg ccccgacctc gccgccgtcg ccgccctgga 43980
caccgtgccc ggcaccctcg tgctgccgtg tcggcagcag tcggccgacg acaccgccgg 44040
cgcggcccac gccggcgccc ggcgcgtgct gaccgctctt caggagtggc tcgccgacga 44100
gcgactggcc ggcacccgtc tggccgtcct cacccacggc gcggtcccgg tcgagcacga 44160
ggacgtcacc gacctcgccc acgcgcccgt gtggggcctg atccgctccg cccgcgccga 44220
acaccccggc aggctggtgc tggtcgacat cgacggcccc gacgcactgc aacagctgcc 44280
cgctgtcctc gccaccggcg aacccgagat cgccgtgcgc tccggccggg tcctcgcacc 44340
ccggctggtc cgcgccccgc gcaccgacga gcccacgagc caggcggccc tgtggccgtc 44400
cgacggcgtc gtcctcgtca ccggcggcac cggcacgctc ggcgccctct gcgcccgcca 44460
cctggtcacc gagcacggcg tacgccggct ggtcctggcc ggacggcgcg gcgacgcggc 44520
ccccgacgcc gtgaccctcg ccggcgaact gcgcgccctc ggcgccgagg tgaccgtcgc 44580
cgcctgcgac gccgccgacc gcaccgaact ggccgccctg ctcgaccgga tcaccgccga 44640
gcaccccctg accggagtcg tccacgccgc cggcgtcctg gacgacggcg tcatcgcctc 44700
ccagaccccc gagcggctcg ccaaggtgct ccgccccaag gtcgacgccg cctggaacct 44760
gcacgaactc accgccccgc accggccggc cgtcttcgtg ctgttctcct ccacctccgg 44820
cctcttcggg gcgcccggac agggcaacta cgcggcgggc aacgccttcg tggacgcgct 44880
cgcggcacac cgccgcgccc agggcctgcc cgccacctcc caggtgtggg gcctgtgggc 44940
gcacgccagc ggcatgaccg gccacctggg cggcgccgac ctgcggcgcg cggcccgcga 45000
cggcgtggtg ccgctgccga cgcccgacgc gctcgccctg ttcgaccgcg ccaccgccgg 45060
ctccgccccc gtcgtcgtcc ccgcctggct ggacctcacc tcgttcgcca ccggcgtcac 45120
cgccgtaccc gcgctgatgc gccggctggt ccgtggcccc gtccggcgcg ccgccaccgc 45180
gggcgccgga ccggacaccc tggccggaaa gctcaccgga ctcaccgccg cggaacgcga 45240
acggaccctg ctcacgctcg tccgctcgca cgccgccgtg gtcctcggcc acaccgacga 45300
caccgccgtg acccccggcc gggcgttcaa ggaactgggc ttcgactcgc tgaccgccgt 45360
cgaactccgc aaccggctgt ccgccgccac cgggctgcgc ctgcccgcga ccctcgtgtt 45420
cgaccacccc aacccgcgct ccctggccgg ccacctgctg gccgaactcc tcggcgaacg 45480
cgccgaggag acggcgccgg tgcccgccgt cgcccgcccc gccgacgacg atcccatcgc 45540
gatcgtcggc atggcgtgcc ggtaccccgg cggcgtgacc tcgcccgagg acctgtggcg 45600
gctgctcgcc gacgagcgcg acgcgctcac cccgttcccc gacgaccggg gctgggacct 45660
cgcgggcctc ttccacccgg atccggagca cgcgggcacg tcgtacgtgc gggagggcgg 45720
cttcctcgcg gacgtcgccg ggttcgacgc ggacttcttc gggatctcgc cgcgcgaggc 45780
gctggcgatg gacccgcagc agcggctggc cctggagacc gcctgggagg ccgtcgaacg 45840
cgccggcatc gacccgaagt ccctgcgcgg cgcggacgtc ggcgtctacc tcggcaccaa 45900
cggccaggac tatgcccagc tcgtgcgcag gaccgtcgag agcgcggagg gctacgtcgg 45960
catcggcaac tccgccagcg tgctgtcggg ccgcatcgcc tacgtcctcg gcctggaagg 46020
ccctgcggtc accgtggaca ccgcgtgctc ggcgtcgctg gtcgccctgc actgggcgat 46080
ccaggcgctg cgcagcggcg agtgctcgat ggcgctggcc ggcggtgtca ccgtcatgtc 46140
cgcccccgac gtcttcgtcg acttctcccg ccagcgcggc ctggccgtgg acggccgctg 46200
caagtccttc gccgccgcgg ccgacggcac cggctggtcc gagggcgccg gcatgctcct 46260
cgtggaacgg ctctccgacg cccgccgcca cggccaccag gtactggccg tcgtacgcgg 46320
caccgcgatc aaccaggacg gcgcgtcgaa cggtctgacg gccccgaacg gtccttcgca 46380
gcagcgggtg atccgtcagg cgctctccgg tgccgggctc acgcccgcgg acgtggacgc 46440
ggtggaggcg cacggtacgg gcacgcggct gggcgacccg atcgaggcgc aggcgctgct 46500
cgccacctac gggcaggagc gggacgagcc gctgtggctc ggttcggtga agtccaacat 46560
cgggcacacg caggccgccg ccggtgtggc cggtgtgatc aagatggtgc aggccatgcg 46620
gcacggcacg ctgccgcgca cgctccacgt ggacgagccg tcacctgagg tcgactgggc 46680
ctcgggcgcg gtggagctgc tgaccgaggc ccgggagtgg gcgcgtgccg gtcggccgcg 46740
ccgtgcgggt gtgtcgtcgt tcggtgtgtc cggcacgaac gcgcatgtgg tgctggaaga 46800
ggctcccgag gagaccgggc gcaccgcgcc ggctgcgctg cccgccgtgc cctggctgtt 46860
gtcggcccgc tccgagaccg cgctgcgcgg acaggtcgag cggctgcgtg cgtacgtcac 46920
ggagcacccg gaggcgcggc cggccgacat cggcctcagc ctcctcaccg cacgctcccg 46980
cttcgagcac agcgccgtcg tcgtcggcac cgaccacgac gcactcctcg ccgcgctggc 47040
ggacccggag ccgctgcacg cacgtgacgg cctgaccgcg ttcgtgttcg cggggcaggg 47100
tgcgcagcgg gtggggatgg gggcggaact ggctgccgcg tatccggtgt tcgctcaggt 47160
gttcgcgcag gtgtgtgcgg cgttcgacgg tgtgctggag cggccgctgg gtgaggtggt 47220
cgccgagggt ggtccggagc tggatcggac ggtttatgcg caggcggggt tgttcgcttt 47280
cgaggtggcg ctgttccggc tgctggagtc gtggggtgtc gcgccggatg tggtgctcgg 47340
gcattccgtg ggtgagttga cggctgcctg tgtggcgggt gtgtggtcgc tcgaggacgc 47400
ggtgcgggtg gtggctgcgc gtgggcggtt gatgcaggcg ttgccggagg gcggtgcgat 47460
ggtcgctctc gaggtgtcgg cgggtgagct ggagttgccg gtgggtgtgg agctggcggc 47520
ggtcaatggc ccgacgtcgg tggtgctgtc cggtgaggag gaggccgtcc tggctgaggc 47580
cgcccgctgg ccggaccgtc gtgccaagcg tctgcgggtc agtcacgcct tccactcgca 47640
tcggatggat ccgatgctgg aggacttccg gcgggtactg gagtccgtga ccttccaggc 47700
tccggaggtt gccttcgtgt cgacggtgac cggtgctgcg gtgacggacg agctgtgcga 47760
cccggggtat tgggtgcgca acgtccggga gaccgtccgc ttcgccgacg ccgtcgccgc 47820
cgtgcgcgcg accggtgccg acgccctggt cgagatcggt cccgatgccg ccctcgctcc 47880
gctcgccgag ggcggtgtgc cgctgctgcg caggggccgg ccggaggccg tcgcgctggt 47940
cgaggggctc gcccggtccc agatggccgt cgactgggag aagttcttcg gcgccggggt 48000
gagccccgtc gacctgccca cgtatccgtt ccagcacagc cggttctggc cggaggtccc 48060
ggtgcgggcc gaggccgatc cggccgcgcg gtggcgttac cgggtgcggt gggagccgct 48120
ccgtcccgcc gtggacgcgg tgccggccgg gcgctggctg gtggccgtgc ccgccgcggg 48180
cgcggatgcg gctctggtgc gggagtgcct gaaggggctc gccggccgag gagtggaggt 48240
ggccgagctc gcggtggcgg gtgcgcccga ccgtgcgcgg ctcgccgaag cggtgtcggc 48300
cacgggcccg gtggacggcg tgctgtccct gctcgccgcc ggtcctgacg cggcggccgg 48360
caccctcgtc ctcgcccagg ccctcggcga cgccgggacc gacgcgccgc tgtggtgcgt 48420
gaccggcgga gccgtcgcgg ccgccgacgg agaacccgcc gacccggagc aggcccaggt 48480
ctggggcctc ggccgggtgc tgtgcctgga ggcgccgcac cgctggggcg gcctcgtcga 48540
cctgcccgcc gagcccgacg agcaggcggt cgtacagctg tgcgccgtcc tcgccggaca 48600
cgacgacgag gaccaggtcg ccgtgcgggc ggccggggtc ttcgggcggc ggctggtccg 48660
cccggccacg ggcgccgcgg cggagggctg gcggccgtcc ggcaccgtgc tgatcaccgg 48720
cggcacgggc gcgctgggcg ggcacaccgc ccgctgggca gcccgctcgg gcgccggccg 48780
ggtggtgctg gtgagccggc gcggacccga cgcggacggc gcggcggaac tcgtggcgga 48840
actcggcgaa ctgggctgcc aggccgtcgc ggaggcgtgc gacgtggccg accgggccgc 48900
gctcggcgcg ctgctcgaca agatcgccgc cgacggcccg ccgctgaccg cagtggtgca 48960
caccgcaggc gtcctggacg acggggtgca cggctcgctg acccccgaac ggctggccac 49020
ggtgctgcgc gccaaggccg acggcgccac cgccctgcat gaactcaccg cccacctgcc 49080
cctggaggcg ttcgtcctgt tcgccgcgct cggcggggtg gtcggcggcg cgggccaggc 49140
caactacgcc gccgccaacg cccacctcga cgcgctcgcc gcgagccgcc gggccgccgg 49200
gctgcccgcc accgcggtgg cgtggggcgc ctgggcgggc ggcgggatgg ccgacgcgga 49260
cgaggtacgc cggcgcctgg accgcgacgg gctgctgccg atggacccgc ggcgggcgct 49320
ggacgctctc ggccgggaga tcgcggccgg cgacccggcc gtggtgctcg ccgacgtcga 49380
ctggacccgg ctcgcgccca acctgcacgc cgtccggccc agcccgctga tctcgaccgt 49440
gcccgaggca cgccgggccg tcgcgcccga acccggcacg gccggcggcg agtccgatcc 49500
gcggcagcgc ctggcggccc tgcccgacgg cgaacgcgcg cgcgtgctgc tcgacctcgt 49560
ccgcgacgcc atcgccgccg tgctcgggta cggcggtccc ggcgcggtcg acatcacgcg 49620
gggcctcgtc gacctgggct tcgactcgct gaccgccgtc gaactgcgca accggctcgc 49680
ccgggccacc ggactcgccc tgccgctcac gctggtcttc gaccaccccg acggggaggc 49740
gctcgccgcc cacctcgccg ccgcactcgc gcccgccgcg gaccggccgc agaccaccga 49800
cctcgaccgg ttcgcccggc tcgacccggc cacggccgac gagccgaccc gggtccgggt 49860
cgccgcggag ctgcgccggc tgctcgacgc gtggacgccg ccaccggccg cgcccgccgg 49920
gtccgccggg tccgccgcgg accccagccg gctgaccacg gcgtccgccg acgagatctt 49980
cgacttcatt cggaacgaac tcgggaagtc ctgaacgtgg agaacgagaa caagctcctc 50040
gaccacctgc ggtgggtcac cggagaactg gcccaggcac ggcagacgct gcgcgagacg 50100
gccgaacgtg ccaccgagcc gatcgcgatc gtcggcatgg cctgccggtt cccgggcggc 50160
gtgagcacgc ccgaggacct gtggcggctg ctcgccgacg agcgtgacgc ggtcggcgag 50220
ttccccgccg accgcggctg ggacctggcc tcgctgcacc acccggaccc cgagcacgcg 50280
ggcacgtcgt acgtgcggga gggcggcttc ctcgcggacg tcgccgggtt cgacgcggac 50340
ttcttcggga tctcgccgcg cgaggcgctg gcgatggacc cgcagcagcg gctcgccctg 50400
gagaccgcct gggaggccgt cgaacgcgcc ggccttgacc cgaagtccct gcggggcgcg 50460

-continued gacgtcggcg tgtacctggg caccaacgga caggactaca tctccgccgc gcgcccgctg 50520
ctgcaccagg tggagggcca cggcggcacc ggcatcgccg gaagcgtgct gtccggacgc 50580
gtcgcctaca ccctcggcct gcgcggcccc gcggccaccg tcgacacggc gtgctccgcc 50640
tccctcgtcg ccctgcactg ggcgatgcgg gcgctgcgcg gcggcgagtg cgcgatggca 50700
ctcgcgggcg gtgtgacggt catgtcgtcc ccggcgacct tcgtggagtt ctcccggcag 50760
cgcggcctcg cctccgacgg ccgctgcaag ccgttcgccg ccgcggcgga cggcaccggc 50820
tggggcgagg gcgccggaat gctgctgctg gagcggctct ccgacgcccg gcgcctcggc 50880
cacccggtgc tcgcggtgct gcgcggctcc gccgtcaacc aggacggcgc cagcagcgcc 50940
ctcaccgcgc ccaacggccc ggcgcaggtc cgcgtcatcc aggcggcgct cgccgacgcc 51000
cggctcgcgc ccgccgacgt cgacctgctg gaggcgcacg gcaccggcac cgtcctcggc 51060
gacccgatcg aggcccaggc cctgctcacc gcctacggcc agaaccgcac cgcccccgcc 51120
tggctcggct cggtcaagtc caacgtcgga cacacccagg ccgcggccgg ggtcgccgga 51180
gtgctcaaga ccgtgctcgc cctgcgtcac ggggtgctgc cccggaccct gcacgtggac 51240
gcgcccaccc cgaaggtcga ctggtcggcg ggcgcggtac ggctgctcac cgaggcccgg 51300
ccgtggcccg ccggcgagcg gccgcggcgc gccggtgtct ccgcgttcgg tgtcagcggc 51360
accaacgcgc acgtcatcgt ggagcaggca cccgagaccg ccgccgaggc gtccggcgcg 51420
gccggcgggc cggtgccgtg ggtgctgtcc ggccgtaccg agagcgcgct gcgggcccag 51480
gccgccgcgc tcgccgccca tctggcggag cggcccggcg accggcccgg ggacgtcgcc 51540
ctgtccctgg ccaccacccg cccggcgttc gaacaccgcg ccgtcgtggt cgggacggac 51600
gtcgacgacc tgctgcgcgg cgtggccgcc gtcgccgcgg gagagcccac gcccggggtg 51660
gtccgcggca ccgccggcca cctcggccgg atcgcgttcg tgttccccgg gcagggctcc 51720
cagtggaccg gcatggcccg cgaactcgcc gacgcctcaa cggagttcgc cgcccgcctg 51780
gacgagtgcg ccgccgccct cgccccgcac gtcgactggt cgctgcgcga cgtcctggcc 51840
gacccggccg ccctggagcg cgtcgatgtc gtccagcccg ccctgtgggc cgtgatggtc 51900
tccctggccg ccctctggca ggcgcacgga gtggagccgg ccgccgtcgt cggccactca 51960
cagggcgaga tcgccgccgc gtgcgtcgcc ggcgccctct ccctggagga cgccgccctg 52020
ctggtcaccg cgcgcgcccg ggcgctgcgc gccctgatcg gccggggcgg catggtgtcc 52080
ctgccgctgc cggaggccgc cgcccgcgaa gtcatcgcag cgtggggcga ccggctgtcg 52140
gtggccgccg tcaacggccc cgccgcgaca gtcgtgtccg gcgacgccgc cggcctggac 52200
gaactcctcg cccaggccga gcgggacggc ctgcgggcca agcgcctccc cgtcgactac 52260
gcctcgcact ccgcgcacgt cgaagccgta cgcgccgagg tactggccgc gaccgccgcc 52320
gtcaccccgc gcgccaccgg caccgccttc gtgtcctcgg tgaccggcgg attcctggac 52380
accaccggtc tggacgccgc ctactggtac cgcaacctgc gcgagccggt ccgtttcgac 52440
cgggcggggc gggccctgct ggacgccggg ttcacgacgt tcatcgaggt cagcgcgcac 52500
cccgtgctca ccgccgcact ccaggagagc gacccggccg tcctcgccgt cggctcgctg 52560
cgccgcgacg acggcggccc cgcccgcttc ctcgcctccc tcgccgaggc cgcggtccgc 52620
ggcgtaccgg tcgactggcg accggccctg accgcggccc gcaccgtgcc tcttcccacc 52680
tacgccttcc agcgcgaacg cctctggctg gaggaggacg ccgggccgat caccccggaa 52740
cgggcccgcg aggacagcgc gttctgggcc gcggtccacg gctccgccga cgacctggcc 52800
gcggtgctcg gcgcggaccc cgccgcccgg gagccgatcg ccgccgttca cccgctgctc 52860
gccgcctggc acgagcggcg cgccgacgag tccgccgtgg actcctggcg ctaccgcgtc 52920
gactggaccc cgctcaccgc gtcgccctcc gccggcgcgc ccaccggccg ctggctggcg 52980
gtcgcggccg acgacccctg gtccgacgcc gtcgtcacgg cactggcgga ccgcatggac 53040
ctcacccgcg tcccggccta cgaccccggc accgtcgcgg aactcaccgc cgggaccgcg 53100
ggcgtcgtcg ccgtgctccg ccccgacgac cccgacccgc tccccggcct cctcgccctc 53160
ctccgggccc acgaccgcgc cgacggcggc ctgccgctgt ggtgcgtcac ccgcggcgcc 53220
gtggcgaccg gcccggcgga caccccggcg gacccggcca ccgcgcagat ctggggcttc 53280
ggccgcgtcg ccgcgctgga acgaccgcag agctggggcg ggctgatcga cctgccggcc 53340
ggcgccaccg tgaccgggga cgcgctggcg ggcacggccc gggccgacgg cccaccggac 53400
gcccgcatcg ccgacgacgt cctcggcgcc cgtctcgccg accggctcgt cgccgcgctg 53460
gcgggtccgg aggaccaggt ggcggtccgc gcctccggcg ccttcggccg ccggctgcgc 53520
cgcgcgcccg cagacgggac cacccccgac tggaggccca ccggaaccat cctcgtcacc 53580
ggcggcaccg gtggtctcgg cgggcacgtg gcccgctggc tcgcccgtgc cggggcggag 53640
cacctcgtgc tcaccgggcg acgcggcccc gaggcgcccg gcgcggcgga actggccgcc 53700
gaactcaccg cgctcggcgc cgaggtcgac atcgtcgcct gcgacgccgc cgaccgtgac 53760
gcactggccc gggtgctggc cgagcacccc gtcgacgccg tgttccacct cgccggcatc 53820
gagcgctacc ggccgctgga cgagctgacc ccggccgatc tcaccgaggt cgccgccgcc 53880
aaggtcaccg gcgccctcct gctggacgaa ctgacccgcg accggcggct gtccgcgttc 53940
gtgctgttca cctcgggcgc cggagtgtgg ggcagcagcg gccaggccgc ctacgccgcc 54000
gccaacaccc gcctcgacgc gctcgccgcc cggcgccgcg ccgagggcct gcccgccacc 54060
gccgtcgcct ggggacactg ggacggcgcc ggcatgtccg acggcccggc ccgcgcccag 54120
atgctccgct ggggcctgcc cgccatggcg ccccaccgcg ccgtcgccgc cctcgccggc 54180
gccctcgccc gggacgaggc ctcgctggtc gtcgccgaca tcgactggcc ggtgttcgcg 54240
ccgacgttca ccctggcccg gcgcagcccg ctcctcgccg gcctgcccga ggccaccgac 54300
ccggccgaca ccgccccgcc gcccgccgcc ccggccggcc ggctggaccg ggccgcgctg 54360
ctggagctgg tgctcgccga gaccggcgcc gtcctcggcc acgcctccgg caccggactg 54420
cccgccgccc gcgccttcca ggaactgggc ttcgactcgc tcaccgccgt ggaactgcgc 54480
aaccggctgc gcgacgcgac cggactgccc ctgcccgcca ccctcgtctt cgaccatccc 54540
accccgcagg cgctcgccga gcgcctggcc ggggaactca ccggcgaaca gcccgccgac 54600
gttccggaca ccacgccggc gccggccgcc gccgccgacg acgacccggt cgtcatcgta 54660
ggcatgggct gccgcttccc cggcggcgcc gactcgcccg aacggctgtg ggacctcgtc 54720
gccgcgggcc gggacgcgat gaccggcttt cccgccgacc gcggctggga cgtcaccgac 54780
accggctaca ccaaggccgg cggattcctc gacgccgccg gtgagttcga cgccgggttc 54840
ttcggcatca gcccccgcga ggccaccagc atggacccgc agcagcggct gctgctggag 54900
acggcgtggg agacggtcga gcgcgccggc atcgacccgg cctcgctgcg cggcagccgg 54960
accggcgtgt tcgtcggcta cggcggccag gactacctca ccagcctgta cggcaccccc 55020
gaggaactac agggccacct cctcaccggc acctccggca gcgtggtctc cggccggctc 55080
gcctacgtcc tcggcctgga gggccccgcg gtcaccatcg acaccgcgtg ctcctcgtcc 55140
ctggtcgccc tgcactgggc gatccgcgcg ctgcgctccg gcgagtgcga cctggccctg 55200
gcaggcggcg tgaccgtgat ggccaccccg ggcgtcttcg tcgagttcgg ccgacagggc 55260
ggcctggccg gcgacggccg ctgcaaggcg ttcgccgacg ccgccgacgg caccggctgg 55320
ggagagggcg ccggcctgct cctggtggag cggctgtccg acgcccgccg aaacggccac 55380
cgcgtcctcg ccgtcgtccg cggctccgcc gtgaactccg acggcgcctc caacggcctc 55440
accgcgccca acggcccctc ccagcagcgg gtcatccggg ccgcgctggc cgacggcggc 55500
ctcaccccgg ccgacatcga cgccgtggag gcacacggca ccggcaccgc cctcggcgac 55560
cccatcgagg cccaggccct acaggtggtc tacggccagg accgcgagcg cccgctgtgg 55620
atcggctcgg tcaagtccaa cctgggccac acccaggccg cctccggcgc cgccggcctc 55680
atcaagacgg tcctggcact gcggcacggc gtgctgccgg ccaccctgca cgtcgaccgg 55740
ccctccgcac aggtcgactg gaccagggga gcggtgtccg tcctcaccga gagcactccg 55800
tggcccggga ccgacgtgcc gcgccgcgcc gccgtgtcct ccttcggggt cagcggcacc 55860
aacgcccatg tcgtcctcga acaggccccg cccgccgggg aagccggacc ggccggggac 55920
ggcggacccg tcccgtggct ggtctccggc cggacgcccg aggccgtacg cgcccaggtg 55980
gagcggctgc gcgccagcct cgccggacac cccgacccgg tcgccgtcgc ccgcgccctc 56040
gccaccacgc gcaccgcgtt cgagtaccgt gtcgccgccg cgggcggcga caccgaggcg 56100
ctgctcgacg ccctcgccga ggcccgaccc gtcaccgccc gccagggccg taccgcgttc 56160
ctgtgcaccg gccagggcgc ccagcgcgcc ggcatgggtg ccggcctgta cgccgcccac 56220
cccgtctacg ccgacgcctt cgacgccgtc tgcgccgagt tcgaccgcct gctggaccgc 56280
ccgctgcgcg acctggtgct gtccggcccc gccgacgtac tcgaccgcac cgcctacgcg 56340
cagcccgcgc tgttcgccgt cgaggccgcc ctcgccgcac tgctgcgcca ctggggcgtg 56400
acccccgacc tgctggccgg ccactcgctc ggcgagatca ccgccgcgca cctggccgga 56460
gtcctctccc tgccggacgc cgcggccctg gtcgccgccc gcggccggct gatggacgcg 56520
ctgccggccg gcggcgcgat ggtcgccgtg gaggccgacg aggaccgtgt acagcccctg 56580
ctgggcgacg acgtctgcct cgccgccgtg aacggcccgc gcgccctggt gctgtccggc 56640
cgcgaggagg ccgtggacgg ggtggccgcg cggctcgccg ccgaggggtg ccggacccgc 56700
cgcctgcggg tgtcccacgc gttccactcc gcactgatgg agccgatgct ggacgagttc 56760
cgcgccaccg tggccgccct cgacctgcgg gcgccctccg tccccgtggt gtccgcgctg 56820
accggccgcc cgctgacggc cgacgaggcc cgctcacccg agcactgggt acggcacgtc 56880
cgcgaggccg tccgcttcca cgacgccgtg cggggacttg ccgccgaggg cgcccgtacgg 56940 tacctggaac tcggcccgga cggtgtgctc accgccctcg cccagagcag cctgccgccc 57000
gccgacaccg acgccgacgg gcgcgacccg ctcgccgtgc ccctgctgcg ggccggccgg 57060
ccggaaccgg agacgctcac cgacgcgctg gcccgcgccg ccgccgacgg cctgaccgtc 57120
gactgggccg gctacttcac gggccgcggc ggcgccccg tcgagctgcc cacctacgcc 57180
ttccagcgcg agcactactg gctgcccgtc gactccggcg ccggcacggc cccggccggg 57240 cacccccctgc tgtccgccgc ggtcgacctg ccggacggcg gcctcgtact caccgggcgg 57300
ctctcgcccg ccgcgcgccc ctggctcgcc cagcacaccg tgcgcggcag cgccctgctg 57360
cccggcaccg ccctgctgga cctggccctc gccgcggccg gccaggcggc cgcgcccggc 57420
gtcgccgaac tgatcctcga agcccccctc gtgctgcccg ccgagggcgc cgtggaggtg 57480
cgcgtcaccg tcggcgccgc cgggaccgac ggccgccgcg cgatcgccct gcacacccgc 57540
gccggcgacg gcgactggac ccggcacgcc accggagccc tgggcgaggt gcccggcgag 57600
cccacggccg ccggcgcctg gccgcccccg gatgcccgcc ccgccgacct cgccgccctg 57660
tacggcgggc tggccgacgc cggcttcggc tacgggcccg cctaccaggg cctccgtgcc 57720
gcctggcggc gcggcgaagg cccggcggcc gaggtgttcg ccgaggccga actgcccgcg 57780
gccgtccccg acgccgaccg ctgccccgta cacccggcgc tgctggacgc cgtcctgcac 57840
gccatcggcg tgggcgggct gatcaccgac ccggcgcacg gcggactccc gttcgcctgg 57900
accggggtac gggtcttcgc ccccggcgcc cgggcggtcc gcgcccggct ctcccgggcc 57960
ggcgccgaag gcgccctcgc cgtcgacctg ttcgacgccg acgggctgcc agtggccgcc 58020
atcggctccc tgcggctgcg cccgcccgcc gctcccgcgg tgcccgacgc cctcttcgag 58080
accgcctgga cgcctgtcga gcagggcacg gccccggccc gccgcctcgc gctgctcggc 58140
gccgacaccg ccctcgcggc cggcctcacc gcggccggcg ccgccctcgc cgacgccacg 58200
gaccgctccg ccgaggtgct cgtcctgccg atcgtcaccg accccggcgc ggcccccgtc 58260
accgagaccc accgggcgac cgccgccgtc ctgacggccc tccgtgacgt cctggccgac 58320
gaggagagca ccgcccgcct cgccgtggtc acccgcggcg ccctcgcgct gtccgccgag 58380
gagtccccgg acccggccgc ccgcgccgtc tggggtctgg tgcggtccgc ccagaccgag 58440
caccccgacc ggatcgtcct cgccgacctg gacgccgccg acgcctcggc ccgcgccctg 58500
cccgccgcgc tgacctgcgg ggaaccgcag ctcgccgtgc ggtccggcgc ggtcagcgca 58560
ccccggctca cccgcgccgg cgccgacgcg ctggtcctgc ccgacggcgg ctggcgcctg 58620
cggcccggcg ccaccggcac cgtcgacggc atgacggccg tgccgcaccc cgacgcgccg 58680
ctcgccgacg gcgaggtacg ggtcgccgtc cgcgcggtcg gcgtcacctt ccgggacgtc 58740
ctcagcgtgc tcggcctcta ccccggggca ccccagccgc tcggcatcga ggcggcgggc 58800
gtggtgaccg ggaccggccc cggcgtgagc gacctcgccc ccggcgaccg ggtgttcgga 58860
ctgctgcccg gctccatggg ctcctccgcc gtcgccgacc ggcgcgtgct cgcgcccgtc 58920
cccgacggct ggggcttcac ccgggccgcc tcggtgccct ccgcgttcct caccgcctgg 58980
ttcgcgctgc gcgatgtggc cggggtgcgg gcgggggagc gggtgctggt gcacgcggcg 59040
gccggtggtg tgggcatggc cgcggtgcgg gtggcgcggc tgctgggcgc cgaggtgtat 59100
gcgacggcga gtcccggcaa gcatggggtg ctgcgggcgg ccggtctgga cgaggcgcgt 59160
gtggcgtcgt cgcgggacac ggagttcgcg cagcggttcc cggagatgga cgtcgtgctg 59220
aactccctca cgggtgagtt cgtggacgcg tcgctgcgac tgctccgtcc cggcggacgg 59280
ttcgtggaac tcggcaagac cgacctgcgc accgacaccg ccggcatcac ctaccgggcc 59340
gtcgacctcg cggacgccgg ccccgaccgc atccaggaga tgctcaccga actcctggac 59400
cgcctcgcgg ccggcgacct cgcccacctg cccgtccgca gcatgcccat gggccgcgcc 59460
cgcgaggcgt tccgcttcat ggcccaggcc cggcacaccg ggaagctcgt cctcaccacc 59520
gccccgtacg gcgacggcac cgtcctcgtc accggcggca ccggcgccct cggcggcctc 59580
gtggcccggc acctcgtcac cgaacacggc atccgcgacc tggtgctcgt cggacgacag 59640
ggcgccgagc cccccgtcac cgccgaactg cgcgccgccg gcgcccgggt ccgcgtggcg 59700
gcctgcgacg tgtccgaccg ggccgcgctc gccgcgctgc tcgcggacat cgagccgccc 59760
ctgaccgcgg tggtgcacgc ggccggcgtc ctcgacgacg gcacgctcac ctcgctgacc 59820
cccgaacggc tcgccgccgt actgcgcccg aaggccgacg ccgcctggca cctgcacgaa 59880
ctcaccgagg acagggacct gtccgccttc gtgctgttct cctcggcggc cggcacgttc 59940
ggcgcccccg gccagggcaa ctacgccgcc gccaacgccg ccctggacgc gctcgccgag 60000
caccgccgct cccgcggcct gcccgccgtc tccctcgcct gggggccgtg ggccgccgag 60060
agcgccatga ccggcggcct cagcagcggc gaccgcgcca ggatgacccg ggccggcgtc 60120
cggcccctgg ccgccaccga ggcactcgcc gtgctcgacg ccgcctgccg caccggagcc 60180
ggcgccctcg ccgcgctccg tctcgacacc gcggcgctca ccgcccgcac cggcgccccg 60240
cacccgctgc tgcgcgacct ggtccgccgt ccggccggcc ccgcccgcga cgacgccgac 60300
acccagcccg cgctgcccca acggctggcc ggactgggcg aggagcagcg ccgccgggcc 60360
gtgctcgacg tcgtacgccg caacgcggca gcggtcctcg gccacgcccg ggcgtccgcc 60420
gtggacaccg cgcgcggctt cctggacctc ggcttcgact cgctgaccgc cgtcgaactg 60480
cgcaaccggc tcaccgaggc caccggcctg cggctgtccg cgaccgccgt cttcgaccac 60540
ccgaccccgg ccgccctggc ccgccatctc ctgaccgaac tggaaccgct ggtccgggcc 60600
gcgcggagcg ccctgcccag cgcgccggac cccgacgccg acctgcgcgg cgccatcgcg 60660
gccatcccgc tcgaacgcct ccggcaggcc ggactcctgg acgaactggc ccgcctggca 60720
ggcgtcgccg taccggccaa ggacgccccg gccgagcagc acgcagcccc cgacgaccac 60780
cccgacgacc ccgcggacgg acccgaggac gacggttccg acgacctcat ggacgcgctg 60840
gacgacatga gcatcgacga cctgatcagg atcgcgcacg acgagcgccc ccgcggaaac 60900
tgaggatcac gaacagcatg agcaacacca acgaagaact cgtcgaggcg ctgcgcagct 60960
cgctgcgcga gaccgagcgg ctgcgccgcc acaaccgctc gctgacggcc gccgccgacg 61020
agccgatcgc catcgtcggc accgcctgcc ggttccccgg cggcatcgac tcgcccgagc 61080
ggctgtggga cgccgtcgcc gccggctcgg acctgatcac cggcttcccc gacgaccgcg 61140
gctgggacct cggcgtccac gaccccgacc ccgagcgggc cggccgcagc tacaccgacc 61200
gcggcggctt cctcaccggc gccgccgact tcgacccggc gttcttcggt atctccccgc 61260
gcgaggcccg cgccatggac ccccagcagc gggtgctgct ggagaccgcc tgggaggcgt 61320
acgaacaggc cggcatcgac ccgcacgccc agcgcggcag ccgcaccggc gtgttcgtcg 61380
gcacctggag ccagggctac ggcatcggcg cccgcgtccc cgaggacgcc gagggctacc 61440
tcgtcaccgg cggcgccacc gccgtcgtct ccggccggat ctcctacgtg ctcggcctgg 61500
agggcccggc cgtcacggtc gacaccgcct gctcctcgtc gctggtcgcc ctgcactggg 61560
cggtgcggtc gctgcgcgcc ggggaatgct cgatggcgct cgccggcggc gtgaccgtca 61620
tggccggccc cggggtgttc gtggagttct cccgggagcg cggcctcgcc cccgacggcc 61680
gctgcaaggc ctactcggcc gacgcggacg gcaccggctg gggcgagggc gtcggcgtgc 61740
tcctgctgga gcggctctcc gacgccgtcc gcaacggcca ccgcgtcctc gccgtcgtgc 61800
gcggctccgc cgtcaactcc gacggcgcca gcagcggcct caccgccccg aacggcccct 61860
cccagcagga ggtcatccgg caggccctcg ccgacgcccg gctcaccccg tccgacgtcg 61920
acgtcgtgga gggccacggc accggcaccc ggctcggcga ccccatcgag gcccaggccc 61980
tgctcgccgc ctacggccag gaccgccccc gcccgctgct gctcggctcc gtgaagtcca 62040
acctcggcca cacccaggcc gccgcgggcg tcgccggcgt catcaagatg gtcgaggcca 62100
tgcgccgcgg catcgcaccc cgcaccctcc acgccaccga gcccaccccc caggtggact 62160
ggtcccgcgg agccgtcgaa ctcctcaccg acaaccgctc ctggcccgac accggggcac 62220
cccgccggtc cgcggtgtcc gcgttcggcg tcagcggcac caacgcccac atcgtcctcg 62280
aacaggcccc cgagcccgcc gacaccgaca ccacccccgcg caccgcacac ccggtcgtgc 62340

-continued

```
cctggctgct gtccgcccac acaccggccg ccctgcgcgc ccaggccgaa cggctctccg  62400
ccggcctgcc cgacgacgcc gaccccctcg acgtcgccgc cgccctggcc accacccgcg  62460
ccgccctgcc gctgcgcgcc gccgtcctcg gcgccgacgc gactcagctg cgcgccggcc  62520
tcgccgcgct cgccgccggc gcacccgccg ccctctccgg cgaagcccgg tccgaccgca  62580
ccacggcctt cctctacacc ggccagggcg cccagcgcgc cggcatgggc gaggaactcg  62640
ccgccgccta cccggcgttc gccgccgcct ggaccgaggt ctgcgcggag ttcgacaccg  62700
tgctgccccg ccccctgcgc caggtgatca ccgaaggcgg ccccgacctc gaccgcaccc  62760
tgtacgcgca ggccgcggtg ttcgccttcg agaccgcgct gaccgcgctg ctcggctcct  62820
gggggatacg ccccgacctc gtcctcggcc actccgtcgg cgaactcgcc gccgcccaca  62880
ccgcgggagt gctgtccctg cggcacgccg tcgtcgtggt cgcggcccgc ggccggctca  62940
tggaggcgct gccggagggc ggcgccatgg tcgccgtcca ggcgagcgag gacgagatcg  63000
agctgcccga gggcgtggcc ctggcggccg tcaacggccc gtcgtcggtg gtcctgtccg  63060
gcgacgaggc cgctgtcctg gccaccgccg cccactgggc cgagcgcgga tgccgcacca  63120
agcggctcac cgtcagccac gccttccact cccaccgcat ggaccccgtc ctgaacggct  63180
tccgccgcgt gctgggcgcc gtcaccctca atacgccgcg catcccgttc gtctccacgg  63240
tcaccggcgc ccccgtcgaa gccggactgc gcgaccccga gtactggctg cgcaacgtcc  63300
gcgacaccgt ccggttcgcc gacggcgtcc ggaccctggc cgacgagggc gcggacacct  63360
tcgtcgaggt cggcccggac gccgtgctcg gcgccctcgt cgccgacgcg ctgcccgacg  63420
accccgaccg gcccgaaata ctcgccgtac ccaccgcccg cgcggaccgg cccgagcccg  63480
agaccctggt cggcgcgctc gcccgcatcc acgcccacgg cgcgcacgtc gactgggccg  63540
ccttcttcgg ctccggcgcc cgccgcgtcg acctgcccac ctacgccttc cagcaccagc  63600
actactggct ggccccggca cccgccgacg acctccccgc cgccggcctc ggcaccgtcg  63660
gccacccgct gctgcgcgcc gccgtcgaac tgcccgccga cgccaccgcg gaccacgccg  63720
cccgccccgg cgccgccgga gccgtcgtct tcaccggcac cctgtccgcc cacacgcacc  63780
cctggctggc cgaccacagc gtcctcggca cgccggtgct ccccggcacc gccctcgccg  63840
aactagccgc cgccgcgggc gaccgcctcg gctgcgccac cgtcgccgaa ctcgtcctca  63900
ccgcgccgct cgccgtcccc gcctccggcg ccgtccggct ccgcgtccac gtcgacgccc  63960
ccgaccgcga cggccaccgc gccgtcaccg tcgactcccg gcccgacgac cagctcgcgg  64020
acggcgccgc ctggacccgc cacgccaccg gacgcctcgc ccccaccggt cccgaacccg  64080
cccaggcgcc caccgcctgg ccgcccgccg acgccgaacc cctccccgtc gacggcctct  64140
acgaccggct caccgcggcc ggcttcggct acggccccgc cttccgcggc gtccgcgcgg  64200
cctggcgcct cggcaccgac ctgctcgccg acgtcgaact gcccgcggac accgacgagt  64260
cgggctttct gctgcacccc gccctgttcg acgccgccct gcacgccctc ggcctcggcg  64320
gcctggtcga gcacggcgga ctgcccttca cctggacggg cgtccgcctg cacgcgaccg  64380
gcgcccgctc cctgcgggtg cggctgaccc cgaccggccc cgacgccgtc gcgctcaccg  64440
cggccgacgc cacgggccgg cccgtcgtca ccgtcaccga cctccgcctg cgcccggcca  64500
ccgaggtccg cggcaccacc acggccgacg ccctgcacca catacggtgg gaaccccgcc  64560
cggcagctgc ggccaccgac gtcaccggca ccgacttcac cgtgttcacc ctgccggccg  64620
ccgggtccga cccgcaggcc gtccgggagg ccacgcgcgc gtccctcgcc cggttgcagg  64680
```

-continued agcatctcgc cgccgtcggg ccggccggcc cgctcgtcgt ggtcacccac ggcgccgtcg 64740
ccgcagaacc cggcgacacc gtccccgacc tggccggcgc ggcggtctgg ggcctggtgc 64800
gctccgccca gtccgagcac cccggccgct tcgtcctgat cgacctggcc gcttccgagg 64860
atgccgctgt cgttccggcc gcgatcgcca ccggagagcc tcagatcgct gtacggaatg 64920
gagcgctgta cgcgccccgg ctggtgcgcg gggcttctcg gccgggtggt gaggtgccgt 64980
tcggtgcggg cgacgtggtg ctggtgaccg gtggcacggg tgctctgggc cggttggtgg 65040
cccggcacct ggtggccgag cacggtgtgc gtcggctggt gctggcgagc cggcgcggag 65100
gcgccgggga gctggtcgcc gagttgggtg agttgggtgc cgctgtggac gtcgtggcct 65160
gcgatgtgtc cgaccgggac gcgctggagc gtctggtcgc ggcccatccg ctgacgggtg 65220
tggtgcacgc ggccggtgtg ctggacgacg gcacggtgga gtcgctgacc cctgaccggg 65280
tggacggggt gctgcgggcg aaggtcgacg gtgcctggca tctgcacgag ctgacggccg 65340
ccctggacct ccgtgccttt gtgctgttct cgtcgctcgc gggtgtggtg ggcagtgcgg 65400
gtcagggtgg ttacgcggcg gcgaacgccg cgctggacgc gctggcggag caccggcggg 65460
ccgagggcct gcccgccacc tccatcgcct ggggaccctg gaccgacggc atggcgagcg 65520
gcctcgaccg ggtggacgcg gcccggctcg cccgcggtgg agtcgtgccc ttcgcccacg 65580
ccgacggcct ggagctgttc gacgccgtct gcgccaccga cgcaccgctg accgtcgccg 65640
cgcgcctgga cctcgccgtg ctgcgcgccc aggcggaggc gctgccgccc gtgctgcgcg 65700
gcctggtgcc ggcgcccgca cgccgtaccg ccgctgccgc ccggcccggc ggcttcgccg 65760
agcggctcgc cgcgctgccc gagaccgagc ggcggcgcgc cgccctggaa ctggtccggg 65820
agaccgcggc gaccgtgctc ggccacgtcg gcccggaggc cgtcgccccc gaccgctcct 65880
tcctcgacct cggcttcgac tcactggccg ccgtcgaact ccgcaaccgg ctcaccgccg 65940
cgaccggcct gcgcctggcc gcgacgatca ccttcgacca ccccacctcc gccgccctcg 66000
cacgccacct cctggacgcg gccctggacg ccggcccgtc ggccacgagc ggcgcgcacc 66060
tgcccgccgc caccgccgta cgcgccgacg agccgatcgc gatcgtgggc atggcctgcc 66120
gctaccccgg cggtgtgacc tcgcccgagg acctgtggcg actcgtgctc gcgggcgccg 66180
acgccgtcac cggcttcccc gaggaccgtg gctgggacct cacctccgtc tacgaccccg 66240
accagtcccg caccgggacg agctacaccc gcgagggcgg attcctcacc ggggcggccg 66300
acttcgacgc cgagttcttc ggcatcagcc cgcgtgaggc gctggccatg gacccgcagc 66360
agaggctgct gctggagacc tcctgggagg cgatcgagcg cgccggcatc gacccgaccg 66420
cgctgcgcgg cagcgccacc ggtgtcttcg ccggcctgat gtaccacgac tacggcagcg 66480
gcaccggcac cctcccggag ggcgtcgagg gctacctggg tctcggcacc gccggcagcg 66540
tgctctcggg ccgggtcgcc tacacgctcg gcctggaggg ccccgcggtc accgtggaca 66600
ccgcgtgctc ctcctcgctg gtcgccctgc actgggcgat ccaggcgctg cgcagcggcg 66660
agtgctcgat ggcgctggcc ggcggtgtca ccgtcatggc cacaccgggc acgttcgtgg 66720
agttctcccg gcagcggggc ctcgcccccg acggccgctg caagtccttc gccgccgcgg 66780
ccgacggagt cggctggtcc gagggcgtcg gcatgctcct cgtggaacgc ctgtcggacg 66840
cccgccgcaa cggccaccaa gtgctggccg tcgtacgcgg atccgcggtg aaccaggacg 66900
gcgcgtcgaa cggtctgacc gccccgaacg gtccctcgca gcagcgggtg atccgccagg 66960
cgctccaggg cgccgggctg acgacggccg acgtcgacgc cgtggaggcg cacggtacgg 67020
gcaccaaact gggcgacccg atcgaggcgc aggccctcct cgccacctac ggccaggagc 67080
gggacgagcc gctgtggctc ggttcggtga agtccaacat cgggcacacg caggccgccg 67140
ccggtgtggc cggtgtgatc aagatggtgc aggccatgcg gcacgggacg ctgccgcgca 67200
cgctccacgt ggacgaggcg tcaccgcacg tcgactggac cgccggcgcg gtggaactgc 67260
tcaccgagga acgcgagtgg acccggacgc gtcggccgcg ccgcgccgcc gtgtcgtcct 67320
tcggcgtgtc cggcaccaac gcccacgtcg tcctcgaaga ggcacccgag gagaccgcac 67380
cccccgtatc ggccgaactg cccctcgtgc cgctgctgct gtccggtcac acctccacgg 67440
cgctcgccgc ccaggcacgc cgactgcacg accacctcgc cgagtccggc acaccggccc 67500
tggaaacggt cggccgctcc cttgccgcgt cgcgggcgtt gttgccgcat cgtgcggtgg 67560
tggtggccgc tgatgtggcc ggtgcgcggg cttctctggc ggcgttggcc gcgggggagc 67620
cggtggaggg tgtggtgtcg ggtgctgccg ggttgccggg tgagggccgg gtggtgttcg 67680
tgttcccggg tcagggggcg cagtgggtgg ggatggcggt ggatctgctg gattcgtcgc 67740
cggtgttcgc ggggcggatg gctgagtgtg cggtggcgtt ggagccgttc gtggagtggt 67800
cgttgcgtgg tgtgctgggt gatccggtgg cgttggagcg ggtggatgtc gttcagccgg 67860
tgttgtgggc ggtgatggtg tcgttggcgg aggtgtggcg ttcgtacggt gtcgtgccgt 67920
cggctgtggt cggtcattcg caggggggaga tcgcggctgc ttgtgtggcg ggtgtgctgt 67980
cgctggcgga cggcgcccgg gtcgtcgccc tgcgcagcag ggctctgacg gcgctggcgg 68040
gcagcggggg gatggtgtcg gtcgccgccg ggccgtccgg tgtcgaggag ttgctggtgg 68100
gctgggcggg ccggttggcg gtggctgcgg tcaacggtcc tgagtcggtc gtcgtcgcgg 68160
gtgagggggt ggcgctggag gagttcctgg ctcattgcgg gggtcggggg gtgcgggctc 68220
ggcgtatcgc tgtcgactat gcctcgcatt cggtgctggt ggagccggtg cgtgaggctc 68280
tgctggctga tctggagggc gtgcggccgg gtgagggcac ggttccgctg ttctccaccg 68340
tgacggggga gtgggcggac ggcacggcgc tggacgccgg ctactggtac cgcaacctgc 68400
gcgaaccggt gggcttcgaa ccggcggtgc gcggcctgct cgactccggc cacgccgtgt 68460
tcgtggagat cagcccgcac ccggtgctga cggccgccgt gcaggagacg gcggatgcca 68520
ccgagcggac cgccgtcgtg gtcggcaccc tccgccgcga ccacgagggt cagcggcaac 68580
tgctcaccca cctcggcgtc ctgcacacca cgggcgccga catcgactgg acgggctgct 68640
tcacgggcgt caccggccgt gccgacctgc ccacctacgc cttccagcac acgcgctact 68700
ggctgacccc ctccggcccg tccgccggcg aactggccgg agcgggcctg accgccgccg 68760
ggcacccgct gctcggcgct gccgtcgacc tcgcggagga cggcggcctc gtcctgaccg 68820
gacgcctcgc cgcggacccg gccgcctgga cggccgatca cgtcgtcctc ggcaccaccc 68880
tgctgcccgg cgcggcgctc gccgaactcg ccctcgccgc cggcgacggc gtcggctgcg 68940
gcaccctgga cgaactcgtc ctcggcgcac ccctggcact gcccgaacgc ggtgccctgc 69000
acctccaggt acgggtgggc cgcgccgagg ccgaccaccg ccgtaccgtc agcgtccacg 69060
cgcgccccga ggacggtgac gcgccctgga cccggcacgc cgagggcgtc ctcgtgcccg 69120
gggacaccgc cgccggcacg ccgctgaccg agtggccgcc cgccgacgcc gaaccggtgg 69180
acgtgtccgc gctctacgac agcctcgccg accgcggcct cgactacggg ccggtcttcc 69240
gtggcgtacg cgcggcctgg cggcacggcg acgacatcct ggcggaggtc gaactgcccg 69300
cggaggccga cgagtcgggc ttcctgctgc acccggccct gctggacgcg gccctgcacc 69360
cgatcggcct cggcggcctg gtcggcgacg gcggactgcc cttcgcctgg cacggcctgc 69420

-continued

```
gtgtgcacgc cgtcggcgcc cgcgccgcgc gggtacggct caccccccctg ggcgacgaga  69480
ccgtcgccgt agacctcgcc gacggcgccg gcgcgcccct ggccgccatt gtctccctgc  69540
gcctgcgagc cgtcacggcc gcacaggtcg ccgccgcccg caccctcacc gacccggccc  69600
tgcacctgga ctggctcccg gtggccggcg ccgcgtccgc gccctcggac gacaccgccg  69660
tggaactgct gcgcttggac gacgcaccgc acgggacgga cgccggtccc gggggcgtgc  69720
ggcaggccgt gcgtacggcc ctcaccgcga tccaggagcg gatcgccgac gaccgggccg  69780
agcggctggt cgtcgtcacc cgcgacaccg acctcgccgg cgccgccgtc ggcggtctgc  69840
tgcggtccgc ccaggccgag cacccgggcc gcttcggcca cgtcgtgctc gacggacacc  69900
ccgactccga gcgcgccctg cccaccgcca ccgccctgac cgacgagccg tgggtcgccg  69960
tgcgcgccgg ggagacatac gtaccgcggc tcgcccggtc cggtgcgcgg ccgggcggcg  70020
acgtgccgtt cggcgccgac gacgtggtgc tggtgaccgg cggcaccggg gtgctgggcg  70080
ccctggtggc ccggcacctg gtgaccgagc acggtgtgcg caggctggtg ctggcgagcc  70140
ggcgcggagg cgccggggag ctggtcgccg agttgggcga attgggcgcg gctgtggatg  70200
tggtggcctg tgatgtgtcc gaccgggagg cgctggagcg tctggtcgcg gcccatccgc  70260
tgacgggtgt ggtgcacgcg gccggtgtgc tggacgacgg cacggtggag tcgctgaccc  70320
ctgaccgggt ggacggggtg ctgcgggcga aggtcgacgg tgcctggcat ctgcacgagc  70380
tgacggccgc cctggacctc cgtgcctttg tgctgttctc gtcgctcgcg ggtgtggtgg  70440
gcagtgcggg tcagggtggt tacgcggcgg cgaacgccgc gttggacgcg ctggcggagt  70500
accggcgggc cgagggcctg cccgccacct ccatcgcctg gggcctgtgg gcgccggcga  70560
gcgccatgac ctccggcgcc gacaccgcgc gcctggcccg gagcggcatc ctcccgctcc  70620
ccgccgaccg ggccctggaa ctgttcgaca ccgcctgcgc cgccgagacg ccgctgaccg  70680
tcgccgcccg cctggacctc acggcgttcc gcgcccaggg cacccgtatg cccgtcgtcc  70740
tgcggagcct cgcgggcccc gccgcccgcc gcacggcacg cgccggcgac gccggcacct  70800
tgcgcgaccg cctcgccgcc cagacccccg ccgaacggac ccggaccgtg ctcgacctgg  70860
tccgaggcca ggccgcggcc gttctcggac acgagtcggc cgccgccatc gccgaggacc  70920
gggccttcct cgaactcggc ttcgactccc tgaccgccgt cgacctgcgc aaccgcctcg  70980
gcacggtgac gggcctccgc ctgcccacca ccaccgtgtt cgaccacccc aaccccgccg  71040
cactgacccg gcacatcctc gccgagctgc tcggcgccac ggccggctcg gcccaggccg  71100
cccccaccgc cgtgcggacc gacgagccga tcgcgatcgt gggcatggcc tgccggtacc  71160
ccggcggagt ggcctctccc gaggacctgt ggcgcgtcgt cgccgagggc cgtgacgtca  71220
tctccccctt cccggaggac cggggctggg acctcggcgc cctgtaccac gccgaccccg  71280
accacacggg gaccagctac gcccgcgagg gcgggttcct gcacgacgcc gccgggttcg  71340
acgccgagtt cttcggcatc agcccgcgtg aggcgctggc catggacccg cagcagcggc  71400
tgctcctgga ggcgtcctgg gaggcgatcg agcgcgccgg catcgacccg accgcgctgc  71460
gcggcagcgc caccggtgtc ttcgccggcc tgatgtacca cgactacgcg gcccggctcg  71520
gcaccacccc ggagggcctc gaaggctacc tgggcatggg caactccggc agcgtcgcct  71580
ccggccgcat ctcctacacc ctgggcctgg aaggcccggc ggtcaccgtg gacaccgcct  71640
gctcctcgtc cctggtcgcc ctgcactggg cgatccaggc gctgcgctcg gggggagtgcg  71700
acctcgccct ggccggcggc gtgtccgtga tggcgacccc gggcacgttc gtggagttct  71760
cccggcagcg gggcctcgcc cccgacggcc gctgcaagtc cttcgccgcc gcggccgacg  71820
```

gggccagctg gtccgagggc gtcggcatgc tgctcgtgga gcgcctgtcg gacgcccgcc 71880
gcaacggtca ccgtgtgctg gccgtcgtgc gcggctcggc ggtgaaccag gacggtgcgt 71940
cgaacggtct gacggccccg aacggtcctt cgcagcagcg ggtgatccgt caggcgctcg 72000
ccggtgccgg gctcacgtcc gcggacgtgg acgcggtgga ggcgcacggt acgggcacgc 72060
ggctgggcga cccgatcgag gcgcaggccc tcctcgccac ctacgggcag gagcgggacg 72120
agccgctgtg gctcggctcg gtcaagtcca acatcggcca tgcgcaggcc gccgccggtg 72180
tggccggtgt gatcaagatg gtccaggcga tgcggaacgg cgtgctcccg cgcacgctcc 72240
acgtcgatga gccgtccccg cacgtcgact ggaccgtcgg cgcggtcgag ctgctgaccg 72300
gggaacagga gtggccgcgg caggaccgcc cgcgccgtgc gggtgtgtcg tcgttcggtg 72360
tgtccggcac gaacgcgcat gtggtgctgg aagaggctcc cgaggagacc gagggcaccg 72420
cgccggctgc gctgcccgcc gtgccctggg tggtgtcggc ccgctccgag accgcgctgc 72480
gtgcgcaggc cgcacggctc gcggactggc tgcacggcga caccgacgtc ctcggcaccg 72540
cctactccct cgccaccggc cgggcggcgc tgccgcaccg cgcggtcgtg gtcgggaccg 72600
accgggccga actctccgac ggactggccg cgctggcggc cggtcgcgcc gccgcgcacg 72660
tcgaatcggg ccgtgcccgc gacaaccgtg tcaccgcgtt cgtgttcgcg gggcagggtg 72720
cgcagcgggc ggggatgggg gcggaactgg ctgccgcgta tccggtgttc gctcaggtgt 72780
tcgcgcaggt gtgtgcggcg ttcgacggtg tgctggagcg gccgctgggt gaggtgatcg 72840
ccgagggtgg tccggagctg gatcggacgg tgtacgcgca ggcggggttg ttcgctttcg 72900
aggtggcgtt gttccggctg ctggagtcgt ggggtgtcgc gccggacgtc gtactcgggc 72960
attccgtggg tgagttggcg gctgcctgtg tggcgggtgt gtggtcgctc gaggacgcgg 73020
tgcgggtggt ggctgcgcgt gggcggttga tgcaggcgct gccgcagggc ggtgcgatgg 73080
tcgctctcga ggtgtcggcg ggtgagctgg agttgccgga gggtgtggag ctggcggcgg 73140
tcaatggtcc gtcgtcggtg gtgctgtccg gtgaggagga ggccgtcctg gctgaggcgg 73200
cccgctggcc ggaccgtcgt gccaagcgtc tgcgggtcag tcacgccttc cactcgcgtc 73260
ggatggatcc gatgctggag gacttccggc gggtactgga gtcggtggcc ttccacgctc 73320
cggagcttgt tttcgtgtcg acggtgaccg gtgctgtggt gacggacgag ttgtgtgacc 73380
cggggtattg ggtgcgcaat gtgcgggaga cggtccggtt cgcggatgcg gtggtggcgg 73440
cggaggccgg tgtcttcgtg gagttggcgc cggacgcggt gttgtcgggg ctggtgggcg 73500
agtccgtcga gggtgtgctg tgtgttcccg cgcagcgggc gggcaggccg gccgcgcggg 73560
ttctcgtgtc ggcgctgggc acgctgcaca cgcacggtgt cgacgtcgcc tggggccggt 73620
tcttcgccgg tagcggtgcc cgtcgtgtcg acctgcccac ctacgccttc caacgcgaac 73680
gctactggct ggacgccccc gcgccgcaga ccggtggcgc ctcggacgac gccttctggg 73740
ccgccgtcca gagcggtgac ctcgccggtc tgctgggtgt cgcggaggac gccgggctgg 73800
acgccgtact gcccacgctc gcgtcctggc acgacaggga acgtgccgac gcggtcgtgg 73860
acggatggcg gcacaaggtc cgctggaccc cgctccccga ggccggcggc gccgtgctga 73920
gcggccggtg gctgctggtc ggcccggagg gggacgaggc gctcgtcgcc gacgtcgcca 73980
ccgccctgcg cgagcacggt gccgaggtca cgcacctcgc gctcccgcgg gacgccgacc 74040
gggagacgac cgccgaactg ctccgcggca ccgacgacac cggtctcacc gcagtgctgt 74100
ccctgctcgc gcgggcggac cgcccggtgc acgccaccct cgccctcgtc caggcgctcg 74160
gcgacgccga agtcaccgtg ccgctgtggt gcgctacctc cgagtccgtc gccgtcgcct 74220
ccacggacgt cgtaccggaa gccgccgtcg acgcggccgg cctctggggg ctcggccggg 74280
tcgtacgcct ggaggcaccg gaccgctggg gcggactggt cgaccttccc ggcgcgctgg 74340
acgcgcgggc ccgccgccgg ctcgccgccg tcctggccgg cgccgaggac gagtgcgcgg 74400
tgcgcgagaa cggcgccttc gccgctcgtc tcgtccgagc cgccgacgca ccccgccgcg 74460
agtggcggcc ccagggcacg gtcctcgtga ccggcggcac cggcgcgctc ggcgcgcggg 74520
tcgcccagcg gctcgcggag cgcggtgcgc ggcacgtgct gctggtgagc aggcgcggtc 74580
cggcggccga cggcgcggcc gaactggtcc gcgccatcga ggcggcgggc gccacggcga 74640
ccgtcgccgc gtgcgatgtc gccgatccgg aggcggtcgc ggccctgctg gagcggatac 74700
ccgccgacgc cccgctgacc gcggtggtgc acacggccag cgtcctcgcc gacgccccgc 74760
tggacacgct caccccggac cggatcaccg ccgtcctccg ggccaaggcc gatgccgcac 74820
gaatcctgca caccgcgacg gccagcctcg acctggacgc gttcgtgctg ttctcctcgc 74880
tcgccggcac cctcggcaac cccgggcagg ccgcctacgc cgccgcgaac gccgtactcg 74940
acacgctcgc cgcgcaccgc cgggccctcg gactgcccgg caccgccgtc gcctggggcc 75000
cctgggccgg cggcggcatg ctcgacgaca cggtggcgga gcgactgcgc cgcgccggtg 75060
tcatcccgct cgaccccgag cacgccctgg tcgccctcga ccgtgccgtg gccgccgcgg 75120
acgcgcacag cgtcatcgcc gacgccgact ggaccggcct caccgccggc tccatgctgg 75180
ccgaactctc cggcccggca cccgtcgagg cgcccacggc gctcaccggt cccgaccgcg 75240
agcgcgccgc actggccctc gtccgctcct gcgccgccgc cgtcctcggc cgctcggccg 75300
ccgtggacgt cgaacccgac accgccttcc gcgagctggg cttcgactcc atggccgccg 75360
tccagctgcg caaccggctc aacgccgcca cgggggtcgt gctcaccgcg accgccgtgt 75420
tcgaccaccc gagcgcccgc gccctggcca cccacctgct cgctctggcg accggggagg 75480
gcgccggctc ggccggcgcg accgaactcc cgggtacggc cgtccacacg gacgagccga 75540
tcgcgatcgt cggcatggcc tgccgcttcc ccggcgacgt gacctcgccc gaggacctgt 75600
ggcggctgct cgccgacggc gtggacgccg tcggccccat cccggcggac cgccagtggg 75660
gacccaccga cgcctacgcc gaaggcggct tcctgcgcgg ggccggcgag ttcgacgcgg 75720
acttcttcgg gatcagcccg cgcgaggcgc tggtcatgga cccgcagcag cggctcgccc 75780
tggagaccgg ctgggaggtg ttcgaacgcg cgggcatcaa cccgcacacg gtgcgcggca 75840
cgtccgtcgg cgtcttcctc ggcaccaacg gccaggacta cgtgtccctc ctcgccggcg 75900
ccaccgaggc ccacgcggga cacatcggca ccggcaactc cgccagcgtg ctgtcgggcc 75960
gcatcgccta cgtcctcggc ctggagggcc ccgcggtcac cgtggacacc gcgtgctcct 76020
cctcgctggt cgccctgcac tgggcgatcc aggcgctgcg cagcggcgag tgctccatgg 76080
ccctggccgg cggtgtcacc gtcatggcca ccccgggcgc cttcgccgag ttctcccacc 76140
agcggggact ggcggaggac ggccgctgca agtccttcgc ggcatcggcg gacggcaccg 76200
gctggggcga gggcgtcggc atgctcctgg tggagcgtct gtcggacgcc cgccgcaacg 76260
gtcaccgtgt gctggccgtc gtgcgcggct cggcggtgaa ccaggacggt gcgtcgaacg 76320
gtctgacggc tccgaacggt ccttcgcagc agcgggtgat ccgtcaggcg ctcgccggtg 76380
ccgggctcac gcccgtggac gtggacgcgg tggaggcgca cggcacgggc acgcggctgg 76440
gcgacccgat cgaggcgcag gcgctcctcg ccacctacgg gcaggagcgg gacgagccgc 76500
tgtggctcgg ttcggtcaag tccaacatcg ggcacacgca ggccgccgcc ggtgtggccg 76560
gtgtgatcaa gatggtggag gcgatgcgga acggaacgct gccgcccacc ctccacgtgg 76620
acgagccgtc cccgcacgtc gactggtccg ccggcgcggt cgagctgctg acggaagcgc 76680
gggagtggaa gcgtgccggt cggccgcgcc gtgcgggtgt gtcgtcgttc ggtgtgtccg 76740
gcacgaacgc gcatgtggtg ctggaagaag cgccggagga gaccgaaccg gcggcttcgg 76800
acgaactgcc ggtcgcaccc tggctgttgt cggcccgctc agagaaggcg ctgctggcac 76860
aggtcgagcg gctgcgcgcg tacgtcacgg agcacccgga ggcgcggccg gccgacatcg 76920
gcctcagcct ggccaccggc cgagccgcgc tggcccaccg tctgagcgga gccggcgaga 76980
ccacggagga actgctcgcc gcccttgaca ccgcccttcc cgccgtggct cgcgaaaccc 77040
cgaccgcgtt cgtgttcgcg gggcagggtg cgcagcgggt ggggatgggg gcggaactgg 77100
ctgccgtgta tccggtgttc gctcaggtgt tcgcgcaggt gtgtgcggcg ttcgacggtg 77160
tgctggagcg gccgttgggt gaggtggtcg ccgagggtgg tccggagctg gatcggacgg 77220
tgtacgcgca ggcggggttg ttcgctttcg aggtggcgtt gttccggctg ctggagtcgt 77280
ggggtgtcgc gccggacgtc gtactcgggc attccgtggg tgagttggcg gctgcctgtg 77340
tggcgggtgt gtggtcgctc gaggacgcgg tgcgggtggt ggctgcgcgt gggcggttga 77400
tgcaggcgct gccgcagggc ggtgcgatgg tcgctctcga ggtgtcggcg ggtgagttgg 77460
agttgccgga gggtgtggag ctggcggcgg tcaatggtcc gacgtcggtg gtgctgtccg 77520
gtgaggagga cgccgtcctg gctgaggcgg cccgctggcc ggaccgtcgt gccaagcgtc 77580
tgcgggtcag tcacgccttc cattcgcgtc ggatggatcc gatgctggag gacttccggc 77640
gggtactgga gtccgtcacc ttccacgctc cgcagcttgc cttcgtgtcg accgtgaccg 77700
gtgctgcggt gacggacgag ttgtgtgacc cggggtattg ggtgcgcaat gtgcgggaga 77760
cggtccggtt cgcggatgcg gtggtggcgg caggggccgg tgtcttcgtg gagttggcgc 77820
cggacgcggt gttgtcgggg ctggtgggcg agtccgtcga gggcgtgctg tgtgttcccg 77880
cgcagcgggc gggcaggccg gccgcgcggg ctctcgtgtc ggcgctgggc acgctgcaca 77940
cgcacggtgt cgacgtcgcc tgggaccggt tcttcgccgg tagcggtgcc cgtcgcgtcg 78000
acctgcccac ctacgccttc caacgcgaac gctactggct cgcgccgccc gcggccggcc 78060
ccgtcggcct cgcgggcgtc ggtctcacgg ccaccggtca ccccctgctc ggcgtcagcg 78120
tcgagctgcc cggcacggac gcggtggcgt tcaccgggag cgtgtcgctg agcacccacc 78180
cgtggctggc cgaccacgcc atcctggggc ctgccctgct gccgggcacg gcgttcctgg 78240
acctcgccct cgcggcgggc gaacacgtcg gctgcccgcg ggtggacgac ctcgcgctgc 78300
acgccccgct ggcgctcccg gcccacggct cggtgcgcat gcaggtcagg gtcgaggggga 78360
ccgaccccga cgggagccgc caggtcggca tctactcacg gcccgaggac gacgaggacg 78420
cctggaccca gcacgcgacc ggcgtgctgg cgcccgaaag cggccccgcc gccgaggcgc 78480
tgaccgagtg gccgccccag ggcgccgaac ccgtgtccgt ggacggcctg tacgacgacc 78540
tggccgccac cgggttcgcg tacggccccc tcttccgcgg cctgcgtgcc gcctgggtgc 78600
gggacggcgc cgtctacgcc gacgtcgccc ttccggacga gacggcctcc gtcgcgggct 78660
acagcgtgca cccggcgctg ctcgacgccg ccctgcacgc gctcggctgc gcgaacctgg 78720
tcgcggactg ggcggacgga cagctgccct tcgcgtggac cggcgcgcgg atccacgccg 78780
tgggcgccag ggcgctgcgc gtccggctcc gggccgagaa cggcgggatc gcgctgaccg 78840
cggccgatgc cggcggacag cccgtggccg ggatcgaagg agtccggctg cggcccgtcg 78900

-continued gcgacgcgcg tgccgtccgt gcggcggcgg gcgcgcgccc ctgccgggtc gagtggctgc 78960
ccgtcgtacc ggcggacgac cccgaggacg acgacatcac cgtcgtcccc gtgaccggcc 79020
gtaccgccgg cggcgacgtc gtggccgagg tgcgtgccgc cgtcgccgcc gccctggccc 79080
ggctccagga atggctggcc gacgaccggt ccgagcgcct ggtcctcgtc acccggggcg 79140
ccgtcgcggc gctgccggac gaggcaccgg acccggtggc cgccgcggtc tggggcctgg 79200
tgcgctccgc ccagtccgag caccccggcc ggttcgtcct ggccgacttg gccgcttccg 79260
aggatgccgc tgtcgtttcg gccgcggtcg ccaccggaga gcctcagatc gccgtacgga 79320
atggagcgct gtacgcgccc cggctggtga ggggggcttc tcggccgggt ggtgaggtgc 79380
cgttcggtgc gggcgacgtg gtgctggtga ccggtgggac gggtgctctg gggcgggtgg 79440
tggcccggca tctggtggcc gagcacggtg tgcgtcggct ggtgctggcg agccggcgag 79500
ggggtgccgg ggagctggtc gccgagttgg gtgagttggg cgcggctgtg gatgtggtgg 79560
cgtgtgatgt gtccgaccgg gaggcgctgg agggtctggt cgcggcctat ccgctgacgg 79620
gtgtggtgca cgcggccggt gtgctggacg acggcacggt ggagtcgctg accgcggagc 79680
gggttgacgg ggtgctgcgg gcgaaggtcg acggtgcctg gcatctgcac gagctgacgt 79740
ccggactgga tctccgtgcg ttcgtgctgt tctcgtcgct cgcgggtgtg gtgggcagtg 79800
cgggtcaggg tggttacgcg gcggcgaacg ccgcgttgga cgcgctggcg gagtaccggc 79860
gggccgaggg cctgcccgcc acctccatcg cctggggacc ctggaccgac ggcatgacca 79920
cagggctgga gcgggcggac cgtgcccgta tcagccggtc gggtacccgg gccctcggca 79980
ccgaggacgg actcgccctc ttcgaccagg ccgtacgcgg cgccgacgcg ctcgccgtcg 80040
ccgcgctgtg ggacctgtcc gcgctgcgcg ccgcgcagtc gctgccgcct ctgttccagg 80100
ggctcgccgg acgaccggtc cggcggaccg tcgccgacgg cgccgggcgg ggcgccgagt 80160
gggccgaccg gttcaccggg ctgtcgccgg ccgaaagcga acgcgccgcc gtcgagtggg 80220
tccgtgagca ggcggcggcc gtgctggggc acgcgtcctc cgccgccgtc gccgctgacc 80280
gggccttcct cgacctgggc ttcgactcgc tcaccgccgt cgaactgcgc aaccggctcg 80340
ccacggcgac cggcctgcgg ctcggcacga ccgccgtgtt cgactacccc accccggccg 80400
ggctggccgc gcacctgctg gagcgcgtgc tcggcgccac gaccggctcg gcgcagccgg 80460
ctcccgccgc cgtaccggcg gacgagccga tcgcgatcgt cggcatggcc tgccgctacc 80520
ccggcggaat cacctccccg gaggagctgt ggcgcgaggt cgccgaaggc cgcgacgcga 80580
tctccgggtt cccgaccgac cgcggctggg acctgcgggc cctgttcgcc gacgaccccg 80640
ggcggcccgg caccagccac acccgcgaag gcggattcct gcacgacgcg ggcgagttcg 80700
acgccgactt cttcggcatc agcccgcgag aggccctggc catggacccg cagcagcggc 80760
tgctgctgga ggcgtcctgg gaggccattg agcgcgcggg catcgacccg gcatcgctgc 80820
gcggcagccg gaccggcgtg tacgccggcg tgatgtacca cgactacgcg gcccgcgtgg 80880
acgtcctgcc cgacggcgtc gagggctacc tcggcaccgg caactcgggc agcatcgcct 80940
ccggccggat cgcctacgcc ctcggcctgg agggccaggc cgtcaccgtc gacaccgcct 81000
gctcctcgtc gctggtcgcc ctgcactggg cggtccggtc gctgcgctcc ggcgagagcg 81060
acctcgcgct cgccggcggt gtcaccgtga tggccacccc gggtgtcttc gtcgacttct 81120
cccggcagcg cggcctcgcc accgacggac gctgcaagtc ctacggcgcc ggcgccgacg 81180
gcaccggctg gtccgagggc gtcggcatgc tcctggtcga acggctctcc gacgcccgtc 81240
gcaacgggca ccgggtgctc gccgtcatcc gcggcaccgc cgtcaaccag gacggcgcgt 81300
ccaacgggct caccgcgccc aacgggccct cgcagcagcg ggtgatccgg caggcgctgg 81360
ccgacgccag cctgcggccg tccgacgtgg acgccgtgga gggccacggc accggcacct 81420
cgctcggcga cccgatcgag gtggaggcgc tgctcgccac ctacggccag gagcgggacg 81480
agccgctgtg gctcggctcg atcaagtcca acatcgggca cacgcaggcc gccgccggcg 81540
tggccggtgt gatcaaaatg gtcgaggcca tgcggcacgg tgtgctgccc cgcacgctgc 81600
acgccgacga gccgtccccg cacatcgact gggcctccgg cgcggtggaa ctcctggccg 81660
agcaacggca gtggccgcgc acggaccggc cgcgccgggc cgccgtgtcc tccttcggtc 81720
tgtccggcac caacgcccat gtggtgctgg aacacacgga ccacggcgac caccactcgg 81780
ccgggaccgg cgaacggccc gccgtccccg tgcccgtccc cgtgccggtg gcgctgtcgg 81840
cgcgtaccga cgcgggactg cgggcccagg cggaccggct cgccgccgcg ctgaccgccg 81900
acccggacct gatcccgctc gacatcgcct actccgcggt gaccgggcgg gcccggctgg 81960
agcgccgggc cagcgtcgtc gcggcgaccc gcgaggaact gctggccgga ctcggcgacc 82020
tgggcccggc cacggtggcc ggcgccgggc acaccgcgtt cctgttcacc gggcagggcg 82080
cccagcgccc cggcaccggc gaggaactgg ccgccgccca cccggtgttc gccgccgcct 82140
acgccgaggt gtgcaccgcg ttcgacgcgg ttctcgaccg gccgctgcgc gaggtcgtcg 82200
ccaccggcga cggtctcgac gacaccggat acgggcagcc ggcggtgttc gcgctggagg 82260
tcgcgttcgg acggctcttc gagtcctggg gcgtcgtacc ggacttcctg ctcggtcact 82320
ccgtcggcga actggccgcc gcccatctgg ccggcgtgtg gtcgctgccc gacgcggtgc 82380
gcgtcgtcgc cgcccgcagc cggctcatgg ccgccctgcc ggcgggcggc gcgatggccg 82440
ccgtcgaggc gtccgcggac gaagtggccg ccgaactcgc cgacggcgcg gtgctcgccg 82500
cggtcaacgg cccccggtcg gtggtcgtct ccggggcacg ggacgcggta ctggccaccg 82560
ccggtctgtg ggccgcgcgc ggctgccgca cccgggaact gaaggtgtcg cacgccttcc 82620
actcgcccct gatggagccc atgctcagcg acttcgcggc ggccctggcc gacgtggagt 82680
tccgcgcgcc gcggatcccc ctggtgtcca cggtgaccgg cgccgtcgcc ggcgacgagc 82740
tgtgcacccc cggctactgg gtccggcacg tccgggacac cgtccggttc gccgacggcg 82800
tccgcgccct cggccaggcc ggcgtggaca ccgtcgtgga actcggcccg gacggcgtcc 82860
tcaccgcgat ggccgctccg ctgctgccgg acaccgccgt ggccctgccc acgctgcgcg 82920
ccggacgccc cgaggcgccc gccgtcgccg ccgcgctcgg cgccctgcac gaccggggca 82980
cggcggtgga ctggccggcc ttcttcaggg gcaccggagc ccggaccgtc gaactgccga 83040
cgaccgcgtt ccagcgcacc cgctactggc tggagtccgc cgcacggacc ggcgacctct 83100
ccgccgccgg gctcgccgcc gccgggcatc cgctgctcgg ggccgccgtc gactcgcccg 83160
acgggatgct gctcaccggc cggctcgaca cggccaccca tccctggctg gccgaccaca 83220
ccgtcctgga caccgtcctg ctgccgggta cggccttcgt ggaactcgcc cgcgcggccg 83280
gcgaacgcgt cggcctgccc cgggtacgcg aactcaccct ggccgcaccg ctcgtactgc 83340
ccgcggacgg ctccgtcctg gtccaggtgc acgtcggcgc cgccgtcgac ggcgagcggc 83400
cggtcaccgt gtccgcccgc accgacgacg gccaggactg ggcacggcac gccaccggcg 83460
tcctcgcccc cgcggcgccg gcgcccggcg ccgacccgct gccctggccg ccgcgggacg 83520
ccgaaccggt ggcgacggcc ggccactacg acgagctggc cgccgccggc ctcggctacg 83580
gccccgcctt ccgcgccctg cgcgcggtct ggcggcgcgg tgacggcccg gccgccgagg 83640
tgttcgccga gatcggtccc gcgccgggca ccgatcccgc gggcttcggc gtgcacccgg 83700
cgctgctcga cacggccctg cacgcggccg ctgtcggcgg actcggcgtc gcgggcgtgc 83760
cgttcacctg gaacgaggtg gcggtgcaca ccgccggcgc ccgctccctg cgggtccgga 83820
tcgccccgga cggaagcggc gggctgtccc tgcgcgccac ggacgacgag ggccgcgccg 83880
tgatcgacgt cggagcgctg cggctgcgtg cgatcgcccc ggaggacctg cgcaccgcgc 83940
cggccgccgc cgaggcgctg ttcgacctgg actgggcgcc cgtctccgtg gcgcggggcg 84000
cgcggcccgc cggacgctgg gcggtgctcg cccccgccga cgcggagctg accgacgtac 84060
tgggagccgg gatcgagacc gtcaaggacc tcgcgacggt gccggacgac ctggacatcg 84120
tgctcgcggc cgtgtccgac aggggcgggg ccggggtcga tgcgcccacg gctgcctccg 84180
tcggcgccgc cgccgagacc gacgtgcccg aggccgtccg ggccatcctg cgcggcgccc 84240
tcggcctggt gcagacatgg gtggcggggg agtccgccgc ccggctggtc ctgctcaccc 84300
gcggcgcggt ggcgctcgcc ggtgagcggc ccgacctggc cggtgccgcc gcctggggcc 84360
tggtgcgcgc ggcgcagtcc gagcaccccg gccggctcgt gctggccgac gtggacgacg 84420
acccggcgtc cctggccgcg ctgcccgccg ccctggcgac cggcgagccg cagctgctga 84480
tccgcgccgg tgcggtccgc gccgcccgtc tggtccgcgc cgcccccgcc gaacccgccg 84540
tacccgccgc cccgttgggc gcacgcggca cggtgctggt caccggagcc accggcagcc 84600
tcggcaccct ggtggtccgg cacctggtcg ccgagcacgg cgtccggcgg ctgctgctgg 84660
tcagccggca gggacggcag ccggagccgg ccgcggaact cgccgcggcc ggagccgaag 84720
tccgcttcgc ggcctgcgac gtcgccgacc gggacgcgct ggccgcgctc ctggcgagcg 84780
tcgaccccga gcaccccgtg acggccgtcg tgcacgccgc gggcgtgctc gacgacggcg 84840
tcgtcgcggc gctcaccccg gaccggctcg acaccgtcct gcggcccaag gcggacgccg 84900
cctggcacct gcacgaactc accggcgagc tggacgcgtt cgtgctgttc tcgtccgccg 84960
cgggactcct cggcgcaccc ggacaggcca actacgcggc cgccaacgcg ttcctggacg 85020
ccctcgcggc gcaccgccgg gccgccggcc tgcccgcggt gtcgatcgcc tggggcccct 85080
gggccgacgg catggccgca cagctcgaca cccggcgcgc ctcccgggcc ggcctgctgc 85140
cgctcgacgc cgcactcggc ctggccctgt tcgacaccgc ccgtaccggg gcgccgaccg 85200
ccccgctcgc cgcccgtctc gacctgccgg gactgcgggc cgcggcggcg gaactcccgc 85260
ccatcctgcg gaccctggtg cccgccccgg cccggacggc gcccgagccg gccgagccgc 85320
tcgcggacac cctggccgcg ctgcccgccg aggagcggga acgccgggca ctcgacgccg 85380
tcctgcggca caccgccgag gtgctcggcc acgccacggc cgacggcgtc gaccgcgaac 85440
gcggcttcca gcagctcggc ttcgactccc tgatgtccgt cgagctgcgc aaccggctgg 85500
gcgccgccgc gggcctgcgg ctgcccgcca cggtgatctt cgatcacccc acgcccgccg 85560
cgctcgcggc ccacctggtg gccgaactgg ccccgggccg ccccaccgtg gcgtccctgc 85620
gcaccagcac gctcgccgaa ctggaggccg cggcgaacga gttcgccggc gaccccgagc 85680
tgcgcgaggg cctgcgcacc cggttgcgcg cactgctgcg caccctggac gacccggcgc 85740
cggacgagcc gctcgaggag accggcgagg agagcctcgc cgaactgctc gacctcgccg 85800
accgggagct gggggacttc tgatgaccga gcacgaccgc acgaccgacc gcgccaccgc 85860
acgaggagcc accgcgttgt cccaggaaca gaccgacgac cgcaaggtcg tggagaccgt 85920
caggcgtctg accaccgacc tgcgccgcgc caagcagcgg ctgcgcgagg cggaggaccg 85980
ggcgcacgag ccgatcgcga tcgtcggcat ggcctgccgg taccccggtg gcgtcggctc 86040

-continued

```
gccggaggac ctgtggcggc tcgtcctgga cggccgggac gccatgggcg ccttccccac  86100
cgaccgcggc tgggacctgg cggccctctt cgccgacgac cccgagcgct ccggcaccag  86160
ccacacccgc gagggcggat tcctgcacga tgcgggcgag ttcgaccccg gcctgttcgg  86220
gatcagcccc cgcgaggcgc tcgccatgga cccgcagcag cggctcctcc tggagaccgc  86280
ctgggaggcc gtcgaacgcg ccggcatcga ccccacctcg ctgcgcggca gccgcaccgg  86340
cgtctacgcc ggcgtgatgt accacgacta cggcaccggc gccgaccctc tgcccgaggg  86400
cgtcgagggc tacctcggcc tcggcaccgc gggcagcgtc gccagcggcc ggatcgccta  86460
cacactgggc ctggagggcc cggccgtcac cgtcgacacc gcctgctcct cgtccctggt  86520
cgccctgcac tccgctgtcc gggcgctgcg cgccggggag tgcacgatgg ccctggcggg  86580
cggcgcgacc gtgctgtcca ccccggccgt cttcgtggac ttctcccgtc agggcggact  86640
cgccgccgac ggacgctgca agtcctactc cgccgaggcc gacggcaccg gctggtccga  86700
gggcgtcggc atgctcctcg tcgaacggct cggcgacgcc gaacggctcg gccaccccgt  86760
cctcgccgtg ctgcgcggct cagcggtcaa ccaggacggt gccagcagcg gcctcaccac  86820
ccccaacggg ccggcccagc agcgcgtcat ccggcaggcg ctcgccgacg cccggctcac  86880
ccccgccgac ctggacctcg tggagggcca cggcaccggc accccgctcg gcgacccgat  86940
cgaggtgcag gccctgctcg ccacctacgg ccaggaccgc gccgaaccgc tctggctggg  87000
ctcggtgaag tccaacatcg gccacaccca ggccgccgcc ggcgtcgccg gagtcatcaa  87060
ggccgtcctg gccctccggc acggtgtact gcccggcacc gcccacctga ccgagccgac  87120
cccgcaggtc gactggaccg ccggcgccgt ggaaccgctg cgggagacgc gcgcctggcc  87180
cgagaccggc aggccgcgcc gcgcggccgt gtcctcgttc ggcatcagcg gcaccaacgc  87240
ccacatcgtc ctggaacagg cccccgcccc cgcggcgccg caggcggccg gagcccaggc  87300
gcccgcggcg ccgcggcccg tcgggaacca ggccaccgcc gcgccgaggt ccatggagga  87360
ccggaccgcc gccgcgccta gcgccggcgg agacccgacc ctcaccgcgc cggccccctc  87420
cgcgccccgc cccgcccccg ccgccctccc cgtcccgctg tccgccgcga ccgagcccgg  87480
tgtccgtgcc caggccctcc ggctggccgc ccacctcacc gagcaccccg aactcgcccc  87540
gcaggacatc gcgttcagcg ccgccaccac gcgcgccgcg ctggcgtccc gggccgtcgt  87600
gctcgccgac gaccgggccg ggctgctgga cgccctcacc gcgctggccg agggacggcc  87660
cggccccgcc gtcgtcaccg gcgccgccgc ggccggcgcg cgccggatca ccttcgtctt  87720
ccccggccag ggcgcccagt gggccggcat ggccgtaccc ctgctggaga cctcgccggt  87780
gttcgcggcg aagtgggccg aatgcgcccg cgtgctcgcc ccctgggtgg actggtcgcc  87840
cgacgaggcg ctgcgctcac cgcaggcact ggaacgggtc gacgtcgtcc agcccgtgct  87900
gtgggccgtc atggtcagcc tcgccgagct gtggcgggcg gcgggcgtac ggcccgacgc  87960
cgtactcggc cattcgcagg gcgagatcgc cgccgcctgc gtcgccggcg ccctgtccct  88020
ggaggacggc gccaaggtcg tcgcgctgcg cgccaaggcc ctgctcgcgc tcgccggccg  88080
cggcggcatg ctctccgtcc cgctgcccga ggcggaggtc cgcgcccggc tcgacagccg  88140
gcccggcctc ggcatcgccg ccgtcaacgg gcccgccacc gtggtggtct ccggcgagac  88200
ggccgccctc gacgaggccc aggccgcctg ggaggccgag ggcgtccggg tgcgccgcat  88260
ccccgtcgac tacgcctccc actccccgca cgtcgccgag gtgcaggacc gcctcgccgc  88320
cgacctcgcc ggcatcgccc cgcgcccggc cgaggtgacc ttcctgtcca cgctcaccgg  88380
```

-continued

```
ggaacccttc gacaccaccg gactcgacgc cggctactgg taccgcaacc tgcgcgagca  88440
ggtccgcttc gaggcggcca cccggcgcgc cctggagcag ggccaccgcg tgttcatcga  88500
ggtcggcccg caccccgtgc tcacgctcgg cgtccagcag accgccgagg ccatggacgt  88560
gcccgccgag gcgatcgcca ccctccgccg cgaccagggc gacctgctcc gcttccgcac  88620
cgcgctcgcc gaggccgccg tcctcggcgc ccccgtcgac tgggccgccg aactcgcccc  88680
gtacgcgccc cgccgggtcg acctgcccac ctacgccttc cagcgcgagc gctactggct  88740
caccccgcag cggcgcgccg ccctggccgc cagcaccggc accgacccgt gggacggccg  88800
gttctgggac atcgtggacc gcgccgacgc cgaggaactc tcccgcgcgc tcggcgtcga  88860
cacggacgac ccgctcaccg cggtcgtgcc ggccctcgcg cgctggcgcc gcctcctgcg  88920
cgagcggtcc gccgtggaca gctggcgcta caccgtcgcc tgggagcggc tcgccgtccc  88980
cgacagcgcc cggctgaccg ggccgtggct gctcgtcgta cccgagcccc gggccggtga  89040
cgccctcgcc gcgcggtgcg ccgccgcgct caccgggcac ggcgccgagg tcaccacgct  89100
caccctgggt gcggacgaca ccgaccgcgc ggcgctcgcg gcccggctga ccggcctccg  89160
cccggccggc gtgctgtccc tgctcgccct ggacgacgcc ccgcaccccg cacacccggc  89220
cctgcccacc ggactggccc tgaccgtcgc cctcgtacag gccctcggcg acgccggcgt  89280
caccgcgccc ctgtggtgcg ccacccgggg cgccgtcgcc accggccccg ccgaccccgt  89340
caccgcaccc gtccaggcgc agatctgggg cctgggccgg gtcgtcgcgc tggagcaccc  89400
cgaccgctgg ggcggcctga tcgacctgcc cgccgagtgg gacgaccgcg ccgcaggccg  89460
gctggccgcc ctgctcgccg caggcggcga cgaggaccag acggtgctgc gcgccaccgg  89520
cgtgtccgcc cgccgcctga cccgcgcgcc gctcggcacg gagcccgccc cccggccctg  89580
gcggtgcgcc ggcaccgtcc tgctcaccgg cggcaccggc gccctcgggc cgcacctggt  89640
gcgctggctg gccggacagg gcgccgagcg catcgtgctg cccggccgcc gcggcgccga  89700
cgccccgatc gcggccgagc tgaccgccga actggccggc accggcaccg aactccactt  89760
cccggtctgc gacgtcaccg accgcgcaga actggccgcg ctcatcgacg gactcgacac  89820
ggccggcacc ccggtgcgca gcgtcctgca cgccgccacc gccctcgaac tgcgcccgct  89880
ggccgacacc cccgtcgaca cgttcgccgg ccagacggcc gccaaggtgc tcggcgcccg  89940
gcacctcgac gaactcttcg ccgaccggga cctggacgcc ttcgtgctgt tctcctcggt  90000
cgccggcgtc tggggcagcg gactgcacgc cccctacgcc gccgccaacg cctacctcga  90060
cgccctcgcc gaggaccgcc gggcccgcgg cctgaccgcg acctccgtcg cctggggcat  90120
ctgggccgcc gtcaacgagt gggacggcgt gaacgcggac gtcgaccccg aacgcgtcgg  90180
ccggcagggc ctgcccttcc tcgacccgga cctcgccgtc gccggcctgc ggcaggcgct  90240
cgaccacgac gagacgaccg tggtgatcgc cgacgtcgac tggacccggt tcgtcccggt  90300
gttctgctcc gcgcgccgcc ggccgctgct ggagtccgtg cccgaggccg ccgccgtcct  90360
gcgcaccgcc accgtcgaca ccggaacggt gtccgcgctg cgcgagcggc tcggctccct  90420
gcccgaggcc ggccgccggc gggccgtcac cgaactggtc cgcgagcacg ccgccgccgt  90480
cctcggccac gactcgcccg ccgcgctccc cgccgaccgc gccttccggg acgtcggctt  90540
cgactccatc accgcggtcg agctgcgcaa ccggctccgc tcggccaccg gcctggccct  90600
gcccgccacc ctcgtcttcg accacccgtc gcccaccgcg ctggccggcc acctgctcgc  90660
gctcgccttc gacaccgccg cggcggacct cgccgcgccc gccgcccgcg ccgccgacga  90720
tgacgacgac ccgatcgccg tcgtcggcct cagctgccgc tacgccggcg gcgtcgcctc  90780
```

cccggacgag ctgtggcggc tcgtcgtggc cggtcaggac gcggtgggcg ccctgcccac 90840
cgaccgtggc tgggacctcg actcgctcta cgactccgac cccgacgccc gcggtcgcag 90900
ctacgtccgc caaggggcct tcctcaccga ccccgccggc ttcgacgccg ccttcttcgg 90960
catcgccccg gcggaggccc gggccaccga cccgcagcag cggctgctcc tggaagccgc 91020
ctgggaggcg ttcgagcacg ccggcatcga cgccaccggc ctgcgcggct cgcgcgtcgg 91080
cgtcttcgcc ggcgccaacg tcggcgacta cgcctccagc cgcggccctg gcgccggcgg 91140
ctccgacgga cagctgctca ccggcaacgt ccccagtgtg atctccggcc ggatctccta 91200
caccttcggt ttcgaggggc cggccgtcac cgtggacacc gcctgctcgt ccgccctggt 91260
cgccctccac ctggcctgcc ggtcggtgcg cggcggcgag agcgacatgg ccctggccgg 91320
cggcgtcgcg ctcatgtcca gcccggccgc cctgatcggc ttctccgcgc agcgcggcct 91380
gtccggcgac ggccgctgca aggccttcgc cgacgccgcc gacggcaccg gtctcgccga 91440
gggcgtcgga ctgctgctgg tggaacgcct ctcccgggcc cgcgcccagg gccaccgcgt 91500
cctcgccctc gtacgcggct cggcgatcaa ccaggacggc gcctccaacg gactcaccgc 91560
cccagcgga cccgcccagc agcgcgtcat caccgccgcg ctcgccgacg ccgggctgcg 91620
gcccgccgac gtcgacgccg tggaggccca tggcaccggc acccgcctcg gcgacccgat 91680
cgaggcccag gccctgctcg ccacctacgg acaggaccgc gccgaaccgc tctggctcgg 91740
ctcggtgaag tccaacatcg gccactccca ggccgcgtcc ggcgcggccg gcgtgatcaa 91800
gaccgtgcag gcgctgcggc acggcctgct gcccgccacg ctccacgtgg accggcccac 91860
cacccaggtc gactggaccg ccggcgccgt cgaggtgctg accgaggccc gggactggcc 91920
ggccgtggac cggcctcggc gggccgccgt gtcggcgttc ggcctgtccg gcaccaacgc 91980
gcacgtgatc ctcgaacagg cccccgccga agacgcccac ccggcccccg aaccggcccc 92040
gggcgaggac tcccacccga cccccgaaac ggccccaggc gaggacgccc cgcggaccgc 92100
gcccgagccc gcgcggcccg tggtgtggcc ggtgcacggc cgtacccggg acgccctgcg 92160
cgcccaggcg gcgcggctgc gcacccacct ggagacccgc cccgacgccc gcccggccga 92220
cgtcggctgg accctcgcgg ccggtcgggc cgtgttcgac caccgcgccg tggtgctcgg 92280
cgccgaccgc gccgagctgc tgcgcggact cgacgccgtc gccgccggca cccccgaccc 92340
cgcggtcgcc gacggcgcgg cccagggcgc cgaccgggcc gtgttcgtct tccccggaca 92400
cggcgcccag tggcccggca tggcccggcg gctcttcgac gacttcccgg tgttccggga 92460
aagcgtgctc cagtgcgccg acgccttcgc cgagttcgtc gactggtccc tgctcgacgt 92520
gctccgcgac gaggagggcg cgccgccgct gcaccgcgtg gacgtcgtcc agcccgccct 92580
gttcaccatg atggtgtcgc tggccgcgct gtggcgctcg tacggcgtgg agccgtcggc 92640
cgtggtcggc cacagccagg gcgagatcgc cgccgcctac gtggcgggcg ccctcgacct 92700
gcgggacgcc gcccggatcg tcgccacccg cggcaaggcc tggctcaccc tggccggcac 92760
cggcggcatg gcctccgtgg cgctgccccg cgccgaggcg gccgagcggc tgcgcccgtt 92820
cggccaccgc ctggacatcg cggccgtcaa cgacccgcgc tcggtcaccg tcgccggcga 92880
cctcgacgcg ctggaggagt tcctgaccgg cctggagacc gagggcgtcc gcgtccgccg 92940
ggtccgccag atcgtcggcg cgggccacac cgcgcacgtc gacgcgctgc gcgaccagct 93000
gatcgagacc ctcgcgccga ccgcgccgcg ctccgcgccg atcgcgttct gctccaccgt 93060
caccggcgga ctgctcgaca ccgccggcct cgaccaccac tactggtacc gcaacgcccg 93120

-continued ccggacggtc ctgttcgaac aggcggtccg cacgctggcg gagcagggct acggcccctt 93180
cctggagatc agcgcgcacc cgatgttcac cgtcgccgtg caggagaccc tggaggacgc 93240
cggcgtcggc gccgcggtcc tcgccacgct gcgccgcgac gagggcggcc ccgaccggtt 93300
cctgcgcgcc gccgccgagg cccacacggc cggcgtcacc gtcgactggc gcccggcctt 93360
cgccggcgcc ggagcccgta cgaccgacct gccgacgtac gccttccagc gcacccggca 93420
ctggctggag ccgggcggcg acagcggcga cgtgaccgcc gcaggcctgg caccggccgg 93480
ccatccgctg ctgggagccg tggtcgaact cgccgacgga gccatggtcc tgaccggccg 93540
gctctccgcc accgcgcagc cctggccggg gcccgaggcg ccggacgccg cgctggtcga 93600
cctcgtcctg gccgccgccg accgggccga ctgcgcgggc gtcggcgaac tgaccgtgta 93660
cgaaccgctg atggcgccgg ccggcggcgc cgacacccgg gtgaccgtcg gcgcacccga 93720
cgcggtgggc agccgcacgg ccgccgtcca cacccgcacc gcggacagcc cgtgggtgcg 93780
ccacgccgag gccacgctcg tcgcccggcc ggcccccggc gagtccctga ccgactggcc 93840
gccggccggc gcggaaccga tcgacccgcc cgcggaggcg ggccgcgccg gtgtcgccgt 93900
gaccgccgcg tggcagcgcg gtgacgacct tttcacagag gtggcgctcg acgacggcgc 93960
cgccgagcgg gccgacgcgt tcgcgctgca tccgctgctg ctggacgccg ccctgagccc 94020
gctgctcgac ggcgagctga cgcccaccgc gtggtcgggc gtccgcctgc acgcgaccgg 94080
ggcgaggacc ctgagagcgc gcgcggaacg catcggcccc gacaccgtgg cgctcaccct 94140
ggccgacccc gagggcggcc cggtgctgac cgccgacacc gtccgtctcg ccgccgcgcc 94200
cgccgcggga gccggccggc gcaccggcaa ggacgccctg ttccggatgg agtgggtgcc 94260
ggcgccgctc gccccggcca cgcccggccg ctgggccgtc ctcggggccg acccgctcgg 94320
cgccgccgac accctgcgct ccctcggcca caccgtgcac ggcgccgacg gcccggccgg 94380
cctgaccgag gtgcccgacg cggtgctgat caccgccgtc ggcgccccgg gcgaggcgcc 94440
cgccgaggca cgcaccgtgc tgcacggcac gctggcggcc ctccagaccc tcctcgccga 94500
cgaccggttc accgccgtac cgctcgtggt cctcacccgg ggcgccgccg ccgaccgggc 94560
cgacgacctc gccggcgccg cggcctgggg cctggtgcgc tccgcacagt cggagcaccc 94620
gggccgcttc gtcctggccg acatcgacga cgacccccgc tcctggcggg cgctgggcgg 94680
cgtaccggcc accggggagc cgcagctggc gctgcgggcc ggtgcggcca ccgtcccgcg 94740
gctggcccgg ctcgccccgc cggacgcccc ggcgccgtgg gacccggacc gcaccgtcct 94800
cgtcaccggc gcctccggag acctcggcgc gctggtggcc cggcacctgg tggccgccca 94860
cggggtacgg cacctgatcc tcgcctcccg gcgcggcccc gccgccccgg gcgccgccgg 94920
actcggcgcc gagctgcggg cctcgggcgc cgccacggtc acgatcgcgg cctgcgacac 94980
cgccgaccgc aaggcactcg cggaactgat cgccgccgta cccgacgagc acccgctcac 95040
cgcggtcgtg cacagcgctt ccgtcctcga cgacggggtg atcgccgccc tcgacccgga 95100
ccggctggac accgcgctgc gcccgaaggc cgacgcggcc tggcacctgc acgaactgac 95160
ccggcatctg aacctgtccg ccttcgtgct gttctcgtcc gtggcgggca ccttcggcgg 95220
cctcggccag ggcaactacg cggcgggcaa cgccttcctg gacgcgctgg cccgccaccg 95280
ccgcgcccac ggcctcccgg cgacctccgt ggcctggggc tggtgggcgg aacgcgccgc 95340
gaagagcggc cacggcactg ccgccgaggc gcccgtcgcc gtcaacggca tgaccccgct 95400
gaccgaggac cacggcctcg ccctgttcga cgcggcctgc cgcggcgacg agccgttcgt 95460
ggtggccggc gcgctgcacc tgcgctcgct gcgcgccgcg gccgacgaac tgccggcgcc 95520

-continued gctgcgcggc ctcgtgcggg cgcccgcccg caaggccgcc gcccaggccg ccgggaccgg 95580
cacgcccacg gtggccgggg aactggccgg ccggccgccc gcgcggcgcg aggcgttcct 95640
cgtggacctg gtgcgcgacg agaccgcgct cgtcctcggc cacaccggcc gggacgacgt 95700
accggcccac caccggttcc tggaccaggg attcgactcc ctggcggcgc tgaagctgcg 95760
caaccggctc gccgccgcca ccggactgcg gctgccgccg acgctcgtct tcgaccaccc 95820
gaccccgacg gagctggccc gccatctgct ggccgaactc gtcccgccgg cggacgcgga 95880
accgcccgcg ttcgacgacg aggacgccgc cacggccgtc ctggtcctgg aggaactcgg 95940
ccagttggac gaggccatca cacggctgcc cgccgacggg cccgaacgca cgcgtatcgc 96000
gggcctgttg acagacctgc tggccaggtg gggtcgatga ggttgcgcac aacactggcc 96060
acaggccctg gaccgtccta tagcatcacc gtgatcgcta cggcaggccg ggccgaccac 96120 cgcccccggcc gcaccgcgcc acgggggcgg gtacgactga gggcgatcga tacgcgtgag 96180
caggcaggca cgtccgccgc acgcacgcac acaaggggga actgatggag aacgttcagg 96240
cctgggttct gcccgccggg ccgcaggaca ggtccggcgg cccggtgcgc ggcgagctga 96300
ccctcacccg cattccggtc gcctccccgg gcgagcacga ggtactggtc gagtccctcg 96360
tcggctgctg ggaggccaac atggagcacg ccctcgcgcg cagccccgtc gacatcgtcc 96420
ggcagcgcgg cgaggagcag atcgtcatcg gcacctgcgg cgtcgtccgc gtgctcagca 96480
ccggttcggc cgtgcgcgga ctgcgtgagg gccaggaatg cctgtggatc ccgttcggcc 96540
acatcgaccg caacggctac gcggagacca tctgcgccta cgacgcgccg ggttcgcccg 96600
gtctgctggc cgagcgcatg gtcgtccccg ccgaccggct cgtgccgctg ccggccgacg 96660
gacgctaccc gctggagcgc tgggcgccgt tcgcccggta cttcaccgcg tgggacaact 96720
ggcgggtcac cagccggtgc tggcgcagcc aggtcgacga cgcctgggac gagcagccgc 96780
tcgtcctcgg ctggggcggc ggggtcgtct tcgccgaact cgaactggcc cgccgcgagg 96840
gcttccgcac ggcgatggtg tccggccgcg agagccggct gaaggagatc gccgcgtccg 96900
gcgcgatcgc cgtcgaccgc cgtgagttcc gcgacctgga ctacctccgg gccaaggagt 96960
ccaccgaccc cgacgccatg gaccgctacc gcgcctccga ggcccggttc ctggagatcg 97020
tcggcgaact ctccggcggc cacggcgtct cggtcttcct ggacaacctc ggcggcggcc 97080
tgcaccgggc cacgatgaag agcctcgccc gcgagggcgt ggtgtccacc gtcggctgga 97140
agaccggcat gcggctgtgg aacctgcgcg ccaccgagtg catcagccgc cacatccacg 97200
tccacaccca cgcctggcgc caccaggacg ccccccgcat ccgtgacgtc atgcaggaga 97260
ccggctggct gcccgacata gccgacgacc cggtgaccgc gttcgcccgc gtccccgaac 97320
tggccgactc ctaccgccgg gacgacctcg acacctactt cccgctgttc tccggcgcgg 97380
ggaggggctg acccgatgag cccgcgttcc tacgacgtgg cggtcgtcgg catggcctgc 97440
gcgttccccg gtgcaccgga cctcgaccgg tactgggcca acgtggtggc cggtgtcgac 97500
tccgtcaccg aagtaccccc ggaccgctgg ccggccgacc gccactgggg cggcgccgac 97560
gcggcccccg gcgagcagtc gccgtcgaaa tggggcggat tcctgccgcc cctgcccttc 97620
gacgccctcg cccacggcgt cccgcccaac tccctcggcg gcatcgagac cgcccagctg 97680
ctcgccctgc acaccgccga ccgggcactg gccgacgccg ggtaccccga gcggccgttc 97740
gaccgggaga ccacctcggt gatcttcgcc gcggaggcgg gggccgacct cgcctccgcg 97800
tacgcggcgc gctcgatgct cggccagcac ctggagtcgg tgccggagga actggacgcc 97860

-continued

```
cggctgcccc ggctgaccga ggactccttc cccggcaccc tcgccaacgt catcgccggc  97920
cgcatcgcca accggctcga cctcggcggc cccacctaca ccgtcgacgc cgcctgcgcg  97980
tcctcgctgg ccgcgctcga ccaggcctgc aaggaactcc tcgccgaaac aagcgacatg  98040
gtgctgtgcg gcgccgtcga cacccacaac gcactccacg accacctgct gttcggctcc  98100
gcgcgggcac tctcgcccac cggccgctgc cgcgccttcg acgcctccgc cgacggcatc  98160
gtcctcgccg aaggcgtcgc ctgcctcgtg ctgaagcggc tcgcggacgc cgaacgggac  98220
ggcgaccgcg tctacgccgt gatcaaggcg gtcggcgcgg gcagcgacgg ccgcggcctc  98280
ggcctgaccg cgccccgccc cgagggccag cggcgcgccc tggaacgcgc ctacgccctc  98340
gcgggcctgt ccccccgcga ggtcggcctt gtcgaggcgc acggcaccgg cacggtgctc  98400
ggcgaccgca ccgaactgga gacgctcacc gaggtgttcc gcacggccgg cgccggtccc  98460
ggagcatgct cgctcggctc ggtgaagtcc ctcatcggcc acgccaagtg cgcggccggc  98520
atggcgggac tgatcaaggc cgtactcgcc gtgcacaccg gcgtccggcc ccccacccgc  98580
ctcaccgagc ccaacgcggc ctgggacccg gcgaccagcc cattcgcctt cgacaccacg  98640
gcccgcccct gggccgagcc ccgacgcgtc gcaggagtca gcgcgttcgg cttcggcggg  98700
gtcaactacc acgccgtcgt ggccgccccc gccccggacc cgtcgcacga gagcgccccg  98760
aggtccgccg gactgctcct gttccgcggc accgaggacg aggtccaaac cgccctgcgg  98820
gacctggccg gccggctggc cgagggcacc gtacggccgt ccgccctcac cggcgtcacc  98880
ggcgccggcc cggcccgggt cgccctcgtc accgagggcg ccgccacgct gggagaacag  98940
ctcgacctgg ctctgcgcct ggaggaccgc cccgagcgcg gcgtccacgt gggagacggc  99000
gcccggcagc ccgtcgcgct gctcttcccc ggccagggca gccagcggcc cggcatgctg  99060
gccgatctct tcgtcgcctt cccgcgcctg caccggttcc tgcgcgccga accggcactg  99120
accggcgccc tcttcccgcc cgccgccttc ggcggcacac ccccgcgcct ggtcgacacc  99180
cggctcgccc agcccgccct cggtctcgga gcactcgccg ccctggacct cctgcgggcc  99240
tgcggcgtcg aacccgacat gaccgccggc cacagctacg gcgaactgcc cgccctcgcc  99300
gccgccggcg ccctccccga gacggccgta atgccgctca gcggcgcccg ggccgaggcc  99360
atgcacaccg cggcgggcca ggaccccggc gcgatggccg cggtcgccgc gcccgccggc  99420
acggtcgccg aactgctcgc ccggcacggc ctggcggacg acgtcacccc ggccaaccgc  99480
aacgcccccg gccaagtggt gctcgccggc tccgccgccg ggatcgacgc cgccgtcgcc  99540
gtactccggg aggccgggca caccgccaag cggctcccgg tcgcggcggc cttccacagc  99600
ccgcggatgg ccccggccgt cgacgccttc gccggcgcgc tggccggcca cgacctgcgc  99660
gcgccccggc tgccggtctg gtcgggcgcc accgcccggc cgtacccggc ggaccccgag  99720
gcgatacgca cccagctcgc cggcgcactc gcccgcccgg tgcggttcgc cgagcagatc  99780
gaggacatgt acgcggccgg cgtccgcgtc ttcgtggagg ccggcccggg cacggtcctg  99840
acccgcctgg ccggcgaggt gctcgccggc cgcccgcaca ccgccctgtc cgtggaggcc  99900
ccgggccgcc cgggcctcgc ccatctgctc ggcaccctcg ccgcgctcgc cgtacgcggc  99960
acacccgtac ggctggacga gctgaccgtc gcccgcgacg agccggtgtc cgcgcccccc 100020
ggatggaccg tcgacggcca cctggtccgc accgcggacg gcacgcccgt ccccggcgga 100080
ctccagccgg ccggcccgcc cgtgaccctc accggcggcg gcgtgcccga cagccgcgac 100140
gagaccgtca tcgaattcct gcgcggcacc cagcggatcg tggccgcaca gcaggaggtc 100200
atgctccgct acctcggcac gcaacccccg gccccggagc cggcccccgc gcacgaccca 100260
```

ccggaatccg ccgcgaccgc cgcgcccacc gtcctggacc tggtggccgc gcgcaccggc 100320
tacccgccgg ccatgctgga cccggacctg gacctggaag ccgccctcgg cgtcgactcg 100380
ctcaagcgca cggagatcgc ctccgccctg gtccgcggca ctccggccgc ggacgccgtc 100440
ggcgaactcg ccgacctgcg caccatccgg gcgatgaccg actggctcgc cacccgcacc 100500
ggccccgacg gccccggccc cgacggcccc ggccgccaga cggccgtgcc ggagcccgaa 100560
accatgcccg ccggcgcctc ggacaccgtg cgccacgtcg tcgaacccgt gcccgaggaa 100620
ccgcccgccg gtccgctgcc gaccctcacc cgggccgccg tcagcggcgg cggtgccgtc 100680
ggcgacgtgc tggccacgct gctcaaggaa cgcggcaccg aggtcgtcag cgaccccgcc 100740
ggctgcgacg ccctcctgct gctcgatgcc ctcgacggcg gcgactacac cctgcccggc 100800
cggttcaccg acataagggc ggccgtcctg ggcggtttac gcaccctgct gctggccacc 100860
tgccacgacg cgggacccgc cggcagcgga gtgcacggcc tcgcccgcgc cctctcccgc 100920
gaacaccccg gcctcgccgt gaccgccgtc gacctgcccg ccggacagcc ggccgaggag 100980
gcggcgcgca ccctgctcgc cgaactcggc ggcagccggc cgtccgtgac ccacaccgac 101040
ggccgccggg ccgtctggcg cacccggccg gccccgctgc ccgccgccga cgtcaccgcc 101100
ggcgacctcg gcctggaccg cgactccgtg gtgctcctca ccggcggcgc gcgcggcatc 101160
accgcccgcg tcgcccgcgc cctggcgacc ctcaccggct gccacctcga actcgtcggc 101220
cgcagcgaac ccgtcaccgg gacggtcctc accgacgccg atctgcggac ccgcctgatc 101280
gccgagggcg ggcgcgaccc ggccggcatc gaacgcgcgg tgcgtgccca cgccgccggc 101340
cggcaggtcc ggcagtgcct ggacgacctc gccggcccgg ccgcctccgt gcgctaccac 101400
cgcgccgacg tacgcgaccc cgagcggctg ggcgccgtcc tggacgacgt gtacgcccgg 101460
cacggccggc tggacaccgt cgtccacgcg gccggccagg tccgcgaccg gctgctgcgg 101520
gacaagagcc ccgacgagtt cgccgaggtg tacgacacga aggtcgcggg cgcccgggcg 101580
ctggccgccc ggctgcggcc gggcctgcgc cacctggtgc tcttcggcag catcgccggg 101640
gtgaccggca accgcggcca gaccgactac gccgccgcca acgacgccct ggacaccatg 101700
gcccggcagt ggtccggccg ggtcgccgac cgggtcctcg ccctggactg gggcccctgg 101760
gcggccgacg cgggcggcat ggtgaccgcc gaactggaac gggcctacgc ccgcaacggc 101820
atcggcctga tcgacccgga cgacggcgta cgggccttcc tgcgcgaact ggccttcggc 101880
cgcgacccgc aggtgctgct caccgtcggg gaccccgccg ggttcgggag cgcccttgac 101940
tgacatactc ctcgccgccg cggccggccc cggagccctg ggcgccgccc tgcgttcggg 102000
ccggcgcggc ggcgccggac cctgccgggt cgccgtgctc gaccccacgg ccgagcggat 102060
cgcacaggcc ctcgccctga tcgaccgggg cgaaccgtgg cacggcggca acgacatccg 102120
gttcgcgccc cggcccgggc cggccggccg caccgtcctg ctcttccccg ggctcgacgc 102180
ccgtaccggc ccgccacccg acgacgtcct gcgctggctg ggccgccccg ccggaccggc 102240
gaccggcgcc gccaccctcg ccgagcgcac ccacgccacc ctgcggctca accgggtgct 102300
ccacgcggcg ctgctgcggg ccgggatcgt cccggacgcc atggcggggc acagcgcggg 102360
ggagtggagc gccctgttcg cggcgggact cttccccgag acggcgttcg acgagttcgc 102420
ccggaccatg ggcgccgccc cggtccccga cgtggtcttc gccgccgtcg gcctgcccgc 102480
cgaagcggcg gcccggctca ccgagggaga gccgcgggtc gtgctgtccc acgacaacgg 102540
gcccgaccag agcgtgctgt gcggcgacga ggacgccgtc acacgctgcc tggaccggat 102600

-continued

```
cgccgacccc gaggtgccgc gcagagtgct gccgttccgg tcggggttcc actcgccgat 102660
gctcgccccg tacctgccgg gcttctcggc cgtgttcgac cgggtgccgc tcgcccgccc 102720
cgccgtcccc gtctggtccg cgaccaccgt cgccccctac ccggacgacg agaccgagct 102780
gcgcgccctg ctcggccggc acctggtgga acccgtccgg ttccgtgccg tgatcgagcg 102840
gctgtacgag cagggcgccc gcgtcttcgt gcaggccggc tgcggcagcc tcacccgctt 102900
cgtcacggcc accctcgccg gccggcccca cctcacggtc agcgcgggct cggcgacccg 102960
gccccaactc gaccagctgc gctgggccgc cgccgcgctg tggacggcgg gtcacacccc 103020
ggacctggcc gccctcggcc tcaccgggcc cgcggcggac ccggtgccga gcacccgcgc 103080
cgtgaccggc gcgcacccga gaaccggcgc gtacccgcgg acccacccgg tggccggcgc 103140
ctacgaggcc gccgtcgccg cggtgagcgc ctccgtggag agcgtctacc ggacctggaa 103200
ggagcggaca tgagcagccg gcgacacgcg gtcgtgaccg gatcgtcccg cggcatcggc 103260
gcggccgtcg ccgcccggct ggcccgggcg ggctgggcgg tcaccggctg ggaccggaca 103320
cccggcgaca ccaccggcct cgccgactgg cgcgaggtgg acgtctccga cgccgagtcc 103380
gtccaggccg ccgcccgcga ggtgaccgcg accgacctcc tcgtcaacag cgcgggcgtc 103440
ggcgccatcg ccccgtccgc ggagctgaag ccccgcacct gggaacgggt cgtcggcgtc 103500
aacctcagcg gcacgttcta ctgcgcccag gcactgttcc ccgccctgtc cgcgcgccgc 103560
ggactggtgg tgaacctcgc ctccgtcatg gcacaccggg ccgtccccgg ccgcgccgcc 103620
tactgcgcgt ccaaggccgg cgtggtcatg ctcaccgagg cgctcggcgt cgaatgggcg 103680
gagcacggcg tccgcgtggt ggccgtcagc cccgcctacg tccgcacccc cctcgtcgcg 103740
gagggcttcg ccaacggcaa cctggacgag tccgccatcg ccgcccgcac cccgctgggc 103800
cggctcgccg agcccgagga gatcgccgac ctcgtcctgt ccctcaccgg cgacgagttc 103860
gcctatctga ccgccaccac cctgcgcttc gacggcggct ggaccgccga cggcgtgttc 103920
ccccgctgaa ccggcccgga cctcgctgaa ccggcccgga ccccgctgaa caggcccacg 103980
gacaaggaga accagacccg atgcccgtca cggacttcgg cgtcctcgcg ctcgcccacg 104040
ccctcggcga tccgcgcgac gtcgccgcca ccgcagccga ccacgtcgac gaccccgacc 104100
gcgtcctgct ctggggctac cgcggctacc accgcgcccc gcagggcacc acctccaccg 104160
cgctcgccgc ccgcgccgcc gagaaggccc tcgccaaggc gggcgtcgac ccccgcgacc 104220
tcgacctcgt cgtggtcgcc gacagcagcg tccccgagta cctgctgtgg gacacctccg 104280
ccgtcgtcgc ccgcgcgatc ggcgccggca cggcgccgac cctgctgctc acccagggct 104340
gcgcgtccgc ggtcaccgcc ttccagcaga tcgccggcat cttcgcgacc cgccccgacg 104400
ccgagacggt cctgctggtc gccgtcaacc aggtcagcga ggcgcacacc aaccgcatgc 104460
gcttcaacac cctgctcggc agcgacggcg ccgcggcggc cgtgctgcgc cgaggtcacg 104520
accggctccg ctggctggcc accgagcagc tcaccgaccc cacgtacgcc gacttctacc 104580
gggtcgagta cggtggcgcc gccgtcccgc acgcccccga gggcgccggc aacctggacg 104640
tcgacccgct gtccctggtg taccggcact tccgccggga gcccgagcac ctggcgaagt 104700
tcgtccgcac cctcaacagc cgcgtccgca ccgtgttcga ggacgcgtgc gacggggccg 104760
gagtcgaccc cggccaggtg aagcggttcc tgttcctcaa cgacaaccag gactccctcg 104820
ccgacgtcgc caaggccgtc ggcgtgcccc tggaccgcac caacgccgaa ctggccaagg 104880
acctcggtca ctgcggcggc gccgaccagc tgatctgcct ggacaccctg ctcgaacgcg 104940
gtgagctcgc cgagggcgac gtggtcgcgc tcgcgggcct gtccatcggc atgcactggt 105000
```

actgcaccct gctcaccgtc tgacccggca ccctcaccga gccctcaccg acagcccgcg 105060
acaccgagag aaacagagag aagaacgacc atggctgagc tgaccatcca ggacctgatc 105120
gacatcttca accgcagcat cggcgaccag gacccggtcg agcccgaggg cgacccgtcg 105180
gacgtcacgt tcgccgccct cggcttcgac tcgctcacca cgctgaacgc cgtacgccgg 105240
atcgagcgca agcacggcgt cgaactcggc gagaacgtga tcagcgaggc ccgtacgccg 105300
cgccagctgc tcgaccgcgt caacgccgcg ctcgccgcgg cctgaagcac gaaaagagac 105360
acgacatgtg cggaatcacc ggatgggtgg cctacggcga cgacctcgcg cggcaccggt 105420
ccgtcgtcca ggcgatgacc gacaccatga tctgccgcgg cccggacgcc gagggcgtct 105480
ggatcgaggg acccgtcgcg ctcggccacc gccggctgtc catcatcgac ccggcgggcg 105540
gcgctcagcc catggtcgcc acacgcgacg gccggaccct ggcggccctg accttctgcg 105600
gagagatcta caacttccgg gagctgcggg ccgaactggc cgccctcggg cacacgttcc 105660
gcaccgacag cgacaccgag gtcgtcctca acgcctacct ccagtggggc gccgacttcg 105720
ccgcccggct caacggcatg ttcgccatcg gcctgtggga cgcgaccacc cgcgaactgc 105780
tgctcgtccg cgacccgatc ggggtcaagc cgctctacta cgcccgcacc tccgacggcg 105840
tcgtgttcgg ctcggaaccg aaggccgtcc tggcccaccg cggcgtgccg cgccgcgtcg 105900
acgcccaggg cctcgccgag atcctggaca tggtccgcac cccggaggtc acgccgttca 105960
ccgacctgtc cgaggtccgc cccggacagg tggtgcgggt gaccgagggc ggcctgaccc 106020
ggacccggta ctggcagctc accgctcgcg agcacaccga cgacctggac accacgatcg 106080
ctaccgtccg ggagctgctg gaggacatcg tctcccgcca gctcatcgcg gacgtcccgg 106140
tcgccaccct gctctccggc ggcctcgact cctcggccat caccgcgctg gcccagcgca 106200
cgctgaccgc cgagggacgc ggcccggtcc gctcgtactc cgtggacttc cagggcgcgg 106260
ccgacgggtt cgagccggac gcggtccgcg gcaccgccga cgcgccgtac gtgcgggact 106320
gcgccgccca tgtgggcgcc gaccacagcg aggtcctgct cgacagcacc gagctggccg 106380
acccggcggt ccgggcggcg atcctgggcg ccaccgacct cccgccggcg tactggggcg 106440
acctgtggcc gtcgctctac ctgctgtgcc gcgagatccg caagcgggcg accgtagtgc 106500
tgtccggcga gtccgccgac gagctgttcg gcggctaccg ctggtaccag cgccccgagg 106560
cggtcgacgc gccgaccttc ccctggctca cccccggctc ggcgcgcatc ttcggcggca 106620
gctcgctgat cgaccagggc ctgctggaga agctggacct ggagggctac cgccgggacc 106680
gctacgccga ggccctggcc gaagtgcccg tgctggccgg ggagtccgcg gtcgaccggc 106740
gcatgcgcga ggtcacctac ctcaacatca cccggttcat gcaggccgtg ctggaccgca 106800
aggaccgcat gagcatggcc gtcggcctgg aggtccgggt gccgttctgc gaccaccgcc 106860
tgatggacta cgtgttcaac gtgccgtggg cgatgaagtc gttcgacggc agggagaaga 106920
gcctgctgcg cgccgccgtc cgcgacgtgc tgccgaactc ggtcctggag cggaccaaga 106980
ccccgttccc cgccacccag gacacccggt acgagcaggc gctgcgcgcc gagctgcgcg 107040
aggtgctggc tgacccggac gcgccggtgc ggccgttgct caacaccgcc cgggtcaacc 107100
gcgtcctcgg ccgtgagctg gacgacttca gcctgccgca cgaccggggc ggcatcgaga 107160
tggcgctgtg gctcaaccgg tggctcgcct cctacgaggt caccgtgacc gtctgagccc 107220
ctggagcgac gcccgcacgg gccgggcgtc gctccgctcc gacgcacggt ccgcgtcaca 107280
tcgccggccg aaacacctcc cggcctcaac cacgctccga acaagtccat ttcgcacaca 107340
gcatgttcca gcaaggggga tttacatgcc cgaccggtcc agcgcagagc accaattgtg 107400
gctgcgcggt ttccaccagc cgaagccggg cgcgccgcgg ctgatctgcc tgccgcacgc 107460
gggaggctcg gcgagcttct acttcccggt ctcccaggcg ctgtcgcccg cggtggacgt 107520
gctggcggtg cagtaccccg gccgccagga ccgccggcag gagtccccgg cagcctccgt 107580
ccaggaactc gcggagggcg tgttccgcgc gttggacgat caggaggaca cgcccctggc 107640
cctgttcggc cacagcatgg gcgccatggt cggcttcgag ctggcccggc tcctggaggc 107700
cgccgggcgg ccacccgcgg tgctcttcat ctccggccgc cgaggcccgt ccatcgtgtg 107760
gacggaaacc gtccacacga tggacgacga acggctgatc gcggaggtcg ccaagctcga 107820
aggcaccgac gcggccctgc tccaggacga ggaggtactg cggatgatcc tgcccgcgct 107880
gcgggccgac taccgtgcgg tggagaccta ccagcgcacc cccggacccc ggctgagttg 107940
ccccttcgtc gtgatgacgg gcgacgccga cccccgggtc acccccgacg aggcgcggac 108000
ctgggcagag gagacggacg gggccttcga actcgaggtg taccccggcg cgcacttcta 108060
cctggtggcg cagcagcagg ccgtgctggc ccggatcgag gccacgatgc ggcggctcgg 108120
ttccaccacc ggagcggtgg tctgagcctg tgaacgagat actcagcgcc gtcctgtcgg 108180
ccgaggcgac cgccgcggac ttcgcggccc tgccgctccc cgagtcctat cgcgccatca 108240
ccgtgcacaa ggacgagacg gagatgttca ccggtgtcgg cccggccgac aaggacccgc 108300
gcaaatcact gcatctggac gaggtgccgg tgcccgaact gggcccgggc gaagccctgg 108360
tggcggtgat ggcctcctcg gtcaactaca actccgtgtg gtcctccatc ttcgagccgc 108420
tgccgacctt cgctttcctg gagcgctacg gccggcgcgg cgaactggcg aagcggcacg 108480
acctgccgta ccacgtgatc ggctccgacc tggctggcgt ggtgctgcgg accggccccg 108540
gggtgcaggc atggaagccc ggtgacgagg tcgtggcgca ctgtctgagc gtggagctgg 108600
agtcgagcga cggccacgac gacaccatga tggaccccga gcagcgcatc tggggcttcg 108660
agaccaactt cggcggtctg gcggagctcg cgttggtgaa gtccaaccag ctgatgccga 108720
aaccccggca cttgacctgg gaggaggccg ccgcgccggg actcgtcaac tccaccgcct 108780
accgacaact ggtgtcgcgc aacggcgcgc agatgaagca gggcgacaac gtgctgatct 108840
ggggcgcgag cggcggcctg ggttcgtacg ccacacagct ggcgctggca ggcggtgcca 108900
acccggtctg tgtggtgtcc acgccgcaga aggcggcgat ctgccgctcc atgggcgctg 108960
aggcggtcat cgaccgtgat gccgaggact accggttctg gcgggacggg aacacccagg 109020
acccccggga atggaagcgt ttcggcaagc gcatccgcga gctgaccggc ggtgaggacg 109080
tggacatcgt cttcgagcac ccgggccgcg agaccttcgg cgcgtccgtg ttcgttgcgc 109140
ggaagggcgg cacgatcgtc acgtgcgcat ccacctcggg ctatgagcat cagtacgaca 109200
atcggtatct gtggatgtcg ctgaagagga tcatcggttc ccacttcgcg aactaccgtg 109260
aggcctggga ggccaaccgg ctcgtcgcga agggcaggat ccaccccacg ctctcgaagg 109320
tctacccctt ggaggagacc ggacaggccg ccttcgacgt gtacggcaac gtgcaccacg 109380
gcaaggtggg ggtcctgggc ctggcgccca cggaaggcct gggtgtgcgg gacgaggaga 109440
tgcgcgccag gcacgtagga gccatcaacc gcttccggcc gtccgcggag ccgcagacag 109500
agccggtctg agggctcgac ccgcaaaaga ccgcacacga tgcccacttc tgcaacagag 109560
cagctttgaa aggcaggacg tcatgagcaa cccgttcgac aaggaagacg gcagcttctt 109620
cgtggtggtg aacatggagg ggcagcactc cctctggccg gccttcgccg agatccctgc 109680
gggctggtcg atcgtccacg gcgagaccga caaggcggcc tgcctggagt acgtcgccgc 109740
tcactggacc gacatgaggc ctcgttcgct gaccgatgcc gcgccgaccc cagagtagaa 109800
ctccccttcg gaaacagtcc gttgacaaca aagtgttcaa atgccagggt tgccgcatgt 109860
catcgattcc gccgcagcca gccgatgcct tcaccgcccc gagcgcgcac gaagccagag 109920
tgcagcgtgc gtacacctct cttttccgca tcgccgaacg gcacgcggcc accgacgggc 109980
agcgtcgtcg gcaggcccag tctcacatga tcagccccta tgaggcggtg aggcttgtgt 110040
cgttcctcct cagcggggcg gcgcagctcg agggagagga accggaggtg gatcgcgcgg 110100
acatcacggc cgcgttgagt cttctcccgc tcgctcgtgc cgagatggac gaagtggagg 110160
ccggaattct caagatggcg catggtcgtg ggatgacgtg gtcggagatc gcgttcggcc 110220
ttggcctcgc aaccccgcag gcggcgaggc agcgccatga gcgcctggcc agccgcatgg 110280
aatccggcgc cgaaaaaaag gccgacggat aggagctcgc catcggcatg gcggcagccg 110340
accgccgcca tgccgatgcg tcatatccgt cagccgagaa tcctggcgaa tccgatgtgg 110400
acgcaccggg ccgacggccg cgagggcgtg cccgggctcc gaacggggcg tcggcgccgg 110460
ggaagtcgtc ggccttgctc gacgtgctca cagccgcgtg aacccgacgg ccacgacgcc 110520
gatgcccacc aggaggcaga ggagccacaa ggcgacctgg gagcccgtgc cgctggcata 110580
gcggcgggcg gtcgcgcgcc cgagggcgcc tatcgcgcat ccgaagacga tgaggaccac 110640
acccacggcc acggcgtcat cccttcctct tcttgttcca tatcccgtac gcgaacatgg 110700
cgacgatccc caccaggatc agaatcgcga cgacggaccc cgcggtgccg gccgggatcc 110760
agcttccacg accgtcagcg gccagcagca tcgctgcact ccttactcag tacgagcact 110820
gggtgtgggt tggcccgcga gcccccaagg gcaccccggg ccggccgatt gtctcaggat 110880
caggattcgg acgccgcgtc ctccacctga ctacccgcga aatcggcgaa gatgccgccc 110940
ccggcaccgg ccaccgcgcg gtggagccac tgtccgcagc ccctgacccg ctcagccact 111000
caccagtgcc tgggcgtgtc gctcagcgac ggacttgggc gccaaccggc cggtggggga 111060
ggtgggctac tcggcccgcg gcgcgggccg tacgggcgtc ttgcacccga tgactcgctc 111120
cgatagccaa ccccgcccca agagcagcgg cccgctccgg gccgcgtcca cgtcgtccag 111180
gacggcgacg ctcactccgg ctcaccgcca cggcggccgg ggagatctga ctacgtccgg 111240
acacaccacg ggctccgagg acgggcagcg gtgctcctcc ttcgtcagat gtacggctcc 111300
gcagcggtgg cacctctgga ggtcatcgaa gccggtcgcg caggcgaagc agaagtccac 111360
cggcggttca gccgcttccg ggtccgttcc ggggtgcagc tggacagcga gccgtcctcc 111420
aaggccgtac gggtggccgc tccggggtcg gtgaacacca ggctccagtg ctccatgagc 111480
agccgggctt tgggaaggac ctcggccccg gcggccaggt gcagcaccgc gtacttcaga 111540
tcccgggcgc tgcccgcccc tttctcgcgc tgcagaagct cgacgacgct gacaaggtag 111600
tcgagaccgt tggcgatggg cgggaagtgc gggtctccgg cgaaccgggt ttcagcctcc 111660
gaggctctgg cgaatgccgg ccagttgggg gttctgccag gccgggaggt agtcggggtg 111720
gtctcgccac tgctcgcctg caccggtcag caggtgccaa gcccgtgtca cgctgtcggt 111780
gtcgccttgg gcgaggaggt acgagacgga ctcggcggtg cccgcgaggc cgtacttgct 111840
ggcattggag acgcggaagt accgggcctg agcctcctcc tccagggtgt cgtcggcgag 111900
cgcggccgcg tgctcctcgt cgatgcgccg gctgatgaag tcgtacagct ctcggacatc 111960
cgcagcggtg ggcacgttcg tggtcatggg gtgcgctcct cctctgaggg cggctcaggc 112020
cggcagcctc atgtaaggga atttatacga gggtgatgaa ggcttggctg cgtaggttag 112080
accgaagagc acttgtcggt gagagctggg aacagcaggc tgccgccggg cctccgaatg 112140
ttgacgagaa gtagcagcgg tcccatgcca cggaaacgtg ctgtcgtcaa cgtgttgacg 112200
tccgtatcct ttggcgggtg agtctgatcg aggtgggtcc agggcaggtc gagctcgtcg 112260
tgcgggggcc gggggtgctg gcgacttctg tccggttgtt cgactggtcg cgtgcggatg 112320
agtacgagac cgtcttcgcg gtggaggcca ttgctgatgg tgtgcgtgca cggctcgaga 112380
acgtgaccgt caccgtctgg gatgacatga gcgcgttctt cgacggcctt gcacgtgatt 112440
tccgtggttg ggatggggag cgggtttgga tcaacaacca cctggtcgtg acggcgactt 112500
tcggctcggg tggtcatgtg tatgtggact ggacgcttca gtccggcttt tttcccggtg 112560
actggaagtg cacggtgacg accgtgatcg aagccggtga agggatgacg gctgtagctg 112620
cggacctgcg ggaatttctg cgccaggagt aggtccccac gtcatccggc aggcacgccc 112680
gtccggtcca gccgacggct tactggtcag cgcgggcgcg ggtggtggtg agacggtagg 112740
agtcgtgccg gtatcgatga tgttgccgcc ccggtccgag cggtcacgcg gacccaagcc 112800
ggtccccgac cggctgtgct tgcagggcat cctgttcgtg ctccacaccg ggatcccgtg 112860
gcagcagctt ccgctggagc tgggtttcgg ctccgacggc atcccgccgg tcgccggccg 112920
agtcggccac ccccgcaagc gccccgacgc gctacttggc gacaagggct acgacagcaa 112980
cgcggaccgc cgagagttgc gtcggcgcgg gatcctgccg gtcatctcct cccgcaaggt 113040
gcagcccgac atccatggcc ccgacatcca tggcctgggc aggatccgct acgtggtgga 113100
gcagatcttc gtcctgctcc accagttcat gcgcctcgct gttcggtggg aacgccgttt 113160
ggctctgcac gacgccttcg tctcggtcgg gtgctcgctc atctgctgga ggaggctcaa 113220
gaggccgctc acctcgcagg cccggcgctc aagcccgtgg cccgtcgggc attctcacgc 113280
cgccaccggg cagtgatctg atgaagtagc tgccccgcag accgatgacc cagccgaagg 113340
catcggagga aacgggcacg tccagacgcc atccgttggc caagcggact cgcaggctgc 113400
ctgaatcggc tgcgtgaacc tcggcgatca cctgatcgag cagctgcggc agccggtcaa 113460
ggttggtccg tgtggatgcg tggacggaca cggcttcgtg gtccgtcgtc agttcggcgg 113520
gactgtgaac ctcgatccgg ttctcaccgg tgtgaagccg caactcgttg ccgatgatca 113580
gctctccgat gccgctccca cgcatcgaga ggatgtccca cccgtcgtcc acacggttgg 113640
ttccgttgtc catgccgcaa gactacggac cccggctacc acgctgccgc acaagatcgt 113700
gtgacgaact ctaacgagct ggtgtgtgac tccggttgaa gggtgatcgc gcgaaggtgg 113760
gttgatccag tccgtgttga tcatggtcgt cgaccgggat atcctcgcgc atcagctgtt 113820
caccggcgtc tcccggcagc atctggcttg ctcggtcgag gagttggccg aaccgtggca 113880
ggcgatcaca ccgcccagaa agccgaacaa gctcgctttg ccgcaggtac acgcagccag 113940
agaagaagcc cggcaccgac actcatcgaa gcgcatcacc gtcgagcacg cgctcaccga 114000
ccacaaacgc tcgaagcagc tgacccgctg gacgcaccgg tgagagggcc ggcccgacac 114060
ctaccgggcc atcgccggcc tcgtctccga ccgcaccgcc aacgcgtgac catgaccccg 114120
atcaggcgaa cacgcctcac ggtcaagagc cggccgctcg ggcaggtgag gccggtctcc 114180
tcctgcgtct ctcgtgtcgc ggcggtgcgg ggggactcgt ggtggtcgag gttcccgccg 114240
gggaactgcc agatctgcct gccagtgcgg cggccgcgca cagcgcgtcg ggcacggtga 114300
gcgtgtaccc ggcctggccg gcggtccgga tcagaacgcc gctgggatcg ctgccgccgc 114360
tgtgagcgtg cggacggacg tcatcggggg agtgaccgga gcgaccgtct ggctcttgtc 114420
gctggtgagg catttctgga aggaatccgg ttgcctcgct gttctcggca gtgccaggtg 114480
gccccgccgt cgctgacgac cgcggcttca cggcccgtcc tgcgggtgga gtcggcggcg 114540
acctgcaaag ccgtcgcgca gtcggtgccc tgcgcggccg acaccgccag gccggtctcg 114600
ccgcggtccg tgccgcggtg cccggcactt cgcacgcgga cacggctgca gggccggaga 114660
cgaccgtcgc cgatacggcc atcaggcctg ccagccacta cccaacttcc ccgagtacta 114720
cctgagccga ggtcgcatcg gcgtacgcac aggcacgctg tccgcccctc agtggacggc 114780
cctcaacgcc ctgctcgccg cagccctgtg ctcgtcgccg gactcggggt acgacaagat 114840
ccaacagcac ctcgacgcgg acgatcacct tcgccggcac ggcggtggcg acgcgtacgg 114900
gcgcggcaac ttcttcgtcg ccttcctcag cacacccgcc gacaccggga tctgggagct 114960
gcagttcggc ggccatcacc tcgcggtcgc ccacacctac gccgacggac gcctgatcgg 115020
tgccacaccc gcgttccgcg gcatcgagcc gttccggtcc ttcacccggc acggcatccc 115080
gaccagcccg aacgagccga acagcaggcc ctctccgccc tgctccagtc cctcgacgcc 115140
tcgcaggcgg cggccggact cagggagcgg cacgacgacc ttctgctcgg cccgcaccgg 115200
gactggaagt tcccccggaa gtccgaaggc atcgccgccc acgatctgac agccgcgcaa 115260
cgtgacctgc tcgtcgcggc catcgcccgt tacgtcggcg acttgcccga agcggacgcc 115320
cgcaggtttc tcgaccgcta ccgggccgaa cttcccgaca cccacgtcgg cttcaccgga 115380
tcgacactgc tgaccgaccc cggtgactac gtccgcatcg acggtccgtc ggtgtggatc 115440
gagttctcca tgcacgacgg catcgtcctg gccgatccgc acccccacgc cgtctggcgc 115500
gacaagcaca ccgactacgg cggactcaag ccctgacgcg gtcccgccgc cccgtatccg 115560
gggcccgacc acgcccccttc cccagctcac accgcgcggc ggtcgcgcgc ggggctcacc 115620
gctggacggc gcgcagtccg tccaggagca gccgcagtcc gaactcgaag tgtgccgcga 115680
agtccgtgct ggtgagcact ggcagggtgg cggcgaggtg tggatatgtc cccgccgcca 115740
cggcctcgtg cagggctccc gcatcggtgg gctccccgtc ccccggcccg agggcggcct 115800
gttcctccag ggtgtggccg acggtgaagt tggtcaccga gtagagcgcc cgcgccgctt 115860
cgccgtcacc gaaacccgcc gcacgcagca caccgacgag gctgtcggcg aagcccaggg 115920
tgttcggacc ggtcgagtgc gtaccggtga agacgcgtgc gccgtcgcga tgggcgagca 115980
gggccgtacg cagcgcgcgg gcgagccgcg ccgctctctc gctccagtcg ccgtcccccg 116040
ccggcccggc ggcgtcggcg acgccgccga ccatccgctc cgccatcgcg gtgagcaggt 116100
cctgtttggt cgcgaagtag cggtacagcg caccggcctg gacgcccaat gcgtcggcga 116160
gccggcgcat ggtcaacgcg tcgagaccgg actcgttcag caggtcgagg gcggtctgga 116220
cggtgcggac ctggctgatc cgggcgggcc ggcctctggt cgggcttgac ggggtgctca 116280
tggacctcac tatactgaac accgttcacg tgaacgctgt tcactaaatg tgggaggaca 116340
tctccgatga acaccgatgt gatcgtcata ggcgccggcc cgaccgggct gatgctcgcc 116400
tgcgagctgg cactggcggg cgtacggacc cgcgtcctgg agcgccgcgc cgaaccgcag 116460
cgcaattcgc gggcgttgag cctgcacccg cgcagcgtgg aactgatgga ccagcgagga 116520
ctgctcgacc ggttcctccc gctcggccgg accgtgccgg gctggcactt cgcagggctg 116580
cgcacccggc tggacttcgg cgccctcgac tcccggcacg gctacaccct cttcctggct 116640
caggagcgca ccgaggcgat cctggaggag cgggcacacg agctgggggc ggagatcagc 116700
cggggatacg agaccctcgg tgtgagccag gacggcggcg gggtcgaggt gcaggtgcgc 116760
gtccccggcg gcggcaccga gaccgtccgc ggcctctacg cggtcgggtg cgacggaggg 116820
cgcagcgtcg tgcggcaggc cgcagggatc gacttccccg gcaccgacga gaccctgacc 116880
ggggtgctcg gggacttcgc ggtcgtcgat ccgcggcccg gcgccctcga tgcggcacga 116940
gcccgcggcg tgatcatcgc gccgctggag ggagggctca cccggttcgt ctacctggat 117000
cccgagcgga tacgggtgcc gtcccgggag cccgtgaccc tggaggagtt ccgtacgtcg 117060
ctcacccgga tcaccggctc cgactgcggg atcgccgagc cccgttggct gtcgcgtttc 117120
ggcaatgcca ctcggctcgc ggagagttac cgtgcgggac gcgtcctgct ggcgggcgac 117180
gccgcccaca tccacttccc cgcggcgggc caggggctca acaccgggct ccaggacgcc 117240
atgaacctgg ggtggaagct ggtcgccgcg gtgggcggct gggcgccgcc cgggctgctg 117300
gacagctacg acggggaacg caggccggtc ggccggtcgg tgaccgagaa caccgaggtg 117360
cagactctgc tggcggagct gacgctggtc gcgcagtacc agcgtccggc cgcggccctg 117420
cgcgagctcc tcgaccaact gctgggcatg acggaggtca accgccggct cgccgaccag 117480
gtctccgcgc tcggcaccca ctatccgccg gcggactcgg acgctgatcc gctggtgggg 117540
cggcgtatgc ccgacatcgg cctgaccgcc gccggttcgg cggcgacacg ggtgtacgaa 117600
ctgctcaccc ggggccgctt cgtcctgctc gccctggccg gagacccggc ctctcgcgag 117660
gccgtcgacg cgggctgggg ctcgcgggtc tcggccgtca ccgtggacaa gtgcgacgag 117720
cattcggacc tcgacggggt ggccgaggtt ctcgtacgcc ccgacggcca cgtcgcgtgg 117780
gccacccgta ccgccgacgc cgacccgcgc ggcgacgagc gggtccaggc gctgaccgct 117840
tgggcgggca cgccctcacc gaggagctga tcatgcccgt gaaccgcgtc agtccaccgt 117900
ccgtgcacaa cccgtccgac cagatcagcc aggtcgtcac cgtcgacgga acccggctcg 117960
cgcatctctc cgggcaggtc gcctgggatg cggaaggatg gcccgtgggg ctcggcgacc 118020
acgaggccca ggcggcacag atcgcacgca acctcgacgc cgcactcgcc gcggtcggcg 118080
ccacccgcga cgacatcatc gaagagaccg tctacgtagt cgactacacc ccgaaactgt 118140
tatccgcgat cttcgggccg ctacgggccg gtgtctcagc agcacctgcg agcacgctgg 118200
tgggcgtgcc cgcgctcttc gcaccggaat acctcctgga ggtccaggtg gtcgccgcgc 118260
tccccgtacc agggggccat gaccgcgcca caccgaccga cgacaccgcg gcgaacgagc 118320
gtgtcagggc acgggagccc cgcaggatcc gtgaaacacc ccccacgggc ga 118372

<210> SEQ ID NO 2
<211> LENGTH: 146
<212> TYPE: PRT
<213> ORGANISM: Streptomyces flaveolus (Streptomyces sp.(DSM 9954))

<400> SEQUENCE: 2

```
Met Trp Arg Pro Ala Pro Pro Ser Arg Met Cys Ser Arg Ser Ala Ser
1               5                   10                  15

Phe Val Ala Ile Arg Thr Phe Ser Arg Ser Ser Ala Ser Ser Thr Ala
            20                  25                  30

Arg Asp Val Arg Tyr Thr Ala Ala Ala Ser Ser Val Val Arg Leu Arg
        35                  40                  45

Glu Ser Glu Cys Arg Arg Gly Asn Asp Thr Leu Ser Ser Ala Pro Tyr
    50                  55                  60

Arg Asp His Ser Ala Pro Pro Arg His Pro Tyr Arg Ser Ala Ala Gln
65                  70                  75                  80

Pro Val Gln Leu His Gln Ala Ala Arg Arg Ala Glu Asn Pro Ala Pro
                85                  90                  95

Pro Ala Ala Arg Arg Ala Ala Ser Arg Thr Arg Arg Pro Lys Thr Pro
```

-continued

```
            100                 105                 110

Ile Arg Arg Leu Pro His Arg Ser His Arg Thr Gly Arg Thr Ala Arg
        115                 120                 125

Pro Gln Gln Gln Arg Leu Leu Ser Pro Val Arg Arg Arg Ala Arg Gln
    130                 135                 140

Ser Pro
145


<210> SEQ ID NO 3
<211> LENGTH: 155
<212> TYPE: PRT
<213> ORGANISM: Streptomyces flaveolus (Streptomyces sp.(DSM 9954))

<400> SEQUENCE: 3

Met Arg Gly Tyr Phe Met Ser Lys Arg Leu Val Val Ser Ser Leu Ala
1               5                   10                  15

Val Ala Ala Ala Val Val Ala Gly Thr Val Val Phe Val Ser Ser Ala
            20                  25                  30

Asp Ala Ala Val Pro Ala Lys Pro Glu Ile Ser Lys Ala Thr Ala His
        35                  40                  45

Tyr Thr Ser Thr Ala Gly Gly Ser Ala Ser Leu Thr Phe Ser Ala Thr
    50                  55                  60

Val Ala Asp Asn Ser Gly Ile Lys Ser Leu Arg Val Leu Ala Trp Pro
65                  70                  75                  80

Ala Ser Ser Gly Leu Ala Pro Thr Ala Gly Glu Met Arg Asp Val Glu
                85                  90                  95

Glu Ala Thr Cys Lys Ala Thr Ser Ala Thr Ala Ser Val Cys Thr Tyr
            100                 105                 110

Thr Val Lys Ser Ser Ala Lys Glu Ala Ala Ala Leu Pro Lys Gly Val
        115                 120                 125

Trp His Val Ser Val Leu Ala Thr Ala Lys Asp His Asp Thr Thr Phe
    130                 135                 140

Ala Pro Gln Gly Ala Thr Phe Thr Val Lys His
145                 150                 155


<210> SEQ ID NO 4
<211> LENGTH: 276
<212> TYPE: PRT
<213> ORGANISM: Streptomyces flaveolus (Streptomyces sp.(DSM 9954))

<400> SEQUENCE: 4

Val Glu Ile Gly Ser Gly Ala Pro Glu Leu Thr Ala Ser Ser Val Tyr
1               5                   10                  15

Gln Gln Arg Arg Asp Gln Ile Ala Ala Ser Ala Ala Ala Tyr Val Pro
            20                  25                  30

Gly Glu Pro Ile Pro Glu Val Glu Tyr Thr Asp Ala Glu His Ala Leu
        35                  40                  45

Trp Arg Leu Val Ser Lys Arg Leu Ala Asp Arg His Arg His Met Ala
    50                  55                  60

Ala Pro Glu Phe Val Glu Ala Ala Glu Arg Leu Glu Val Gly Gly Asp
65                  70                  75                  80

Gly Val Pro Gln Leu Arg Glu Val Ser Asp Arg Leu Asp Gln Leu Thr
                85                  90                  95

Gly Phe Arg Leu Arg Pro Ala Ser Gly Val Val Pro Phe Ala Leu Phe
            100                 105                 110

Cys Gly Ser Leu Ala Asp Gly Tyr Phe His Ser Thr Gln Tyr Leu Arg
```

```
        115                 120                 125

Asp Ser Ala Thr Pro Phe Tyr Ser Thr Glu Pro Asp Ile Leu His Glu
    130                 135                 140

Val Ile Gly His Gly Ser Ala Leu Ala Asp Asp Arg Phe Ala Asn Leu
145                 150                 155                 160

Tyr Arg Leu Ala Gly Glu Ala Val Arg Arg Val Glu Ser Glu Asp Ala
                165                 170                 175

Val Gln Phe Val Ala Lys Thr Phe Trp Phe Thr Leu Glu Cys Gly Leu
            180                 185                 190

Leu Asp Ala Ala Asp Gly Pro Arg Ala Tyr Gly Ala Ser Val Val Ser
        195                 200                 205

Ser Tyr Gly Glu Leu Glu His Phe Arg Ser Ala Glu Ile Arg Pro Leu
    210                 215                 220

Asp Ile Ala Asp Met Ala His Val Asp Tyr Asp Ile Thr Gln Tyr Gln
225                 230                 235                 240

Thr Thr Phe Tyr Ser Ala Arg Ser Leu Thr His Leu Glu Asp Val Ala
                245                 250                 255

Gly Glu Phe Trp Ala Ser Cys Asp Asp Thr Ser Ile Glu Lys Leu Met
            260                 265                 270

Ala Val Asp Ile
        275


<210> SEQ ID NO 5
<211> LENGTH: 446
<212> TYPE: PRT
<213> ORGANISM: Streptomyces flaveolus (Streptomyces sp.(DSM 9954))

<400> SEQUENCE: 5

Met Thr Arg Leu Ala Glu Gln Ser Ser Thr Ala Gln Gln Ser Pro Glu
1               5                   10                  15

Ser Glu Val Leu Asp Val Thr Gly Ile Gly Phe Gly Ala Ala Asn Leu
            20                  25                  30

Ala Leu Ala Val Ala Leu His Glu Ser Glu Ala Ala Gly Lys Ala Leu
        35                  40                  45

Phe Leu Glu Lys Gln Lys Glu Phe Gly Trp His Arg Gly Met Leu Leu
    50                  55                  60

Gly Gly Ser Ser Leu Gln Val Ser Phe Leu Lys Asp Ile Ala Thr Met
65                  70                  75                  80

Arg Asn Pro Thr Ser Asp Phe Gly Phe Leu Ser Tyr Leu Gln Glu Lys
                85                  90                  95

Asp Arg Leu Val Asp Phe Ile Asn Gln His Thr Leu Leu Pro Ser Arg
            100                 105                 110

Ile Glu Tyr His Asp Tyr Leu Gln Trp Ala Ala Asp Arg Leu Asn His
        115                 120                 125

Leu Val Glu Tyr Gly Val Glu Ala Thr Gly Val Arg Pro Val Thr Glu
    130                 135                 140

Ala Gly Glu Val Val Ala Leu Asp Val Leu Ala Gly Asp Arg Val Val
145                 150                 155                 160

Ala Arg Thr Arg Asn Leu Val Leu Ala Ser Gly Leu Arg Pro Arg Leu
                165                 170                 175

Pro Glu Gly Ala Glu Thr Gly Glu Arg Val Trp His Ser Ser Gln Leu
            180                 185                 190

Leu His Arg Leu Pro Ala Phe Asp Glu Arg Pro Pro Arg Arg Ala Val
        195                 200                 205
```

```
Val Val Gly Ala Gly Gln Ser Ala Ala Glu Val Ala Ala His Leu Met
    210                 215                 220

Asp Arg Tyr Pro Gln Ala Glu Val Cys Ala Val Phe Ala Arg Tyr Gly
225                 230                 235                 240

Tyr Ser Val Ala Asp Ser Ser Pro Phe Ala Asn Arg Val Phe Asp Pro
                245                 250                 255

Ala Ala Val Asp Asp Phe Tyr Phe Ala Pro Pro Glu Val Lys Gln Ala
            260                 265                 270

Ile Met Arg Tyr His Gly Gly Thr Asn Tyr Ala Val Val Asp Glu Asp
        275                 280                 285

Val Leu Gln Gly Leu Tyr Arg Arg Gln Tyr Glu Gln Lys Val Ser Gly
    290                 295                 300

Ala Pro Arg Leu Arg Val Met Asn Ala Ser Arg Leu Val Ser Val Glu
305                 310                 315                 320

Pro Arg Gln Glu Ser Ala Ala Val Arg Val Glu Phe Leu Pro Thr Gly
                325                 330                 335

Glu His Thr Asp Leu Asp Ala Asp Leu Val Val Tyr Ala Thr Gly Tyr
            340                 345                 350

Asp Ser Thr Asp Pro Ala Glu Leu Leu Gly Gly Val Ser Gly Ala Leu
        355                 360                 365

Arg Arg Asp Glu Ala Gly Glu Leu Leu Ile Gly Arg Asp Tyr Arg Leu
    370                 375                 380

Gly Thr Thr Gly Asp Phe Arg Cys Gly Ile Tyr Val Gln Gly Ala Thr
385                 390                 395                 400

Glu Ala Thr His Gly Ile Ala Ser Thr Leu Leu Ser Met Val Ala Val
                405                 410                 415

Arg Ala Gly Glu Ile Ala Arg Ser Ile Thr Gly Gly Arg Cys Asp Pro
            420                 425                 430

Asp Arg Ser Thr Gly Ser Lys Ala Ala Ala Gly Asn Arg Gly
        435                 440                 445


<210> SEQ ID NO 6
<211> LENGTH: 231
<212> TYPE: PRT
<213> ORGANISM: Streptomyces flaveolus (Streptomyces sp.(DSM 9954))

<400> SEQUENCE: 6

Val Tyr Glu Arg Pro Leu Tyr Arg Glu Asp Cys Asp Gly Val Val Leu
1               5                   10                  15

Ala Phe Leu Arg His Asn Pro Leu Ala Met Val Val Thr Ser His Asp
            20                  25                  30

Asp Val Pro Val Ala Thr His Ala Pro Val Leu Phe Arg His Gly Pro
        35                  40                  45

Asp Gly Ala Asp Ala Glu Ala Val Ala Ala Gly Thr Val Pro Leu Ala
    50                  55                  60

Gly Ser Thr Leu Ile Gly His Met Asn Val Glu Asn Pro Gln Trp Arg
65                  70                  75                  80

Arg Met Arg Ser Gly Asp Arg Ala Leu Ile Val Phe Gln Gly Pro His
                85                  90                  95

Gly Tyr Val Ser Pro Thr Val Tyr Gly Val Thr Pro Ala Ala Pro Thr
            100                 105                 110

Trp Asp Phe Ile Ala Val His Val Asn Gly Thr Val Glu Pro Thr Ala
        115                 120                 125

Asp Pro Ala Ala Val Leu Asp Ile Val Ser Asp Thr Ala Arg Arg Leu
    130                 135                 140
```

```
Glu Ser Gly Phe Gly Arg Gly Trp Asp Gln Glu Ser Ser Leu Asp Tyr
145                 150                 155                 160

Phe Arg Gln Ile Ala Pro Gly Val Gly Ala Phe Thr Leu Arg Val Asp
                165                 170                 175

Ser Val Gln Thr Met Phe Lys Leu Ser Gln Glu Lys Pro Ala Pro Met
            180                 185                 190

Arg Arg Arg Val Val Glu Gln Phe Glu Ala Ser Glu Ser Gly Thr His
        195                 200                 205

Arg Ala Leu Ala Ser Val Met Arg Asp Arg Gly Leu Thr Glu Ala Asp
    210                 215                 220

Glu Glu Arg Glu Thr Ala Gly
225                 230


<210> SEQ ID NO 7
<211> LENGTH: 3609
<212> TYPE: PRT
<213> ORGANISM: Streptomyces flaveolus (Streptomyces sp.(DSM 9954))

<400> SEQUENCE: 7

Met Thr Gln Gly Ser Ser Arg Arg Pro Gly Leu Asp Ser Ala Leu Asn
1               5                   10                  15

Arg Leu Arg Glu Arg Thr Ala Arg Thr Gly Thr Thr Pro Ala Gly Ile
            20                  25                  30

Ser Arg Val Pro Arg Asp Arg Pro Leu Glu Leu Ser Phe Ala Gln Gln
        35                  40                  45

Arg Leu Trp Phe Leu Asp Arg Leu Met Pro Asp Ser Ala Phe Tyr Asn
    50                  55                  60

Phe Gly Thr Ala Val Arg Val Arg Gly Pro Leu Gly Ala Gly Leu Leu
65                  70                  75                  80

Ala Arg Ala Leu Ser Cys Val Val Ala Arg His Glu Thr Leu Arg Thr
                85                  90                  95

Val Phe Ala Asp His Glu Gly Val Ala Gly Ala Val Val Leu Pro Pro
            100                 105                 110

Glu Pro Val Pro Val Pro Val Thr Asp Ala Val Asp Glu Ala Asp Ala
        115                 120                 125

Glu Arg Leu Ala Gly Glu Glu Ala Ala Arg Pro Phe Asp Leu Thr Lys
    130                 135                 140

Gly Pro Leu Leu Arg Ala Arg Leu Leu Arg Leu Ala Asp Asp Asp His
145                 150                 155                 160

Val Leu Leu Leu Thr Val His His Ile Ala Thr Asp Gly Trp Ser His
                165                 170                 175

Gly Leu Leu Trp Ala Glu Leu Thr Ala Ala Tyr Thr Ala Leu Ala Asp
            180                 185                 190

Gly Arg Gln Pro Ala Leu Pro Glu Leu Pro Val Gln Tyr Ala Asp Phe
        195                 200                 205

Ala Ala Trp Gln Arg Arg Thr Leu Ser Pro Ala Val Leu Glu Arg Arg
    210                 215                 220

Leu Ala Tyr Trp Gln Asp Arg Leu Ala Gly Leu Pro Pro Leu Asp Leu
225                 230                 235                 240

Pro Leu Asp Arg Pro Arg Pro Ala Val Ala Ser Ala Glu Gly Gly Val
                245                 250                 255

Val Thr Trp Arg Leu Pro Ala Asp Ala Val Ala Ala Ala Arg Ala Val
            260                 265                 270

Ala Ala Arg Gln Gly Ala Thr Leu His Met Thr Leu Leu Ala Ala Phe
```

-continued

```
        275                 280                 285

Ser Ala Val Leu Gly Arg His Ala Arg Thr Glu Asp Val Ala Val Ala
    290                 295                 300

Gln Pro Val Ala Gly Arg Pro Leu Ala Glu Val Glu Gln Leu Ile Gly
305                 310                 315                 320

Phe Phe Val Asn Thr Val Val Thr Arg Thr Asp Leu Gly Gly Asp Pro
                325                 330                 335

Thr Phe Ala Glu Leu Val Glu Arg Val Arg Ala Ala Ser Val Asp Glu
            340                 345                 350

Met Ala His Gln Asp Val Pro Phe Glu Tyr Leu Val Glu Arg Leu Val
        355                 360                 365

Pro Glu Arg Asp Leu Ser Arg Asn Pro Leu Ala Gln Val Val Phe Gln
    370                 375                 380

Tyr Val Pro Arg Pro Ala Ala Arg Pro Ala Pro Phe Pro Gly Thr Thr
385                 390                 395                 400

Ala Glu Pro Phe Ala Gly Asp Arg Ala Phe Thr Arg Met Asp Leu Glu
                405                 410                 415

Val Tyr Leu Gly Glu Asp Ala Glu Gly Gly Val Glu Gly Leu Ile Asn
            420                 425                 430

Tyr Ser Arg Ala Leu Phe Asp Arg Glu Thr Val Glu Arg Leu Ala Arg
        435                 440                 445

His Leu Thr Ala Leu Leu Arg Ala Ala Cys Ala Glu Pro Asp Arg Pro
    450                 455                 460

Leu Ser Arg Leu Thr Met Thr Asp Ala Gly Glu Asp Ala Ala Leu Asp
465                 470                 475                 480

Arg Ala Ala Arg Gly Thr Gly Val Pro Leu Pro Glu Ala Ser Leu Pro
                485                 490                 495

Glu Leu Phe Ala Ala Gln Ala Ala Arg Thr Pro Asp Ala Val Ala Val
            500                 505                 510

Ala Asp Gly Thr Glu His Leu Thr Tyr Ala Gln Leu Asp Arg Ala Ala
        515                 520                 525

Asn Arg Leu Ala His Val Leu Ala Gly His Gly Ala Gly Pro Glu Ser
    530                 535                 540

Val Val Ala Leu Ala Thr Glu Arg Ser Ala His Leu Val Val Ala Val
545                 550                 555                 560

Leu Ala Val Leu Lys Ala Gly Gly Ala Tyr Leu Pro Leu Asp Ala Arg
                565                 570                 575

Asn Pro Ala Ala Arg Thr Arg Ala Val Leu Ala Asp Thr Gly Ala Ala
            580                 585                 590

Leu Leu Leu Thr Asp Gly Gly Pro Ala Pro Ala Gly Thr Glu His Leu
        595                 600                 605

Pro Ala Val Asp Leu Arg Ala Val Pro Gly Thr Ala Pro Asp Thr Ala
    610                 615                 620

Leu Pro Asn Thr Val Gly Pro Asp Gly Leu Ala Tyr Val Met Ser Thr
625                 630                 635                 640

Ser Gly Ser Thr Gly Thr Pro Lys Ala Val Ala Thr Thr His Arg Ala
                645                 650                 655

Val Ala Ala Leu Ala Leu His Arg Arg Trp Ser Gly Gly Ala His Glu
            660                 665                 670

Arg Val Leu Leu His Ser Pro Gln Ala Phe Asp Ala Ser Thr Tyr Glu
        675                 680                 685

Leu Trp Ser Pro Leu Leu Ser Gly Arg Arg Val Val Val Ala Pro Pro
    690                 695                 700
```

-continued

Gly Ala Leu Gly Pro Ala Ala Leu Ala Arg Val Val Ala Asp Gln Gly
705 710 715 720

Val Thr Ala Leu Trp Leu Thr Ser Gly Leu Phe Asp Leu Val Val Glu
725 730 735

Glu Asp Val Thr Cys Leu Ala Gly Val Arg Glu Leu Val Val Gly Gly
740 745 750

Asp Thr Val Ser Pro Ala Thr Val Ala Arg Val Arg Gly Ala His Pro
755 760 765

Asp Leu Thr Val Val Asn Gly Tyr Gly Pro Thr Glu Thr Thr Thr Phe
770 775 780

Ala Thr Leu His Pro Ile Ala Pro Ala Asp Pro Ala Pro Gly Gly Arg
785 790 795 800

Val Pro Ile Gly Ser Pro Leu Asp Asn Thr Arg Ala His Val Leu Asp
805 810 815

Asp Arg Leu Arg Pro Val Pro Phe Gly Val Pro Gly Glu Leu Tyr Val
820 825 830

Gly Gly Pro Arg Leu Ala Arg Gly Tyr Ala Gly Arg Pro Ala Ala Thr
835 840 845

Ala Glu Arg Phe Leu Pro Asp Pro Ser Gly Pro Ala Gly Ser Arg Met
850 855 860

Tyr Arg Thr Gly Asp Val Val Arg Arg Arg Pro Asp Gly Val Leu Glu
865 870 875 880

Phe Leu Gly Arg Ala Asp Asp Gln Ala Lys Leu Arg Gly Leu Arg Val
885 890 895

Glu Pro Gly Glu Val Glu Ala Val Leu Ala Ala His Pro Ala Val Ala
900 905 910

His Ala Ala Val Val Val Arg Gly Asp Gly Pro Ala Gly Lys Arg Leu
915 920 925

Val Ala His Val Val Pro Arg Ala Gly Arg Thr Thr Asp Thr Ala Ala
930 935 940

Leu Arg Ala His Ala Ala Ala Ala Leu Pro Asp Tyr Leu Val Pro Ser
945 950 955 960

Ala Phe Val Leu Ala Asp Ala Leu Pro Leu Thr Ala Thr Gly Lys Val
965 970 975

Asp Arg Ala Ala Leu Pro Ala Pro Ala Glu Thr Ala Asp Ala Gly Leu
980 985 990

Ala Ala Pro Arg Thr Asp Ala Glu Arg Ala Leu Cys Glu Ile Phe Ala
995 1000 1005

Glu Leu Leu Asp Ala Asp Ala Phe Gly Ala Glu Asp Asp Phe Phe Val
1010 1015 1020

Arg Gly Gly His Ser Leu Leu Ala Thr Arg Leu Val Ala Arg Ile Ala
1025 1030 1035 1040

Arg Ala Phe Gly Thr Glu Val Pro Leu Arg Glu Val Phe Glu His Arg
1045 1050 1055

Thr Pro Arg Ala Leu Ala Ser Val Val Ala Gly Ala Ala Leu Pro Ala
1060 1065 1070

Asp Pro Ala Pro Pro Leu Val Pro Ala Asp Arg Asp Arg Leu Leu Pro
1075 1080 1085

Leu Ser Phe Ala Gln Gln Arg Met Trp Phe Leu Asp Gln Leu Ala Pro
1090 1095 1100

Gly Ser Ala Ser Tyr Thr Ser Gly Gly Ala Leu Arg Val Arg Gly Pro
1105 1110 1115 1120

Leu Asp Pro Glu Arg Leu Ala Gly Ala Leu Ser Ala Val Val Ala Arg
1125 1130 1135

His Glu Thr Leu Arg Thr Thr Phe Thr Val Ala Asp Gly Val Pro Ala
1140 1145 1150

Ala Val Ile Gly Ala Ala Ala Pro Val Ala Pro Arg Ile Val Asp Val
1155 1160 1165

Pro Asp Ala Asp Ala Ala Arg Ala Ala Ala Ser Ala Glu Leu Ser Thr
1170 1175 1180

Gly Phe Asp Leu Thr Arg Gly Pro Leu Leu Arg Ala Thr Leu Leu Arg
1185 1190 1195 1200

Leu Ala Pro Asp Asp His Val Leu Val Val Ala Val His His Ile Ala
1205 1210 1215

Thr Asp Gly Trp Ser Gln Ala Leu Leu Trp Ala Glu Ile Ala Ala Ala
1220 1225 1230

Tyr Asp Gly Ala Pro Leu Pro Glu Leu Pro Val Gln Tyr Gly Asp His
1235 1240 1245

Ala Val Trp Gln Arg Ser Trp Leu Thr Gly Glu Val Leu Glu Arg Arg
1250 1255 1260

Ala Gly Tyr Trp Thr Gly Arg Leu Ala Gly Leu Ala Pro Leu Glu Leu
1265 1270 1275 1280

Pro Leu Asp Lys Ala Arg Pro Ala Val Ala Thr Gly Arg Ala Gly Thr
1285 1290 1295

Leu Pro Trp Gln Leu Pro Ala Glu Leu Ile Arg Asp Ala Arg Ala Val
1300 1305 1310

Ala Ala Arg Glu Gly Ala Thr Leu Tyr Met Val Leu Leu Ala Ala Phe
1315 1320 1325

Thr Leu Val Leu Ser Arg Tyr Ala Arg Thr Glu Asp Ile Ala Val Gly
1330 1335 1340

Ser Pro Thr Ala Gly Arg Thr Arg Ala Glu Thr Glu Ala Leu Ile Gly
1345 1350 1355 1360

Phe Phe Val Asn Val Val Ala Val Arg Thr Asp Leu Ser Gly Asp Pro
1365 1370 1375

Thr Phe Arg Glu Leu Leu Gly Arg Val Arg Glu Ser Val Val Gly Ala
1380 1385 1390

Val Glu His Gln Asp Val Pro Phe Glu His Leu Val Glu Arg Leu Arg
1395 1400 1405

Pro Glu Arg Asp Leu Ser Arg Asn Pro Leu Val Gln Val Ala Phe Gln
1410 1415 1420

Leu Leu Ala Asp Ala Pro Arg Arg Pro Trp Trp Gln Gly Ala Arg Ala
1425 1430 1435 1440

Glu Pro Phe Asp Ile Asp His Ala Tyr Thr Arg Met Asp Leu Glu Val
1445 1450 1455

His Ala Val Glu Thr Gly Asp Glu Val Gly Ala Thr Val Leu Tyr Ala
1460 1465 1470

Ala Asp Leu Phe Asp Ala Asp Thr Val Arg Gln Leu Met His His Val
1475 1480 1485

Ser Val Val Leu Gly Glu Val Leu Ala Asp Pro Asp Arg Pro Val Ser
1490 1495 1500

Ala Ala Thr Met Leu Asp Glu Thr Asp Arg His Arg Thr Leu Val Ala
1505 1510 1515 1520

Trp Asn Asp Thr Ala Ala Pro Leu Pro Asp Gly Cys Val Pro Arg Leu
1525 1530 1535

Tyr Ala Glu Gln Ala Ala Arg Thr Pro Asp Ala Val Ala Leu Ile Cys

```
            1540                1545                1550

Gly Asp Glu Arg Val Thr Tyr Ala Glu Leu Asp Arg Arg Ala Asn Arg
        1555                1560                1565

Phe Ala His Leu Leu Leu Ala His Gly Val Gly Ala Asp Glu Pro Val
    1570                1575                1580

Gly Val Ala Thr Gly Arg Ser Thr Gly Met Val Ala Ala Val Leu Gly
1585                1590                1595                1600

Val Leu Lys Ala Gly Ala Ala Tyr Val Pro Leu Asp Pro Arg Asn Pro
                1605                1610                1615

Pro Gly Arg Thr Glu Arg Ile Val Ala Thr Ser Gly Leu Arg Val Val
            1620                1625                1630

Ile Ala Asp Arg Pro Val Pro Gly Thr Asp Gly Ile Thr Val Leu Asp
        1635                1640                1645

Val Thr Asp Pro Gly Pro Gly Pro Asp Thr Asp Pro Gly Ile Asp Pro
    1650                1655                1660

His Pro Asp Thr Thr Ala Tyr Val Ile Tyr Thr Ser Gly Ser Ser Gly
1665                1670                1675                1680

Glu Pro Lys Gly Val Ala Val Thr His Arg Asn Val Val Val Leu Ala
                1685                1690                1695

Ala Asp Arg Arg Trp Ser Asn Gly Asn His Glu Arg Val Leu Leu His
            1700                1705                1710

Tyr Pro Leu Ala Thr Asp Ile Ser Thr Tyr Glu Leu Trp Pro Phe Leu
        1715                1720                1725

Leu Thr Gly Lys Gln Ile Val Val Ala Thr Asp Glu His Val Glu Pro
    1730                1735                1740

His Thr Phe Asp Arg Leu Ile Arg Glu His Gly Val Thr Ala Met Cys
1745                1750                1755                1760

Leu Pro Ala Pro Leu Phe Ser Leu Leu Ala Glu Glu Cys Met Glu Cys
                1765                1770                1775

Phe Gly Gly Leu Arg Glu Val Leu Thr Gly Gly Glu Ala Val Ser Gly
            1780                1785                1790

Glu Thr Val Ala Gln Val Met Ala Ala His Pro His Leu Thr Val Ala
        1795                1800                1805

Asp Ala Tyr Gly Pro Thr Glu Ala Thr Ala Phe Thr Thr Leu Phe Pro
    1810                1815                1820

Met Glu Pro Gly Phe Arg Leu Ala Gly Ser Arg Val Pro Ile Gly Ala
1825                1830                1835                1840

Pro Ile Asp Asn Thr Arg Val Tyr Val Leu Asp Asp Thr Leu Arg Pro
                1845                1850                1855

Ala Pro Leu Gly Val Ala Gly Glu Leu Val Ile Gly Gly Pro Arg Val
            1860                1865                1870

Ala Arg Gly Tyr Leu Gly Arg Pro Asp Leu Thr Ala Glu Lys Phe Val
        1875                1880                1885

Pro Asp Pro Trp Gly Gly Pro Gly Glu Arg Met Tyr Arg Thr Gly Asp
    1890                1895                1900

Val Val Arg Trp Leu Pro Gly Gly Ala Leu Glu Phe Leu Gly Arg Ala
1905                1910                1915                1920

Asp Val Gln Val Lys Ile Arg Gly Phe Arg Val Glu Pro Gly Glu Val
                1925                1930                1935

Glu Ala Ala Leu Leu Arg His Pro Ala Val Ser Gln Val Thr Val Ala
            1940                1945                1950

Val Arg Glu Asp Ile Pro Gly Asp Lys Arg Leu Val Ala Tyr Val Val
        1955                1960                1965
```

-continued

```
Leu Glu Pro Glu Ala Gly Ala Ser Val Leu Pro Ala Leu Arg Ala His
    1970                1975                1980

Ala Ala Gly Ser Val Pro Asp Tyr Met Val Pro Ser Ala Phe Val Ala
1985                1990                1995                2000

Leu Asp Ala Phe Pro Leu Ser Thr Thr Gly Lys Ile Asp Arg Arg Ala
                2005                2010                2015

Leu Pro Ala Pro Asp Thr Arg Ser Val Ala Glu Ser Gly Tyr Val Pro
            2020                2025                2030

Pro Ala Thr Glu Ala Glu Arg Val Leu Cys Glu Ile Phe Ala Glu Val
        2035                2040                2045

Leu Asp Val His Pro Val Gly Ala Asp Asp Asp Phe Phe Ala Leu Gly
    2050                2055                2060

Gly His Ser Leu Leu Ala Thr Arg Ala Ile Ala Arg Ile Arg Ala Arg
2065                2070                2075                2080

Phe Gly Pro Asp Val Pro Leu Gln Ala Val Phe Glu Arg Arg Ser Pro
                2085                2090                2095

Arg Arg Leu Ala Glu Thr Leu Gly Glu Pro Gly Thr Ala Thr Asp Val
            2100                2105                2110

Ile Arg Pro Ala Arg Arg Asp Gly Ala Ala Leu Pro Leu Ser Ser Ser
        2115                2120                2125

Gln Arg Arg Leu Trp Phe Leu Asp Arg Leu Thr Pro Asp Ser Gly Phe
    2130                2135                2140

Trp Asn Val Ala Met Gly Val Arg Ala His Gly Pro Leu Asp Val Asp
2145                2150                2155                2160

Ala Leu Gly Arg Ala Leu Ser Leu Val Val Ser Arg His Glu Ala Leu
                2165                2170                2175

Arg Thr Val Phe Ala Ala Asp Ala Gly Glu Pro Met Ala Val Val Arg
            2180                2185                2190

Pro Ala Thr Pro Leu Arg Leu Glu Val Thr Asp Val Ala Asp Glu Ala
        2195                2200                2205

Glu Val Arg Ala Leu Ala Glu Ala Asp Ala Ala Arg Pro Phe Asp Leu
    2210                2215                2220

Ala Arg Gly Pro Leu Leu Arg Ala Arg Val Leu Arg Leu Ala Ala Glu
2225                2230                2235                2240

Asp His Ala Val Leu Ile Thr Ala His His Ala Val Thr Asp Gly Trp
                2245                2250                2255

Ser His Ala Val Phe Trp Gly Glu Leu Ala Glu Ala Tyr Arg Ala Glu
            2260                2265                2270

Leu Ser Gly Asp Pro Ala Glu Leu Pro Glu Leu Pro Val Gln Tyr Gly
        2275                2280                2285

Asp Phe Ala Val Trp Gln Gln Gly Arg Leu Thr Gly Ala Glu Leu Glu
    2290                2295                2300

Arg Tyr Leu Thr Tyr Trp Arg Ala Arg Leu Ala Gly Leu Arg Pro Leu
2305                2310                2315                2320

Glu Leu Pro Leu Asp Arg Pro Arg Pro Ala Val Ala Gly Ser Ala Gly
                2325                2330                2335

Ala Ser Gln Pro Trp Glu Leu Pro Glu Asp Leu Val Arg Ala Ala Arg
            2340                2345                2350

Ala Phe Gly Asp Thr Glu Gly Ala Thr Leu Tyr Met Thr Leu Leu Thr
        2355                2360                2365

Ala Phe Thr Val Val Leu Ala Arg Phe Ala Gly Thr Glu Asp Val Ala
    2370                2375                2380
```

-continued

```
Val Gly Ala Pro Val Ala Gly Arg Thr Arg Pro Glu Val Glu Arg Leu
2385                2390                2395                2400

Ile Gly Phe Phe Val Asn Met Leu Val Leu Arg Thr Asp Val Ser Gly
                2405                2410                2415

Asp Pro Thr Phe Arg Asp Leu Leu Gly Arg Val Arg Glu Thr Val Val
            2420                2425                2430

Gly Ala Met Asp His Gln Asp Leu Pro Phe Glu His Leu Val Glu Thr
        2435                2440                2445

Leu Ala Pro Glu Arg Asp Leu Ser Arg Asn Pro Leu Val Gln Val Val
    2450                2455                2460

Phe Gln Leu Met Arg Ala Pro Gly Asp Lys Gly Asp Arg Leu Gly Ala
2465                2470                2475                2480

Ala Arg Leu Glu Pro Leu Leu Asp Glu His Ala Phe Thr Arg Val Asp
                2485                2490                2495

Leu Glu Val His Leu Thr Glu Asp Gly Asp Arg Val Arg Gly Thr Val
            2500                2505                2510

Leu His Ser Thr Ala Leu Phe Glu Ala Asp Thr Val Arg Arg Leu Leu
        2515                2520                2525

His His His Thr Val Leu Leu Arg Ala Ala Leu Ala Asp Pro Asp Ala
    2530                2535                2540

Pro Leu Ser Ala Leu Ser Leu Leu Asp Asp Asp Asp Arg Arg Leu Leu
2545                2550                2555                2560

Leu Glu Arg Trp Asn Asp Thr Ala Leu Pro Tyr Arg Asp Val Pro Leu
                2565                2570                2575

Val Glu Leu Phe Ala Glu Gln Val Ala Arg Thr Pro Gly Ala Arg Ala
            2580                2585                2590

Val Glu Cys Glu Asp Asp Val Leu Thr Tyr Ala Ala Leu Asp His Glu
        2595                2600                2605

Ala Glu Arg Ile Ala Ala Gly Leu Arg Ala Gln Gly Val Gly Pro Asp
    2610                2615                2620

Asp Leu Val Gly Leu Cys Leu Glu Arg Gly Thr Val Gln Met Ala Ala
2625                2630                2635                2640

Leu Ile Gly Ile Leu Lys Ala Gly Ala Ala Tyr Val Pro Ile Asp Pro
                2645                2650                2655

Ser His Pro Arg Asp Arg Ile Arg Leu Ile Val Asp Asp Ala Arg Met
            2660                2665                2670

Thr Val Ala Val Thr Asp Arg Ala His Ala Asp Val Phe Ala Glu Gly
        2675                2680                2685

Thr Ala Leu Val Leu Val Asp Ala Pro Ala Gly Gln Glu Pro Pro Ala
    2690                2695                2700

Ala Thr Ala Ala Gly Arg Pro Gly Pro Asp Ser Leu Ala Tyr Val Val
2705                2710                2715                2720

Tyr Thr Ser Gly Ser Thr Gly Val Pro Lys Gly Ile Ala Met Pro Ala
                2725                2730                2735

Arg Cys Val Val Asn Met Leu Ala Trp Gln Lys Lys Thr Val Pro Gly
            2740                2745                2750

Gly Pro Gly Thr Arg Thr Ala Gln Phe Thr Ala Leu Thr Phe Asp Val
        2755                2760                2765

His Val Gln Glu Val Leu Ser Ala Leu Leu Tyr Gly Glu Thr Leu Val
    2770                2775                2780

Ile Pro Thr Glu Glu Thr Arg Arg Asp Pro Ala Arg Phe Ala Arg Trp
2785                2790                2795                2800

Leu Asp Glu Arg Ala Val Glu Gln Ile Phe Val Pro Asn Leu Met Ile
```

-continued

```
                2805                2810                2815

Arg Ala Leu Ala Glu Glu Ala Gly Ala Gly Arg Ala Arg Leu Thr Ser
            2820                2825                2830

Leu Arg His Ile Ser Gln Ala Gly Glu Pro Leu Ser Leu Asp Thr Val
        2835                2840                2845

Leu Arg Glu Phe Cys Ala Ala Arg Pro Arg Leu Arg Leu His Asn His
    2850                2855                2860

Tyr Gly Ser Thr Glu Ile Gln Val Val Thr Ser Phe Thr Leu Pro Ala
2865                2870                2875                2880

Asp Val Ala Asp Trp Pro Arg Thr Ala His Leu Gly Glu Pro Val Asp
                2885                2890                2895

Asn Ser Arg Ala Tyr Val Leu Asp Asp Arg Leu Arg Pro Val Pro Val
            2900                2905                2910

Gly Val Ala Gly Glu Leu Cys Phe Ala Gly Pro Gly Leu Ala Arg Gly
        2915                2920                2925

Tyr Val Gly Lys Pro Glu Leu Thr Ala Gln Lys Phe Val Pro Asp Pro
    2930                2935                2940

Phe Gly Pro Pro Gly Ser Arg Leu Tyr Arg Thr Gly Asp Leu Gly Arg
2945                2950                2955                2960

Trp Arg Pro Asp Gly Ser Leu Glu Tyr Leu Gly Arg Leu Asp His Gln
                2965                2970                2975

Val Lys Ile Arg Gly Phe Arg Val Glu Leu Gly Glu Val Glu Ala Val
            2980                2985                2990

Leu Leu Arg His Pro Glu Val Thr Arg Ala Val Ile Val Ala Arg Glu
        2995                3000                3005

Asp Ala Pro Gly Val Lys Arg Leu Val Gly Tyr Val Val Pro Val Pro
    3010                3015                3020

Gly Thr Asp Gly Gly Leu Pro Ala Arg Leu Arg Ala His Leu Ala Asp
3025                3030                3035                3040

Ala Val Pro Asp Tyr Met Val Pro Ser Ala Leu Val Ala Leu Asp Ala
                3045                3050                3055

Phe Pro Leu Thr Thr Thr Gly Lys Ile Asp Arg Ala Ala Leu Pro Ala
            3060                3065                3070

Pro Asp Leu Arg Thr Thr Leu Asp Thr Gly Phe Thr Ala Pro Arg Thr
        3075                3080                3085

Gly Ala Glu Gln Thr Leu Cys Glu Val Phe Ala Glu Val Leu Glu Thr
    3090                3095                3100

Gly Gly Val Gly Ile Asp Asp Asp Phe Phe Ala Leu Gly Gly His Ser
3105                3110                3115                3120

Leu Val Ala Ala Arg Thr Val Ala Arg Ile Arg Glu Ala Leu Gly Ala
                3125                3130                3135

Glu Val Ser Leu Arg Glu Leu Phe Gln His Arg Thr Pro Arg Ala Leu
            3140                3145                3150

Ala Glu Val Val Ala Val Ala Pro Arg Thr Ala Val Pro Pro Leu Val
        3155                3160                3165

Pro Val Ser Arg Gln Glu Pro Leu Pro Leu Ser Leu Gly Gln Leu Arg
    3170                3175                3180

Leu Trp Arg Leu His Glu Ala Asp Pro Gly Asp Pro Val Trp Thr Ile
3185                3190                3195                3200

Pro Leu Ala Val Arg Ile Thr Gly Glu Leu Asp Ala Asp Leu Leu Gly
                3205                3210                3215

Arg Ala Leu Thr Glu Val Val Arg Arg His Glu Ala Leu Arg Thr Val
            3220                3225                3230
```

```
Phe Val Pro Gly Asp Glu Pro Ala Ser Val Ile Leu Pro Ala Thr Asp
        3235                3240                3245

Ile Val Leu Asp Pro Val Asp Val Ala Asp Glu Thr Ala Ala Arg Ala
    3250                3255                3260

Leu Ala Asp Glu Ala Ala Ala Arg Pro Phe Asp Leu Val Arg Gly Pro
3265                3270                3275                3280

Val Leu Arg Pro Ala Leu Leu Arg Ile Ala Pro Asp Asp His Val Leu
                3285                3290                3295

Leu Leu Thr Val His His Ile Ala Thr Asp Gly Trp Ser Gln Gly Val
            3300                3305                3310

Leu Trp Thr Glu Leu Ser Gly Ala Tyr Ala Ala Leu Arg Glu Asn Arg
        3315                3320                3325

Pro Ala Glu Leu Pro Glu Leu Pro Val Gln Tyr Gly Asp Phe Ala Phe
    3330                3335                3340

Trp Gln Arg Ser Trp Leu Thr Gly Ala Ala Leu Asp Ala Gln Leu Gly
3345                3350                3355                3360

His Trp Arg Arg Arg Leu Asp Gly Leu Arg Pro Leu Ala Leu Pro Gly
                3365                3370                3375

Val Pro Ala Asp Ala Ala His Asp Ala Thr Gly Val Leu Thr Glu Trp
            3380                3385                3390

Arg Leu Pro Ala Gly Leu Val Ala Thr Ala Arg Arg Val Gly Ala Glu
        3395                3400                3405

His Asp Ala Thr Leu Tyr Met Thr Leu Leu Ala Ala Phe Thr Ala Thr
    3410                3415                3420

Leu Ala Arg Trp Ala Gly Thr Asp Asp Leu Ala Val Gly Ser Pro Val
3425                3430                3435                3440

Ala Gly Arg Thr Arg Ala Glu Val Glu Gly Leu Ile Gly Phe Phe Ala
                3445                3450                3455

Asn Phe Val Pro Leu Arg Val Asp Leu Ser Gly Asp Pro Ser Phe Ala
            3460                3465                3470

Gly Leu Leu Glu Arg Val Arg Asp Thr Ala Leu Asp Ala Tyr Ala His
        3475                3480                3485

Gln Ala Leu Pro Trp Glu Arg Val Val Glu Gly Leu Gly Leu Asp Pro
    3490                3495                3500

Glu Gln Pro Leu Val Asp Val Val Phe Gln Leu Val Asn Val Glu Leu
3505                3510                3515                3520

Gly Glu Leu Gly Leu Pro Gly Ala Arg Val Glu Gln Phe Thr Gly Gln
                3525                3530                3535

Gln Ala Tyr Ala Arg Trp His Leu Glu Val His Leu Val Glu Asp Pro
            3540                3545                3550

Asp Gly Gly Leu Thr Gly His Val Val His Arg Ala Ala Ala Leu Gly
        3555                3560                3565

Arg Arg Val Val Asp Gly Leu Leu Ala Gly Thr Ala Ala Leu Leu Gln
    3570                3575                3580

Ala Ala Leu Ala Glu Pro Gly Leu Pro Val Ser Ala Leu His Ala Pro
3585                3590                3595                3600

Asp Pro Leu Glu Gly Thr Thr His Asp
                3605
```

<210> SEQ ID NO 8
<211> LENGTH: 2217
<212> TYPE: PRT
<213> ORGANISM: Streptomyces flaveolus (Streptomyces sp.(DSM 9954))

<400> SEQUENCE: 8

Met Thr Glu Pro Leu Thr Asp Pro Lys Ala Ala Gln Pro Pro Ala Leu
1 5 10 15

Ala His Arg Leu Ala Gly Leu Pro Glu Pro Glu Arg Arg Arg Val Val
20 25 30

Leu Asp Leu Val Arg Thr Gln Val Ala Glu Val Leu Asp Leu Gly Thr
35 40 45

Ala Ala Asp Val Pro Pro Asp Arg Ala Ile Arg Glu Leu Gly Leu Arg
50 55 60

Ser Leu Thr Ala Val Gln Leu Leu Leu Arg Leu Ser Arg Gly Thr Gly
65 70 75 80

Val Lys Leu Pro Thr Thr Ala Ile Tyr Asp His Pro Thr Ala Arg Ala
85 90 95

Leu Ala Asp Val Leu Val Asp Ala Ala Ser Gly Arg His Val Arg Leu
100 105 110

Ala Glu Asp Asp Glu Pro Val Gln Arg Ala Ala Asp Asp Asp Pro Val
115 120 125

Ala Val Val Gly Met Ala Cys Arg Phe Pro Gly Gly Val Thr Thr Pro
130 135 140

Asp Glu Leu Trp Arg Leu Val Leu Glu Glu Arg Asp Ala Ile Thr Pro
145 150 155 160

Phe Pro Ala Asp Arg Gly Trp Asp Leu Ala Ala Leu Ala Asp Pro Asp
165 170 175

Gly Pro Ser Ala Ser Arg Thr Arg His Gly Gly Phe Leu Asp Asp Val
180 185 190

Ala Leu Phe Asp Ala Gly Phe Phe Gly Ile Ser Pro Arg Glu Ala Gln
195 200 205

Leu Met Asp Pro Gln Gln Arg Leu Leu Leu Glu Thr Ser Trp Glu Ala
210 215 220

Leu Glu Arg Ala Gly Val Ala Pro Gly Ser Trp Arg Gly Gly Arg Val
225 230 235 240

Gly Val Phe Val Gly Ala Asn Ala Gln Ser Tyr Ser Ser Leu Leu Ala
245 250 255

Gly Ile Pro Glu Gly Gly Asp Gly His Ala Leu Thr Gly Arg Leu Ala
260 265 270

Ser Val Val Ala Gly Arg Ile Ser Tyr Val Leu Gly Leu Glu Gly Pro
275 280 285

Ala Phe Thr Val Asp Thr Ala Cys Ser Ser Ser Leu Val Ala Leu His
290 295 300

Gln Ala Val Arg Ser Leu Arg Ser Gly Glu Ser Thr Leu Ala Leu Ala
305 310 315 320

Gly Gly Val Thr Val Met Pro Thr Pro Glu Leu Phe Val Asp Phe Thr
325 330 335

Lys Gln Gly Gly Leu Ser Glu Asp Gly Arg Cys Arg Ser Tyr Ala Lys
340 345 350

Ala Ala Asp Gly Leu Gly Trp Ser Glu Gly Val Gly Met Leu Leu Leu
355 360 365

Glu Arg Leu Ser Asp Ala Arg Arg Asn Gly His Pro Val Leu Ala Leu
370 375 380

Leu Pro Gly Thr Ala Val Asn Gln Asp Gly Ala Ser Asn Gly Leu Thr
385 390 395 400

Ala Pro Ser Gly Ala Ala Gln Gln Arg Val Val Arg Gln Ala Leu Ala
405 410 415

```
Asp Ala Gly Leu Arg Pro Ala Asp Val Asp Ala Val Glu Gly His Gly
            420                 425                 430

Thr Gly Thr Ala Leu Gly Asp Pro Ile Glu Ala Gln Ala Leu Leu Ser
        435                 440                 445

Ser Tyr Gly Gln Asp Arg Asp Arg Pro Leu Trp Leu Gly Ser Leu Lys
    450                 455                 460

Ser Asn Leu Gly His Ala Gln Ala Ala Ala Gly Val Gly Gly Val Ile
465                 470                 475                 480

Lys Thr Val Leu Ala Leu Arg His Gly Leu Leu Pro Lys Thr Leu His
                485                 490                 495

Val Asp Glu Pro Thr Pro His Val Asp Trp Val Ser Gly Asp Val Arg
            500                 505                 510

Leu Leu Thr Glu Ala Arg Pro Trp Pro Arg Gly Glu Arg Pro Arg Arg
        515                 520                 525

Ala Gly Val Ser Ser Phe Gly Val Ser Gly Thr Asn Ala His Val Ile
    530                 535                 540

Val Ala Glu Ala Pro Glu Pro Glu Glu Ala Thr Ala Pro Pro Ala Gly
545                 550                 555                 560

Ala Leu Pro Val Pro Trp Gln Leu Ser Ala Arg Thr Glu Ala Ala Leu
                565                 570                 575

Leu Glu Gln Ala Ala Arg Leu Arg Glu Phe Val Ala Ala Asp Pro Gly
            580                 585                 590

Leu Glu Pro Ala Ser Val Gly Phe Thr Leu Ala Thr Arg Arg Thr Ala
        595                 600                 605

Phe Glu His Arg Ala Ala Val Val Gly Arg Asp Arg Ala Glu Leu Leu
    610                 615                 620

Ala Ala Leu Asp Val Leu Ala Ala Gly Gly Ala Asp Pro Ala Val Val
625                 630                 635                 640

Arg Gly Thr Ala Gly Ala Asp Gly Ser Val Val Phe Val Phe Ala Gly
                645                 650                 655

Gln Gly Gly Gln Trp Leu Gly Met Gly Val Glu Leu Leu Asp Thr His
            660                 665                 670

Pro Val Phe Ala Ala Arg Met Ala Glu Cys Glu Arg Ala Leu Ala Pro
        675                 680                 685

Tyr Leu Asp Trp Ser Val Val Asp Val Leu Arg Gly Ala Glu Asp Ala
    690                 695                 700

Pro Pro Leu Ser Arg Val Asp Val Val Gln Pro Val Leu Phe Ala Leu
705                 710                 715                 720

Met Val Ser Leu Ala Ala Val Trp Arg Ser His Gly Val Val Pro Ala
                725                 730                 735

Ala Val Val Gly His Ser Gln Gly Glu Ile Ala Ala Ala Cys Val Ala
            740                 745                 750

Gly Ala Leu Thr Leu Asp Asp Ala Ala Lys Thr Val Ala Leu Arg Ala
        755                 760                 765

Lys Ala Val Ala Asp Leu Pro Gly Arg Cys Gly Met Ala Phe Val Ala
    770                 775                 780

Ala Pro Ala Ala Asn Val Glu Arg Met Leu Glu Arg Trp Pro Gly Arg
785                 790                 795                 800

Leu Gly Ile Ala Ala Ala Asn Ser Pro Arg Ser Leu Val Val Ala Gly
                805                 810                 815

Asp Arg Asp Ala Leu Glu Glu Leu Leu Asp Leu Cys Asp Asp Glu Gly
            820                 825                 830
```

```
Leu Arg Ala Gly Arg Val Ala Ala Asp Tyr Ala Ser His Ser Pro Gln
        835                 840                 845

Val Glu Ala Val Arg Gln Arg Leu Leu Ala Asp Leu Lys Gly Ile Arg
    850                 855                 860

Pro Arg Asp Gly Asp Val Pro Leu Tyr Ser Thr Val Thr Ala Asp Trp
865                 870                 875                 880

Ile Asp Gly Ser Glu Leu Gly Ala Arg Tyr Trp Tyr Arg Asn Leu Arg
                885                 890                 895

Glu Pro Val Leu Phe Gln Asn Ala Ile Ser Asp Leu Leu Ala Ala Gly
            900                 905                 910

His His Gly Phe Val Glu Ile Ser Pro His Pro Val Leu Thr Val Ala
        915                 920                 925

Met Gln Gln Thr Ala Glu Ala Ala Gly Thr Glu Leu Arg Val Ala Ala
    930                 935                 940

Thr Leu Arg Arg Asp Glu Ser Asp Arg Leu Arg Leu Thr Thr Ala Leu
945                 950                 955                 960

Ala Glu Val Ala Ala Asp Gly Val Pro Val Asp Trp Arg Pro Leu Phe
                965                 970                 975

Asp Ala Thr Gly Ala Arg Pro Val Glu Leu Pro Ala Tyr Pro Phe Gln
            980                 985                 990

Arg Glu Arg Tyr Trp Leu Thr Pro Gln Ala Ala Ala Gly Asp Leu Thr
        995                 1000                1005

Ala Val Gly Leu Thr Ala Gly Gly His Pro Leu Leu Ala Ala Glu Ala
    1010                1015                1020

Glu Leu Pro Asp Glu Asp Gly Leu Leu Leu Thr Gly Arg Ile Ser Pro
1025                1030                1035                1040

Glu Thr His Pro Trp Leu Thr Glu His Thr Val Leu Gly Thr Ala Leu
                1045                1050                1055

Leu Pro Gly Thr Ala Val Leu Glu Met Val Ala His Ala Gly His Arg
            1060                1065                1070

Leu Asp Arg Ala Gln Ile Glu Glu Leu Thr Leu Ala Ala Pro Ile Gly
        1075                1080                1085

Val Pro Ala Asp Gly Leu Thr Leu Arg Val Thr Val His Gly Ala Asp
    1090                1095                1100

Gly Ser Gly Arg Arg Thr Val Ala Val His Ser His Ser Gly Asp Gly
1105                1110                1115                1120

Trp Thr Arg His Ala Thr Gly Val Leu Ala Pro Ala Glu Pro Ala Glu
                1125                1130                1135

Pro Ala Glu Pro Glu Thr Gly Ala Trp Pro Pro Ala Gly Ala Glu Pro
            1140                1145                1150

Val Pro Val Asp Gly Val Tyr Asp Arg Phe Ala Ala Arg Gly Tyr Gly
        1155                1160                1165

Tyr Gly Pro Ala Phe Gln Gly Leu Arg Ala Leu Trp Arg Arg Asp Thr
    1170                1175                1180

Glu Val Tyr Ala Glu Val Glu Leu Pro Asp Thr Val Asp Thr Ala Gly
1185                1190                1195                1200

His Leu Val His Pro Ala Leu Leu Asp Ala Val Thr Gln Ala Val Pro
                1205                1210                1215

Ala Ala Glu Pro Glu Asp Ala Pro Leu Leu Leu Pro Phe Thr Trp Thr
            1220                1225                1230

Gly Val Thr Val His Pro Gly Pro Ala Arg Val Leu Arg Val Arg Ala
        1235                1240                1245

Ala Arg Glu Ser Ala Asp Thr Leu Ser Leu Thr Ala Thr Asp Arg Glu
```

```
    1250                1255                1260

Gly Arg Pro Val Val Glu Leu Ala Ala Leu Arg Leu Arg Pro Ala Ser
1265                1270                1275                1280

Ala Gly Gln Leu Arg Ala Val Ala Ala Ala Gly Thr Arg Asp Ala Leu
                1285                1290                1295

Phe Arg Val Thr Trp Gln Thr Pro Asp Ala Glu Thr Pro Ala Ala Ala
            1300                1305                1310

Arg Cys Ala Val Leu Gly Asp Gly Pro Glu Gly Leu Ala Ala Pro Leu
        1315                1320                1325

Ser Thr Ala Leu Ala Asp Ile Asp Ala Gly Ala Val Asp Leu Val Leu
    1330                1335                1340

Ala Pro Val Ser Thr Gly Ala Asp Val Val Ala Ala Ala His Arg Ala
1345                1350                1355                1360

Thr Ala Gln Val Leu Glu Leu Leu His Glu Trp Leu Ala Asp Asp Arg
                1365                1370                1375

Phe Gly Gln Ala Arg Leu Ala Ile Val Thr Arg His Ala Val Ala Ala
            1380                1385                1390

Arg Pro Gly Glu Glu Pro Asp Pro Ala Ala Ala Ala Val Trp Gly Leu
        1395                1400                1405

Val Arg Ser Ala Gln Thr Glu His Pro Asp Arg Phe Leu Leu Val Asp
    1410                1415                1420

Thr Asp Gly Thr Pro Ala Ser Leu Asp Ala Val Pro Ala Val Gly Asp
1425                1430                1435                1440

Glu Pro Gln Thr Ala Leu Arg Asp Gly Glu Arg Leu Val Ala Arg Leu
                1445                1450                1455

Thr Arg Ala Ala Glu Thr Ala Leu Arg Pro Pro Val Gly Ala Asp Ala
            1460                1465                1470

Trp Arg Val Asp Val Val Arg Pro Gly Ser Ile Asp Gly Val Asp Ala
        1475                1480                1485

Val Ala Ala Pro Asp Ala Thr Ala Pro Leu Ala Pro Gly Gln Val Arg
    1490                1495                1500

Ile Ala Val Arg Ala Ala Gly Leu Asn Phe Arg Asp Val Leu Cys Ala
1505                1510                1515                1520

Leu Asp Met Tyr Pro Asp Glu Val Asp Ala Ile Gly Ser Glu Ala Ala
                1525                1530                1535

Gly Thr Val Val Ala Val Ala Pro Asp Val Thr Asp Leu Ala Val Gly
            1540                1545                1550

Asp Arg Val Leu Gly Met Val Pro Gly Gly Phe Gly Thr Leu Ala Val
        1555                1560                1565

Val Asp Arg Arg Leu Val Val Pro Val Pro Ala Gly Trp Ser Trp Val
    1570                1575                1580

Arg Ala Ala Ala Leu Pro Ser Val Phe Ala Thr Ala Trp Phe Ala Leu
1585                1590                1595                1600

Arg Asp Val Ala Gly Val Arg Ala Gly Glu Arg Val Leu Val His Ala
                1605                1610                1615

Ala Ala Gly Gly Val Gly Met Ala Ala Val Arg Val Ala Arg Leu Leu
            1620                1625                1630

Gly Ala Glu Val Tyr Ala Thr Ala Ser Pro Gly Lys His Glu Val Leu
        1635                1640                1645

Arg Ala Ala Gly Leu Asp Glu Ala Arg Val Ala Ser Ser Arg Asp Thr
    1650                1655                1660

Glu Phe Ala Gln Arg Phe Pro Glu Met Asp Val Val Leu Asn Ser Leu
1665                1670                1675                1680
```

Thr Gly Glu Phe Val Asp Ala Ser Leu Arg Leu Leu Arg Pro Gly Gly
1685 1690 1695

Arg Phe Val Glu Leu Gly Lys Thr Asp Arg Arg Asp Pro Ala Gly Leu
1700 1705 1710

Pro Gly Val Asp Tyr Leu Pro Phe Asp Leu Leu Leu Asp Ala Gly Pro
1715 1720 1725

Asp Arg Val Gln Ser Leu Leu Thr Glu Val Val Ala His Ala Glu Ala
1730 1735 1740

Gly Glu Leu Thr Gly Leu Pro Thr Arg Thr Trp Pro Leu Ala Asp Ala
1745 1750 1755 1760

Arg Thr Ala Phe Arg Phe Met Ala Gln Ala Arg His Thr Gly Lys Ile
1765 1770 1775

Val Leu Thr Val Ala Pro Tyr Ala Asp Gly Thr Val Leu Ile Thr Gly
1780 1785 1790

Ala Gly Val Leu Gly Gly Met Leu Ala Arg His Leu Val Ser Glu His
1795 1800 1805

Gly Ala Arg Asp Leu Val Leu Ala Ser Arg Arg Gly Ala Ala Ala Pro
1810 1815 1820

Gly Ser Ala Asp Leu Val Ala Glu Leu Ala Ala Ala Gly Ala Thr Val
1825 1830 1835 1840

Arg Phe Glu Thr Cys Asp Val Thr Asp Arg Ala Ala Leu Asp Ala Leu
1845 1850 1855

Leu Ala Lys Leu Thr Ala Glu Ala Pro Leu Thr Ala Val Val His Thr
1860 1865 1870

Ala Gly Ala Leu Asp Asp Gly Val Leu Thr Glu Leu Gly Ala Gly Arg
1875 1880 1885

Leu Pro Gly Val Leu Arg Pro Lys Ala Asp Ala Ala Trp His Leu His
1890 1895 1900

Glu Leu Thr Glu Asp Lys Asp Leu Ser Ala Phe Val Leu Phe Ser Ser
1905 1910 1915 1920

Ala Ala Ala Thr Leu Gly Thr Pro Ala Gln Ala Asn Tyr Ala Ala Ala
1925 1930 1935

Asn Ala Phe Leu Asp Ala Leu Ala Glu Arg Arg Arg Ala Ala Gly Leu
1940 1945 1950

Pro Gly Thr Ala Ala Ala Trp Gly Leu Trp Ala Asp Ala Thr Gly Leu
1955 1960 1965

Thr Arg His Leu Asp Ala Ala Asp Val Ala Arg Ala Gly Arg Asn Arg
1970 1975 1980

Ile Val Pro Met Ala Ala Ala Glu Gly Leu Ala Leu Phe Asp Thr Ala
1985 1990 1995 2000

Thr Ala Thr Gly Asp Ala Val Thr Val Thr Ala Arg Leu Asp Leu Ala
2005 2010 2015

Thr Ala Ser Ala Ala Pro Thr Pro Pro Leu Leu Arg Gly Leu Val Ala
2020 2025 2030

Thr Pro Ala Gly Pro Ala Ala Ala Arg Pro Val Pro Gly Ala Ala Ala
2035 2040 2045

Leu Val Ala Arg Ile Thr Gly Leu Pro Ala Pro Glu Arg Ala Pro Ala
2050 2055 2060

Leu Leu Asp Val Val Arg Gly Gln Val Ala Asp Val Leu Gly His Arg
2065 2070 2075 2080

Gly Arg Asp Ala Val Ala Pro Asp Arg Gly Phe Lys Glu Leu Gly Phe
2085 2090 2095

Asp Ser Leu Thr Ala Val Glu Leu Arg Asn Arg Leu Gly Thr Ala Thr
2100 2105 2110

Gly Leu Arg Leu Pro Thr Thr Ile Val Phe Asp His Pro Asn Pro Ala
2115 2120 2125

Ala Leu Ala Asp His Leu Leu Asp Ala Leu Leu Pro Ser Glu Ser Gly
2130 2135 2140

Glu Ala Ser Ala Asp Arg Ile Ile Ala Glu Leu Ala Arg Val Glu Ser
2145 2150 2155 2160

Ala Leu Gly Ala Leu Pro Ala Asp Gly Thr Asp Arg Ala Arg Val Ala
2165 2170 2175

Ala His Leu Arg Asp Leu Ala Ala Arg Trp Asp Ala Gly Thr Thr Asp
2180 2185 2190

Gly Thr Pro Glu Arg Ala Ala Leu Asp Gly Val Thr Ala Asp Glu Leu
2195 2200 2205

Phe Asp Leu Ile Asp Arg Gly Val Ser
2210 2215

<210> SEQ ID NO 9
<211> LENGTH: 4206
<212> TYPE: PRT
<213> ORGANISM: Streptomyces flaveolus (Streptomyces sp.(DSM 9954))

<400> SEQUENCE: 9

Met Ala Asp Glu Ala Lys Leu Leu Asp Tyr Leu Lys Gln Val Thr Gly
1 5 10 15

Asp Leu Gln Val Ala Arg Arg Arg Leu Arg Glu Ala Glu Ala Arg Asp
20 25 30

Arg Glu Pro Ile Ala Ile Val Gly Met Ala Cys Arg Tyr Pro Gly Gly
35 40 45

Val Thr Ser Pro Glu Asp Leu Trp Arg Leu Val Thr Asp Gly Thr Asp
50 55 60

Ala Val Ser Ala Phe Pro Ala Asp Arg Gly Trp Asp Met Ala Ser Val
65 70 75 80

Tyr Asp Pro Asp Pro Asp Arg Pro Gly Thr Ser Tyr Ala Arg Glu Gly
85 90 95

Gly Phe Leu Asp Gly Ala Ala Asp Phe Asp Ala Gly Phe Phe Gly Ile
100 105 110

Ser Pro Arg Glu Ala Leu Ala Met Asp Pro Gln Gln Arg Leu Val Leu
115 120 125

Glu Thr Ser Trp Glu Ala Leu Glu Arg Ala Gly Ile Asp Pro Ala Gly
130 135 140

Leu Arg Ser Thr Ala Thr Gly Val Phe Val Gly Phe Ser Ser Glu Asp
145 150 155 160

Tyr Ser Asp Ile Thr Gly Pro Val Ala Thr Glu Leu Glu Gly Tyr Val
165 170 175

Val Thr Gly Thr Ser Pro Ser Val Leu Ser Gly Arg Val Ala Tyr Thr
180 185 190

Leu Gly Leu Glu Gly Pro Ala Leu Ser Val Asp Thr Ala Cys Ser Ser
195 200 205

Ser Leu Val Ala Leu His Leu Ala Val Arg Ser Leu Arg Ala Gly Glu
210 215 220

Cys Thr Leu Ala Leu Thr Gly Gly Ala Thr Val Leu Ser Thr Pro Gly
225 230 235 240

Val Phe Thr Glu Tyr Ser Arg Gln Arg Ala Leu Ala Ala Asp Gly Arg
245 250 255

```
Cys Lys Ala Phe Ala Ala Ala Ala Asp Gly Phe Gly Phe Ala Glu Gly
            260                 265                 270

Ala Gly Met Leu Val Leu Glu Arg Leu Ser Asp Ala Arg Arg Asn Gly
        275                 280                 285

His Pro Val Leu Ala Val Val Arg Gly Thr Ala Ile Asn Gln Asp Gly
    290                 295                 300

Ala Ser Ser Gly Leu Thr Ala Pro Asn Gly Leu Ala Gln Gln Arg Val
305                 310                 315                 320

Ile Arg Gln Ala Leu Ala Asp Ala Arg Leu Ala Ala Ser Gln Val Asp
                325                 330                 335

Ala Val Glu Ala His Gly Thr Gly Thr Arg Leu Gly Asp Pro Ile Glu
            340                 345                 350

Ala Gln Ala Leu Leu Ala Thr Tyr Gly Gln Glu Arg Asp Glu Pro Leu
        355                 360                 365

Trp Leu Gly Ser Val Lys Ser Asn Ile Gly His Thr Gln Ala Ala Ala
    370                 375                 380

Gly Val Ala Gly Val Ile Lys Met Val Gln Ala Met Arg His Gly Thr
385                 390                 395                 400

Leu Pro Arg Thr Leu His Val Asp Glu Ala Ser Pro His Val Asp Trp
                405                 410                 415

Thr Ala Gly Ala Val Glu Leu Leu Thr Glu Glu Arg Asp Trp Pro Gly
            420                 425                 430

Gly Glu Gln Pro Arg Arg Ala Gly Val Ser Ser Phe Gly Val Ser Gly
        435                 440                 445

Thr Asn Ala His Ala Ile Leu Glu Gln Ala Pro Ala Arg Pro Glu Pro
    450                 455                 460

Thr Asp Glu Ala Thr Asp Arg Thr Leu Pro Val Val Pro Trp Thr Leu
465                 470                 475                 480

Ser Ser Arg Thr Ala Ala Gly Leu Arg Ala Gln Ala Glu Arg Leu Leu
                485                 490                 495

Ala His Arg Pro Ala His Asp Ala Ala Pro His Asp Val Ala Leu Ala
            500                 505                 510

Leu Ala Thr Thr Arg Thr Ala Phe Glu His Arg Val Val Val Leu Gly
        515                 520                 525

Ala Asp His Asp Thr Leu Leu Ala Gly Leu Thr Ala Val Ala Glu Gly
    530                 535                 540

Ala Glu Ser Ala Asp Val Val Arg Gly Arg Ala Val Gly Asp Gly Arg
545                 550                 555                 560

Ala Val Phe Val Phe Pro Gly Gln Gly Ala Gln Trp Val Gly Met Ala
                565                 570                 575

Val Asp Leu Leu Asp Ser Ser Pro Val Phe Ala Gly Arg Met Ala Glu
            580                 585                 590

Cys Ala Val Ala Leu Glu Pro Phe Val Gly Trp Ser Leu Arg Gly Val
        595                 600                 605

Leu Gly Asp Pro Val Ala Leu Glu Arg Val Asp Val Val Gln Pro Val
    610                 615                 620

Leu Trp Ala Val Met Val Ser Leu Ala Glu Val Trp Arg Ser Tyr Gly
625                 630                 635                 640

Val Val Pro Ser Ala Val Val Gly His Ser Gln Gly Glu Ile Ala Ala
                645                 650                 655

Ala Cys Val Ala Gly Val Leu Ser Leu Ala Asp Gly Ala Arg Val Val
            660                 665                 670
```

```
Ala Leu Arg Ser Arg Ala Leu Thr Ala Leu Ala Gly Ser Gly Gly Met
        675                 680                 685

Val Ser Val Ala Ala Gly Pro Ser Gly Val Glu Glu Leu Leu Val Gly
    690                 695                 700

Trp Ala Gly Arg Leu Ala Val Ala Ala Val Asn Gly Pro Glu Ser Val
705                 710                 715                 720

Val Val Ala Gly Glu Gly Val Ala Leu Glu Glu Phe Leu Ala His Cys
            725                 730                 735

Gly Gly Arg Gly Val Arg Ala Arg Arg Ile Ala Val Asp Tyr Ala Ser
        740                 745                 750

His Ser Val Leu Val Glu Pro Val Arg Glu Ala Leu Leu Ala Asp Leu
        755                 760                 765

Glu Gly Val Arg Pro Gly Glu Gly Thr Val Pro Leu Phe Ser Thr Val
    770                 775                 780

Thr Gly Glu Trp Ala Asp Gly Thr Ala Leu Asp Ala Gly Tyr Trp Tyr
785                 790                 795                 800

Arg Asn Leu Arg Glu Pro Val Arg Tyr Ala Asp Ala Val Ala Ala Leu
            805                 810                 815

Leu Ala Gln Gly His Arg Gly Phe Ile Glu Val Ser Pro His Pro Val
            820                 825                 830

Leu Thr Val Gly Thr Gln Glu Thr Val Glu Arg Thr Glu Thr Gly Ala
        835                 840                 845

Ala Val Val Gly Thr Leu Gln Arg Asp Arg Ala Gly Leu Pro Thr Leu
    850                 855                 860

Leu Thr Asn Leu Ala Glu Ala His Thr His Gly Val Arg Ile Asp Trp
865                 870                 875                 880

Thr Ala Phe Phe Arg Gly Thr Gly Ala His Pro Ala Asp Leu Pro Thr
            885                 890                 895

Tyr Ala Phe Gln Arg Asp Arg Tyr Trp Pro Pro Val Asp Ala Ala Ala
            900                 905                 910

Arg Pro Leu Pro Pro Ala Ala Thr Pro Val Ala Leu Pro Ala Gln Arg
        915                 920                 925

Thr Ala Asp Glu Gly Thr Pro Trp Arg Asp Glu Leu Ala Gly Leu Thr
    930                 935                 940

Pro Ala Glu Arg Arg His Arg Val Met Asp Leu Val Arg Leu Arg Thr
945                 950                 955                 960

Ala Ala Val Leu Gly His Ala Asp Pro Ala Ala Ile Glu Pro His Arg
            965                 970                 975

Gly Phe Ala Ala Leu Gly Phe Asp Ser Leu Ala Ser Leu Arg Leu Arg
            980                 985                 990

Thr Ala Leu Thr Glu Ala Thr Gly Leu Thr Leu Ala Ser Ser Val Val
        995                 1000                1005

Phe Asp His Pro Asn Pro Ala Ala Leu Thr Asp His Leu Leu Thr Arg
    1010                1015                1020

Leu Asp Gly Ala Pro Val Pro Ala Arg Pro Ala Val Arg Ala Thr Pro
1025                1030                1035                1040

Ala Asp Glu Pro Leu Ala Val Val Gly Met Ala Cys Arg Phe Pro Gly
            1045                1050                1055

Gly Val Ala Ser Pro Asp Asp Leu Trp Gln Leu Leu Ala Glu Gly Arg
            1060                1065                1070

Asp Val Ile Gly Asp Phe Pro Ala Asp Arg Gly Trp Asp Leu Asp Gly
        1075                1080                1085

Leu Tyr Asp Pro Asp Pro Asp Arg Ala Gly His Thr Tyr Leu Arg Gln
```

1090 1095 1100

Gly Gly Phe Leu Asn Asp Ala Ala Gly Phe Asp Ala Asp Phe Phe Gly
1105 1110 1115 1120

Ile Ser Pro Arg Glu Ala Leu Ala Met Asp Pro Gln Gln Arg Leu Phe
1125 1130 1135

Leu Glu Val Ala Trp Glu Ala Phe Glu His Ala Gly Val Asp Pro His
1140 1145 1150

Gly Leu Arg Gly Ser Ala Thr Gly Val Phe Ala Gly Val Thr Asp Gln
1155 1160 1165

Arg Tyr Asp Ser Arg His Gly Ala Val Ala Gly Val Asp Glu Gly Leu
1170 1175 1180

Leu Gly Thr Gly Asn Tyr Ala Ser Val Leu Ser Gly Arg Val Ala Tyr
1185 1190 1195 1200

Thr Leu Gly Leu Glu Gly Pro Ala Val Ser Val Asp Thr Ala Cys Ser
1205 1210 1215

Ser Ser Leu Val Ala Leu His Leu Ala Gly Gln Ser Leu Arg Ser Gly
1220 1225 1230

Glu Cys Ser Leu Ala Leu Ala Gly Gly Val Met Val Met Ser Thr Pro
1235 1240 1245

Arg Ala Phe Val Glu Phe Ser Arg Gln Arg Gly Leu Ala Pro Asp Gly
1250 1255 1260

Arg Cys Lys Ala Phe Ala Ala Ala Ala Asp Gly Ile Gly Trp Ser Glu
1265 1270 1275 1280

Gly Ala Gly Val Val Val Leu Glu Arg Leu Ser Asp Ala Arg Arg Asn
1285 1290 1295

Gly His Pro Val Leu Ala Val Val Arg Gly Ser Ala Ile Asn Gln Asp
1300 1305 1310

Gly Ala Ser Ser Gly Leu Thr Ala Pro Asn Gly Ser Ala Gln Gln Arg
1315 1320 1325

Val Ile Arg Ser Ala Leu Ala Ala Ala Gly Leu Thr Ala Ala Asp Val
1330 1335 1340

Asp Val Val Glu Ala His Gly Thr Gly Thr Thr Leu Gly Asp Pro Ile
1345 1350 1355 1360

Glu Ala Asn Ala Leu Leu Ala Thr Tyr Gly Gln Asp Arg Ala Gln Pro
1365 1370 1375

Leu Arg Leu Gly Ser Leu Lys Ser Asn Ile Gly His Thr Gly Pro Ala
1380 1385 1390

Ala Gly Val Ala Gly Val Ile Lys Thr Val Leu Ala Leu Arg Ala Gly
1395 1400 1405

Glu Val Pro Arg Thr Leu His Val Asp Ala Pro Ser Pro His Ile Asp
1410 1415 1420

Trp Ala Ser Gly Ser Val Glu Leu Val Thr Gly Ala Ala Val Trp Pro
1425 1430 1435 1440

Pro Thr Asp Arg Pro Arg Arg Ala Gly Val Ser Ser Phe Gly Ala Ser
1445 1450 1455

Gly Thr Asn Ala His Leu Ile Leu Glu Glu Ala Pro Ala Glu Pro Ala
1460 1465 1470

Ala Pro Ala Arg Gly Ala Ala Pro Arg Trp Val Pro Trp Leu Leu Ser
1475 1480 1485

Ala Arg Ser Gln Ala Ala Leu Ala Glu Gln Ala Thr Arg Leu Ala Ala
1490 1495 1500

His Leu Asp Thr His Pro Gly Leu Asp Pro Val Asp Leu Ser Trp Ser
1505 1510 1515 1520

```
Leu Ala Ala Ser Arg Ala Leu Leu Pro His Arg Ala Val Val Val Ala
                1525                1530                1535

Ala Asp Val Ala Gly Ala Arg Ala Ser Leu Ala Ala Leu Ala Ala Gly
            1540                1545                1550

Glu Pro Val Glu Gly Val Val Ser Gly Val Ala Gly Leu Pro Gly Glu
        1555                1560                1565

Gly Arg Val Val Phe Val Phe Pro Gly Gln Gly Ala Gln Trp Val Gly
    1570                1575                1580

Met Ala Val Asp Leu Leu Asp Ser Ser Pro Val Phe Ala Gly Arg Met
1585                1590                1595                1600

Ala Glu Cys Ala Val Ala Leu Glu Pro Phe Val Gly Trp Ser Leu Arg
                1605                1610                1615

Gly Val Leu Gly Asp Pro Val Ala Leu Glu Arg Val Asp Val Val Gln
            1620                1625                1630

Pro Val Leu Trp Ala Val Met Val Ser Leu Ala Glu Val Trp Arg Ser
        1635                1640                1645

Tyr Gly Val Val Pro Ser Ala Val Val Gly His Ser Gln Gly Glu Ile
    1650                1655                1660

Ala Ala Ala Cys Val Ala Gly Val Leu Ser Leu Ala Asp Gly Ala Arg
1665                1670                1675                1680

Ile Val Ala Leu Arg Ser Arg Leu Ile Ala Glu Arg Leu Ala Gly Arg
                1685                1690                1695

Gly Gly Met Val Ser Val Ala Leu Pro Glu Ala Thr Val Thr Arg Arg
            1700                1705                1710

Leu Ala Pro Trp Ser Gly Arg Val Cys Val Ala Ala Leu Asn Gly Pro
        1715                1720                1725

Ser Ser Val Val Leu Ser Gly Asp Pro Asp Ala Leu Asp Glu Val Met
    1730                1735                1740

Ala Ala Trp Ser Ala Asp Gly Val Arg Leu Arg Arg Ile Ala Val Asp
1745                1750                1755                1760

Tyr Ala Ser His Ser Ala His Val Glu Ser Leu Glu Ala Glu Leu Arg
                1765                1770                1775

Ala Ala Leu Ala Glu Leu Arg Pro Gly Glu Ala Gly Ile Ala Phe His
            1780                1785                1790

Ser Thr Leu Leu Gly Gly Pro Leu Gly Glu Thr Arg Leu Asp Ala Gly
        1795                1800                1805

Tyr Trp Tyr Arg Asn Leu Arg Glu Pro Val Arg Phe Glu Pro Val Val
    1810                1815                1820

Arg Gly Leu Leu Asp Ser Gly His Ala Val Phe Val Glu Ile Ser Pro
1825                1830                1835                1840

His Pro Val Leu Thr Ala Ala Val Gln Glu Thr Ala Glu Ala Thr Glu
                1845                1850                1855

Arg Thr Ala Val Val Val Gly Thr Leu Arg Arg Asp Glu Asp Gly Pro
            1860                1865                1870

Arg Arg Leu Leu Thr Ser Leu Ala Glu Ala Ala Val His Gly Val Ser
        1875                1880                1885

Val Asp Trp Thr Val Gly Cys Pro Asp Gly Arg His Val Asp Leu Pro
    1890                1895                1900

Thr Tyr Ala Phe Gln Arg Arg Arg Phe Trp Pro Ser Gly Pro Val Ala
1905                1910                1915                1920

Ser Asp Ala Ala Gly Leu Gly Leu Thr Gly Ala Gly His Pro Leu Leu
                1925                1930                1935
```

-continued

Gly Ala Val Thr Pro Leu Ala Gly Ser Gly Gly Gln Val Phe Thr Gly
1940 1945 1950

Arg Val Pro Ala Gly Thr Glu Leu Pro Ala Gly Ala Val Leu Asp Leu
1955 1960 1965

Ala Leu His Ala Ala Asp Gly Arg Thr Leu Gly Glu Leu Thr Glu Glu
1970 1975 1980

Ala Pro Leu Asp Thr Val Gly Glu Ala Arg Arg Leu Gln Val Thr Leu
1985 1990 1995 2000

Gly Ala Glu Asn Glu Asp Gly Ala Arg Pro Val Ala Val His Ser Arg
2005 2010 2015

Pro Ala Asp Ala Asp Asp Asp Gln Pro Trp Thr Arg His Ala Thr Gly
2020 2025 2030

Val Leu Leu Pro His Thr Gly Thr Ala Pro Ala Ala Ala Pro Gly Asp
2035 2040 2045

Pro Asp Thr Asp Val Thr Val Glu Leu Thr Asp Val Thr Val Glu Leu
2050 2055 2060

Thr Asp Glu Thr Ala Gly Gly Trp Gly Val His Pro Ala Leu Leu Thr
2065 2070 2075 2080

Asp Ala Leu Ala Ala Val His Pro Gly Leu Val Pro Gly Ala Trp His
2085 2090 2095

Gly Val Thr Leu His Ala Val Gly Ala Thr Arg Leu Arg Val Arg Leu
2100 2105 2110

His Pro Ala Gly Glu His Thr Val Thr Leu His Ala Thr Asp Asp Ser
2115 2120 2125

Gly Ala Ala Val Leu Thr Val Asp Ala Val Thr Leu Arg Pro Pro Ala
2130 2135 2140

Thr Ala Gly Pro Gly Arg Asp His Glu Leu Tyr Arg Val Glu Trp Thr
2145 2150 2155 2160

Pro Val Pro Leu Pro Ala Ala Asp Val Asp Gly Ile Ala Val Leu Gly
2165 2170 2175

Gly Leu Pro Leu Pro Gly Tyr Pro Ser Cys Pro Asp Leu Ala Ala Val
2180 2185 2190

Ala Ala Leu Asp Thr Val Pro Gly Thr Leu Val Leu Pro Cys Arg Gln
2195 2200 2205

Gln Ser Ala Asp Asp Thr Ala Gly Ala Ala His Ala Gly Ala Arg Arg
2210 2215 2220

Val Leu Thr Ala Leu Gln Glu Trp Leu Ala Asp Glu Arg Leu Ala Gly
2225 2230 2235 2240

Thr Arg Leu Ala Val Leu Thr His Gly Ala Val Pro Val Glu His Glu
2245 2250 2255

Asp Val Thr Asp Leu Ala His Ala Pro Val Trp Gly Leu Ile Arg Ser
2260 2265 2270

Ala Arg Ala Glu His Pro Gly Arg Leu Val Leu Val Asp Ile Asp Gly
2275 2280 2285

Pro Asp Ala Leu Gln Gln Leu Pro Ala Val Leu Ala Thr Gly Glu Pro
2290 2295 2300

Glu Ile Ala Val Arg Ser Gly Arg Val Leu Ala Pro Arg Leu Val Arg
2305 2310 2315 2320

Ala Pro Arg Thr Asp Glu Pro Thr Ser Gln Ala Ala Leu Trp Pro Ser
2325 2330 2335

Asp Gly Val Val Leu Val Thr Gly Gly Thr Gly Thr Leu Gly Ala Leu
2340 2345 2350

Cys Ala Arg His Leu Val Thr Glu His Gly Val Arg Arg Leu Val Leu

```
        2355                2360                2365

Ala Gly Arg Arg Gly Asp Ala Ala Pro Asp Ala Val Thr Leu Ala Gly
    2370                2375                2380

Glu Leu Arg Ala Leu Gly Ala Glu Val Thr Val Ala Ala Cys Asp Ala
2385                2390                2395                2400

Ala Asp Arg Thr Glu Leu Ala Ala Leu Leu Asp Arg Ile Thr Ala Glu
                2405                2410                2415

His Pro Leu Thr Gly Val Val His Ala Ala Gly Val Leu Asp Asp Gly
            2420                2425                2430

Val Ile Ala Ser Gln Thr Pro Glu Arg Leu Ala Lys Val Leu Arg Pro
        2435                2440                2445

Lys Val Asp Ala Ala Trp Asn Leu His Glu Leu Thr Ala Pro His Arg
    2450                2455                2460

Pro Ala Val Phe Val Leu Phe Ser Ser Thr Ser Gly Leu Phe Gly Ala
2465                2470                2475                2480

Pro Gly Gln Gly Asn Tyr Ala Ala Gly Asn Ala Phe Val Asp Ala Leu
                2485                2490                2495

Ala Ala His Arg Arg Ala Gln Gly Leu Pro Ala Thr Ser Gln Val Trp
            2500                2505                2510

Gly Leu Trp Ala His Ala Ser Gly Met Thr Gly His Leu Gly Gly Ala
        2515                2520                2525

Asp Leu Arg Arg Ala Ala Arg Asp Gly Val Val Pro Leu Pro Thr Pro
    2530                2535                2540

Asp Ala Leu Ala Leu Phe Asp Arg Ala Thr Ala Gly Ser Ala Pro Val
2545                2550                2555                2560

Val Val Pro Ala Trp Leu Asp Leu Thr Ser Phe Ala Thr Gly Val Thr
                2565                2570                2575

Ala Val Pro Ala Leu Met Arg Arg Leu Val Arg Gly Pro Val Arg Arg
            2580                2585                2590

Ala Ala Thr Ala Gly Ala Gly Pro Asp Thr Leu Ala Gly Lys Leu Thr
        2595                2600                2605

Gly Leu Thr Ala Ala Glu Arg Glu Arg Thr Leu Leu Thr Leu Val Arg
    2610                2615                2620

Ser His Ala Ala Val Val Leu Gly His Thr Asp Asp Thr Ala Val Thr
2625                2630                2635                2640

Pro Gly Arg Ala Phe Lys Glu Leu Gly Phe Asp Ser Leu Thr Ala Val
                2645                2650                2655

Glu Leu Arg Asn Arg Leu Ser Ala Ala Thr Gly Leu Arg Leu Pro Ala
            2660                2665                2670

Thr Leu Val Phe Asp His Pro Asn Pro Arg Ser Leu Ala Gly His Leu
        2675                2680                2685

Leu Ala Glu Leu Leu Gly Glu Arg Ala Glu Glu Thr Ala Pro Val Pro
    2690                2695                2700

Ala Val Ala Arg Pro Ala Asp Asp Asp Pro Ile Ala Ile Val Gly Met
2705                2710                2715                2720

Ala Cys Arg Tyr Pro Gly Gly Val Thr Ser Pro Glu Asp Leu Trp Arg
                2725                2730                2735

Leu Leu Ala Asp Glu Arg Asp Ala Leu Thr Pro Phe Pro Asp Asp Arg
            2740                2745                2750

Gly Trp Asp Leu Ala Gly Leu Phe His Pro Asp Pro Glu His Ala Gly
        2755                2760                2765

Thr Ser Tyr Val Arg Glu Gly Gly Phe Leu Ala Asp Val Ala Gly Phe
    2770                2775                2780
```

Asp Ala Asp Phe Phe Gly Ile Ser Pro Arg Glu Ala Leu Ala Met Asp
2785 2790 2795 2800

Pro Gln Gln Arg Leu Ala Leu Glu Thr Ala Trp Glu Ala Val Glu Arg
2805 2810 2815

Ala Gly Ile Asp Pro Lys Ser Leu Arg Gly Ala Asp Val Gly Val Tyr
2820 2825 2830

Leu Gly Thr Asn Gly Gln Asp Tyr Ala Gln Leu Val Arg Arg Thr Val
2835 2840 2845

Glu Ser Ala Glu Gly Tyr Val Gly Ile Gly Asn Ser Ala Ser Val Leu
2850 2855 2860

Ser Gly Arg Ile Ala Tyr Val Leu Gly Leu Glu Gly Pro Ala Val Thr
2865 2870 2875 2880

Val Asp Thr Ala Cys Ser Ala Ser Leu Val Ala Leu His Trp Ala Ile
2885 2890 2895

Gln Ala Leu Arg Ser Gly Glu Cys Ser Met Ala Leu Ala Gly Gly Val
2900 2905 2910

Thr Val Met Ser Ala Pro Asp Val Phe Val Asp Phe Ser Arg Gln Arg
2915 2920 2925

Gly Leu Ala Val Asp Gly Arg Cys Lys Ser Phe Ala Ala Ala Ala Asp
2930 2935 2940

Gly Thr Gly Trp Ser Glu Gly Ala Gly Met Leu Leu Val Glu Arg Leu
2945 2950 2955 2960

Ser Asp Ala Arg Arg His Gly His Gln Val Leu Ala Val Val Arg Gly
2965 2970 2975

Thr Ala Ile Asn Gln Asp Gly Ala Ser Asn Gly Leu Thr Ala Pro Asn
2980 2985 2990

Gly Pro Ser Gln Gln Arg Val Ile Arg Gln Ala Leu Ser Gly Ala Gly
2995 3000 3005

Leu Thr Pro Ala Asp Val Asp Ala Val Glu Ala His Gly Thr Gly Thr
3010 3015 3020

Arg Leu Gly Asp Pro Ile Glu Ala Gln Ala Leu Leu Ala Thr Tyr Gly
3025 3030 3035 3040

Gln Glu Arg Asp Glu Pro Leu Trp Leu Gly Ser Val Lys Ser Asn Ile
3045 3050 3055

Gly His Thr Gln Ala Ala Ala Gly Val Ala Gly Val Ile Lys Met Val
3060 3065 3070

Gln Ala Met Arg His Gly Thr Leu Pro Arg Thr Leu His Val Asp Glu
3075 3080 3085

Pro Ser Pro Glu Val Asp Trp Ala Ser Gly Ala Val Glu Leu Leu Thr
3090 3095 3100

Glu Ala Arg Glu Trp Ala Arg Ala Gly Arg Pro Arg Arg Ala Gly Val
3105 3110 3115 3120

Ser Ser Phe Gly Val Ser Gly Thr Asn Ala His Val Val Leu Glu Glu
3125 3130 3135

Ala Pro Glu Glu Thr Gly Arg Thr Ala Pro Ala Ala Leu Pro Ala Val
3140 3145 3150

Pro Trp Leu Leu Ser Ala Arg Ser Glu Thr Ala Leu Arg Gly Gln Val
3155 3160 3165

Glu Arg Leu Arg Ala Tyr Val Thr Glu His Pro Glu Ala Arg Pro Ala
3170 3175 3180

Asp Ile Gly Leu Ser Leu Leu Thr Ala Arg Ser Arg Phe Glu His Ser
3185 3190 3195 3200

-continued

Ala Val Val Val Gly Thr Asp His Asp Ala Leu Leu Ala Ala Leu Ala
3205 3210 3215

Asp Pro Glu Pro Leu His Ala Arg Asp Gly Leu Thr Ala Phe Val Phe
3220 3225 3230

Ala Gly Gln Gly Ala Gln Arg Val Gly Met Gly Ala Glu Leu Ala Ala
3235 3240 3245

Ala Tyr Pro Val Phe Ala Gln Val Phe Ala Gln Val Cys Ala Ala Phe
3250 3255 3260

Asp Gly Val Leu Glu Arg Pro Leu Gly Glu Val Val Ala Glu Gly Gly
3265 3270 3275 3280

Pro Glu Leu Asp Arg Thr Val Tyr Ala Gln Ala Gly Leu Phe Ala Phe
3285 3290 3295

Glu Val Ala Leu Phe Arg Leu Leu Glu Ser Trp Gly Val Ala Pro Asp
3300 3305 3310

Val Val Leu Gly His Ser Val Gly Glu Leu Thr Ala Ala Cys Val Ala
3315 3320 3325

Gly Val Trp Ser Leu Glu Asp Ala Val Arg Val Val Ala Ala Arg Gly
3330 3335 3340

Arg Leu Met Gln Ala Leu Pro Glu Gly Gly Ala Met Val Ala Leu Glu
3345 3350 3355 3360

Val Ser Ala Gly Glu Leu Glu Leu Pro Val Gly Val Glu Leu Ala Ala
3365 3370 3375

Val Asn Gly Pro Thr Ser Val Val Leu Ser Gly Glu Glu Glu Ala Val
3380 3385 3390

Leu Ala Glu Ala Ala Arg Trp Pro Asp Arg Arg Ala Lys Arg Leu Arg
3395 3400 3405

Val Ser His Ala Phe His Ser His Arg Met Asp Pro Met Leu Glu Asp
3410 3415 3420

Phe Arg Arg Val Leu Glu Ser Val Thr Phe Gln Ala Pro Glu Val Ala
3425 3430 3435 3440

Phe Val Ser Thr Val Thr Gly Ala Ala Val Thr Asp Glu Leu Cys Asp
3445 3450 3455

Pro Gly Tyr Trp Val Arg Asn Val Arg Glu Thr Val Arg Phe Ala Asp
3460 3465 3470

Ala Val Ala Ala Val Arg Ala Thr Gly Ala Asp Ala Leu Val Glu Ile
3475 3480 3485

Gly Pro Asp Ala Ala Leu Ala Pro Leu Ala Glu Gly Gly Val Pro Leu
3490 3495 3500

Leu Arg Arg Gly Arg Pro Glu Ala Val Ala Leu Val Glu Gly Leu Ala
3505 3510 3515 3520

Arg Ser Gln Met Ala Val Asp Trp Glu Lys Phe Phe Gly Ala Gly Val
3525 3530 3535

Ser Pro Val Asp Leu Pro Thr Tyr Pro Phe Gln His Ser Arg Phe Trp
3540 3545 3550

Pro Glu Val Pro Val Arg Ala Glu Ala Asp Pro Ala Ala Arg Trp Arg
3555 3560 3565

Tyr Arg Val Arg Trp Glu Pro Leu Arg Pro Ala Val Asp Ala Val Pro
3570 3575 3580

Ala Gly Arg Trp Leu Val Ala Val Pro Ala Ala Gly Ala Asp Ala Ala
3585 3590 3595 3600

Leu Val Arg Glu Cys Leu Lys Gly Leu Ala Gly Arg Gly Val Glu Val
3605 3610 3615

Ala Glu Leu Ala Val Ala Gly Ala Pro Asp Arg Ala Arg Leu Ala Glu 3620 3625 3630

Ala Val Ser Ala Thr Gly Pro Val Asp Gly Val Leu Ser Leu Leu Ala
3635 3640 3645

Ala Gly Pro Asp Ala Ala Ala Gly Thr Leu Val Leu Ala Gln Ala Leu
3650 3655 3660

Gly Asp Ala Gly Thr Asp Ala Pro Leu Trp Cys Val Thr Gly Gly Ala
3665 3670 3675 3680

Val Ala Ala Ala Asp Gly Glu Pro Ala Asp Pro Glu Gln Ala Gln Val
3685 3690 3695

Trp Gly Leu Gly Arg Val Leu Cys Leu Glu Ala Pro His Arg Trp Gly
3700 3705 3710

Gly Leu Val Asp Leu Pro Ala Glu Pro Asp Glu Gln Ala Val Val Gln
3715 3720 3725

Leu Cys Ala Val Leu Ala Gly His Asp Asp Glu Asp Gln Val Ala Val
3730 3735 3740

Arg Ala Ala Gly Val Phe Gly Arg Arg Leu Val Arg Pro Ala Thr Gly
3745 3750 3755 3760

Ala Ala Ala Glu Gly Trp Arg Pro Ser Gly Thr Val Leu Ile Thr Gly
3765 3770 3775

Gly Thr Gly Ala Leu Gly Gly His Thr Ala Arg Trp Ala Ala Arg Ser
3780 3785 3790

Gly Ala Gly Arg Val Val Leu Val Ser Arg Arg Gly Pro Asp Ala Asp
3795 3800 3805

Gly Ala Ala Glu Leu Val Ala Glu Leu Gly Glu Leu Gly Cys Gln Ala
3810 3815 3820

Val Ala Glu Ala Cys Asp Val Ala Asp Arg Ala Ala Leu Gly Ala Leu
3825 3830 3835 3840

Leu Asp Lys Ile Ala Ala Asp Gly Pro Pro Leu Thr Ala Val Val His
3845 3850 3855

Thr Ala Gly Val Leu Asp Asp Gly Val His Gly Ser Leu Thr Pro Glu
3860 3865 3870

Arg Leu Ala Thr Val Leu Arg Ala Lys Ala Asp Gly Ala Thr Ala Leu
3875 3880 3885

His Glu Leu Thr Ala His Leu Pro Leu Glu Ala Phe Val Leu Phe Ala
3890 3895 3900

Ala Leu Gly Gly Val Val Gly Gly Ala Gly Gln Ala Asn Tyr Ala Ala
3905 3910 3915 3920

Ala Asn Ala His Leu Asp Ala Leu Ala Ala Ser Arg Arg Ala Ala Gly
3925 3930 3935

Leu Pro Ala Thr Ala Val Ala Trp Gly Ala Trp Ala Gly Gly Gly Met
3940 3945 3950

Ala Asp Ala Asp Glu Val Arg Arg Arg Leu Asp Arg Asp Gly Leu Leu
3955 3960 3965

Pro Met Asp Pro Arg Arg Ala Leu Asp Ala Leu Gly Arg Glu Ile Ala
3970 3975 3980

Ala Gly Asp Pro Ala Val Val Leu Ala Asp Val Asp Trp Thr Arg Leu
3985 3990 3995 4000

Ala Pro Asn Leu His Ala Val Arg Pro Ser Pro Leu Ile Ser Thr Val
4005 4010 4015

Pro Glu Ala Arg Arg Ala Val Ala Pro Glu Pro Gly Thr Ala Gly Gly
4020 4025 4030

Glu Ser Asp Pro Arg Gln Arg Leu Ala Ala Leu Pro Asp Gly Glu Arg
4035 4040 4045

Ala Arg Val Leu Leu Asp Leu Val Arg Asp Ala Ile Ala Ala Val Leu
4050 4055 4060

Gly Tyr Gly Gly Pro Gly Ala Val Asp Ile Thr Arg Gly Leu Val Asp
4065 4070 4075 4080

Leu Gly Phe Asp Ser Leu Thr Ala Val Glu Leu Arg Asn Arg Leu Ala
4085 4090 4095

Arg Ala Thr Gly Leu Ala Leu Pro Leu Thr Leu Val Phe Asp His Pro
4100 4105 4110

Asp Gly Glu Ala Leu Ala Ala His Leu Ala Ala Ala Leu Ala Pro Ala
4115 4120 4125

Ala Asp Arg Pro Gln Thr Thr Asp Leu Asp Arg Phe Ala Arg Leu Asp
4130 4135 4140

Pro Ala Thr Ala Asp Glu Pro Thr Arg Val Arg Val Ala Ala Glu Leu
4145 4150 4155 4160

Arg Arg Leu Leu Asp Ala Trp Thr Pro Pro Pro Ala Ala Pro Ala Gly
4165 4170 4175

Ser Ala Gly Ser Ala Ala Asp Pro Ser Arg Leu Thr Thr Ala Ser Ala
4180 4185 4190

Asp Glu Ile Phe Asp Phe Ile Arg Asn Glu Leu Gly Lys Ser
4195 4200 4205

<210> SEQ ID NO 10
<211> LENGTH: 3628
<212> TYPE: PRT
<213> ORGANISM: Streptomyces flaveolus (Streptomyces sp.(DSM 9954))

<400> SEQUENCE: 10

Val Glu Asn Glu Asn Lys Leu Leu Asp His Leu Arg Trp Val Thr Gly
1 5 10 15

Glu Leu Ala Gln Ala Arg Gln Thr Leu Arg Glu Thr Ala Glu Arg Ala
20 25 30

Thr Glu Pro Ile Ala Ile Val Gly Met Ala Cys Arg Phe Pro Gly Gly
35 40 45

Val Ser Thr Pro Glu Asp Leu Trp Arg Leu Leu Ala Asp Glu Arg Asp
50 55 60

Ala Val Gly Glu Phe Pro Ala Asp Arg Gly Trp Asp Leu Ala Ser Leu
65 70 75 80

His His Pro Asp Pro Glu His Ala Gly Thr Ser Tyr Val Arg Glu Gly
85 90 95

Gly Phe Leu Ala Asp Val Ala Gly Phe Asp Ala Asp Phe Phe Gly Ile
100 105 110

Ser Pro Arg Glu Ala Leu Ala Met Asp Pro Gln Gln Arg Leu Ala Leu
115 120 125

Glu Thr Ala Trp Glu Ala Val Glu Arg Ala Gly Leu Asp Pro Lys Ser
130 135 140

Leu Arg Gly Ala Asp Val Gly Val Tyr Leu Gly Thr Asn Gly Gln Asp
145 150 155 160

Tyr Ile Ser Ala Ala Arg Pro Leu Leu His Gln Val Glu Gly His Gly
165 170 175

Gly Thr Gly Ile Ala Gly Ser Val Leu Ser Gly Arg Val Ala Tyr Thr
180 185 190

Leu Gly Leu Arg Gly Pro Ala Ala Thr Val Asp Thr Ala Cys Ser Ala
195 200 205

Ser Leu Val Ala Leu His Trp Ala Met Arg Ala Leu Arg Gly Gly Glu

```
    210                 215                 220

Cys Ala Met Ala Leu Ala Gly Gly Val Thr Val Met Ser Ser Pro Ala
225                 230                 235                 240

Thr Phe Val Glu Phe Ser Arg Gln Arg Gly Leu Ala Ser Asp Gly Arg
                245                 250                 255

Cys Lys Pro Phe Ala Ala Ala Ala Asp Gly Thr Gly Trp Gly Glu Gly
            260                 265                 270

Ala Gly Met Leu Leu Leu Glu Arg Leu Ser Asp Ala Arg Arg Leu Gly
        275                 280                 285

His Pro Val Leu Ala Val Leu Arg Gly Ser Ala Val Asn Gln Asp Gly
    290                 295                 300

Ala Ser Ser Ala Leu Thr Ala Pro Asn Gly Pro Ala Gln Val Arg Val
305                 310                 315                 320

Ile Gln Ala Ala Leu Ala Asp Ala Arg Leu Ala Pro Ala Asp Val Asp
                325                 330                 335

Leu Leu Glu Ala His Gly Thr Gly Thr Val Leu Gly Asp Pro Ile Glu
            340                 345                 350

Ala Gln Ala Leu Leu Thr Ala Tyr Gly Gln Asn Arg Thr Ala Pro Ala
        355                 360                 365

Trp Leu Gly Ser Val Lys Ser Asn Val Gly His Thr Gln Ala Ala Ala
    370                 375                 380

Gly Val Ala Gly Val Leu Lys Thr Val Leu Ala Leu Arg His Gly Val
385                 390                 395                 400

Leu Pro Arg Thr Leu His Val Asp Ala Pro Thr Pro Lys Val Asp Trp
                405                 410                 415

Ser Ala Gly Ala Val Arg Leu Leu Thr Glu Ala Arg Pro Trp Pro Ala
            420                 425                 430

Gly Glu Arg Pro Arg Arg Ala Gly Val Ser Ala Phe Gly Val Ser Gly
        435                 440                 445

Thr Asn Ala His Val Ile Val Glu Gln Ala Pro Glu Thr Ala Ala Glu
    450                 455                 460

Ala Ser Gly Ala Ala Gly Gly Pro Val Pro Trp Val Leu Ser Gly Arg
465                 470                 475                 480

Thr Glu Ser Ala Leu Arg Ala Gln Ala Ala Ala Leu Ala Ala His Leu
                485                 490                 495

Ala Glu Arg Pro Gly Asp Arg Pro Gly Asp Val Ala Leu Ser Leu Ala
            500                 505                 510

Thr Thr Arg Pro Ala Phe Glu His Arg Ala Val Val Val Gly Thr Asp
        515                 520                 525

Val Asp Asp Leu Leu Arg Gly Val Ala Ala Val Ala Ala Gly Glu Pro
    530                 535                 540

Thr Pro Gly Val Val Arg Gly Thr Ala Gly His Leu Gly Arg Ile Ala
545                 550                 555                 560

Phe Val Phe Pro Gly Gln Gly Ser Gln Trp Thr Gly Met Ala Arg Glu
                565                 570                 575

Leu Ala Asp Ala Ser Thr Glu Phe Ala Ala Arg Leu Asp Glu Cys Ala
            580                 585                 590

Ala Ala Leu Ala Pro His Val Asp Trp Ser Leu Arg Asp Val Leu Ala
        595                 600                 605

Asp Pro Ala Ala Leu Glu Arg Val Asp Val Val Gln Pro Ala Leu Trp
    610                 615                 620

Ala Val Met Val Ser Leu Ala Ala Leu Trp Gln Ala His Gly Val Glu
625                 630                 635                 640
```

```
Pro Ala Ala Val Val Gly His Ser Gln Gly Glu Ile Ala Ala Ala Cys
                645                 650                 655

Val Ala Gly Ala Leu Ser Leu Glu Asp Ala Ala Leu Leu Val Thr Ala
            660                 665                 670

Arg Ala Arg Ala Leu Arg Ala Leu Ile Gly Arg Gly Gly Met Val Ser
        675                 680                 685

Leu Pro Leu Pro Glu Ala Ala Ala Arg Glu Val Ile Ala Ala Trp Gly
    690                 695                 700

Asp Arg Leu Ser Val Ala Ala Val Asn Gly Pro Ala Ala Thr Val Val
705                 710                 715                 720

Ser Gly Asp Ala Ala Gly Leu Asp Glu Leu Leu Ala Gln Ala Glu Arg
                725                 730                 735

Asp Gly Leu Arg Ala Lys Arg Leu Pro Val Asp Tyr Ala Ser His Ser
            740                 745                 750

Ala His Val Glu Ala Val Arg Ala Glu Val Leu Ala Ala Thr Ala Ala
        755                 760                 765

Val Thr Pro Arg Ala Thr Gly Thr Ala Phe Val Ser Ser Val Thr Gly
    770                 775                 780

Gly Phe Leu Asp Thr Thr Gly Leu Asp Ala Ala Tyr Trp Tyr Arg Asn
785                 790                 795                 800

Leu Arg Glu Pro Val Arg Phe Asp Arg Ala Gly Arg Ala Leu Leu Asp
                805                 810                 815

Ala Gly Phe Thr Thr Phe Ile Glu Val Ser Ala His Pro Val Leu Thr
            820                 825                 830

Ala Ala Leu Gln Glu Ser Asp Pro Ala Val Leu Ala Val Gly Ser Leu
        835                 840                 845

Arg Arg Asp Asp Gly Gly Pro Ala Arg Phe Leu Ala Ser Leu Ala Glu
    850                 855                 860

Ala Ala Val Arg Gly Val Pro Val Asp Trp Arg Pro Ala Leu Thr Ala
865                 870                 875                 880

Ala Arg Thr Val Pro Leu Pro Thr Tyr Ala Phe Gln Arg Glu Arg Leu
                885                 890                 895

Trp Leu Glu Glu Asp Ala Gly Pro Ile Thr Pro Glu Arg Ala Arg Glu
            900                 905                 910

Asp Ser Ala Phe Trp Ala Ala Val His Gly Ser Ala Asp Asp Leu Ala
        915                 920                 925

Ala Val Leu Gly Ala Asp Pro Ala Ala Arg Glu Pro Ile Ala Ala Val
    930                 935                 940

His Pro Leu Leu Ala Ala Trp His Glu Arg Arg Ala Asp Glu Ser Ala
945                 950                 955                 960

Val Asp Ser Trp Arg Tyr Arg Val Asp Trp Thr Pro Leu Thr Ala Ser
                965                 970                 975

Pro Ser Ala Gly Ala Pro Thr Gly Arg Trp Leu Ala Val Ala Ala Asp
            980                 985                 990

Asp Pro Trp Ser Asp Ala Val Val Thr Ala Leu Ala Asp Arg Met Asp
        995                 1000                1005

Leu Thr Arg Val Pro Ala Tyr Asp Pro Gly Thr Val Ala Glu Leu Thr
    1010                1015                1020

Ala Gly Thr Ala Gly Val Val Ala Val Leu Arg Pro Asp Asp Pro Asp
1025                1030                1035                1040

Pro Leu Pro Gly Leu Leu Ala Leu Leu Arg Ala His Asp Arg Ala Asp
                1045                1050                1055
```

```
Gly Gly Leu Pro Leu Trp Cys Val Thr Arg Gly Ala Val Ala Thr Gly
            1060                1065                1070

Pro Ala Asp Thr Pro Ala Asp Pro Ala Thr Ala Gln Ile Trp Gly Phe
        1075                1080                1085

Gly Arg Val Ala Ala Leu Glu Arg Pro Gln Ser Trp Gly Gly Leu Ile
    1090                1095                1100

Asp Leu Pro Ala Gly Ala Thr Val Thr Gly Asp Ala Leu Ala Gly Thr
1105                1110                1115                1120

Ala Arg Ala Asp Gly Pro Pro Asp Ala Arg Ile Ala Asp Asp Val Leu
                1125                1130                1135

Gly Ala Arg Leu Ala Asp Arg Leu Val Ala Ala Leu Ala Gly Pro Glu
            1140                1145                1150

Asp Gln Val Ala Val Arg Ala Ser Gly Ala Phe Gly Arg Arg Leu Arg
        1155                1160                1165

Arg Ala Pro Ala Asp Gly Thr Thr Pro Asp Trp Arg Pro Thr Gly Thr
    1170                1175                1180

Ile Leu Val Thr Gly Gly Thr Gly Gly Leu Gly Gly His Val Ala Arg
1185                1190                1195                1200

Trp Leu Ala Arg Ala Gly Ala Glu His Leu Val Leu Thr Gly Arg Arg
                1205                1210                1215

Gly Pro Glu Ala Pro Gly Ala Ala Glu Leu Ala Ala Glu Leu Thr Ala
            1220                1225                1230

Leu Gly Ala Glu Val Asp Ile Val Ala Cys Asp Ala Ala Asp Arg Asp
        1235                1240                1245

Ala Leu Ala Arg Val Leu Ala Glu His Pro Val Asp Ala Val Phe His
    1250                1255                1260

Leu Ala Gly Ile Glu Arg Tyr Arg Pro Leu Asp Glu Leu Thr Pro Ala
1265                1270                1275                1280

Asp Leu Thr Glu Val Ala Ala Ala Lys Val Thr Gly Ala Leu Leu Leu
                1285                1290                1295

Asp Glu Leu Thr Arg Asp Arg Arg Leu Ser Ala Phe Val Leu Phe Thr
            1300                1305                1310

Ser Gly Ala Gly Val Trp Gly Ser Ser Gly Gln Ala Ala Tyr Ala Ala
        1315                1320                1325

Ala Asn Thr Arg Leu Asp Ala Leu Ala Ala Arg Arg Arg Ala Glu Gly
    1330                1335                1340

Leu Pro Ala Thr Ala Val Ala Trp Gly His Trp Asp Gly Ala Gly Met
1345                1350                1355                1360

Ser Asp Gly Pro Ala Arg Ala Gln Met Leu Arg Trp Gly Leu Pro Ala
                1365                1370                1375

Met Ala Pro His Arg Ala Val Ala Ala Leu Ala Gly Ala Leu Ala Arg
            1380                1385                1390

Asp Glu Ala Ser Leu Val Val Ala Asp Ile Asp Trp Pro Val Phe Ala
        1395                1400                1405

Pro Thr Phe Thr Leu Ala Arg Arg Ser Pro Leu Leu Ala Gly Leu Pro
    1410                1415                1420

Glu Ala Thr Asp Pro Ala Asp Thr Ala Pro Pro Pro Ala Ala Pro Ala
1425                1430                1435                1440

Gly Arg Leu Asp Arg Ala Ala Leu Leu Glu Leu Val Leu Ala Glu Thr
                1445                1450                1455

Gly Ala Val Leu Gly His Ala Ser Gly Thr Gly Leu Pro Ala Ala Arg
            1460                1465                1470

Ala Phe Gln Glu Leu Gly Phe Asp Ser Leu Thr Ala Val Glu Leu Arg
```

```
        1475                1480                1485

Asn Arg Leu Arg Asp Ala Thr Gly Leu Pro Leu Pro Ala Thr Leu Val
    1490                1495                1500

Phe Asp His Pro Thr Pro Gln Ala Leu Ala Glu Arg Leu Ala Gly Glu
1505                1510                1515                1520

Leu Thr Gly Glu Gln Pro Ala Asp Val Pro Asp Thr Thr Pro Ala Pro
                1525                1530                1535

Ala Ala Ala Ala Asp Asp Asp Pro Val Val Ile Val Gly Met Gly Cys
            1540                1545                1550

Arg Phe Pro Gly Gly Ala Asp Ser Pro Glu Arg Leu Trp Asp Leu Val
        1555                1560                1565

Ala Ala Gly Arg Asp Ala Met Thr Gly Phe Pro Ala Asp Arg Gly Trp
    1570                1575                1580

Asp Val Thr Asp Thr Gly Tyr Thr Lys Ala Gly Gly Phe Leu Asp Ala
1585                1590                1595                1600

Ala Gly Glu Phe Asp Ala Gly Phe Phe Gly Ile Ser Pro Arg Glu Ala
                1605                1610                1615

Thr Ser Met Asp Pro Gln Gln Arg Leu Leu Leu Glu Thr Ala Trp Glu
            1620                1625                1630

Thr Val Glu Arg Ala Gly Ile Asp Pro Ala Ser Leu Arg Gly Ser Arg
        1635                1640                1645

Thr Gly Val Phe Val Gly Tyr Gly Gly Gln Asp Tyr Leu Thr Ser Leu
    1650                1655                1660

Tyr Gly Thr Pro Glu Glu Leu Gln Gly His Leu Leu Thr Gly Thr Ser
1665                1670                1675                1680

Gly Ser Val Val Ser Gly Arg Leu Ala Tyr Val Leu Gly Leu Glu Gly
                1685                1690                1695

Pro Ala Val Thr Ile Asp Thr Ala Cys Ser Ser Ser Leu Val Ala Leu
            1700                1705                1710

His Trp Ala Ile Arg Ala Leu Arg Ser Gly Glu Cys Asp Leu Ala Leu
        1715                1720                1725

Ala Gly Gly Val Thr Val Met Ala Thr Pro Gly Val Phe Val Glu Phe
    1730                1735                1740

Gly Arg Gln Gly Gly Leu Ala Gly Asp Gly Arg Cys Lys Ala Phe Ala
1745                1750                1755                1760

Asp Ala Ala Asp Gly Thr Gly Trp Gly Glu Gly Ala Gly Leu Leu Leu
                1765                1770                1775

Val Glu Arg Leu Ser Asp Ala Arg Arg Asn Gly His Arg Val Leu Ala
            1780                1785                1790

Val Val Arg Gly Ser Ala Val Asn Ser Asp Gly Ala Ser Asn Gly Leu
        1795                1800                1805

Thr Ala Pro Asn Gly Pro Ser Gln Gln Arg Val Ile Arg Ala Ala Leu
    1810                1815                1820

Ala Asp Gly Gly Leu Thr Pro Ala Asp Ile Asp Ala Val Glu Ala His
1825                1830                1835                1840

Gly Thr Gly Thr Ala Leu Gly Asp Pro Ile Glu Ala Gln Ala Leu Gln
                1845                1850                1855

Val Val Tyr Gly Gln Asp Arg Glu Arg Pro Leu Trp Ile Gly Ser Val
            1860                1865                1870

Lys Ser Asn Leu Gly His Thr Gln Ala Ala Ser Gly Ala Ala Gly Leu
        1875                1880                1885

Ile Lys Thr Val Leu Ala Leu Arg His Gly Val Leu Pro Ala Thr Leu
    1890                1895                1900
```

His Val Asp Arg Pro Ser Ala Gln Val Asp Trp Thr Arg Gly Ala Val
1905 1910 1915 1920

Ser Val Leu Thr Glu Ser Thr Pro Trp Pro Gly Thr Asp Val Pro Arg
1925 1930 1935

Arg Ala Ala Val Ser Ser Phe Gly Val Ser Gly Thr Asn Ala His Val
1940 1945 1950

Val Leu Glu Gln Ala Pro Pro Ala Gly Glu Ala Gly Pro Ala Gly Asp
1955 1960 1965

Gly Gly Pro Val Pro Trp Leu Val Ser Gly Arg Thr Pro Glu Ala Val
1970 1975 1980

Arg Ala Gln Val Glu Arg Leu Arg Ala Ser Leu Ala Gly His Pro Asp
1985 1990 1995 2000

Pro Val Ala Val Ala Arg Ala Leu Ala Thr Thr Arg Thr Ala Phe Glu
2005 2010 2015

Tyr Arg Val Ala Ala Ala Gly Gly Asp Thr Glu Ala Leu Leu Asp Ala
2020 2025 2030

Leu Ala Glu Ala Arg Pro Val Thr Ala Arg Gln Gly Arg Thr Ala Phe
2035 2040 2045

Leu Cys Thr Gly Gln Gly Ala Gln Arg Ala Gly Met Gly Ala Gly Leu
2050 2055 2060

Tyr Ala Ala His Pro Val Tyr Ala Asp Ala Phe Asp Ala Val Cys Ala
2065 2070 2075 2080

Glu Phe Asp Arg Leu Leu Asp Arg Pro Leu Arg Asp Leu Val Leu Ser
2085 2090 2095

Gly Pro Ala Asp Val Leu Asp Arg Thr Ala Tyr Ala Gln Pro Ala Leu
2100 2105 2110

Phe Ala Val Glu Ala Ala Leu Ala Ala Leu Leu Arg His Trp Gly Val
2115 2120 2125

Thr Pro Asp Leu Leu Ala Gly His Ser Leu Gly Glu Ile Thr Ala Ala
2130 2135 2140

His Leu Ala Gly Val Leu Ser Leu Pro Asp Ala Ala Ala Leu Val Ala
2145 2150 2155 2160

Ala Arg Gly Arg Leu Met Asp Ala Leu Pro Ala Gly Gly Ala Met Val
2165 2170 2175

Ala Val Glu Ala Asp Glu Asp Arg Val Gln Pro Leu Leu Gly Asp Asp
2180 2185 2190

Val Cys Leu Ala Ala Val Asn Gly Pro Arg Ala Leu Val Leu Ser Gly
2195 2200 2205

Arg Glu Glu Ala Val Asp Gly Val Ala Ala Arg Leu Ala Ala Glu Gly
2210 2215 2220

Cys Arg Thr Arg Arg Leu Arg Val Ser His Ala Phe His Ser Ala Leu
2225 2230 2235 2240

Met Glu Pro Met Leu Asp Glu Phe Arg Ala Thr Val Ala Ala Leu Asp
2245 2250 2255

Leu Arg Ala Pro Ser Val Pro Val Val Ser Ala Leu Thr Gly Arg Pro
2260 2265 2270

Leu Thr Ala Asp Glu Ala Arg Ser Pro Glu His Trp Val Arg His Val
2275 2280 2285

Arg Glu Ala Val Arg Phe His Asp Ala Val Arg Gly Leu Ala Ala Glu
2290 2295 2300

Gly Ala Val Arg Tyr Leu Glu Leu Gly Pro Asp Gly Val Leu Thr Ala
2305 2310 2315 2320

-continued

```
Leu Ala Gln Ser Ser Leu Pro Pro Ala Asp Thr Asp Ala Asp Gly Arg
                2325                2330                2335

Asp Pro Leu Ala Val Pro Leu Leu Arg Ala Gly Arg Pro Glu Pro Glu
            2340                2345                2350

Thr Leu Thr Asp Ala Leu Ala Arg Ala Ala Ala Asp Gly Leu Thr Val
        2355                2360                2365

Asp Trp Ala Gly Tyr Phe Thr Gly Arg Gly Gly Ala Pro Val Glu Leu
    2370                2375                2380

Pro Thr Tyr Ala Phe Gln Arg Glu His Tyr Trp Leu Pro Val Asp Ser
2385                2390                2395                2400

Gly Ala Gly Thr Ala Pro Ala Gly His Pro Leu Leu Ser Ala Ala Val
                2405                2410                2415

Asp Leu Pro Asp Gly Gly Leu Val Leu Thr Gly Arg Leu Ser Pro Ala
            2420                2425                2430

Ala Arg Pro Trp Leu Ala Gln His Thr Val Arg Gly Ser Ala Leu Leu
        2435                2440                2445

Pro Gly Thr Ala Leu Leu Asp Leu Ala Leu Ala Ala Ala Gly Gln Ala
    2450                2455                2460

Ala Ala Pro Gly Val Ala Glu Leu Ile Leu Glu Ala Pro Leu Val Leu
2465                2470                2475                2480

Pro Ala Glu Gly Ala Val Glu Val Arg Val Thr Val Gly Ala Ala Gly
                2485                2490                2495

Thr Asp Gly Arg Arg Ala Ile Ala Leu His Thr Arg Ala Gly Asp Gly
            2500                2505                2510

Asp Trp Thr Arg His Ala Thr Gly Ala Leu Gly Glu Val Pro Gly Glu
        2515                2520                2525

Pro Thr Ala Ala Gly Ala Trp Pro Pro Pro Asp Ala Arg Pro Ala Asp
    2530                2535                2540

Leu Ala Ala Leu Tyr Gly Gly Leu Ala Asp Ala Gly Phe Gly Tyr Gly
2545                2550                2555                2560

Pro Ala Tyr Gln Gly Leu Arg Ala Ala Trp Arg Arg Gly Glu Gly Pro
                2565                2570                2575

Ala Ala Glu Val Phe Ala Glu Ala Glu Leu Pro Ala Ala Val Pro Asp
            2580                2585                2590

Ala Asp Arg Cys Pro Val His Pro Ala Leu Leu Asp Ala Val Leu His
        2595                2600                2605

Ala Ile Gly Val Gly Gly Leu Ile Thr Asp Pro Ala His Gly Gly Leu
    2610                2615                2620

Pro Phe Ala Trp Thr Gly Val Arg Val Phe Ala Pro Gly Ala Arg Ala
2625                2630                2635                2640

Val Arg Ala Arg Leu Ser Arg Ala Gly Ala Glu Gly Ala Leu Ala Val
                2645                2650                2655

Asp Leu Phe Asp Ala Asp Gly Leu Pro Val Ala Ala Ile Gly Ser Leu
            2660                2665                2670

Arg Leu Arg Pro Pro Ala Ala Pro Ala Val Pro Asp Ala Leu Phe Glu
        2675                2680                2685

Thr Ala Trp Thr Pro Val Glu Gln Gly Thr Ala Pro Ala Arg Arg Leu
    2690                2695                2700

Ala Leu Leu Gly Ala Asp Thr Ala Leu Ala Ala Gly Leu Thr Ala Ala
2705                2710                2715                2720

Gly Ala Ala Leu Ala Asp Ala Thr Asp Arg Ser Ala Glu Val Leu Val
                2725                2730                2735

Leu Pro Ile Val Thr Asp Pro Gly Ala Ala Pro Val Thr Glu Thr His
```

```
            2740                2745                2750

Arg Ala Thr Ala Ala Val Leu Thr Ala Leu Arg Asp Val Leu Ala Asp
        2755                2760                2765

Glu Glu Ser Thr Ala Arg Leu Ala Val Val Thr Arg Gly Ala Leu Ala
    2770                2775                2780

Leu Ser Ala Glu Glu Ser Pro Asp Pro Ala Ala Arg Ala Val Trp Gly
2785                2790                2795                2800

Leu Val Arg Ser Ala Gln Thr Glu His Pro Asp Arg Ile Val Leu Ala
                2805                2810                2815

Asp Leu Asp Ala Ala Asp Ala Ser Ala Arg Ala Leu Pro Ala Ala Leu
            2820                2825                2830

Thr Cys Gly Glu Pro Gln Leu Ala Val Arg Ser Gly Ala Val Ser Ala
        2835                2840                2845

Pro Arg Leu Thr Arg Ala Gly Ala Asp Ala Leu Val Leu Pro Asp Gly
    2850                2855                2860

Gly Trp Arg Leu Arg Pro Gly Ala Thr Gly Thr Val Asp Gly Met Thr
2865                2870                2875                2880

Ala Val Pro His Pro Asp Ala Pro Leu Ala Asp Gly Glu Val Arg Val
                2885                2890                2895

Ala Val Arg Ala Val Gly Val Thr Phe Arg Asp Val Leu Ser Val Leu
            2900                2905                2910

Gly Leu Tyr Pro Gly Ala Pro Gln Pro Leu Gly Ile Glu Ala Ala Gly
        2915                2920                2925

Val Val Thr Gly Thr Gly Pro Gly Val Ser Asp Leu Ala Pro Gly Asp
    2930                2935                2940

Arg Val Phe Gly Leu Leu Pro Gly Ser Met Gly Ser Ser Ala Val Ala
2945                2950                2955                2960

Asp Arg Arg Val Leu Ala Pro Val Pro Asp Gly Trp Gly Phe Thr Arg
                2965                2970                2975

Ala Ala Ser Val Pro Ser Ala Phe Leu Thr Ala Trp Phe Ala Leu Arg
            2980                2985                2990

Asp Val Ala Gly Val Arg Ala Gly Glu Arg Val Leu Val His Ala Ala
        2995                3000                3005

Ala Gly Gly Val Gly Met Ala Ala Val Arg Val Ala Arg Leu Leu Gly
    3010                3015                3020

Ala Glu Val Tyr Ala Thr Ala Ser Pro Gly Lys His Gly Val Leu Arg
3025                3030                3035                3040

Ala Ala Gly Leu Asp Glu Ala Arg Val Ala Ser Ser Arg Asp Thr Glu
                3045                3050                3055

Phe Ala Gln Arg Phe Pro Glu Met Asp Val Val Leu Asn Ser Leu Thr
            3060                3065                3070

Gly Glu Phe Val Asp Ala Ser Leu Arg Leu Leu Arg Pro Gly Gly Arg
        3075                3080                3085

Phe Val Glu Leu Gly Lys Thr Asp Leu Arg Thr Asp Thr Ala Gly Ile
    3090                3095                3100

Thr Tyr Arg Ala Val Asp Leu Ala Asp Ala Gly Pro Asp Arg Ile Gln
3105                3110                3115                3120

Glu Met Leu Thr Glu Leu Leu Asp Arg Leu Ala Ala Gly Asp Leu Ala
                3125                3130                3135

His Leu Pro Val Arg Ser Met Pro Met Gly Arg Ala Arg Glu Ala Phe
            3140                3145                3150

Arg Phe Met Ala Gln Ala Arg His Thr Gly Lys Leu Val Leu Thr Thr
        3155                3160                3165
```

Ala Pro Tyr Gly Asp Gly Thr Val Leu Val Thr Gly Gly Thr Gly Ala
3170 3175 3180

Leu Gly Gly Leu Val Ala Arg His Leu Val Thr Glu His Gly Ile Arg
3185 3190 3195 3200

Asp Leu Val Leu Val Gly Arg Gln Gly Ala Glu Pro Pro Val Thr Ala
3205 3210 3215

Glu Leu Arg Ala Ala Gly Ala Arg Val Arg Val Ala Ala Cys Asp Val
3220 3225 3230

Ser Asp Arg Ala Ala Leu Ala Ala Leu Leu Ala Asp Ile Glu Pro Pro
3235 3240 3245

Leu Thr Ala Val Val His Ala Ala Gly Val Leu Asp Asp Gly Thr Leu
3250 3255 3260

Thr Ser Leu Thr Pro Glu Arg Leu Ala Ala Val Leu Arg Pro Lys Ala
3265 3270 3275 3280

Asp Ala Ala Trp His Leu His Glu Leu Thr Glu Asp Arg Asp Leu Ser
3285 3290 3295

Ala Phe Val Leu Phe Ser Ser Ala Ala Gly Thr Phe Gly Ala Pro Gly
3300 3305 3310

Gln Gly Asn Tyr Ala Ala Ala Asn Ala Ala Leu Asp Ala Leu Ala Glu
3315 3320 3325

His Arg Arg Ser Arg Gly Leu Pro Ala Val Ser Leu Ala Trp Gly Pro
3330 3335 3340

Trp Ala Ala Glu Ser Ala Met Thr Gly Gly Leu Ser Ser Gly Asp Arg
3345 3350 3355 3360

Ala Arg Met Thr Arg Ala Gly Val Arg Pro Leu Ala Ala Thr Glu Ala
3365 3370 3375

Leu Ala Val Leu Asp Ala Ala Cys Arg Thr Gly Ala Gly Ala Leu Ala
3380 3385 3390

Ala Leu Arg Leu Asp Thr Ala Ala Leu Thr Ala Arg Thr Gly Ala Pro
3395 3400 3405

His Pro Leu Leu Arg Asp Leu Val Arg Arg Pro Ala Gly Pro Ala Arg
3410 3415 3420

Asp Asp Ala Asp Thr Gln Pro Ala Leu Pro Gln Arg Leu Ala Gly Leu
3425 3430 3435 3440

Gly Glu Glu Gln Arg Arg Arg Ala Val Leu Asp Val Val Arg Arg Asn
3445 3450 3455

Ala Ala Ala Val Leu Gly His Ala Arg Ala Ser Ala Val Asp Thr Ala
3460 3465 3470

Arg Gly Phe Leu Asp Leu Gly Phe Asp Ser Leu Thr Ala Val Glu Leu
3475 3480 3485

Arg Asn Arg Leu Thr Glu Ala Thr Gly Leu Arg Leu Ser Ala Thr Ala
3490 3495 3500

Val Phe Asp His Pro Thr Pro Ala Ala Leu Ala Arg His Leu Leu Thr
3505 3510 3515 3520

Glu Leu Glu Pro Leu Val Arg Ala Ala Arg Ser Ala Leu Pro Ser Ala
3525 3530 3535

Pro Asp Pro Asp Ala Asp Leu Arg Gly Ala Ile Ala Ala Ile Pro Leu
3540 3545 3550

Glu Arg Leu Arg Gln Ala Gly Leu Leu Asp Glu Leu Ala Arg Leu Ala
3555 3560 3565

Gly Val Ala Val Pro Ala Lys Asp Ala Pro Ala Glu Gln His Ala Ala
3570 3575 3580

```
Pro Asp Asp His Pro Asp Asp Pro Ala Asp Gly Pro Glu Asp Asp Gly
3585                3590                3595                3600

Ser Asp Asp Leu Met Asp Ala Leu Asp Asp Met Ser Ile Asp Asp Leu
                3605                3610                3615

Ile Arg Ile Ala His Asp Glu Arg Pro Arg Gly Asn
            3620                3625


<210> SEQ ID NO 11
<211> LENGTH: 8301
<212> TYPE: PRT
<213> ORGANISM: Streptomyces flaveolus (Streptomyces sp.(DSM 9954))

<400> SEQUENCE: 11

Met Ser Asn Thr Asn Glu Glu Leu Val Glu Ala Leu Arg Ser Ser Leu
1               5                   10                  15

Arg Glu Thr Glu Arg Leu Arg Arg His Asn Arg Ser Leu Thr Ala Ala
            20                  25                  30

Ala Asp Glu Pro Ile Ala Ile Val Gly Thr Ala Cys Arg Phe Pro Gly
        35                  40                  45

Gly Ile Asp Ser Pro Glu Arg Leu Trp Asp Ala Val Ala Ala Gly Ser
    50                  55                  60

Asp Leu Ile Thr Gly Phe Pro Asp Asp Arg Gly Trp Asp Leu Gly Val
65                  70                  75                  80

His Asp Pro Asp Pro Glu Arg Ala Gly Arg Ser Tyr Thr Asp Arg Gly
                85                  90                  95

Gly Phe Leu Thr Gly Ala Ala Asp Phe Asp Pro Ala Phe Phe Gly Ile
            100                 105                 110

Ser Pro Arg Glu Ala Arg Ala Met Asp Pro Gln Gln Arg Val Leu Leu
        115                 120                 125

Glu Thr Ala Trp Glu Ala Tyr Glu Gln Ala Gly Ile Asp Pro His Ala
    130                 135                 140

Gln Arg Gly Ser Arg Thr Gly Val Phe Val Gly Thr Trp Ser Gln Gly
145                 150                 155                 160

Tyr Gly Ile Gly Ala Arg Val Pro Glu Asp Ala Glu Gly Tyr Leu Val
                165                 170                 175

Thr Gly Gly Ala Thr Ala Val Val Ser Gly Arg Ile Ser Tyr Val Leu
            180                 185                 190

Gly Leu Glu Gly Pro Ala Val Thr Val Asp Thr Ala Cys Ser Ser Ser
        195                 200                 205

Leu Val Ala Leu His Trp Ala Val Arg Ser Leu Arg Ala Gly Glu Cys
    210                 215                 220

Ser Met Ala Leu Ala Gly Gly Val Thr Val Met Ala Gly Pro Gly Val
225                 230                 235                 240

Phe Val Glu Phe Ser Arg Glu Arg Gly Leu Ala Pro Asp Gly Arg Cys
                245                 250                 255

Lys Ala Tyr Ser Ala Asp Ala Asp Gly Thr Gly Trp Gly Glu Gly Val
            260                 265                 270

Gly Val Leu Leu Leu Glu Arg Leu Ser Asp Ala Val Arg Asn Gly His
        275                 280                 285

Arg Val Leu Ala Val Val Arg Gly Ser Ala Val Asn Ser Asp Gly Ala
    290                 295                 300

Ser Ser Gly Leu Thr Ala Pro Asn Gly Pro Ser Gln Gln Glu Val Ile
305                 310                 315                 320

Arg Gln Ala Leu Ala Asp Ala Arg Leu Thr Pro Ser Asp Val Asp Val
                325                 330                 335
```

```
Val Glu Gly His Gly Thr Gly Thr Arg Leu Gly Asp Pro Ile Glu Ala
            340                 345                 350

Gln Ala Leu Leu Ala Ala Tyr Gly Gln Asp Arg Pro Arg Pro Leu Leu
        355                 360                 365

Leu Gly Ser Val Lys Ser Asn Leu Gly His Thr Gln Ala Ala Ala Gly
    370                 375                 380

Val Ala Gly Val Ile Lys Met Val Glu Ala Met Arg Arg Gly Ile Ala
385                 390                 395                 400

Pro Arg Thr Leu His Ala Thr Glu Pro Thr Pro Gln Val Asp Trp Ser
                405                 410                 415

Arg Gly Ala Val Glu Leu Leu Thr Asp Asn Arg Ser Trp Pro Asp Thr
            420                 425                 430

Gly Ala Pro Arg Arg Ser Ala Val Ser Ala Phe Gly Val Ser Gly Thr
        435                 440                 445

Asn Ala His Ile Val Leu Glu Gln Ala Pro Glu Pro Ala Asp Thr Asp
    450                 455                 460

Thr Thr Pro Arg Thr Ala His Pro Val Val Pro Trp Leu Leu Ser Ala
465                 470                 475                 480

His Thr Pro Ala Ala Leu Arg Ala Gln Ala Glu Arg Leu Ser Ala Gly
                485                 490                 495

Leu Pro Asp Asp Ala Asp Pro Leu Asp Val Ala Ala Ala Leu Ala Thr
            500                 505                 510

Thr Arg Ala Ala Leu Pro Leu Arg Ala Ala Val Leu Gly Ala Asp Ala
        515                 520                 525

Thr Gln Leu Arg Ala Gly Leu Ala Ala Leu Ala Ala Gly Ala Pro Ala
    530                 535                 540

Ala Leu Ser Gly Glu Ala Arg Ser Asp Arg Thr Thr Ala Phe Leu Tyr
545                 550                 555                 560

Thr Gly Gln Gly Ala Gln Arg Ala Gly Met Gly Glu Glu Leu Ala Ala
                565                 570                 575

Ala Tyr Pro Ala Phe Ala Ala Ala Trp Thr Glu Val Cys Ala Glu Phe
            580                 585                 590

Asp Thr Val Leu Pro Arg Pro Leu Arg Gln Val Ile Thr Glu Gly Gly
        595                 600                 605

Pro Asp Leu Asp Arg Thr Leu Tyr Ala Gln Ala Ala Val Phe Ala Phe
    610                 615                 620

Glu Thr Ala Leu Thr Ala Leu Leu Gly Ser Trp Gly Ile Arg Pro Asp
625                 630                 635                 640

Leu Val Leu Gly His Ser Val Gly Glu Leu Ala Ala Ala His Thr Ala
                645                 650                 655

Gly Val Leu Ser Leu Arg His Ala Val Val Val Val Ala Ala Arg Gly
            660                 665                 670

Arg Leu Met Glu Ala Leu Pro Glu Gly Gly Ala Met Val Ala Val Gln
        675                 680                 685

Ala Ser Glu Asp Glu Ile Glu Leu Pro Glu Gly Val Ala Leu Ala Ala
    690                 695                 700

Val Asn Gly Pro Ser Ser Val Val Leu Ser Gly Asp Glu Ala Ala Val
705                 710                 715                 720

Leu Ala Thr Ala Ala His Trp Ala Glu Arg Gly Cys Arg Thr Lys Arg
                725                 730                 735

Leu Thr Val Ser His Ala Phe His Ser His Arg Met Asp Pro Val Leu
            740                 745                 750
```

```
Asn Gly Phe Arg Arg Val Leu Gly Ala Val Thr Leu Asn Thr Pro Arg
        755                 760                 765

Ile Pro Phe Val Ser Thr Val Thr Gly Ala Pro Val Glu Ala Gly Leu
    770                 775                 780

Arg Asp Pro Glu Tyr Trp Leu Arg Asn Val Arg Asp Thr Val Arg Phe
785                 790                 795                 800

Ala Asp Gly Val Arg Thr Leu Ala Asp Glu Gly Ala Asp Thr Phe Val
                805                 810                 815

Glu Val Gly Pro Asp Ala Val Leu Gly Ala Leu Val Ala Asp Ala Leu
            820                 825                 830

Pro Asp Asp Pro Asp Arg Pro Glu Ile Leu Ala Val Pro Thr Ala Arg
        835                 840                 845

Ala Asp Arg Pro Glu Pro Glu Thr Leu Val Gly Ala Leu Ala Arg Ile
    850                 855                 860

His Ala His Gly Ala His Val Asp Trp Ala Ala Phe Phe Gly Ser Gly
865                 870                 875                 880

Ala Arg Arg Val Asp Leu Pro Thr Tyr Ala Phe Gln His Gln His Tyr
                885                 890                 895

Trp Leu Ala Pro Ala Pro Ala Asp Asp Leu Pro Ala Ala Gly Leu Gly
            900                 905                 910

Thr Val Gly His Pro Leu Leu Arg Ala Ala Val Glu Leu Pro Ala Asp
        915                 920                 925

Ala Thr Ala Asp His Ala Ala Arg Pro Gly Ala Ala Gly Ala Val Val
    930                 935                 940

Phe Thr Gly Thr Leu Ser Ala His Thr His Pro Trp Leu Ala Asp His
945                 950                 955                 960

Ser Val Leu Gly Thr Pro Val Leu Pro Gly Thr Ala Leu Ala Glu Leu
                965                 970                 975

Ala Ala Ala Ala Gly Asp Arg Leu Gly Cys Ala Thr Val Ala Glu Leu
            980                 985                 990

Val Leu Thr Ala Pro Leu Ala Val Pro Ala Ser Gly Ala Val Arg Leu
        995                 1000                1005

Arg Val His Val Asp Ala Pro Asp Arg Asp Gly His Arg Ala Val Thr
    1010                1015                1020

Val Asp Ser Arg Pro Asp Asp Gln Leu Ala Asp Gly Ala Ala Trp Thr
1025                1030                1035                1040

Arg His Ala Thr Gly Arg Leu Ala Pro Thr Gly Pro Glu Pro Ala Gln
                1045                1050                1055

Ala Pro Thr Ala Trp Pro Pro Ala Asp Ala Glu Pro Leu Pro Val Asp
            1060                1065                1070

Gly Leu Tyr Asp Arg Leu Thr Ala Ala Gly Phe Gly Tyr Gly Pro Ala
        1075                1080                1085

Phe Arg Gly Val Arg Ala Ala Trp Arg Leu Gly Thr Asp Leu Leu Ala
    1090                1095                1100

Asp Val Glu Leu Pro Ala Asp Thr Asp Glu Ser Gly Phe Leu Leu His
1105                1110                1115                1120

Pro Ala Leu Phe Asp Ala Ala Leu His Ala Leu Gly Leu Gly Gly Leu
                1125                1130                1135

Val Glu His Gly Gly Leu Pro Phe Thr Trp Thr Gly Val Arg Leu His
            1140                1145                1150

Ala Thr Gly Ala Arg Ser Leu Arg Val Arg Leu Thr Pro Thr Gly Pro
        1155                1160                1165

Asp Ala Val Ala Leu Thr Ala Ala Asp Ala Thr Gly Arg Pro Val Val
```

```
    1170                1175                1180

Thr Val Thr Asp Leu Arg Leu Arg Pro Ala Thr Glu Val Arg Gly Thr
1185                1190                1195                1200

Thr Thr Ala Asp Ala Leu His His Ile Arg Trp Glu Pro Arg Pro Ala
                1205                1210                1215

Ala Ala Ala Thr Asp Val Thr Gly Thr Asp Phe Thr Val Phe Thr Leu
            1220                1225                1230

Pro Ala Ala Gly Ser Asp Pro Gln Ala Val Arg Glu Ala Thr Arg Ala
        1235                1240                1245

Ser Leu Ala Arg Leu Gln Glu His Leu Ala Ala Val Gly Pro Ala Gly
    1250                1255                1260

Pro Leu Val Val Val Thr His Gly Ala Val Ala Ala Glu Pro Gly Asp
1265                1270                1275                1280

Thr Val Pro Asp Leu Ala Gly Ala Ala Val Trp Gly Leu Val Arg Ser
                1285                1290                1295

Ala Gln Ser Glu His Pro Gly Arg Phe Val Leu Ile Asp Leu Ala Ala
            1300                1305                1310

Ser Glu Asp Ala Ala Val Val Pro Ala Ala Ile Ala Thr Gly Glu Pro
        1315                1320                1325

Gln Ile Ala Val Arg Asn Gly Ala Leu Tyr Ala Pro Arg Leu Val Arg
    1330                1335                1340

Gly Ala Ser Arg Pro Gly Gly Glu Val Pro Phe Gly Ala Gly Asp Val
1345                1350                1355                1360

Val Leu Val Thr Gly Gly Thr Gly Ala Leu Gly Arg Leu Val Ala Arg
                1365                1370                1375

His Leu Val Ala Glu His Gly Val Arg Arg Leu Val Leu Ala Ser Arg
            1380                1385                1390

Arg Gly Gly Ala Gly Glu Leu Val Ala Glu Leu Gly Glu Leu Gly Ala
        1395                1400                1405

Ala Val Asp Val Val Ala Cys Asp Val Ser Asp Arg Asp Ala Leu Glu
    1410                1415                1420

Arg Leu Val Ala Ala His Pro Leu Thr Gly Val Val His Ala Ala Gly
1425                1430                1435                1440

Val Leu Asp Asp Gly Thr Val Glu Ser Leu Thr Pro Asp Arg Val Asp
                1445                1450                1455

Gly Val Leu Arg Ala Lys Val Asp Gly Ala Trp His Leu His Glu Leu
            1460                1465                1470

Thr Ala Ala Leu Asp Leu Arg Ala Phe Val Leu Phe Ser Ser Leu Ala
        1475                1480                1485

Gly Val Val Gly Ser Ala Gly Gln Gly Gly Tyr Ala Ala Ala Asn Ala
    1490                1495                1500

Ala Leu Asp Ala Leu Ala Glu His Arg Arg Ala Glu Gly Leu Pro Ala
1505                1510                1515                1520

Thr Ser Ile Ala Trp Gly Pro Trp Thr Asp Gly Met Ala Ser Gly Leu
                1525                1530                1535

Asp Arg Val Asp Ala Ala Arg Leu Ala Arg Gly Gly Val Val Pro Phe
            1540                1545                1550

Ala His Ala Asp Gly Leu Glu Leu Phe Asp Ala Val Cys Ala Thr Asp
        1555                1560                1565

Ala Pro Leu Thr Val Ala Ala Arg Leu Asp Leu Ala Val Leu Arg Ala
    1570                1575                1580

Gln Ala Glu Ala Leu Pro Pro Val Leu Arg Gly Leu Val Pro Ala Pro
1585                1590                1595                1600
```

```
Ala Arg Arg Thr Ala Ala Ala Ala Arg Pro Gly Gly Phe Ala Glu Arg
                1605                1610                1615

Leu Ala Ala Leu Pro Glu Thr Glu Arg Arg Arg Ala Ala Leu Glu Leu
            1620                1625                1630

Val Arg Glu Thr Ala Ala Thr Val Leu Gly His Val Gly Pro Glu Ala
        1635                1640                1645

Val Ala Pro Asp Arg Ser Phe Leu Asp Leu Gly Phe Asp Ser Leu Ala
    1650                1655                1660

Ala Val Glu Leu Arg Asn Arg Leu Thr Ala Ala Thr Gly Leu Arg Leu
1665                1670                1675                1680

Ala Ala Thr Ile Thr Phe Asp His Pro Thr Ser Ala Ala Leu Ala Arg
                1685                1690                1695

His Leu Leu Asp Ala Ala Leu Asp Ala Gly Pro Ser Ala Thr Ser Gly
            1700                1705                1710

Ala His Leu Pro Ala Ala Thr Ala Val Arg Ala Asp Glu Pro Ile Ala
        1715                1720                1725

Ile Val Gly Met Ala Cys Arg Tyr Pro Gly Gly Val Thr Ser Pro Glu
    1730                1735                1740

Asp Leu Trp Arg Leu Val Leu Ala Gly Ala Asp Ala Val Thr Gly Phe
1745                1750                1755                1760

Pro Glu Asp Arg Gly Trp Asp Leu Thr Ser Val Tyr Asp Pro Asp Gln
                1765                1770                1775

Ser Arg Thr Gly Thr Ser Tyr Thr Arg Glu Gly Gly Phe Leu Thr Gly
            1780                1785                1790

Ala Ala Asp Phe Asp Ala Glu Phe Phe Gly Ile Ser Pro Arg Glu Ala
        1795                1800                1805

Leu Ala Met Asp Pro Gln Gln Arg Leu Leu Leu Glu Thr Ser Trp Glu
    1810                1815                1820

Ala Ile Glu Arg Ala Gly Ile Asp Pro Thr Ala Leu Arg Gly Ser Ala
1825                1830                1835                1840

Thr Gly Val Phe Ala Gly Leu Met Tyr His Asp Tyr Gly Ser Gly Thr
                1845                1850                1855

Gly Thr Leu Pro Glu Gly Val Glu Gly Tyr Leu Gly Leu Gly Thr Ala
            1860                1865                1870

Gly Ser Val Leu Ser Gly Arg Val Ala Tyr Thr Leu Gly Leu Glu Gly
        1875                1880                1885

Pro Ala Val Thr Val Asp Thr Ala Cys Ser Ser Ser Leu Val Ala Leu
    1890                1895                1900

His Trp Ala Ile Gln Ala Leu Arg Ser Gly Glu Cys Ser Met Ala Leu
1905                1910                1915                1920

Ala Gly Gly Val Thr Val Met Ala Thr Pro Gly Thr Phe Val Glu Phe
                1925                1930                1935

Ser Arg Gln Arg Gly Leu Ala Pro Asp Gly Arg Cys Lys Ser Phe Ala
            1940                1945                1950

Ala Ala Ala Asp Gly Val Gly Trp Ser Glu Gly Val Gly Met Leu Leu
        1955                1960                1965

Val Glu Arg Leu Ser Asp Ala Arg Arg Asn Gly His Gln Val Leu Ala
    1970                1975                1980

Val Val Arg Gly Ser Ala Val Asn Gln Asp Gly Ala Ser Asn Gly Leu
1985                1990                1995                2000

Thr Ala Pro Asn Gly Pro Ser Gln Gln Arg Val Ile Arg Gln Ala Leu
                2005                2010                2015
```

Gln Gly Ala Gly Leu Thr Thr Ala Asp Val Asp Ala Val Glu Ala His
2020 2025 2030

Gly Thr Gly Thr Lys Leu Gly Asp Pro Ile Glu Ala Gln Ala Leu Leu
2035 2040 2045

Ala Thr Tyr Gly Gln Glu Arg Asp Glu Pro Leu Trp Leu Gly Ser Val
2050 2055 2060

Lys Ser Asn Ile Gly His Thr Gln Ala Ala Ala Gly Val Ala Gly Val
2065 2070 2075 2080

Ile Lys Met Val Gln Ala Met Arg His Gly Thr Leu Pro Arg Thr Leu
2085 2090 2095

His Val Asp Glu Ala Ser Pro His Val Asp Trp Thr Ala Gly Ala Val
2100 2105 2110

Glu Leu Leu Thr Glu Glu Arg Glu Trp Thr Arg Thr Arg Arg Pro Arg
2115 2120 2125

Arg Ala Ala Val Ser Ser Phe Gly Val Ser Gly Thr Asn Ala His Val
2130 2135 2140

Val Leu Glu Glu Ala Pro Glu Glu Thr Ala Pro Pro Val Ser Ala Glu
2145 2150 2155 2160

Leu Pro Leu Val Pro Leu Leu Leu Ser Gly His Thr Ser Thr Ala Leu
2165 2170 2175

Ala Ala Gln Ala Arg Arg Leu His Asp His Leu Ala Glu Ser Gly Thr
2180 2185 2190

Pro Ala Leu Glu Thr Val Gly Arg Ser Leu Ala Ala Ser Arg Ala Leu
2195 2200 2205

Leu Pro His Arg Ala Val Val Val Ala Ala Asp Val Ala Gly Ala Arg
2210 2215 2220

Ala Ser Leu Ala Ala Leu Ala Ala Gly Glu Pro Val Glu Gly Val Val
2225 2230 2235 2240

Ser Gly Ala Ala Gly Leu Pro Gly Glu Gly Arg Val Val Phe Val Phe
2245 2250 2255

Pro Gly Gln Gly Ala Gln Trp Val Gly Met Ala Val Asp Leu Leu Asp
2260 2265 2270

Ser Ser Pro Val Phe Ala Gly Arg Met Ala Glu Cys Ala Val Ala Leu
2275 2280 2285

Glu Pro Phe Val Glu Trp Ser Leu Arg Gly Val Leu Gly Asp Pro Val
2290 2295 2300

Ala Leu Glu Arg Val Asp Val Val Gln Pro Val Leu Trp Ala Val Met
2305 2310 2315 2320

Val Ser Leu Ala Glu Val Trp Arg Ser Tyr Gly Val Val Pro Ser Ala
2325 2330 2335

Val Val Gly His Ser Gln Gly Glu Ile Ala Ala Ala Cys Val Ala Gly
2340 2345 2350

Val Leu Ser Leu Ala Asp Gly Ala Arg Val Val Ala Leu Arg Ser Arg
2355 2360 2365

Ala Leu Thr Ala Leu Ala Gly Ser Gly Gly Met Val Ser Val Ala Ala
2370 2375 2380

Gly Pro Ser Gly Val Glu Glu Leu Leu Val Gly Trp Ala Gly Arg Leu
2385 2390 2395 2400

Ala Val Ala Ala Val Asn Gly Pro Glu Ser Val Val Val Ala Gly Glu
2405 2410 2415

Gly Val Ala Leu Glu Glu Phe Leu Ala His Cys Gly Gly Arg Gly Val
2420 2425 2430

Arg Ala Arg Arg Ile Ala Val Asp Tyr Ala Ser His Ser Val Leu Val

-continued

```
        2435                2440                2445

Glu Pro Val Arg Glu Ala Leu Leu Ala Asp Leu Glu Gly Val Arg Pro
    2450                2455                2460

Gly Glu Gly Thr Val Pro Leu Phe Ser Thr Val Thr Gly Glu Trp Ala
2465                2470                2475                2480

Asp Gly Thr Ala Leu Asp Ala Gly Tyr Trp Tyr Arg Asn Leu Arg Glu
                2485                2490                2495

Pro Val Gly Phe Glu Pro Ala Val Arg Gly Leu Leu Asp Ser Gly His
            2500                2505                2510

Ala Val Phe Val Glu Ile Ser Pro His Pro Val Leu Thr Ala Ala Val
        2515                2520                2525

Gln Glu Thr Ala Asp Ala Thr Glu Arg Thr Ala Val Val Val Gly Thr
    2530                2535                2540

Leu Arg Arg Asp His Glu Gly Gln Arg Gln Leu Leu Thr His Leu Gly
2545                2550                2555                2560

Val Leu His Thr Thr Gly Ala Asp Ile Asp Trp Thr Gly Cys Phe Thr
                2565                2570                2575

Gly Val Thr Gly Arg Ala Asp Leu Pro Thr Tyr Ala Phe Gln His Thr
            2580                2585                2590

Arg Tyr Trp Leu Thr Pro Ser Gly Pro Ser Ala Gly Glu Leu Ala Gly
        2595                2600                2605

Ala Gly Leu Thr Ala Ala Gly His Pro Leu Leu Gly Ala Ala Val Asp
    2610                2615                2620

Leu Ala Glu Asp Gly Gly Leu Val Leu Thr Gly Arg Leu Ala Ala Asp
2625                2630                2635                2640

Pro Ala Ala Trp Thr Ala Asp His Val Val Leu Gly Thr Thr Leu Leu
                2645                2650                2655

Pro Gly Ala Ala Leu Ala Glu Leu Ala Leu Ala Ala Gly Asp Gly Val
            2660                2665                2670

Gly Cys Gly Thr Leu Asp Glu Leu Val Leu Gly Ala Pro Leu Ala Leu
        2675                2680                2685

Pro Glu Arg Gly Ala Leu His Leu Gln Val Arg Val Gly Arg Ala Glu
    2690                2695                2700

Ala Asp His Arg Arg Thr Val Ser Val His Ala Arg Pro Glu Asp Gly
2705                2710                2715                2720

Asp Ala Pro Trp Thr Arg His Ala Glu Gly Val Leu Val Pro Gly Asp
                2725                2730                2735

Thr Ala Ala Gly Thr Pro Leu Thr Glu Trp Pro Pro Ala Asp Ala Glu
            2740                2745                2750

Pro Val Asp Val Ser Ala Leu Tyr Asp Ser Leu Ala Asp Arg Gly Leu
        2755                2760                2765

Asp Tyr Gly Pro Val Phe Arg Gly Val Arg Ala Ala Trp Arg His Gly
    2770                2775                2780

Asp Asp Ile Leu Ala Glu Val Glu Leu Pro Ala Glu Ala Asp Glu Ser
2785                2790                2795                2800

Gly Phe Leu Leu His Pro Ala Leu Leu Asp Ala Ala Leu His Pro Ile
                2805                2810                2815

Gly Leu Gly Gly Leu Val Gly Asp Gly Gly Leu Pro Phe Ala Trp His
            2820                2825                2830

Gly Leu Arg Val His Ala Val Gly Ala Arg Ala Ala Arg Val Arg Leu
        2835                2840                2845

Thr Pro Leu Gly Asp Glu Thr Val Ala Val Asp Leu Ala Asp Gly Ala
    2850                2855                2860
```

```
Gly Ala Pro Leu Ala Ala Ile Val Ser Leu Arg Leu Arg Ala Val Thr
2865                2870                2875                2880

Ala Ala Gln Val Ala Ala Ala Arg Thr Leu Thr Asp Pro Ala Leu His
                2885                2890                2895

Leu Asp Trp Leu Pro Val Ala Gly Ala Ala Ser Ala Pro Ser Asp Asp
            2900                2905                2910

Thr Ala Val Glu Leu Leu Arg Leu Asp Asp Ala Pro His Gly Thr Asp
        2915                2920                2925

Ala Gly Pro Gly Gly Val Arg Gln Ala Val Arg Thr Ala Leu Thr Ala
    2930                2935                2940

Ile Gln Glu Arg Ile Ala Asp Asp Arg Ala Glu Arg Leu Val Val Val
2945                2950                2955                2960

Thr Arg Asp Thr Asp Leu Ala Gly Ala Ala Val Gly Gly Leu Leu Arg
                2965                2970                2975

Ser Ala Gln Ala Glu His Pro Gly Arg Phe Gly His Val Val Leu Asp
            2980                2985                2990

Gly His Pro Asp Ser Glu Arg Ala Leu Pro Thr Ala Thr Ala Leu Thr
        2995                3000                3005

Asp Glu Pro Trp Val Ala Val Arg Ala Gly Glu Thr Tyr Val Pro Arg
    3010                3015                3020

Leu Ala Arg Ser Gly Ala Arg Pro Gly Gly Asp Val Pro Phe Gly Ala
3025                3030                3035                3040

Asp Asp Val Val Leu Val Thr Gly Gly Thr Gly Val Leu Gly Ala Leu
                3045                3050                3055

Val Ala Arg His Leu Val Thr Glu His Gly Val Arg Arg Leu Val Leu
            3060                3065                3070

Ala Ser Arg Arg Gly Gly Ala Gly Glu Leu Val Ala Glu Leu Gly Glu
        3075                3080                3085

Leu Gly Ala Ala Val Asp Val Val Ala Cys Asp Val Ser Asp Arg Glu
    3090                3095                3100

Ala Leu Glu Arg Leu Val Ala Ala His Pro Leu Thr Gly Val Val His
3105                3110                3115                3120

Ala Ala Gly Val Leu Asp Asp Gly Thr Val Glu Ser Leu Thr Pro Asp
                3125                3130                3135

Arg Val Asp Gly Val Leu Arg Ala Lys Val Asp Gly Ala Trp His Leu
            3140                3145                3150

His Glu Leu Thr Ala Ala Leu Asp Leu Arg Ala Phe Val Leu Phe Ser
        3155                3160                3165

Ser Leu Ala Gly Val Val Gly Ser Ala Gly Gln Gly Gly Tyr Ala Ala
    3170                3175                3180

Ala Asn Ala Ala Leu Asp Ala Leu Ala Glu Tyr Arg Arg Ala Glu Gly
3185                3190                3195                3200

Leu Pro Ala Thr Ser Ile Ala Trp Gly Leu Trp Ala Pro Ala Ser Ala
                3205                3210                3215

Met Thr Ser Gly Ala Asp Thr Ala Arg Leu Ala Arg Ser Gly Ile Leu
            3220                3225                3230

Pro Leu Pro Ala Asp Arg Ala Leu Glu Leu Phe Asp Thr Ala Cys Ala
        3235                3240                3245

Ala Glu Thr Pro Leu Thr Val Ala Ala Arg Leu Asp Leu Thr Ala Phe
    3250                3255                3260

Arg Ala Gln Gly Thr Arg Met Pro Val Val Leu Arg Ser Leu Ala Gly
3265                3270                3275                3280
```

-continued

```
Pro Ala Ala Arg Arg Thr Ala Arg Ala Gly Asp Ala Gly Thr Leu Arg
                3285                3290                3295

Asp Arg Leu Ala Ala Gln Thr Pro Ala Glu Arg Thr Arg Thr Val Leu
            3300                3305                3310

Asp Leu Val Arg Gly Gln Ala Ala Ala Val Leu Gly His Glu Ser Ala
        3315                3320                3325

Ala Ala Ile Ala Glu Asp Arg Ala Phe Leu Glu Leu Gly Phe Asp Ser
    3330                3335                3340

Leu Thr Ala Val Asp Leu Arg Asn Arg Leu Gly Thr Val Thr Gly Leu
3345                3350                3355                3360

Arg Leu Pro Thr Thr Thr Val Phe Asp His Pro Asn Pro Ala Ala Leu
                3365                3370                3375

Thr Arg His Ile Leu Ala Glu Leu Leu Gly Ala Thr Ala Gly Ser Ala
            3380                3385                3390

Gln Ala Ala Pro Thr Ala Val Arg Thr Asp Glu Pro Ile Ala Ile Val
        3395                3400                3405

Gly Met Ala Cys Arg Tyr Pro Gly Gly Val Ala Ser Pro Glu Asp Leu
    3410                3415                3420

Trp Arg Val Val Ala Glu Gly Arg Asp Val Ile Ser Pro Phe Pro Glu
3425                3430                3435                3440

Asp Arg Gly Trp Asp Leu Gly Ala Leu Tyr His Ala Asp Pro Asp His
                3445                3450                3455

Thr Gly Thr Ser Tyr Ala Arg Glu Gly Gly Phe Leu His Asp Ala Ala
            3460                3465                3470

Gly Phe Asp Ala Glu Phe Phe Gly Ile Ser Pro Arg Glu Ala Leu Ala
        3475                3480                3485

Met Asp Pro Gln Gln Arg Leu Leu Leu Glu Ala Ser Trp Glu Ala Ile
    3490                3495                3500

Glu Arg Ala Gly Ile Asp Pro Thr Ala Leu Arg Gly Ser Ala Thr Gly
3505                3510                3515                3520

Val Phe Ala Gly Leu Met Tyr His Asp Tyr Ala Ala Arg Leu Gly Thr
                3525                3530                3535

Thr Pro Glu Gly Leu Glu Gly Tyr Leu Gly Met Gly Asn Ser Gly Ser
            3540                3545                3550

Val Ala Ser Gly Arg Ile Ser Tyr Thr Leu Gly Leu Glu Gly Pro Ala
        3555                3560                3565

Val Thr Val Asp Thr Ala Cys Ser Ser Ser Leu Val Ala Leu His Trp
    3570                3575                3580

Ala Ile Gln Ala Leu Arg Ser Gly Glu Cys Asp Leu Ala Leu Ala Gly
3585                3590                3595                3600

Gly Val Ser Val Met Ala Thr Pro Gly Thr Phe Val Glu Phe Ser Arg
                3605                3610                3615

Gln Arg Gly Leu Ala Pro Asp Gly Arg Cys Lys Ser Phe Ala Ala Ala
            3620                3625                3630

Ala Asp Gly Ala Ser Trp Ser Glu Gly Val Gly Met Leu Leu Val Glu
        3635                3640                3645

Arg Leu Ser Asp Ala Arg Arg Asn Gly His Arg Val Leu Ala Val Val
    3650                3655                3660

Arg Gly Ser Ala Val Asn Gln Asp Gly Ala Ser Asn Gly Leu Thr Ala
3665                3670                3675                3680

Pro Asn Gly Pro Ser Gln Gln Arg Val Ile Arg Gln Ala Leu Ala Gly
                3685                3690                3695

Ala Gly Leu Thr Ser Ala Asp Val Asp Ala Val Glu Ala His Gly Thr
```

```
            3700                3705                3710

Gly Thr Arg Leu Gly Asp Pro Ile Glu Ala Gln Ala Leu Leu Ala Thr
        3715                3720                3725

Tyr Gly Gln Glu Arg Asp Glu Pro Leu Trp Leu Gly Ser Val Lys Ser
    3730                3735                3740

Asn Ile Gly His Ala Gln Ala Ala Ala Gly Val Ala Gly Val Ile Lys
3745                3750                3755                3760

Met Val Gln Ala Met Arg Asn Gly Val Leu Pro Arg Thr Leu His Val
                3765                3770                3775

Asp Glu Pro Ser Pro His Val Asp Trp Thr Val Gly Ala Val Glu Leu
            3780                3785                3790

Leu Thr Gly Glu Gln Glu Trp Pro Arg Gln Asp Arg Pro Arg Arg Ala
        3795                3800                3805

Gly Val Ser Ser Phe Gly Val Ser Gly Thr Asn Ala His Val Val Leu
    3810                3815                3820

Glu Glu Ala Pro Glu Glu Thr Glu Gly Thr Ala Pro Ala Ala Leu Pro
3825                3830                3835                3840

Ala Val Pro Trp Val Val Ser Ala Arg Ser Glu Thr Ala Leu Arg Ala
                3845                3850                3855

Gln Ala Ala Arg Leu Ala Asp Trp Leu His Gly Asp Thr Asp Val Leu
            3860                3865                3870

Gly Thr Ala Tyr Ser Leu Ala Thr Gly Arg Ala Ala Leu Pro His Arg
        3875                3880                3885

Ala Val Val Val Gly Thr Asp Arg Ala Glu Leu Ser Asp Gly Leu Ala
    3890                3895                3900

Ala Leu Ala Ala Gly Arg Ala Ala Ala His Val Glu Ser Gly Arg Ala
3905                3910                3915                3920

Arg Asp Asn Arg Val Thr Ala Phe Val Phe Ala Gly Gln Gly Ala Gln
                3925                3930                3935

Arg Ala Gly Met Gly Ala Glu Leu Ala Ala Ala Tyr Pro Val Phe Ala
            3940                3945                3950

Gln Val Phe Ala Gln Val Cys Ala Ala Phe Asp Gly Val Leu Glu Arg
        3955                3960                3965

Pro Leu Gly Glu Val Ile Ala Glu Gly Gly Pro Glu Leu Asp Arg Thr
    3970                3975                3980

Val Tyr Ala Gln Ala Gly Leu Phe Ala Phe Glu Val Ala Leu Phe Arg
3985                3990                3995                4000

Leu Leu Glu Ser Trp Gly Val Ala Pro Asp Val Val Leu Gly His Ser
                4005                4010                4015

Val Gly Glu Leu Ala Ala Ala Cys Val Ala Gly Val Trp Ser Leu Glu
            4020                4025                4030

Asp Ala Val Arg Val Val Ala Ala Arg Gly Arg Leu Met Gln Ala Leu
        4035                4040                4045

Pro Gln Gly Gly Ala Met Val Ala Leu Glu Val Ser Ala Gly Glu Leu
    4050                4055                4060

Glu Leu Pro Glu Gly Val Glu Leu Ala Ala Val Asn Gly Pro Ser Ser
4065                4070                4075                4080

Val Val Leu Ser Gly Glu Glu Glu Ala Val Leu Ala Glu Ala Ala Arg
                4085                4090                4095

Trp Pro Asp Arg Arg Ala Lys Arg Leu Arg Val Ser His Ala Phe His
            4100                4105                4110

Ser Arg Arg Met Asp Pro Met Leu Glu Asp Phe Arg Arg Val Leu Glu
        4115                4120                4125
```

```
Ser Val Ala Phe His Ala Pro Glu Leu Val Phe Val Ser Thr Val Thr
    4130                4135                4140

Gly Ala Val Val Thr Asp Glu Leu Cys Asp Pro Gly Tyr Trp Val Arg
4145                4150                4155                4160

Asn Val Arg Glu Thr Val Arg Phe Ala Asp Ala Val Val Ala Ala Glu
                4165                4170                4175

Ala Gly Val Phe Val Glu Leu Ala Pro Asp Ala Val Leu Ser Gly Leu
            4180                4185                4190

Val Gly Glu Ser Val Glu Gly Val Leu Cys Val Pro Ala Gln Arg Ala
        4195                4200                4205

Gly Arg Pro Ala Ala Arg Val Leu Val Ser Ala Leu Gly Thr Leu His
    4210                4215                4220

Thr His Gly Val Asp Val Ala Trp Gly Arg Phe Phe Ala Gly Ser Gly
4225                4230                4235                4240

Ala Arg Arg Val Asp Leu Pro Thr Tyr Ala Phe Gln Arg Glu Arg Tyr
                4245                4250                4255

Trp Leu Asp Ala Pro Ala Pro Gln Thr Gly Gly Ala Ser Asp Asp Ala
            4260                4265                4270

Phe Trp Ala Ala Val Gln Ser Gly Asp Leu Ala Gly Leu Leu Gly Val
        4275                4280                4285

Ala Glu Asp Ala Gly Leu Asp Ala Val Leu Pro Thr Leu Ala Ser Trp
    4290                4295                4300

His Asp Arg Glu Arg Ala Asp Ala Val Val Asp Gly Trp Arg His Lys
4305                4310                4315                4320

Val Arg Trp Thr Pro Leu Pro Glu Ala Gly Gly Ala Val Leu Ser Gly
                4325                4330                4335

Arg Trp Leu Leu Val Gly Pro Glu Gly Asp Glu Ala Leu Val Ala Asp
            4340                4345                4350

Val Ala Thr Ala Leu Arg Glu His Gly Ala Glu Val Thr His Leu Ala
        4355                4360                4365

Leu Pro Arg Asp Ala Asp Arg Glu Thr Thr Ala Glu Leu Leu Arg Gly
    4370                4375                4380

Thr Asp Asp Thr Gly Leu Thr Ala Val Leu Ser Leu Leu Ala Arg Ala
4385                4390                4395                4400

Asp Arg Pro Val His Ala Thr Leu Ala Leu Val Gln Ala Leu Gly Asp
                4405                4410                4415

Ala Glu Val Thr Val Pro Leu Trp Cys Ala Thr Ser Glu Ser Val Ala
            4420                4425                4430

Val Ala Ser Thr Asp Val Val Pro Glu Ala Ala Val Asp Ala Ala Gly
        4435                4440                4445

Leu Trp Gly Leu Gly Arg Val Val Arg Leu Glu Ala Pro Asp Arg Trp
    4450                4455                4460

Gly Gly Leu Val Asp Leu Pro Gly Ala Leu Asp Ala Arg Ala Arg Arg
4465                4470                4475                4480

Arg Leu Ala Ala Val Leu Ala Gly Ala Glu Asp Glu Cys Ala Val Arg
                4485                4490                4495

Glu Asn Gly Ala Phe Ala Ala Arg Leu Val Arg Ala Ala Asp Ala Pro
            4500                4505                4510

Arg Arg Glu Trp Arg Pro Gln Gly Thr Val Leu Val Thr Gly Gly Thr
        4515                4520                4525

Gly Ala Leu Gly Ala Arg Val Ala Gln Arg Leu Ala Glu Arg Gly Ala
    4530                4535                4540
```

Arg His Val Leu Leu Val Ser Arg Arg Gly Pro Ala Ala Asp Gly Ala
4545 4550 4555 4560

Ala Glu Leu Val Arg Ala Ile Glu Ala Ala Gly Ala Thr Ala Thr Val
4565 4570 4575

Ala Ala Cys Asp Val Ala Asp Pro Glu Ala Val Ala Ala Leu Leu Glu
4580 4585 4590

Arg Ile Pro Ala Asp Ala Pro Leu Thr Ala Val Val His Thr Ala Ser
4595 4600 4605

Val Leu Ala Asp Ala Pro Leu Asp Thr Leu Thr Pro Asp Arg Ile Thr
4610 4615 4620

Ala Val Leu Arg Ala Lys Ala Asp Ala Ala Arg Ile Leu His Thr Ala
4625 4630 4635 4640

Thr Ala Ser Leu Asp Leu Asp Ala Phe Val Leu Phe Ser Ser Leu Ala
4645 4650 4655

Gly Thr Leu Gly Asn Pro Gly Gln Ala Ala Tyr Ala Ala Ala Asn Ala
4660 4665 4670

Val Leu Asp Thr Leu Ala Ala His Arg Arg Ala Leu Gly Leu Pro Gly
4675 4680 4685

Thr Ala Val Ala Trp Gly Pro Trp Ala Gly Gly Gly Met Leu Asp Asp
4690 4695 4700

Thr Val Ala Glu Arg Leu Arg Arg Ala Gly Val Ile Pro Leu Asp Pro
4705 4710 4715 4720

Glu His Ala Leu Val Ala Leu Asp Arg Ala Val Ala Ala Ala Asp Ala
4725 4730 4735

His Ser Val Ile Ala Asp Ala Asp Trp Thr Gly Leu Thr Ala Gly Ser
4740 4745 4750

Met Leu Ala Glu Leu Ser Gly Pro Ala Pro Val Glu Ala Pro Thr Ala
4755 4760 4765

Leu Thr Gly Pro Asp Arg Glu Arg Ala Ala Leu Ala Leu Val Arg Ser
4770 4775 4780

Cys Ala Ala Ala Val Leu Gly Arg Ser Ala Ala Val Asp Val Glu Pro
4785 4790 4795 4800

Asp Thr Ala Phe Arg Glu Leu Gly Phe Asp Ser Met Ala Ala Val Gln
4805 4810 4815

Leu Arg Asn Arg Leu Asn Ala Ala Thr Gly Val Val Leu Thr Ala Thr
4820 4825 4830

Ala Val Phe Asp His Pro Ser Ala Arg Ala Leu Ala Thr His Leu Leu
4835 4840 4845

Ala Leu Ala Thr Gly Glu Gly Ala Gly Ser Ala Gly Ala Thr Glu Leu
4850 4855 4860

Pro Gly Thr Ala Val His Thr Asp Glu Pro Ile Ala Ile Val Gly Met
4865 4870 4875 4880

Ala Cys Arg Phe Pro Gly Asp Val Thr Ser Pro Glu Asp Leu Trp Arg
4885 4890 4895

Leu Leu Ala Asp Gly Val Asp Ala Val Gly Pro Ile Pro Ala Asp Arg
4900 4905 4910

Gln Trp Gly Pro Thr Asp Ala Tyr Ala Glu Gly Gly Phe Leu Arg Gly
4915 4920 4925

Ala Gly Glu Phe Asp Ala Asp Phe Phe Gly Ile Ser Pro Arg Glu Ala
4930 4935 4940

Leu Val Met Asp Pro Gln Gln Arg Leu Ala Leu Glu Thr Gly Trp Glu
4945 4950 4955 4960

Val Phe Glu Arg Ala Gly Ile Asn Pro His Thr Val Arg Gly Thr Ser

-continued

```
            4965                4970                4975

Val Gly Val Phe Leu Gly Thr Asn Gly Gln Asp Tyr Val Ser Leu Leu
            4980                4985                4990

Ala Gly Ala Thr Glu Ala His Ala Gly His Ile Gly Thr Gly Asn Ser
        4995                5000                5005

Ala Ser Val Leu Ser Gly Arg Ile Ala Tyr Val Leu Gly Leu Glu Gly
    5010                5015                5020

Pro Ala Val Thr Val Asp Thr Ala Cys Ser Ser Ser Leu Val Ala Leu
5025                5030                5035                5040

His Trp Ala Ile Gln Ala Leu Arg Ser Gly Glu Cys Ser Met Ala Leu
                5045                5050                5055

Ala Gly Gly Val Thr Val Met Ala Thr Pro Gly Ala Phe Ala Glu Phe
            5060                5065                5070

Ser His Gln Arg Gly Leu Ala Glu Asp Gly Arg Cys Lys Ser Phe Ala
        5075                5080                5085

Ala Ser Ala Asp Gly Thr Gly Trp Gly Glu Gly Val Gly Met Leu Leu
    5090                5095                5100

Val Glu Arg Leu Ser Asp Ala Arg Arg Asn Gly His Arg Val Leu Ala
5105                5110                5115                5120

Val Val Arg Gly Ser Ala Val Asn Gln Asp Gly Ala Ser Asn Gly Leu
                5125                5130                5135

Thr Ala Pro Asn Gly Pro Ser Gln Gln Arg Val Ile Arg Gln Ala Leu
            5140                5145                5150

Ala Gly Ala Gly Leu Thr Pro Val Asp Val Asp Ala Val Glu Ala His
        5155                5160                5165

Gly Thr Gly Thr Arg Leu Gly Asp Pro Ile Glu Ala Gln Ala Leu Leu
    5170                5175                5180

Ala Thr Tyr Gly Gln Glu Arg Asp Glu Pro Leu Trp Leu Gly Ser Val
5185                5190                5195                5200

Lys Ser Asn Ile Gly His Thr Gln Ala Ala Ala Gly Val Ala Gly Val
                5205                5210                5215

Ile Lys Met Val Glu Ala Met Arg Asn Gly Thr Leu Pro Pro Thr Leu
            5220                5225                5230

His Val Asp Glu Pro Ser Pro His Val Asp Trp Ser Ala Gly Ala Val
        5235                5240                5245

Glu Leu Leu Thr Glu Ala Arg Glu Trp Lys Arg Ala Gly Arg Pro Arg
    5250                5255                5260

Arg Ala Gly Val Ser Ser Phe Gly Val Ser Gly Thr Asn Ala His Val
5265                5270                5275                5280

Val Leu Glu Glu Ala Pro Glu Glu Thr Glu Pro Ala Ala Ser Asp Glu
                5285                5290                5295

Leu Pro Val Ala Pro Trp Leu Leu Ser Ala Arg Ser Glu Lys Ala Leu
            5300                5305                5310

Leu Ala Gln Val Glu Arg Leu Arg Ala Tyr Val Thr Glu His Pro Glu
        5315                5320                5325

Ala Arg Pro Ala Asp Ile Gly Leu Ser Leu Ala Thr Gly Arg Ala Ala
    5330                5335                5340

Leu Ala His Arg Leu Ser Gly Ala Gly Glu Thr Thr Glu Glu Leu Leu
5345                5350                5355                5360

Ala Ala Leu Asp Thr Ala Leu Pro Ala Val Ala Arg Glu Thr Pro Thr
                5365                5370                5375

Ala Phe Val Phe Ala Gly Gln Gly Ala Gln Arg Val Gly Met Gly Ala
            5380                5385                5390
```

Glu Leu Ala Ala Val Tyr Pro Val Phe Ala Gln Val Phe Ala Gln Val
5395 5400 5405

Cys Ala Ala Phe Asp Gly Val Leu Glu Arg Pro Leu Gly Glu Val Val
5410 5415 5420

Ala Glu Gly Gly Pro Glu Leu Asp Arg Thr Val Tyr Ala Gln Ala Gly
5425 5430 5435 5440

Leu Phe Ala Phe Glu Val Ala Leu Phe Arg Leu Leu Glu Ser Trp Gly
5445 5450 5455

Val Ala Pro Asp Val Val Leu Gly His Ser Val Gly Glu Leu Ala Ala
5460 5465 5470

Ala Cys Val Ala Gly Val Trp Ser Leu Glu Asp Ala Val Arg Val Val
5475 5480 5485

Ala Ala Arg Gly Arg Leu Met Gln Ala Leu Pro Gln Gly Gly Ala Met
5490 5495 5500

Val Ala Leu Glu Val Ser Ala Gly Glu Leu Glu Leu Pro Glu Gly Val
5505 5510 5515 5520

Glu Leu Ala Ala Val Asn Gly Pro Thr Ser Val Val Leu Ser Gly Glu
5525 5530 5535

Glu Asp Ala Val Leu Ala Glu Ala Ala Arg Trp Pro Asp Arg Arg Ala
5540 5545 5550

Lys Arg Leu Arg Val Ser His Ala Phe His Ser Arg Arg Met Asp Pro
5555 5560 5565

Met Leu Glu Asp Phe Arg Arg Val Leu Glu Ser Val Thr Phe His Ala
5570 5575 5580

Pro Gln Leu Ala Phe Val Ser Thr Val Thr Gly Ala Ala Val Thr Asp
5585 5590 5595 5600

Glu Leu Cys Asp Pro Gly Tyr Trp Val Arg Asn Val Arg Glu Thr Val
5605 5610 5615

Arg Phe Ala Asp Ala Val Val Ala Ala Gly Ala Gly Val Phe Val Glu
5620 5625 5630

Leu Ala Pro Asp Ala Val Leu Ser Gly Leu Val Gly Glu Ser Val Glu
5635 5640 5645

Gly Val Leu Cys Val Pro Ala Gln Arg Ala Gly Arg Pro Ala Ala Arg
5650 5655 5660

Ala Leu Val Ser Ala Leu Gly Thr Leu His Thr His Gly Val Asp Val
5665 5670 5675 5680

Ala Trp Asp Arg Phe Phe Ala Gly Ser Gly Ala Arg Arg Val Asp Leu
5685 5690 5695

Pro Thr Tyr Ala Phe Gln Arg Glu Arg Tyr Trp Leu Ala Pro Pro Ala
5700 5705 5710

Ala Gly Pro Val Gly Leu Ala Gly Val Gly Leu Thr Ala Thr Gly His
5715 5720 5725

Pro Leu Leu Gly Val Ser Val Glu Leu Pro Gly Thr Asp Ala Val Ala
5730 5735 5740

Phe Thr Gly Ser Val Ser Leu Ser Thr His Pro Trp Leu Ala Asp His
5745 5750 5755 5760

Ala Ile Leu Gly Pro Ala Leu Leu Pro Gly Thr Ala Phe Leu Asp Leu
5765 5770 5775

Ala Leu Ala Ala Gly Glu His Val Gly Cys Pro Arg Val Asp Asp Leu
5780 5785 5790

Ala Leu His Ala Pro Leu Ala Leu Pro Ala His Gly Ser Val Arg Met
5795 5800 5805

```
Gln Val Arg Val Glu Gly Thr Asp Pro Asp Gly Ser Arg Gln Val Gly
    5810                5815                5820

Ile Tyr Ser Arg Pro Glu Asp Asp Glu Asp Ala Trp Thr Gln His Ala
5825                5830                5835                5840

Thr Gly Val Leu Ala Pro Glu Ser Gly Pro Ala Ala Glu Ala Leu Thr
                5845                5850                5855

Glu Trp Pro Pro Gln Gly Ala Glu Pro Val Ser Val Asp Gly Leu Tyr
            5860                5865                5870

Asp Asp Leu Ala Ala Thr Gly Phe Ala Tyr Gly Pro Leu Phe Arg Gly
        5875                5880                5885

Leu Arg Ala Ala Trp Val Arg Asp Gly Ala Val Tyr Ala Asp Val Ala
    5890                5895                5900

Leu Pro Asp Glu Thr Ala Ser Val Ala Gly Tyr Ser Val His Pro Ala
5905                5910                5915                5920

Leu Leu Asp Ala Ala Leu His Ala Leu Gly Cys Ala Asn Leu Val Ala
                5925                5930                5935

Asp Trp Ala Asp Gly Gln Leu Pro Phe Ala Trp Thr Gly Ala Arg Ile
            5940                5945                5950

His Ala Val Gly Ala Arg Ala Leu Arg Val Arg Leu Arg Ala Glu Asn
        5955                5960                5965

Gly Gly Ile Ala Leu Thr Ala Ala Asp Ala Gly Gly Gln Pro Val Ala
    5970                5975                5980

Gly Ile Glu Gly Val Arg Leu Arg Pro Val Gly Asp Ala Arg Ala Val
5985                5990                5995                6000

Arg Ala Ala Ala Gly Ala Arg Pro Cys Arg Val Glu Trp Leu Pro Val
                6005                6010                6015

Val Pro Ala Asp Asp Pro Glu Asp Asp Asp Ile Thr Val Val Pro Val
            6020                6025                6030

Thr Gly Arg Thr Ala Gly Gly Asp Val Val Ala Glu Val Arg Ala Ala
        6035                6040                6045

Val Ala Ala Ala Leu Ala Arg Leu Gln Glu Trp Leu Ala Asp Asp Arg
    6050                6055                6060

Ser Glu Arg Leu Val Leu Val Thr Arg Gly Ala Val Ala Ala Leu Pro
6065                6070                6075                6080

Asp Glu Ala Pro Asp Pro Val Ala Ala Ala Val Trp Gly Leu Val Arg
                6085                6090                6095

Ser Ala Gln Ser Glu His Pro Gly Arg Phe Val Leu Ala Asp Leu Ala
            6100                6105                6110

Ala Ser Glu Asp Ala Ala Val Val Ser Ala Ala Val Ala Thr Gly Glu
        6115                6120                6125

Pro Gln Ile Ala Val Arg Asn Gly Ala Leu Tyr Ala Pro Arg Leu Val
    6130                6135                6140

Arg Gly Ala Ser Arg Pro Gly Gly Glu Val Pro Phe Gly Ala Gly Asp
6145                6150                6155                6160

Val Val Leu Val Thr Gly Gly Thr Gly Ala Leu Gly Arg Val Val Ala
                6165                6170                6175

Arg His Leu Val Ala Glu His Gly Val Arg Arg Leu Val Leu Ala Ser
            6180                6185                6190

Arg Arg Gly Gly Ala Gly Glu Leu Val Ala Glu Leu Gly Glu Leu Gly
        6195                6200                6205

Ala Ala Val Asp Val Val Ala Cys Asp Val Ser Asp Arg Glu Ala Leu
    6210                6215                6220

Glu Gly Leu Val Ala Ala Tyr Pro Leu Thr Gly Val Val His Ala Ala
```

```
6225                6230                6235                6240

Gly Val Leu Asp Asp Gly Thr Val Glu Ser Leu Thr Ala Glu Arg Val
                6245                6250                6255

Asp Gly Val Leu Arg Ala Lys Val Asp Gly Ala Trp His Leu His Glu
            6260                6265                6270

Leu Thr Ser Gly Leu Asp Leu Arg Ala Phe Val Leu Phe Ser Ser Leu
        6275                6280                6285

Ala Gly Val Val Gly Ser Ala Gly Gln Gly Gly Tyr Ala Ala Ala Asn
    6290                6295                6300

Ala Ala Leu Asp Ala Leu Ala Glu Tyr Arg Arg Ala Glu Gly Leu Pro
6305                6310                6315                6320

Ala Thr Ser Ile Ala Trp Gly Pro Trp Thr Asp Gly Met Thr Thr Gly
                6325                6330                6335

Leu Glu Arg Ala Asp Arg Ala Arg Ile Ser Arg Ser Gly Thr Arg Ala
            6340                6345                6350

Leu Gly Thr Glu Asp Gly Leu Ala Leu Phe Asp Gln Ala Val Arg Gly
        6355                6360                6365

Ala Asp Ala Leu Ala Val Ala Ala Leu Trp Asp Leu Ser Ala Leu Arg
    6370                6375                6380

Ala Ala Gln Ser Leu Pro Pro Leu Phe Gln Gly Leu Ala Gly Arg Pro
6385                6390                6395                6400

Val Arg Arg Thr Val Ala Asp Gly Ala Gly Arg Gly Ala Glu Trp Ala
                6405                6410                6415

Asp Arg Phe Thr Gly Leu Ser Pro Ala Glu Ser Glu Arg Ala Ala Val
            6420                6425                6430

Glu Trp Val Arg Glu Gln Ala Ala Ala Val Leu Gly His Ala Ser Ser
        6435                6440                6445

Ala Ala Val Ala Ala Asp Arg Ala Phe Leu Asp Leu Gly Phe Asp Ser
    6450                6455                6460

Leu Thr Ala Val Glu Leu Arg Asn Arg Leu Ala Thr Ala Thr Gly Leu
6465                6470                6475                6480

Arg Leu Gly Thr Thr Ala Val Phe Asp Tyr Pro Thr Pro Ala Gly Leu
                6485                6490                6495

Ala Ala His Leu Leu Glu Arg Val Leu Gly Ala Thr Thr Gly Ser Ala
            6500                6505                6510

Gln Pro Ala Pro Ala Ala Val Pro Ala Asp Glu Pro Ile Ala Ile Val
        6515                6520                6525

Gly Met Ala Cys Arg Tyr Pro Gly Gly Ile Thr Ser Pro Glu Glu Leu
    6530                6535                6540

Trp Arg Glu Val Ala Glu Gly Arg Asp Ala Ile Ser Gly Phe Pro Thr
6545                6550                6555                6560

Asp Arg Gly Trp Asp Leu Arg Ala Leu Phe Ala Asp Asp Pro Gly Arg
                6565                6570                6575

Pro Gly Thr Ser His Thr Arg Glu Gly Gly Phe Leu His Asp Ala Gly
            6580                6585                6590

Glu Phe Asp Ala Asp Phe Phe Gly Ile Ser Pro Arg Glu Ala Leu Ala
        6595                6600                6605

Met Asp Pro Gln Gln Arg Leu Leu Leu Glu Ala Ser Trp Glu Ala Ile
    6610                6615                6620

Glu Arg Ala Gly Ile Asp Pro Ala Ser Leu Arg Gly Ser Arg Thr Gly
6625                6630                6635                6640

Val Tyr Ala Gly Val Met Tyr His Asp Tyr Ala Ala Arg Val Asp Val
                6645                6650                6655
```

```
Leu Pro Asp Gly Val Glu Gly Tyr Leu Gly Thr Gly Asn Ser Gly Ser
            6660                6665                6670

Ile Ala Ser Gly Arg Ile Ala Tyr Ala Leu Gly Leu Glu Gly Gln Ala
        6675                6680                6685

Val Thr Val Asp Thr Ala Cys Ser Ser Ser Leu Val Ala Leu His Trp
    6690                6695                6700

Ala Val Arg Ser Leu Arg Ser Gly Glu Ser Asp Leu Ala Leu Ala Gly
6705                6710                6715                6720

Gly Val Thr Val Met Ala Thr Pro Gly Val Phe Val Asp Phe Ser Arg
                6725                6730                6735

Gln Arg Gly Leu Ala Thr Asp Gly Arg Cys Lys Ser Tyr Gly Ala Gly
            6740                6745                6750

Ala Asp Gly Thr Gly Trp Ser Glu Gly Val Gly Met Leu Leu Val Glu
        6755                6760                6765

Arg Leu Ser Asp Ala Arg Arg Asn Gly His Arg Val Leu Ala Val Ile
    6770                6775                6780

Arg Gly Thr Ala Val Asn Gln Asp Gly Ala Ser Asn Gly Leu Thr Ala
6785                6790                6795                6800

Pro Asn Gly Pro Ser Gln Gln Arg Val Ile Arg Gln Ala Leu Ala Asp
                6805                6810                6815

Ala Ser Leu Arg Pro Ser Asp Val Asp Ala Val Glu Gly His Gly Thr
            6820                6825                6830

Gly Thr Ser Leu Gly Asp Pro Ile Glu Val Glu Ala Leu Leu Ala Thr
        6835                6840                6845

Tyr Gly Gln Glu Arg Asp Glu Pro Leu Trp Leu Gly Ser Ile Lys Ser
    6850                6855                6860

Asn Ile Gly His Thr Gln Ala Ala Ala Gly Val Ala Gly Val Ile Lys
6865                6870                6875                6880

Met Val Glu Ala Met Arg His Gly Val Leu Pro Arg Thr Leu His Ala
                6885                6890                6895

Asp Glu Pro Ser Pro His Ile Asp Trp Ala Ser Gly Ala Val Glu Leu
            6900                6905                6910

Leu Ala Glu Gln Arg Gln Trp Pro Arg Thr Asp Arg Pro Arg Arg Ala
        6915                6920                6925

Ala Val Ser Ser Phe Gly Leu Ser Gly Thr Asn Ala His Val Val Leu
    6930                6935                6940

Glu His Thr Asp His Gly Asp His His Ser Ala Gly Thr Gly Glu Arg
6945                6950                6955                6960

Pro Ala Val Pro Val Pro Val Pro Val Pro Val Ala Leu Ser Ala Arg
                6965                6970                6975

Thr Asp Ala Gly Leu Arg Ala Gln Ala Asp Arg Leu Ala Ala Ala Leu
            6980                6985                6990

Thr Ala Asp Pro Asp Leu Ile Pro Leu Asp Ile Ala Tyr Ser Ala Val
        6995                7000                7005

Thr Gly Arg Ala Arg Leu Glu Arg Arg Ala Ser Val Val Ala Ala Thr
    7010                7015                7020

Arg Glu Glu Leu Leu Ala Gly Leu Gly Asp Leu Gly Pro Ala Thr Val
7025                7030                7035                7040

Ala Gly Ala Gly His Thr Ala Phe Leu Phe Thr Gly Gln Gly Ala Gln
                7045                7050                7055

Arg Pro Gly Thr Gly Glu Glu Leu Ala Ala Ala His Pro Val Phe Ala
            7060                7065                7070
```

-continued

```
Ala Ala Tyr Ala Glu Val Cys Thr Ala Phe Asp Ala Val Leu Asp Arg
        7075                7080                7085

Pro Leu Arg Glu Val Val Ala Thr Gly Asp Gly Leu Asp Asp Thr Gly
    7090                7095                7100

Tyr Gly Gln Pro Ala Val Phe Ala Leu Glu Val Ala Phe Gly Arg Leu
7105                7110                7115                7120

Phe Glu Ser Trp Gly Val Val Pro Asp Phe Leu Leu Gly His Ser Val
                7125                7130                7135

Gly Glu Leu Ala Ala Ala His Leu Ala Gly Val Trp Ser Leu Pro Asp
            7140                7145                7150

Ala Val Arg Val Val Ala Ala Arg Ser Arg Leu Met Ala Ala Leu Pro
        7155                7160                7165

Ala Gly Gly Ala Met Ala Ala Val Glu Ala Ser Ala Asp Glu Val Ala
    7170                7175                7180

Ala Glu Leu Ala Asp Gly Ala Val Leu Ala Ala Val Asn Gly Pro Arg
7185                7190                7195                7200

Ser Val Val Val Ser Gly Ala Arg Asp Ala Val Leu Ala Thr Ala Gly
                7205                7210                7215

Leu Trp Ala Ala Arg Gly Cys Arg Thr Arg Glu Leu Lys Val Ser His
            7220                7225                7230

Ala Phe His Ser Pro Leu Met Glu Pro Met Leu Ser Asp Phe Ala Ala
        7235                7240                7245

Ala Leu Ala Asp Val Glu Phe Arg Ala Pro Arg Ile Pro Leu Val Ser
    7250                7255                7260

Thr Val Thr Gly Ala Val Ala Gly Asp Glu Leu Cys Thr Pro Gly Tyr
7265                7270                7275                7280

Trp Val Arg His Val Arg Asp Thr Val Arg Phe Ala Asp Gly Val Arg
                7285                7290                7295

Ala Leu Gly Gln Ala Gly Val Asp Thr Val Val Glu Leu Gly Pro Asp
            7300                7305                7310

Gly Val Leu Thr Ala Met Ala Ala Pro Leu Leu Pro Asp Thr Ala Val
        7315                7320                7325

Ala Leu Pro Thr Leu Arg Ala Gly Arg Pro Glu Ala Pro Ala Val Ala
    7330                7335                7340

Ala Ala Leu Gly Ala Leu His Asp Arg Gly Thr Ala Val Asp Trp Pro
7345                7350                7355                7360

Ala Phe Phe Arg Gly Thr Gly Ala Arg Thr Val Glu Leu Pro Thr Thr
                7365                7370                7375

Ala Phe Gln Arg Thr Arg Tyr Trp Leu Glu Ser Ala Ala Arg Thr Gly
            7380                7385                7390

Asp Leu Ser Ala Ala Gly Leu Ala Ala Ala Gly His Pro Leu Leu Gly
        7395                7400                7405

Ala Ala Val Asp Ser Pro Asp Gly Met Leu Leu Thr Gly Arg Leu Asp
    7410                7415                7420

Thr Ala Thr His Pro Trp Leu Ala Asp His Thr Val Leu Asp Thr Val
7425                7430                7435                7440

Leu Leu Pro Gly Thr Ala Phe Val Glu Leu Ala Arg Ala Ala Gly Glu
                7445                7450                7455

Arg Val Gly Leu Pro Arg Val Arg Glu Leu Thr Leu Ala Ala Pro Leu
            7460                7465                7470

Val Leu Pro Ala Asp Gly Ser Val Leu Val Gln Val His Val Gly Ala
        7475                7480                7485

Ala Val Asp Gly Glu Arg Pro Val Thr Val Ser Ala Arg Thr Asp Asp
```

```
    7490                7495                7500

Gly Gln Asp Trp Ala Arg His Ala Thr Gly Val Leu Ala Pro Ala Ala
7505                7510                7515                7520

Pro Ala Pro Gly Ala Asp Pro Leu Pro Trp Pro Pro Arg Asp Ala Glu
                7525                7530                7535

Pro Val Ala Thr Ala Gly His Tyr Asp Glu Leu Ala Ala Ala Gly Leu
            7540                7545                7550

Gly Tyr Gly Pro Ala Phe Arg Ala Leu Arg Ala Val Trp Arg Arg Gly
        7555                7560                7565

Asp Gly Pro Ala Ala Glu Val Phe Ala Glu Ile Gly Pro Ala Pro Gly
    7570                7575                7580

Thr Asp Pro Ala Gly Phe Gly Val His Pro Ala Leu Leu Asp Thr Ala
7585                7590                7595                7600

Leu His Ala Ala Ala Val Gly Gly Leu Gly Val Ala Gly Val Pro Phe
                7605                7610                7615

Thr Trp Asn Glu Val Ala Val His Thr Ala Gly Ala Arg Ser Leu Arg
            7620                7625                7630

Val Arg Ile Ala Pro Asp Gly Ser Gly Gly Leu Ser Leu Arg Ala Thr
        7635                7640                7645

Asp Asp Glu Gly Arg Ala Val Ile Asp Val Gly Ala Leu Arg Leu Arg
    7650                7655                7660

Ala Ile Ala Pro Glu Asp Leu Arg Thr Ala Pro Ala Ala Ala Glu Ala
7665                7670                7675                7680

Leu Phe Asp Leu Asp Trp Ala Pro Val Ser Val Ala Arg Gly Ala Arg
                7685                7690                7695

Pro Ala Gly Arg Trp Ala Val Leu Ala Pro Ala Asp Ala Glu Leu Thr
            7700                7705                7710

Asp Val Leu Gly Ala Gly Ile Glu Thr Val Lys Asp Leu Ala Thr Val
        7715                7720                7725

Pro Asp Asp Leu Asp Ile Val Leu Ala Ala Val Ser Asp Arg Gly Gly
    7730                7735                7740

Ala Gly Val Asp Ala Pro Thr Ala Ala Ser Val Gly Ala Ala Ala Glu
7745                7750                7755                7760

Thr Asp Val Pro Glu Ala Val Arg Ala Ile Leu Arg Gly Ala Leu Gly
                7765                7770                7775

Leu Val Gln Thr Trp Val Ala Gly Glu Ser Ala Ala Arg Leu Val Leu
            7780                7785                7790

Leu Thr Arg Gly Ala Val Ala Leu Ala Gly Glu Arg Pro Asp Leu Ala
        7795                7800                7805

Gly Ala Ala Ala Trp Gly Leu Val Arg Ala Ala Gln Ser Glu His Pro
    7810                7815                7820

Gly Arg Leu Val Leu Ala Asp Val Asp Asp Asp Pro Ala Ser Leu Ala
7825                7830                7835                7840

Ala Leu Pro Ala Ala Leu Ala Thr Gly Glu Pro Gln Leu Leu Ile Arg
                7845                7850                7855

Ala Gly Ala Val Arg Ala Ala Arg Leu Val Arg Ala Ala Pro Ala Glu
            7860                7865                7870

Pro Ala Val Pro Ala Ala Pro Leu Gly Ala Arg Gly Thr Val Leu Val
        7875                7880                7885

Thr Gly Ala Thr Gly Ser Leu Gly Thr Leu Val Val Arg His Leu Val
    7890                7895                7900

Ala Glu His Gly Val Arg Arg Leu Leu Leu Val Ser Arg Gln Gly Arg
7905                7910                7915                7920
```

Gln Pro Glu Pro Ala Ala Glu Leu Ala Ala Ala Gly Ala Glu Val Arg
7925 7930 7935

Phe Ala Ala Cys Asp Val Ala Asp Arg Asp Ala Leu Ala Ala Leu Leu
7940 7945 7950

Ala Ser Val Asp Pro Glu His Pro Val Thr Ala Val Val His Ala Ala
7955 7960 7965

Gly Val Leu Asp Asp Gly Val Val Ala Ala Leu Thr Pro Asp Arg Leu
7970 7975 7980

Asp Thr Val Leu Arg Pro Lys Ala Asp Ala Ala Trp His Leu His Glu
7985 7990 7995 8000

Leu Thr Gly Glu Leu Asp Ala Phe Val Leu Phe Ser Ser Ala Ala Gly
8005 8010 8015

Leu Leu Gly Ala Pro Gly Gln Ala Asn Tyr Ala Ala Ala Asn Ala Phe
8020 8025 8030

Leu Asp Ala Leu Ala Ala His Arg Arg Ala Ala Gly Leu Pro Ala Val
8035 8040 8045

Ser Ile Ala Trp Gly Pro Trp Ala Asp Gly Met Ala Ala Gln Leu Asp
8050 8055 8060

Thr Arg Arg Ala Ser Arg Ala Gly Leu Leu Pro Leu Asp Ala Ala Leu
8065 8070 8075 8080

Gly Leu Ala Leu Phe Asp Thr Ala Arg Thr Gly Ala Pro Thr Ala Pro
8085 8090 8095

Leu Ala Ala Arg Leu Asp Leu Pro Gly Leu Arg Ala Ala Ala Ala Glu
8100 8105 8110

Leu Pro Pro Ile Leu Arg Thr Leu Val Pro Ala Pro Ala Arg Thr Ala
8115 8120 8125

Pro Glu Pro Ala Glu Pro Leu Ala Asp Thr Leu Ala Ala Leu Pro Ala
8130 8135 8140

Glu Glu Arg Glu Arg Arg Ala Leu Asp Ala Val Leu Arg His Thr Ala
8145 8150 8155 8160

Glu Val Leu Gly His Ala Thr Ala Asp Gly Val Asp Arg Glu Arg Gly
8165 8170 8175

Phe Gln Gln Leu Gly Phe Asp Ser Leu Met Ser Val Glu Leu Arg Asn
8180 8185 8190

Arg Leu Gly Ala Ala Ala Gly Leu Arg Leu Pro Ala Thr Val Ile Phe
8195 8200 8205

Asp His Pro Thr Pro Ala Ala Leu Ala Ala His Leu Val Ala Glu Leu
8210 8215 8220

Ala Pro Gly Arg Pro Thr Val Ala Ser Leu Arg Thr Ser Thr Leu Ala
8225 8230 8235 8240

Glu Leu Glu Ala Ala Ala Asn Glu Phe Ala Gly Asp Pro Glu Leu Arg
8245 8250 8255

Glu Gly Leu Arg Thr Arg Leu Arg Ala Leu Leu Arg Thr Leu Asp Asp
8260 8265 8270

Pro Ala Pro Asp Glu Pro Leu Glu Glu Thr Gly Glu Glu Ser Leu Ala
8275 8280 8285

Glu Leu Leu Asp Leu Ala Asp Arg Glu Leu Gly Asp Phe
8290 8295 8300

<210> SEQ ID NO 12
<211> LENGTH: 3405
<212> TYPE: PRT
<213> ORGANISM: Streptomyces flaveolus (Streptomyces sp.(DSM 9954))

<400> SEQUENCE: 12

```
Met Thr Glu His Asp Arg Thr Thr Asp Arg Ala Thr Ala Arg Gly Ala
1               5                   10                  15

Thr Ala Leu Ser Gln Glu Gln Thr Asp Asp Arg Lys Val Val Glu Thr
            20                  25                  30

Val Arg Arg Leu Thr Thr Asp Leu Arg Arg Ala Lys Gln Arg Leu Arg
        35                  40                  45

Glu Ala Glu Asp Arg Ala His Glu Pro Ile Ala Ile Val Gly Met Ala
    50                  55                  60

Cys Arg Tyr Pro Gly Gly Val Gly Ser Pro Glu Asp Leu Trp Arg Leu
65                  70                  75                  80

Val Leu Asp Gly Arg Asp Ala Met Gly Ala Phe Pro Thr Asp Arg Gly
                85                  90                  95

Trp Asp Leu Ala Ala Leu Phe Ala Asp Asp Pro Glu Arg Ser Gly Thr
            100                 105                 110

Ser His Thr Arg Glu Gly Gly Phe Leu His Asp Ala Gly Glu Phe Asp
        115                 120                 125

Pro Gly Leu Phe Gly Ile Ser Pro Arg Glu Ala Leu Ala Met Asp Pro
    130                 135                 140

Gln Gln Arg Leu Leu Leu Glu Thr Ala Trp Glu Ala Val Glu Arg Ala
145                 150                 155                 160

Gly Ile Asp Pro Thr Ser Leu Arg Gly Ser Arg Thr Gly Val Tyr Ala
                165                 170                 175

Gly Val Met Tyr His Asp Tyr Gly Thr Gly Ala Asp Pro Leu Pro Glu
            180                 185                 190

Gly Val Glu Gly Tyr Leu Gly Leu Gly Thr Ala Gly Ser Val Ala Ser
        195                 200                 205

Gly Arg Ile Ala Tyr Thr Leu Gly Leu Glu Gly Pro Ala Val Thr Val
    210                 215                 220

Asp Thr Ala Cys Ser Ser Ser Leu Val Ala Leu His Ser Ala Val Arg
225                 230                 235                 240

Ala Leu Arg Ala Gly Glu Cys Thr Met Ala Leu Ala Gly Gly Ala Thr
                245                 250                 255

Val Leu Ser Thr Pro Ala Val Phe Val Asp Phe Ser Arg Gln Gly Gly
            260                 265                 270

Leu Ala Ala Asp Gly Arg Cys Lys Ser Tyr Ser Ala Glu Ala Asp Gly
        275                 280                 285

Thr Gly Trp Ser Glu Gly Val Gly Met Leu Leu Val Glu Arg Leu Gly
    290                 295                 300

Asp Ala Glu Arg Leu Gly His Pro Val Leu Ala Val Leu Arg Gly Ser
305                 310                 315                 320

Ala Val Asn Gln Asp Gly Ala Ser Ser Gly Leu Thr Thr Pro Asn Gly
                325                 330                 335

Pro Ala Gln Gln Arg Val Ile Arg Gln Ala Leu Ala Asp Ala Arg Leu
            340                 345                 350

Thr Pro Ala Asp Leu Asp Leu Val Glu Gly His Gly Thr Gly Thr Pro
        355                 360                 365

Leu Gly Asp Pro Ile Glu Val Gln Ala Leu Leu Ala Thr Tyr Gly Gln
    370                 375                 380

Asp Arg Ala Glu Pro Leu Trp Leu Gly Ser Val Lys Ser Asn Ile Gly
385                 390                 395                 400

His Thr Gln Ala Ala Ala Gly Val Ala Gly Val Ile Lys Ala Val Leu
                405                 410                 415
```

```
Ala Leu Arg His Gly Val Leu Pro Gly Thr Ala His Leu Thr Glu Pro
            420                 425                 430

Thr Pro Gln Val Asp Trp Thr Ala Gly Ala Val Glu Pro Leu Arg Glu
        435                 440                 445

Thr Arg Ala Trp Pro Glu Thr Gly Arg Pro Arg Arg Ala Ala Val Ser
    450                 455                 460

Ser Phe Gly Ile Ser Gly Thr Asn Ala His Ile Val Leu Glu Gln Ala
465                 470                 475                 480

Pro Ala Pro Ala Ala Pro Gln Ala Ala Gly Ala Gln Ala Pro Ala Ala
                485                 490                 495

Pro Arg Pro Val Gly Asn Gln Ala Thr Ala Ala Pro Arg Ser Met Glu
            500                 505                 510

Asp Arg Thr Ala Ala Ala Pro Ser Ala Gly Gly Asp Pro Thr Leu Thr
        515                 520                 525

Ala Pro Ala Pro Ser Ala Pro Arg Pro Ala Pro Ala Ala Leu Pro Val
    530                 535                 540

Pro Leu Ser Ala Ala Thr Glu Pro Gly Val Arg Ala Gln Ala Leu Arg
545                 550                 555                 560

Leu Ala Ala His Leu Thr Glu His Pro Glu Leu Ala Pro Gln Asp Ile
                565                 570                 575

Ala Phe Ser Ala Ala Thr Thr Arg Ala Ala Leu Ala Ser Arg Ala Val
            580                 585                 590

Val Leu Ala Asp Asp Arg Ala Gly Leu Leu Asp Ala Leu Thr Ala Leu
        595                 600                 605

Ala Glu Gly Arg Pro Gly Pro Ala Val Val Thr Gly Ala Ala Ala Ala
    610                 615                 620

Gly Ala Arg Arg Ile Thr Phe Val Phe Pro Gly Gln Gly Ala Gln Trp
625                 630                 635                 640

Ala Gly Met Ala Val Pro Leu Leu Glu Thr Ser Pro Val Phe Ala Ala
                645                 650                 655

Lys Trp Ala Glu Cys Ala Arg Val Leu Ala Pro Trp Val Asp Trp Ser
            660                 665                 670

Pro Asp Glu Ala Leu Arg Ser Pro Gln Ala Leu Glu Arg Val Asp Val
        675                 680                 685

Val Gln Pro Val Leu Trp Ala Val Met Val Ser Leu Ala Glu Leu Trp
    690                 695                 700

Arg Ala Ala Gly Val Arg Pro Asp Ala Val Leu Gly His Ser Gln Gly
705                 710                 715                 720

Glu Ile Ala Ala Ala Cys Val Ala Gly Ala Leu Ser Leu Glu Asp Gly
                725                 730                 735

Ala Lys Val Val Ala Leu Arg Ala Lys Ala Leu Leu Ala Leu Ala Gly
            740                 745                 750

Arg Gly Gly Met Leu Ser Val Pro Leu Pro Glu Ala Glu Val Arg Ala
        755                 760                 765

Arg Leu Asp Ser Arg Pro Gly Leu Gly Ile Ala Ala Val Asn Gly Pro
    770                 775                 780

Ala Thr Val Val Val Ser Gly Glu Thr Ala Ala Leu Asp Glu Ala Gln
785                 790                 795                 800

Ala Ala Trp Glu Ala Glu Gly Val Arg Val Arg Arg Ile Pro Val Asp
                805                 810                 815

Tyr Ala Ser His Ser Pro His Val Ala Glu Val Gln Asp Arg Leu Ala
            820                 825                 830
```

-continued

```
Ala Asp Leu Ala Gly Ile Ala Pro Arg Pro Ala Glu Val Thr Phe Leu
        835                 840                 845

Ser Thr Leu Thr Gly Glu Pro Phe Asp Thr Thr Gly Leu Asp Ala Gly
    850                 855                 860

Tyr Trp Tyr Arg Asn Leu Arg Glu Gln Val Arg Phe Glu Ala Ala Thr
865                 870                 875                 880

Arg Arg Ala Leu Glu Gln Gly His Arg Val Phe Ile Glu Val Gly Pro
                885                 890                 895

His Pro Val Leu Thr Leu Gly Val Gln Gln Thr Ala Glu Ala Met Asp
            900                 905                 910

Val Pro Ala Glu Ala Ile Ala Thr Leu Arg Arg Asp Gln Gly Asp Leu
        915                 920                 925

Leu Arg Phe Arg Thr Ala Leu Ala Glu Ala Ala Val Leu Gly Ala Pro
    930                 935                 940

Val Asp Trp Ala Ala Glu Leu Ala Pro Tyr Ala Pro Arg Arg Val Asp
945                 950                 955                 960

Leu Pro Thr Tyr Ala Phe Gln Arg Glu Arg Tyr Trp Leu Thr Pro Gln
                965                 970                 975

Arg Arg Ala Ala Leu Ala Ala Ser Thr Gly Thr Asp Pro Trp Asp Gly
            980                 985                 990

Arg Phe Trp Asp Ile Val Asp Arg Ala Asp Ala Glu Glu Leu Ser Arg
        995                 1000                1005

Ala Leu Gly Val Asp Thr Asp Asp Pro Leu Thr Ala Val Val Pro Ala
    1010                1015                1020

Leu Ala Arg Trp Arg Arg Leu Leu Arg Glu Arg Ser Ala Val Asp Ser
1025                1030                1035                1040

Trp Arg Tyr Thr Val Ala Trp Glu Arg Leu Ala Val Pro Asp Ser Ala
                1045                1050                1055

Arg Leu Thr Gly Pro Trp Leu Leu Val Val Pro Glu Pro Arg Ala Gly
            1060                1065                1070

Asp Ala Leu Ala Ala Arg Cys Ala Ala Ala Leu Thr Gly His Gly Ala
        1075                1080                1085

Glu Val Thr Thr Leu Thr Leu Gly Ala Asp Asp Thr Asp Arg Ala Ala
    1090                1095                1100

Leu Ala Ala Arg Leu Thr Gly Leu Arg Pro Ala Gly Val Leu Ser Leu
1105                1110                1115                1120

Leu Ala Leu Asp Asp Ala Pro His Pro Ala His Pro Ala Leu Pro Thr
                1125                1130                1135

Gly Leu Ala Leu Thr Val Ala Leu Val Gln Ala Leu Gly Asp Ala Gly
            1140                1145                1150

Val Thr Ala Pro Leu Trp Cys Ala Thr Arg Gly Ala Val Ala Thr Gly
        1155                1160                1165

Pro Ala Asp Pro Val Thr Ala Pro Val Gln Ala Gln Ile Trp Gly Leu
    1170                1175                1180

Gly Arg Val Val Ala Leu Glu His Pro Asp Arg Trp Gly Gly Leu Ile
1185                1190                1195                1200

Asp Leu Pro Ala Glu Trp Asp Asp Arg Ala Ala Gly Arg Leu Ala Ala
                1205                1210                1215

Leu Leu Ala Ala Gly Gly Asp Glu Asp Gln Thr Val Leu Arg Ala Thr
            1220                1225                1230

Gly Val Ser Ala Arg Arg Leu Thr Arg Ala Pro Leu Gly Thr Glu Pro
        1235                1240                1245

Ala Pro Arg Pro Trp Arg Cys Ala Gly Thr Val Leu Leu Thr Gly Gly
```

```
    1250                1255                1260

Thr Gly Ala Leu Gly Pro His Leu Val Arg Trp Leu Ala Gly Gln Gly
1265                1270                1275                1280

Ala Glu Arg Ile Val Leu Pro Gly Arg Arg Gly Ala Asp Ala Pro Ile
                1285                1290                1295

Ala Ala Glu Leu Thr Ala Glu Leu Ala Gly Thr Gly Thr Glu Leu His
            1300                1305                1310

Phe Pro Val Cys Asp Val Thr Asp Arg Ala Glu Leu Ala Ala Leu Ile
        1315                1320                1325

Asp Gly Leu Asp Thr Ala Gly Thr Pro Val Arg Ser Val Leu His Ala
    1330                1335                1340

Ala Thr Ala Leu Glu Leu Arg Pro Leu Ala Asp Thr Pro Val Asp Thr
1345                1350                1355                1360

Phe Ala Gly Gln Thr Ala Ala Lys Val Leu Gly Ala Arg His Leu Asp
                1365                1370                1375

Glu Leu Phe Ala Asp Arg Asp Leu Asp Ala Phe Val Leu Phe Ser Ser
            1380                1385                1390

Val Ala Gly Val Trp Gly Ser Gly Leu His Ala Pro Tyr Ala Ala Ala
        1395                1400                1405

Asn Ala Tyr Leu Asp Ala Leu Ala Glu Asp Arg Arg Ala Arg Gly Leu
    1410                1415                1420

Thr Ala Thr Ser Val Ala Trp Gly Ile Trp Ala Ala Val Asn Glu Trp
1425                1430                1435                1440

Asp Gly Val Asn Ala Asp Val Asp Pro Glu Arg Val Gly Arg Gln Gly
                1445                1450                1455

Leu Pro Phe Leu Asp Pro Asp Leu Ala Val Ala Gly Leu Arg Gln Ala
            1460                1465                1470

Leu Asp His Asp Glu Thr Thr Val Val Ile Ala Asp Val Asp Trp Thr
        1475                1480                1485

Arg Phe Val Pro Val Phe Cys Ser Ala Arg Arg Arg Pro Leu Leu Glu
    1490                1495                1500

Ser Val Pro Glu Ala Ala Ala Val Leu Arg Thr Ala Thr Val Asp Thr
1505                1510                1515                1520

Gly Thr Val Ser Ala Leu Arg Glu Arg Leu Gly Ser Leu Pro Glu Ala
                1525                1530                1535

Gly Arg Arg Arg Ala Val Thr Glu Leu Val Arg Glu His Ala Ala Ala
            1540                1545                1550

Val Leu Gly His Asp Ser Pro Ala Ala Leu Pro Ala Asp Arg Ala Phe
        1555                1560                1565

Arg Asp Val Gly Phe Asp Ser Ile Thr Ala Val Glu Leu Arg Asn Arg
    1570                1575                1580

Leu Arg Ser Ala Thr Gly Leu Ala Leu Pro Ala Thr Leu Val Phe Asp
1585                1590                1595                1600

His Pro Ser Pro Thr Ala Leu Ala Gly His Leu Leu Ala Leu Ala Phe
                1605                1610                1615

Asp Thr Ala Ala Ala Asp Leu Ala Ala Pro Ala Ala Arg Ala Ala Asp
            1620                1625                1630

Asp Asp Asp Asp Pro Ile Ala Val Val Gly Leu Ser Cys Arg Tyr Ala
        1635                1640                1645

Gly Gly Val Ala Ser Pro Asp Glu Leu Trp Arg Leu Val Val Ala Gly
    1650                1655                1660

Gln Asp Ala Val Gly Ala Leu Pro Thr Asp Arg Gly Trp Asp Leu Asp
1665                1670                1675                1680
```

-continued

```
Ser Leu Tyr Asp Ser Asp Pro Asp Ala Arg Gly Arg Ser Tyr Val Arg
                1685                1690                1695

Gln Gly Ala Phe Leu Thr Asp Pro Ala Gly Phe Asp Ala Ala Phe Phe
            1700                1705                1710

Gly Ile Ala Pro Ala Glu Ala Arg Ala Thr Asp Pro Gln Gln Arg Leu
        1715                1720                1725

Leu Leu Glu Ala Ala Trp Glu Ala Phe Glu His Ala Gly Ile Asp Ala
    1730                1735                1740

Thr Gly Leu Arg Gly Ser Arg Val Gly Val Phe Ala Gly Ala Asn Val
1745                1750                1755                1760

Gly Asp Tyr Ala Ser Ser Arg Gly Pro Gly Ala Gly Gly Ser Asp Gly
                1765                1770                1775

Gln Leu Leu Thr Gly Asn Val Pro Ser Val Ile Ser Gly Arg Ile Ser
            1780                1785                1790

Tyr Thr Phe Gly Phe Glu Gly Pro Ala Val Thr Val Asp Thr Ala Cys
        1795                1800                1805

Ser Ser Ala Leu Val Ala Leu His Leu Ala Cys Arg Ser Val Arg Gly
    1810                1815                1820

Gly Glu Ser Asp Met Ala Leu Ala Gly Gly Val Ala Leu Met Ser Ser
1825                1830                1835                1840

Pro Ala Ala Leu Ile Gly Phe Ser Ala Gln Arg Gly Leu Ser Gly Asp
                1845                1850                1855

Gly Arg Cys Lys Ala Phe Ala Asp Ala Ala Asp Gly Thr Gly Leu Ala
            1860                1865                1870

Glu Gly Val Gly Leu Leu Leu Val Glu Arg Leu Ser Arg Ala Arg Ala
        1875                1880                1885

Gln Gly His Arg Val Leu Ala Leu Val Arg Gly Ser Ala Ile Asn Gln
    1890                1895                1900

Asp Gly Ala Ser Asn Gly Leu Thr Ala Pro Ser Gly Pro Ala Gln Gln
1905                1910                1915                1920

Arg Val Ile Thr Ala Ala Leu Ala Asp Ala Gly Leu Arg Pro Ala Asp
                1925                1930                1935

Val Asp Ala Val Glu Ala His Gly Thr Gly Thr Arg Leu Gly Asp Pro
            1940                1945                1950

Ile Glu Ala Gln Ala Leu Leu Ala Thr Tyr Gly Gln Asp Arg Ala Glu
        1955                1960                1965

Pro Leu Trp Leu Gly Ser Val Lys Ser Asn Ile Gly His Ser Gln Ala
    1970                1975                1980

Ala Ser Gly Ala Ala Gly Val Ile Lys Thr Val Gln Ala Leu Arg His
1985                1990                1995                2000

Gly Leu Leu Pro Ala Thr Leu His Val Asp Arg Pro Thr Thr Gln Val
                2005                2010                2015

Asp Trp Thr Ala Gly Ala Val Glu Val Leu Thr Glu Ala Arg Asp Trp
            2020                2025                2030

Pro Ala Val Asp Arg Pro Arg Arg Ala Ala Val Ser Ala Phe Gly Leu
        2035                2040                2045

Ser Gly Thr Asn Ala His Val Ile Leu Glu Gln Ala Pro Ala Glu Asp
    2050                2055                2060

Ala His Pro Ala Pro Glu Pro Ala Pro Gly Glu Asp Ser His Pro Thr
2065                2070                2075                2080

Pro Glu Thr Ala Pro Gly Glu Asp Ala Pro Arg Thr Ala Pro Glu Pro
                2085                2090                2095
```

```
Ala Arg Pro Val Val Trp Pro Val His Gly Arg Thr Arg Asp Ala Leu
            2100                2105                2110

Arg Ala Gln Ala Ala Arg Leu Arg Thr His Leu Glu Thr Arg Pro Asp
        2115                2120                2125

Ala Arg Pro Ala Asp Val Gly Trp Thr Leu Ala Ala Gly Arg Ala Val
    2130                2135                2140

Phe Asp His Arg Ala Val Val Leu Gly Ala Asp Arg Ala Glu Leu Leu
2145                2150                2155                2160

Arg Gly Leu Asp Ala Val Ala Ala Gly Thr Pro Asp Pro Ala Val Ala
                2165                2170                2175

Asp Gly Ala Ala Gln Gly Ala Asp Arg Ala Val Phe Val Phe Pro Gly
            2180                2185                2190

His Gly Ala Gln Trp Pro Gly Met Ala Arg Arg Leu Phe Asp Asp Phe
        2195                2200                2205

Pro Val Phe Arg Glu Ser Val Leu Gln Cys Ala Asp Ala Phe Ala Glu
    2210                2215                2220

Phe Val Asp Trp Ser Leu Leu Asp Val Leu Arg Asp Glu Glu Gly Ala
2225                2230                2235                2240

Pro Pro Leu His Arg Val Asp Val Val Gln Pro Ala Leu Phe Thr Met
                2245                2250                2255

Met Val Ser Leu Ala Ala Leu Trp Arg Ser Tyr Gly Val Glu Pro Ser
            2260                2265                2270

Ala Val Val Gly His Ser Gln Gly Glu Ile Ala Ala Ala Tyr Val Ala
        2275                2280                2285

Gly Ala Leu Asp Leu Arg Asp Ala Ala Arg Ile Val Ala Thr Arg Gly
    2290                2295                2300

Lys Ala Trp Leu Thr Leu Ala Gly Thr Gly Gly Met Ala Ser Val Ala
2305                2310                2315                2320

Leu Pro Arg Ala Glu Ala Ala Glu Arg Leu Arg Pro Phe Gly His Arg
                2325                2330                2335

Leu Asp Ile Ala Ala Val Asn Asp Pro Arg Ser Val Thr Val Ala Gly
            2340                2345                2350

Asp Leu Asp Ala Leu Glu Glu Phe Leu Thr Gly Leu Glu Thr Glu Gly
        2355                2360                2365

Val Arg Val Arg Arg Val Arg Gln Ile Val Gly Ala Gly His Thr Ala
    2370                2375                2380

His Val Asp Ala Leu Arg Asp Gln Leu Ile Glu Thr Leu Ala Pro Thr
2385                2390                2395                2400

Ala Pro Arg Ser Ala Pro Ile Ala Phe Cys Ser Thr Val Thr Gly Gly
                2405                2410                2415

Leu Leu Asp Thr Ala Gly Leu Asp His His Tyr Trp Tyr Arg Asn Ala
            2420                2425                2430

Arg Arg Thr Val Leu Phe Glu Gln Ala Val Arg Thr Leu Ala Glu Gln
        2435                2440                2445

Gly Tyr Gly Pro Phe Leu Glu Ile Ser Ala His Pro Met Phe Thr Val
    2450                2455                2460

Ala Val Gln Glu Thr Leu Glu Asp Ala Gly Val Gly Ala Ala Val Leu
2465                2470                2475                2480

Ala Thr Leu Arg Arg Asp Glu Gly Gly Pro Asp Arg Phe Leu Arg Ala
                2485                2490                2495

Ala Ala Glu Ala His Thr Ala Gly Val Thr Val Asp Trp Arg Pro Ala
            2500                2505                2510

Phe Ala Gly Ala Gly Ala Arg Thr Thr Asp Leu Pro Thr Tyr Ala Phe
```

```
        2515                2520                2525

Gln Arg Thr Arg His Trp Leu Glu Pro Gly Gly Asp Ser Gly Asp Val
    2530                2535                2540

Thr Ala Ala Gly Leu Ala Pro Ala Gly His Pro Leu Leu Gly Ala Val
2545                2550                2555                2560

Val Glu Leu Ala Asp Gly Ala Met Val Leu Thr Gly Arg Leu Ser Ala
                2565                2570                2575

Thr Ala Gln Pro Trp Pro Gly Pro Glu Ala Pro Asp Ala Ala Leu Val
            2580                2585                2590

Asp Leu Val Leu Ala Ala Ala Asp Arg Ala Asp Cys Ala Gly Val Gly
        2595                2600                2605

Glu Leu Thr Val Tyr Glu Pro Leu Met Ala Pro Ala Gly Gly Ala Asp
    2610                2615                2620

Thr Arg Val Thr Val Gly Ala Pro Asp Ala Val Gly Ser Arg Thr Ala
2625                2630                2635                2640

Ala Val His Thr Arg Thr Ala Asp Ser Pro Trp Val Arg His Ala Glu
                2645                2650                2655

Ala Thr Leu Val Ala Arg Pro Ala Pro Gly Glu Ser Leu Thr Asp Trp
            2660                2665                2670

Pro Pro Ala Gly Ala Glu Pro Ile Asp Pro Pro Ala Glu Ala Gly Arg
        2675                2680                2685

Ala Gly Val Ala Val Thr Ala Ala Trp Gln Arg Gly Asp Asp Leu Phe
    2690                2695                2700

Thr Glu Val Ala Leu Asp Asp Gly Ala Ala Glu Arg Ala Asp Ala Phe
2705                2710                2715                2720

Ala Leu His Pro Leu Leu Leu Asp Ala Ala Leu Ser Pro Leu Leu Asp
                2725                2730                2735

Gly Glu Leu Thr Pro Thr Ala Trp Ser Gly Val Arg Leu His Ala Thr
            2740                2745                2750

Gly Ala Arg Thr Leu Arg Ala Arg Ala Glu Arg Ile Gly Pro Asp Thr
        2755                2760                2765

Val Ala Leu Thr Leu Ala Asp Pro Glu Gly Gly Pro Val Leu Thr Ala
    2770                2775                2780

Asp Thr Val Arg Leu Ala Ala Ala Pro Ala Ala Gly Ala Gly Arg Arg
2785                2790                2795                2800

Thr Gly Lys Asp Ala Leu Phe Arg Met Glu Trp Val Pro Ala Pro Leu
                2805                2810                2815

Ala Pro Ala Thr Pro Gly Arg Trp Ala Val Leu Gly Ala Asp Pro Leu
            2820                2825                2830

Gly Ala Ala Asp Thr Leu Arg Ser Leu Gly His Thr Val His Gly Ala
        2835                2840                2845

Asp Gly Pro Ala Gly Leu Thr Glu Val Pro Asp Ala Val Leu Ile Thr
    2850                2855                2860

Ala Val Gly Ala Pro Gly Glu Ala Pro Ala Glu Ala Arg Thr Val Leu
2865                2870                2875                2880

His Gly Thr Leu Ala Ala Leu Gln Thr Leu Leu Ala Asp Asp Arg Phe
                2885                2890                2895

Thr Ala Val Pro Leu Val Val Leu Thr Arg Gly Ala Ala Ala Asp Arg
            2900                2905                2910

Ala Asp Asp Leu Ala Gly Ala Ala Ala Trp Gly Leu Val Arg Ser Ala
        2915                2920                2925

Gln Ser Glu His Pro Gly Arg Phe Val Leu Ala Asp Ile Asp Asp Asp
    2930                2935                2940
```

```
Pro Arg Ser Trp Arg Ala Leu Gly Gly Val Pro Ala Thr Gly Glu Pro
2945                2950                2955                2960

Gln Leu Ala Leu Arg Ala Gly Ala Ala Thr Val Pro Arg Leu Ala Arg
                2965                2970                2975

Leu Ala Pro Pro Asp Ala Pro Ala Pro Trp Asp Pro Asp Arg Thr Val
            2980                2985                2990

Leu Val Thr Gly Ala Ser Gly Asp Leu Gly Ala Leu Val Ala Arg His
        2995                3000                3005

Leu Val Ala Ala His Gly Val Arg His Leu Ile Leu Ala Ser Arg Arg
    3010                3015                3020

Gly Pro Ala Ala Pro Gly Ala Ala Gly Leu Gly Ala Glu Leu Arg Ala
3025                3030                3035                3040

Ser Gly Ala Ala Thr Val Thr Ile Ala Ala Cys Asp Thr Ala Asp Arg
                3045                3050                3055

Lys Ala Leu Ala Glu Leu Ile Ala Ala Val Pro Asp Glu His Pro Leu
            3060                3065                3070

Thr Ala Val Val His Ser Ala Ser Val Leu Asp Asp Gly Val Ile Ala
        3075                3080                3085

Ala Leu Asp Pro Asp Arg Leu Asp Thr Ala Leu Arg Pro Lys Ala Asp
    3090                3095                3100

Ala Ala Trp His Leu His Glu Leu Thr Arg His Leu Asn Leu Ser Ala
3105                3110                3115                3120

Phe Val Leu Phe Ser Ser Val Ala Gly Thr Phe Gly Gly Leu Gly Gln
                3125                3130                3135

Gly Asn Tyr Ala Ala Gly Asn Ala Phe Leu Asp Ala Leu Ala Arg His
            3140                3145                3150

Arg Arg Ala His Gly Leu Pro Ala Thr Ser Val Ala Trp Gly Trp Trp
        3155                3160                3165

Ala Glu Arg Ala Ala Lys Ser Gly His Gly Thr Ala Ala Glu Ala Pro
    3170                3175                3180

Val Ala Val Asn Gly Met Thr Pro Leu Thr Glu Asp His Gly Leu Ala
3185                3190                3195                3200

Leu Phe Asp Ala Ala Cys Arg Gly Asp Glu Pro Phe Val Val Ala Gly
                3205                3210                3215

Ala Leu His Leu Arg Ser Leu Arg Ala Ala Ala Asp Glu Leu Pro Ala
            3220                3225                3230

Pro Leu Arg Gly Leu Val Arg Ala Pro Ala Arg Lys Ala Ala Ala Gln
        3235                3240                3245

Ala Ala Gly Thr Gly Thr Pro Thr Val Ala Gly Glu Leu Ala Gly Arg
    3250                3255                3260

Pro Pro Ala Arg Arg Glu Ala Phe Leu Val Asp Leu Val Arg Asp Glu
3265                3270                3275                3280

Thr Ala Leu Val Leu Gly His Thr Gly Arg Asp Asp Val Pro Ala His
                3285                3290                3295

His Arg Phe Leu Asp Gln Gly Phe Asp Ser Leu Ala Ala Leu Lys Leu
            3300                3305                3310

Arg Asn Arg Leu Ala Ala Ala Thr Gly Leu Arg Leu Pro Pro Thr Leu
        3315                3320                3325

Val Phe Asp His Pro Thr Pro Thr Glu Leu Ala Arg His Leu Leu Ala
    3330                3335                3340

Glu Leu Val Pro Pro Ala Asp Ala Glu Pro Pro Ala Phe Asp Asp Glu
3345                3350                3355                3360
```

```
Asp Ala Ala Thr Ala Val Leu Val Leu Glu Glu Leu Gly Gln Leu Asp
                3365                3370                3375

Glu Ala Ile Thr Arg Leu Pro Ala Asp Gly Pro Glu Arg Thr Arg Ile
            3380                3385                3390

Ala Gly Leu Leu Thr Asp Leu Leu Ala Arg Trp Gly Arg
        3395                3400                3405


<210> SEQ ID NO 13
<211> LENGTH: 388
<212> TYPE: PRT
<213> ORGANISM: Streptomyces flaveolus (Streptomyces sp.(DSM 9954))

<400> SEQUENCE: 13

Met Glu Asn Val Gln Ala Trp Val Leu Pro Ala Gly Pro Gln Asp Arg
1               5                   10                  15

Ser Gly Gly Pro Val Arg Gly Glu Leu Thr Leu Thr Arg Ile Pro Val
            20                  25                  30

Ala Ser Pro Gly Glu His Glu Val Leu Val Glu Ser Leu Val Gly Cys
        35                  40                  45

Trp Glu Ala Asn Met Glu His Ala Leu Ala Arg Ser Pro Val Asp Ile
    50                  55                  60

Val Arg Gln Arg Gly Glu Glu Gln Ile Val Ile Gly Thr Cys Gly Val
65                  70                  75                  80

Val Arg Val Leu Ser Thr Gly Ser Ala Val Arg Gly Leu Arg Glu Gly
                85                  90                  95

Gln Glu Cys Leu Trp Ile Pro Phe Gly His Ile Asp Arg Asn Gly Tyr
            100                 105                 110

Ala Glu Thr Ile Cys Ala Tyr Asp Ala Pro Gly Ser Pro Gly Leu Leu
        115                 120                 125

Ala Glu Arg Met Val Val Pro Ala Asp Arg Leu Val Pro Leu Pro Ala
    130                 135                 140

Asp Gly Arg Tyr Pro Leu Glu Arg Trp Ala Pro Phe Ala Arg Tyr Phe
145                 150                 155                 160

Thr Ala Trp Asp Asn Trp Arg Val Thr Ser Arg Cys Trp Arg Ser Gln
                165                 170                 175

Val Asp Asp Ala Trp Asp Glu Gln Pro Leu Val Leu Gly Trp Gly Gly
            180                 185                 190

Gly Val Val Phe Ala Glu Leu Glu Leu Ala Arg Arg Glu Gly Phe Arg
        195                 200                 205

Thr Ala Met Val Ser Gly Arg Glu Ser Arg Leu Lys Glu Ile Ala Ala
    210                 215                 220

Ser Gly Ala Ile Ala Val Asp Arg Arg Glu Phe Arg Asp Leu Asp Tyr
225                 230                 235                 240

Leu Arg Ala Lys Glu Ser Thr Asp Pro Asp Ala Met Asp Arg Tyr Arg
                245                 250                 255

Ala Ser Glu Ala Arg Phe Leu Glu Ile Val Gly Glu Leu Ser Gly Gly
            260                 265                 270

His Gly Val Ser Val Phe Leu Asp Asn Leu Gly Gly Gly Leu His Arg
        275                 280                 285

Ala Thr Met Lys Ser Leu Ala Arg Glu Gly Val Val Ser Thr Val Gly
    290                 295                 300

Trp Lys Thr Gly Met Arg Leu Trp Asn Leu Arg Ala Thr Glu Cys Ile
305                 310                 315                 320

Ser Arg His Ile His Val His Thr His Ala Trp Arg His Gln Asp Ala
                325                 330                 335
```

Pro Arg Ile Arg Asp Val Met Gln Glu Thr Gly Trp Leu Pro Asp Ile
340 345 350

Ala Asp Asp Pro Val Thr Ala Phe Ala Arg Val Pro Glu Leu Ala Asp
355 360 365

Ser Tyr Arg Arg Asp Asp Leu Asp Thr Tyr Phe Pro Leu Phe Ser Gly
370 375 380

Ala Gly Arg Gly
385

<210> SEQ ID NO 14
<211> LENGTH: 1515
<212> TYPE: PRT
<213> ORGANISM: Streptomyces flaveolus (Streptomyces sp.(DSM 9954))

<400> SEQUENCE: 14

Met Ser Pro Arg Ser Tyr Asp Val Ala Val Val Gly Met Ala Cys Ala
1 5 10 15

Phe Pro Gly Ala Pro Asp Leu Asp Arg Tyr Trp Ala Asn Val Val Ala
20 25 30

Gly Val Asp Ser Val Thr Glu Val Pro Pro Asp Arg Trp Pro Ala Asp
35 40 45

Arg His Trp Gly Gly Ala Asp Ala Ala Pro Gly Glu Gln Ser Pro Ser
50 55 60

Lys Trp Gly Gly Phe Leu Pro Pro Leu Pro Phe Asp Ala Leu Ala His
65 70 75 80

Gly Val Pro Pro Asn Ser Leu Gly Gly Ile Glu Thr Ala Gln Leu Leu
85 90 95

Ala Leu His Thr Ala Asp Arg Ala Leu Ala Asp Ala Gly Tyr Pro Glu
100 105 110

Arg Pro Phe Asp Arg Glu Thr Thr Ser Val Ile Phe Ala Ala Glu Ala
115 120 125

Gly Ala Asp Leu Ala Ser Ala Tyr Ala Ala Arg Ser Met Leu Gly Gln
130 135 140

His Leu Glu Ser Val Pro Glu Glu Leu Asp Ala Arg Leu Pro Arg Leu
145 150 155 160

Thr Glu Asp Ser Phe Pro Gly Thr Leu Ala Asn Val Ile Ala Gly Arg
165 170 175

Ile Ala Asn Arg Leu Asp Leu Gly Gly Pro Thr Tyr Thr Val Asp Ala
180 185 190

Ala Cys Ala Ser Ser Leu Ala Ala Leu Asp Gln Ala Cys Lys Glu Leu
195 200 205

Leu Ala Glu Thr Ser Asp Met Val Leu Cys Gly Ala Val Asp Thr His
210 215 220

Asn Ala Leu His Asp His Leu Leu Phe Gly Ser Ala Arg Ala Leu Ser
225 230 235 240

Pro Thr Gly Arg Cys Arg Ala Phe Asp Ala Ser Ala Asp Gly Ile Val
245 250 255

Leu Ala Glu Gly Val Ala Cys Leu Val Leu Lys Arg Leu Ala Asp Ala
260 265 270

Glu Arg Asp Gly Asp Arg Val Tyr Ala Val Ile Lys Ala Val Gly Ala
275 280 285

Gly Ser Asp Gly Arg Gly Leu Gly Leu Thr Ala Pro Arg Pro Glu Gly
290 295 300

Gln Arg Arg Ala Leu Glu Arg Ala Tyr Ala Leu Ala Gly Leu Ser Pro

-continued

```
305                 310                 315                 320

Arg Glu Val Gly Leu Val Glu Ala His Gly Thr Gly Thr Val Leu Gly
                325                 330                 335

Asp Arg Thr Glu Leu Glu Thr Leu Thr Glu Val Phe Arg Thr Ala Gly
            340                 345                 350

Ala Gly Pro Gly Ala Cys Ser Leu Gly Ser Val Lys Ser Leu Ile Gly
        355                 360                 365

His Ala Lys Cys Ala Ala Gly Met Ala Gly Leu Ile Lys Ala Val Leu
    370                 375                 380

Ala Val His Thr Gly Val Arg Pro Pro Thr Arg Leu Thr Glu Pro Asn
385                 390                 395                 400

Ala Ala Trp Asp Pro Ala Thr Ser Pro Phe Ala Phe Asp Thr Thr Ala
                405                 410                 415

Arg Pro Trp Ala Glu Pro Arg Arg Val Ala Gly Val Ser Ala Phe Gly
            420                 425                 430

Phe Gly Gly Val Asn Tyr His Ala Val Val Ala Ala Pro Ala Pro Asp
        435                 440                 445

Pro Ser His Glu Ser Ala Pro Arg Ser Ala Gly Leu Leu Leu Phe Arg
    450                 455                 460

Gly Thr Glu Asp Glu Val Gln Thr Ala Leu Arg Asp Leu Ala Gly Arg
465                 470                 475                 480

Leu Ala Glu Gly Thr Val Arg Pro Ser Ala Leu Thr Gly Val Thr Gly
                485                 490                 495

Ala Gly Pro Ala Arg Val Ala Leu Val Thr Glu Gly Ala Ala Thr Leu
            500                 505                 510

Gly Glu Gln Leu Asp Leu Ala Leu Arg Leu Glu Asp Arg Pro Glu Arg
        515                 520                 525

Gly Val His Val Gly Asp Gly Ala Arg Gln Pro Val Ala Leu Leu Phe
    530                 535                 540

Pro Gly Gln Gly Ser Gln Arg Pro Gly Met Leu Ala Asp Leu Phe Val
545                 550                 555                 560

Ala Phe Pro Arg Leu His Arg Phe Leu Arg Ala Glu Pro Ala Leu Thr
                565                 570                 575

Gly Ala Leu Phe Pro Pro Ala Ala Phe Gly Gly Thr Pro Pro Arg Leu
            580                 585                 590

Val Asp Thr Arg Leu Ala Gln Pro Ala Leu Gly Leu Gly Ala Leu Ala
        595                 600                 605

Ala Leu Asp Leu Leu Arg Ala Cys Gly Val Glu Pro Asp Met Thr Ala
    610                 615                 620

Gly His Ser Tyr Gly Glu Leu Pro Ala Leu Ala Ala Ala Gly Ala Leu
625                 630                 635                 640

Pro Glu Thr Ala Val Met Pro Leu Ser Gly Ala Arg Ala Glu Ala Met
                645                 650                 655

His Thr Ala Ala Gly Gln Asp Pro Gly Ala Met Ala Ala Val Ala Ala
            660                 665                 670

Pro Ala Gly Thr Val Ala Glu Leu Leu Ala Arg His Gly Leu Ala Asp
        675                 680                 685

Asp Val Thr Pro Ala Asn Arg Asn Ala Pro Gly Gln Val Val Leu Ala
    690                 695                 700

Gly Ser Ala Ala Gly Ile Asp Ala Ala Val Ala Val Leu Arg Glu Ala
705                 710                 715                 720

Gly His Thr Ala Lys Arg Leu Pro Val Ala Ala Ala Phe His Ser Pro
                725                 730                 735
```

-continued

```
Arg Met Ala Pro Ala Val Asp Ala Phe Ala Gly Ala Leu Ala Gly His
            740                 745                 750

Asp Leu Arg Ala Pro Arg Leu Pro Val Trp Ser Gly Ala Thr Ala Arg
        755                 760                 765

Pro Tyr Pro Ala Asp Pro Glu Ala Ile Arg Thr Gln Leu Ala Gly Ala
    770                 775                 780

Leu Ala Arg Pro Val Arg Phe Ala Glu Gln Ile Glu Asp Met Tyr Ala
785                 790                 795                 800

Ala Gly Val Arg Val Phe Val Glu Ala Gly Pro Gly Thr Val Leu Thr
                805                 810                 815

Arg Leu Ala Gly Glu Val Leu Ala Gly Arg Pro His Thr Ala Leu Ser
            820                 825                 830

Val Glu Ala Pro Gly Arg Pro Gly Leu Ala His Leu Leu Gly Thr Leu
        835                 840                 845

Ala Ala Leu Ala Val Arg Gly Thr Pro Val Arg Leu Asp Glu Leu Thr
    850                 855                 860

Val Ala Arg Asp Glu Pro Val Ser Ala Pro Pro Gly Trp Thr Val Asp
865                 870                 875                 880

Gly His Leu Val Arg Thr Ala Asp Gly Thr Pro Val Pro Gly Gly Leu
                885                 890                 895

Gln Pro Ala Gly Pro Pro Val Thr Leu Thr Gly Gly Gly Val Pro Asp
            900                 905                 910

Ser Arg Asp Glu Thr Val Ile Glu Phe Leu Arg Gly Thr Gln Arg Ile
        915                 920                 925

Val Ala Ala Gln Gln Glu Val Met Leu Arg Tyr Leu Gly Thr Gln Pro
    930                 935                 940

Pro Ala Pro Glu Pro Ala Pro Ala His Asp Pro Pro Glu Ser Ala Ala
945                 950                 955                 960

Thr Ala Ala Pro Thr Val Leu Asp Leu Val Ala Ala Arg Thr Gly Tyr
                965                 970                 975

Pro Pro Ala Met Leu Asp Pro Asp Leu Asp Leu Glu Ala Ala Leu Gly
            980                 985                 990

Val Asp Ser Leu Lys Arg Thr Glu Ile Ala Ser Ala Leu Val Arg Gly
        995                 1000                1005

Thr Pro Ala Ala Asp Ala Val Gly Glu Leu Ala Asp Leu Arg Thr Ile
    1010                1015                1020

Arg Ala Met Thr Asp Trp Leu Ala Thr Arg Thr Gly Pro Asp Gly Pro
1025                1030                1035                1040

Gly Pro Asp Gly Pro Gly Arg Gln Thr Ala Val Pro Glu Pro Glu Thr
                1045                1050                1055

Met Pro Ala Gly Ala Ser Asp Thr Val Arg His Val Val Glu Pro Val
            1060                1065                1070

Pro Glu Glu Pro Pro Ala Gly Pro Leu Pro Thr Leu Thr Arg Ala Ala
        1075                1080                1085

Val Ser Gly Gly Gly Ala Val Gly Asp Val Leu Ala Thr Leu Leu Lys
    1090                1095                1100

Glu Arg Gly Thr Glu Val Val Ser Asp Pro Ala Gly Cys Asp Ala Leu
1105                1110                1115                1120

Leu Leu Leu Asp Ala Leu Asp Gly Gly Asp Tyr Thr Leu Pro Gly Arg
                1125                1130                1135

Phe Thr Asp Ile Arg Ala Ala Val Leu Gly Gly Leu Arg Thr Leu Leu
            1140                1145                1150
```

-continued

Leu Ala Thr Cys His Asp Ala Gly Pro Ala Gly Ser Gly Val His Gly
        1155                1160                1165

Leu Ala Arg Ala Leu Ser Arg Glu His Pro Gly Leu Ala Val Thr Ala
    1170                1175                1180

Val Asp Leu Pro Ala Gly Gln Pro Ala Glu Glu Ala Ala Arg Thr Leu
1185                1190                1195                1200

Leu Ala Glu Leu Gly Gly Ser Arg Pro Ser Val Thr His Thr Asp Gly
                1205                1210                1215

Arg Arg Ala Val Trp Arg Thr Arg Pro Ala Pro Leu Pro Ala Ala Asp
            1220                1225                1230

Val Thr Ala Gly Asp Leu Gly Leu Asp Arg Asp Ser Val Val Leu Leu
        1235                1240                1245

Thr Gly Gly Ala Arg Gly Ile Thr Ala Arg Val Ala Arg Ala Leu Ala
    1250                1255                1260

Thr Leu Thr Gly Cys His Leu Glu Leu Val Gly Arg Ser Glu Pro Val
1265                1270                1275                1280

Thr Gly Thr Val Leu Thr Asp Ala Asp Leu Arg Thr Arg Leu Ile Ala
                1285                1290                1295

Glu Gly Gly Arg Asp Pro Ala Gly Ile Glu Arg Ala Val Arg Ala His
            1300                1305                1310

Ala Ala Gly Arg Gln Val Arg Gln Cys Leu Asp Asp Leu Ala Gly Pro
        1315                1320                1325

Ala Ala Ser Val Arg Tyr His Arg Ala Asp Val Arg Asp Pro Glu Arg
    1330                1335                1340

Leu Gly Ala Val Leu Asp Asp Val Tyr Ala Arg His Gly Arg Leu Asp
1345                1350                1355                1360

Thr Val Val His Ala Ala Gly Gln Val Arg Asp Arg Leu Leu Arg Asp
                1365                1370                1375

Lys Ser Pro Asp Glu Phe Ala Glu Val Tyr Asp Thr Lys Val Ala Gly
            1380                1385                1390

Ala Arg Ala Leu Ala Ala Arg Leu Arg Pro Gly Leu Arg His Leu Val
        1395                1400                1405

Leu Phe Gly Ser Ile Ala Gly Val Thr Gly Asn Arg Gly Gln Thr Asp
    1410                1415                1420

Tyr Ala Ala Ala Asn Asp Ala Leu Asp Thr Met Ala Arg Gln Trp Ser
1425                1430                1435                1440

Gly Arg Val Ala Asp Arg Val Leu Ala Leu Asp Trp Gly Pro Trp Ala
                1445                1450                1455

Ala Asp Ala Gly Gly Met Val Thr Ala Glu Leu Glu Arg Ala Tyr Ala
            1460                1465                1470

Arg Asn Gly Ile Gly Leu Ile Asp Pro Asp Asp Gly Val Arg Ala Phe
        1475                1480                1485

Leu Arg Glu Leu Ala Phe Gly Arg Asp Pro Gln Val Leu Leu Thr Val
    1490                1495                1500

Gly Asp Pro Ala Gly Phe Gly Ser Ala Leu Asp
1505                1510                1515

<210> SEQ ID NO 15
<211> LENGTH: 425
<212> TYPE: PRT
<213> ORGANISM: Streptomyces flaveolus (Streptomyces sp.(DSM 9954))

<400> SEQUENCE: 15

Leu Thr Asp Ile Leu Leu Ala Ala Ala Ala Gly Pro Gly Ala Leu Gly
1               5                   10                  15

-continued

```
Ala Ala Leu Arg Ser Gly Arg Arg Gly Gly Ala Gly Pro Cys Arg Val
            20                  25                  30

Ala Val Leu Asp Pro Thr Ala Glu Arg Ile Ala Gln Ala Leu Ala Leu
        35                  40                  45

Ile Asp Arg Gly Glu Pro Trp His Gly Gly Asn Asp Ile Arg Phe Ala
    50                  55                  60

Pro Arg Pro Gly Pro Ala Gly Arg Thr Val Leu Leu Phe Pro Gly Leu
65                  70                  75                  80

Asp Ala Arg Thr Gly Pro Pro Pro Asp Asp Val Leu Arg Trp Leu Gly
                85                  90                  95

Arg Pro Ala Gly Pro Ala Thr Gly Ala Ala Thr Leu Ala Glu Arg Thr
            100                 105                 110

His Ala Thr Leu Arg Leu Asn Arg Val Leu His Ala Ala Leu Leu Arg
        115                 120                 125

Ala Gly Ile Val Pro Asp Ala Met Ala Gly His Ser Ala Gly Glu Trp
    130                 135                 140

Ser Ala Leu Phe Ala Ala Gly Leu Phe Pro Glu Thr Ala Phe Asp Glu
145                 150                 155                 160

Phe Ala Arg Thr Met Gly Ala Ala Pro Val Pro Asp Val Val Phe Ala
                165                 170                 175

Ala Val Gly Leu Pro Ala Glu Ala Ala Ala Arg Leu Thr Glu Gly Glu
            180                 185                 190

Pro Arg Val Val Leu Ser His Asp Asn Gly Pro Asp Gln Ser Val Leu
        195                 200                 205

Cys Gly Asp Glu Asp Ala Val Thr Arg Cys Leu Asp Arg Ile Ala Asp
    210                 215                 220

Pro Glu Val Pro Arg Arg Val Leu Pro Phe Arg Ser Gly Phe His Ser
225                 230                 235                 240

Pro Met Leu Ala Pro Tyr Leu Pro Gly Phe Ser Ala Val Phe Asp Arg
                245                 250                 255

Val Pro Leu Ala Arg Pro Ala Val Pro Val Trp Ser Ala Thr Thr Val
            260                 265                 270

Ala Pro Tyr Pro Asp Asp Glu Thr Glu Leu Arg Ala Leu Leu Gly Arg
        275                 280                 285

His Leu Val Glu Pro Val Arg Phe Arg Ala Val Ile Glu Arg Leu Tyr
    290                 295                 300

Glu Gln Gly Ala Arg Val Phe Val Gln Ala Gly Cys Gly Ser Leu Thr
305                 310                 315                 320

Arg Phe Val Thr Ala Thr Leu Ala Gly Arg Pro His Leu Thr Val Ser
                325                 330                 335

Ala Gly Ser Ala Thr Arg Pro Gln Leu Asp Gln Leu Arg Trp Ala Ala
            340                 345                 350

Ala Ala Leu Trp Thr Ala Gly His Thr Pro Asp Leu Ala Ala Leu Gly
        355                 360                 365

Leu Thr Gly Pro Ala Ala Asp Pro Val Pro Ser Thr Arg Ala Val Thr
    370                 375                 380

Gly Ala His Pro Arg Thr Gly Ala Tyr Pro Arg Thr His Pro Val Ala
385                 390                 395                 400

Gly Ala Tyr Glu Ala Ala Val Ala Ala Val Ser Ala Ser Val Glu Ser
                405                 410                 415

Val Tyr Arg Thr Trp Lys Glu Arg Thr
            420                 425
```

```
<210> SEQ ID NO 16
<211> LENGTH: 239
<212> TYPE: PRT
<213> ORGANISM: Streptomyces flaveolus (Streptomyces sp.(DSM 9954))

<400> SEQUENCE: 16

Met Ser Ser Arg Arg His Ala Val Val Thr Gly Ser Ser Arg Gly Ile
1               5                   10                  15

Gly Ala Ala Val Ala Ala Arg Leu Ala Arg Ala Gly Trp Ala Val Thr
            20                  25                  30

Gly Trp Asp Arg Thr Pro Gly Asp Thr Thr Gly Leu Ala Asp Trp Arg
        35                  40                  45

Glu Val Asp Val Ser Asp Ala Glu Ser Val Gln Ala Ala Ala Arg Glu
    50                  55                  60

Val Thr Ala Thr Asp Leu Leu Val Asn Ser Ala Gly Val Gly Ala Ile
65                  70                  75                  80

Ala Pro Ser Ala Glu Leu Lys Pro Arg Thr Trp Glu Arg Val Val Gly
                85                  90                  95

Val Asn Leu Ser Gly Thr Phe Tyr Cys Ala Gln Ala Leu Phe Pro Ala
            100                 105                 110

Leu Ser Ala Arg Arg Gly Leu Val Val Asn Leu Ala Ser Val Met Ala
        115                 120                 125

His Arg Ala Val Pro Gly Arg Ala Ala Tyr Cys Ala Ser Lys Ala Gly
    130                 135                 140

Val Val Met Leu Thr Glu Ala Leu Gly Val Glu Trp Ala Glu His Gly
145                 150                 155                 160

Val Arg Val Val Ala Val Ser Pro Ala Tyr Val Arg Thr Pro Leu Val
                165                 170                 175

Ala Glu Gly Phe Ala Asn Gly Asn Leu Asp Glu Ser Ala Ile Ala Ala
            180                 185                 190

Arg Thr Pro Leu Gly Arg Leu Ala Glu Pro Glu Glu Ile Ala Asp Leu
        195                 200                 205

Val Leu Ser Leu Thr Gly Asp Glu Phe Ala Tyr Leu Thr Ala Thr Thr
    210                 215                 220

Leu Arg Phe Asp Gly Gly Trp Thr Ala Asp Gly Val Phe Pro Arg
225                 230                 235


<210> SEQ ID NO 17
<211> LENGTH: 340
<212> TYPE: PRT
<213> ORGANISM: Streptomyces flaveolus (Streptomyces sp.(DSM 9954))

<400> SEQUENCE: 17

Met Pro Val Thr Asp Phe Gly Val Leu Ala Leu Ala His Ala Leu Gly
1               5                   10                  15

Asp Pro Arg Asp Val Ala Ala Thr Ala Ala Asp His Val Asp Asp Pro
            20                  25                  30

Asp Arg Val Leu Leu Trp Gly Tyr Arg Gly Tyr His Arg Ala Pro Gln
        35                  40                  45

Gly Thr Thr Ser Thr Ala Leu Ala Ala Arg Ala Ala Glu Lys Ala Leu
    50                  55                  60

Ala Lys Ala Gly Val Asp Pro Arg Asp Leu Asp Leu Val Val Val Ala
65                  70                  75                  80

Asp Ser Ser Val Pro Glu Tyr Leu Leu Trp Asp Thr Ser Ala Val Val
                85                  90                  95
```

```
Ala Arg Ala Ile Gly Ala Gly Thr Ala Pro Thr Leu Leu Leu Thr Gln
            100                 105                 110

Gly Cys Ala Ser Ala Val Thr Ala Phe Gln Gln Ile Ala Gly Ile Phe
        115                 120                 125

Ala Thr Arg Pro Asp Ala Glu Thr Val Leu Leu Val Ala Val Asn Gln
    130                 135                 140

Val Ser Glu Ala His Thr Asn Arg Met Arg Phe Asn Thr Leu Leu Gly
145                 150                 155                 160

Ser Asp Gly Ala Ala Ala Ala Val Leu Arg Arg Gly His Asp Arg Leu
                165                 170                 175

Arg Trp Leu Ala Thr Glu Gln Leu Thr Asp Pro Thr Tyr Ala Asp Phe
            180                 185                 190

Tyr Arg Val Glu Tyr Gly Gly Ala Ala Val Pro His Ala Pro Glu Gly
        195                 200                 205

Ala Gly Asn Leu Asp Val Asp Pro Leu Ser Leu Val Tyr Arg His Phe
    210                 215                 220

Arg Arg Glu Pro Glu His Leu Ala Lys Phe Val Arg Thr Leu Asn Ser
225                 230                 235                 240

Arg Val Arg Thr Val Phe Glu Asp Ala Cys Asp Gly Ala Gly Val Asp
                245                 250                 255

Pro Gly Gln Val Lys Arg Phe Leu Phe Leu Asn Asp Asn Gln Asp Ser
            260                 265                 270

Leu Ala Asp Val Ala Lys Ala Val Gly Val Pro Leu Asp Arg Thr Asn
        275                 280                 285

Ala Glu Leu Ala Lys Asp Leu Gly His Cys Gly Gly Ala Asp Gln Leu
    290                 295                 300

Ile Cys Leu Asp Thr Leu Leu Glu Arg Gly Glu Leu Ala Glu Gly Asp
305                 310                 315                 320

Val Val Ala Leu Ala Gly Leu Ser Ile Gly Met His Trp Tyr Cys Thr
                325                 330                 335

Leu Leu Thr Val
            340


<210> SEQ ID NO 18
<211> LENGTH: 84
<212> TYPE: PRT
<213> ORGANISM: Streptomyces flaveolus (Streptomyces sp.(DSM 9954))

<400> SEQUENCE: 18

Met Ala Glu Leu Thr Ile Gln Asp Leu Ile Asp Ile Phe Asn Arg Ser
1               5                   10                  15

Ile Gly Asp Gln Asp Pro Val Glu Pro Glu Gly Asp Pro Ser Asp Val
            20                  25                  30

Thr Phe Ala Ala Leu Gly Phe Asp Ser Leu Thr Thr Leu Asn Ala Val
        35                  40                  45

Arg Arg Ile Glu Arg Lys His Gly Val Glu Leu Gly Glu Asn Val Ile
    50                  55                  60

Ser Glu Ala Arg Thr Pro Arg Gln Leu Leu Asp Arg Val Asn Ala Ala
65                  70                  75                  80

Leu Ala Ala Ala


<210> SEQ ID NO 19
<211> LENGTH: 616
<212> TYPE: PRT
<213> ORGANISM: Streptomyces flaveolus (Streptomyces sp.(DSM 9954))
```

-continued

<400> SEQUENCE: 19

```
Met Cys Gly Ile Thr Gly Trp Val Ala Tyr Gly Asp Asp Leu Ala Arg
1               5                   10                  15

His Arg Ser Val Val Gln Ala Met Thr Asp Thr Met Ile Cys Arg Gly
            20                  25                  30

Pro Asp Ala Glu Gly Val Trp Ile Glu Gly Pro Val Ala Leu Gly His
        35                  40                  45

Arg Arg Leu Ser Ile Ile Asp Pro Ala Gly Gly Ala Gln Pro Met Val
    50                  55                  60

Ala Thr Arg Asp Gly Arg Thr Leu Ala Ala Leu Thr Phe Cys Gly Glu
65                  70                  75                  80

Ile Tyr Asn Phe Arg Glu Leu Arg Ala Glu Leu Ala Ala Leu Gly His
                85                  90                  95

Thr Phe Arg Thr Asp Ser Asp Thr Glu Val Val Leu Asn Ala Tyr Leu
            100                 105                 110

Gln Trp Gly Ala Asp Phe Ala Ala Arg Leu Asn Gly Met Phe Ala Ile
        115                 120                 125

Gly Leu Trp Asp Ala Thr Thr Arg Glu Leu Leu Leu Val Arg Asp Pro
    130                 135                 140

Ile Gly Val Lys Pro Leu Tyr Tyr Ala Arg Thr Ser Asp Gly Val Val
145                 150                 155                 160

Phe Gly Ser Glu Pro Lys Ala Val Leu Ala His Arg Gly Val Pro Arg
                165                 170                 175

Arg Val Asp Ala Gln Gly Leu Ala Glu Ile Leu Asp Met Val Arg Thr
            180                 185                 190

Pro Glu Val Thr Pro Phe Thr Asp Leu Ser Glu Val Arg Pro Gly Gln
        195                 200                 205

Val Val Arg Val Thr Glu Gly Gly Leu Thr Arg Thr Arg Tyr Trp Gln
    210                 215                 220

Leu Thr Ala Arg Glu His Thr Asp Asp Leu Asp Thr Thr Ile Ala Thr
225                 230                 235                 240

Val Arg Glu Leu Leu Glu Asp Ile Val Ser Arg Gln Leu Ile Ala Asp
                245                 250                 255

Val Pro Val Ala Thr Leu Leu Ser Gly Gly Leu Asp Ser Ser Ala Ile
            260                 265                 270

Thr Ala Leu Ala Gln Arg Thr Leu Thr Ala Glu Gly Arg Gly Pro Val
        275                 280                 285

Arg Ser Tyr Ser Val Asp Phe Gln Gly Ala Ala Asp Gly Phe Glu Pro
    290                 295                 300

Asp Ala Val Arg Gly Thr Ala Asp Ala Pro Tyr Val Arg Asp Cys Ala
305                 310                 315                 320

Ala His Val Gly Ala Asp His Ser Glu Val Leu Leu Asp Ser Thr Glu
                325                 330                 335

Leu Ala Asp Pro Ala Val Arg Ala Ala Ile Leu Gly Ala Thr Asp Leu
            340                 345                 350

Pro Pro Ala Tyr Trp Gly Asp Leu Trp Pro Ser Leu Tyr Leu Leu Cys
        355                 360                 365

Arg Glu Ile Arg Lys Arg Ala Thr Val Val Leu Ser Gly Glu Ser Ala
    370                 375                 380

Asp Glu Leu Phe Gly Gly Tyr Arg Trp Tyr Gln Arg Pro Glu Ala Val
385                 390                 395                 400

Asp Ala Pro Thr Phe Pro Trp Leu Thr Pro Gly Ser Ala Arg Ile Phe
                405                 410                 415
```

Gly Gly Ser Ser Leu Ile Asp Gln Gly Leu Leu Glu Lys Leu Asp Leu
420 425 430

Glu Gly Tyr Arg Arg Asp Arg Tyr Ala Glu Ala Leu Ala Glu Val Pro
435 440 445

Val Leu Ala Gly Glu Ser Ala Val Asp Arg Arg Met Arg Glu Val Thr
450 455 460

Tyr Leu Asn Ile Thr Arg Phe Met Gln Ala Val Leu Asp Arg Lys Asp
465 470 475 480

Arg Met Ser Met Ala Val Gly Leu Glu Val Arg Val Pro Phe Cys Asp
485 490 495

His Arg Leu Met Asp Tyr Val Phe Asn Val Pro Trp Ala Met Lys Ser
500 505 510

Phe Asp Gly Arg Glu Lys Ser Leu Leu Arg Ala Ala Val Arg Asp Val
515 520 525

Leu Pro Asn Ser Val Leu Glu Arg Thr Lys Thr Pro Phe Pro Ala Thr
530 535 540

Gln Asp Thr Arg Tyr Glu Gln Ala Leu Arg Ala Glu Leu Arg Glu Val
545 550 555 560

Leu Ala Asp Pro Asp Ala Pro Val Arg Pro Leu Leu Asn Thr Ala Arg
565 570 575

Val Asn Arg Val Leu Gly Arg Glu Leu Asp Asp Phe Ser Leu Pro His
580 585 590

Asp Arg Gly Gly Ile Glu Met Ala Leu Trp Leu Asn Arg Trp Leu Ala
595 600 605

Ser Tyr Glu Val Thr Val Thr Val
610 615

<210> SEQ ID NO 20
<211> LENGTH: 259
<212> TYPE: PRT
<213> ORGANISM: Streptomyces flaveolus (Streptomyces sp.(DSM 9954))

<400> SEQUENCE: 20

Met Pro Asp Arg Ser Ser Ala Glu His Gln Leu Trp Leu Arg Gly Phe
1 5 10 15

His Gln Pro Lys Pro Gly Ala Pro Arg Leu Ile Cys Leu Pro His Ala
20 25 30

Gly Gly Ser Ala Ser Phe Tyr Phe Pro Val Ser Gln Ala Leu Ser Pro
35 40 45

Ala Val Asp Val Leu Ala Val Gln Tyr Pro Gly Arg Gln Asp Arg Arg
50 55 60

Gln Glu Ser Pro Ala Ala Ser Val Gln Glu Leu Ala Glu Gly Val Phe
65 70 75 80

Arg Ala Leu Asp Asp Gln Glu Asp Thr Pro Leu Ala Leu Phe Gly His
85 90 95

Ser Met Gly Ala Met Val Gly Phe Glu Leu Ala Arg Leu Leu Glu Ala
100 105 110

Ala Gly Arg Pro Pro Ala Val Leu Phe Ile Ser Gly Arg Arg Gly Pro
115 120 125

Ser Ile Val Trp Thr Glu Thr Val His Thr Met Asp Asp Glu Arg Leu
130 135 140

Ile Ala Glu Val Ala Lys Leu Glu Gly Thr Asp Ala Ala Leu Leu Gln
145 150 155 160

Asp Glu Glu Val Leu Arg Met Ile Leu Pro Ala Leu Arg Ala Asp Tyr

```
                165                 170                 175

Arg Ala Val Glu Thr Tyr Gln Arg Thr Pro Gly Pro Arg Leu Ser Cys
            180                 185                 190

Pro Phe Val Val Met Thr Gly Asp Ala Asp Pro Arg Val Thr Pro Asp
        195                 200                 205

Glu Ala Arg Thr Trp Ala Glu Glu Thr Asp Gly Ala Phe Glu Leu Glu
    210                 215                 220

Val Tyr Pro Gly Ala His Phe Tyr Leu Val Ala Gln Gln Gln Ala Val
225                 230                 235                 240

Leu Ala Arg Ile Glu Ala Thr Met Arg Arg Leu Gly Ser Thr Thr Gly
                245                 250                 255

Ala Val Val


<210> SEQ ID NO 21
<211> LENGTH: 453
<212> TYPE: PRT
<213> ORGANISM: Streptomyces flaveolus (Streptomyces sp.(DSM 9954))

<400> SEQUENCE: 21

Val Asn Glu Ile Leu Ser Ala Val Leu Ser Ala Glu Ala Thr Ala Ala
1               5                   10                  15

Asp Phe Ala Ala Leu Pro Leu Pro Glu Ser Tyr Arg Ala Ile Thr Val
            20                  25                  30

His Lys Asp Glu Thr Glu Met Phe Thr Gly Val Gly Pro Ala Asp Lys
        35                  40                  45

Asp Pro Arg Lys Ser Leu His Leu Asp Glu Val Pro Val Pro Glu Leu
    50                  55                  60

Gly Pro Gly Glu Ala Leu Val Ala Val Met Ala Ser Ser Val Asn Tyr
65                  70                  75                  80

Asn Ser Val Trp Ser Ser Ile Phe Glu Pro Leu Pro Thr Phe Ala Phe
                85                  90                  95

Leu Glu Arg Tyr Gly Arg Arg Gly Glu Leu Ala Lys Arg His Asp Leu
            100                 105                 110

Pro Tyr His Val Ile Gly Ser Asp Leu Ala Gly Val Val Leu Arg Thr
        115                 120                 125

Gly Pro Gly Val Gln Ala Trp Lys Pro Gly Asp Glu Val Val Ala His
    130                 135                 140

Cys Leu Ser Val Glu Leu Glu Ser Ser Asp Gly His Asp Asp Thr Met
145                 150                 155                 160

Met Asp Pro Glu Gln Arg Ile Trp Gly Phe Glu Thr Asn Phe Gly Gly
                165                 170                 175

Leu Ala Glu Leu Ala Leu Val Lys Ser Asn Gln Leu Met Pro Lys Pro
            180                 185                 190

Arg His Leu Thr Trp Glu Glu Ala Ala Ala Pro Gly Leu Val Asn Ser
        195                 200                 205

Thr Ala Tyr Arg Gln Leu Val Ser Arg Asn Gly Ala Gln Met Lys Gln
    210                 215                 220

Gly Asp Asn Val Leu Ile Trp Gly Ala Ser Gly Gly Leu Gly Ser Tyr
225                 230                 235                 240

Ala Thr Gln Leu Ala Leu Ala Gly Gly Ala Asn Pro Val Cys Val Val
                245                 250                 255

Ser Thr Pro Gln Lys Ala Ala Ile Cys Arg Ser Met Gly Ala Glu Ala
            260                 265                 270

Val Ile Asp Arg Asp Ala Glu Asp Tyr Arg Phe Trp Arg Asp Gly Asn
```

```
        275                 280                 285

Thr Gln Asp Pro Arg Glu Trp Lys Arg Phe Gly Lys Arg Ile Arg Glu
    290                 295                 300

Leu Thr Gly Gly Glu Asp Val Asp Ile Val Phe Glu His Pro Gly Arg
305                 310                 315                 320

Glu Thr Phe Gly Ala Ser Val Phe Val Ala Arg Lys Gly Gly Thr Ile
                325                 330                 335

Val Thr Cys Ala Ser Thr Ser Gly Tyr Glu His Gln Tyr Asp Asn Arg
            340                 345                 350

Tyr Leu Trp Met Ser Leu Lys Arg Ile Ile Gly Ser His Phe Ala Asn
        355                 360                 365

Tyr Arg Glu Ala Trp Glu Ala Asn Arg Leu Val Ala Lys Gly Arg Ile
    370                 375                 380

His Pro Thr Leu Ser Lys Val Tyr Pro Leu Glu Glu Thr Gly Gln Ala
385                 390                 395                 400

Ala Phe Asp Val Tyr Gly Asn Val His His Gly Lys Val Gly Val Leu
                405                 410                 415

Gly Leu Ala Pro Thr Glu Gly Leu Gly Val Arg Asp Glu Glu Met Arg
            420                 425                 430

Ala Arg His Val Gly Ala Ile Asn Arg Phe Arg Pro Ser Ala Glu Pro
        435                 440                 445

Gln Thr Glu Pro Val
    450
```

<210> SEQ ID NO 22
<211> LENGTH: 71
<212> TYPE: PRT
<213> ORGANISM: Streptomyces flaveolus (Streptomyces sp.(DSM 9954))

<400> SEQUENCE: 22

```
Met Ser Asn Pro Phe Asp Lys Glu Asp Gly Ser Phe Phe Val Val Val
1               5                   10                  15

Asn Met Glu Gly Gln His Ser Leu Trp Pro Ala Phe Ala Glu Ile Pro
            20                  25                  30

Ala Gly Trp Ser Ile Val His Gly Glu Thr Asp Lys Ala Ala Cys Leu
        35                  40                  45

Glu Tyr Val Ala Ala His Trp Thr Asp Met Arg Pro Arg Ser Leu Thr
    50                  55                  60

Asp Ala Ala Pro Thr Pro Glu
65                  70
```

<210> SEQ ID NO 23
<211> LENGTH: 178
<212> TYPE: PRT
<213> ORGANISM: Streptomyces flaveolus (Streptomyces sp.(DSM 9954))

<400> SEQUENCE: 23

```
Met Pro Arg Arg Pro Gln Ser Arg Thr Pro Leu Arg Lys Gln Ser Val
1               5                   10                  15

Asp Asn Lys Val Phe Lys Cys Gln Gly Cys Arg Met Ser Ser Ile Pro
            20                  25                  30

Pro Gln Pro Ala Asp Ala Phe Thr Ala Pro Ser Ala His Glu Ala Arg
        35                  40                  45

Val Gln Arg Ala Tyr Thr Ser Leu Phe Arg Ile Ala Glu Arg His Ala
    50                  55                  60

Ala Thr Asp Gly Gln Arg Arg Arg Gln Ala Gln Ser His Met Ile Ser
```

```
65                  70                  75                  80

Pro Tyr Glu Ala Val Arg Leu Val Ser Phe Leu Leu Ser Gly Ala Ala
                85                  90                  95

Gln Leu Glu Gly Glu Glu Pro Glu Val Asp Arg Ala Asp Ile Thr Ala
            100                 105                 110

Ala Leu Ser Leu Leu Pro Leu Ala Arg Ala Glu Met Asp Glu Val Glu
        115                 120                 125

Ala Gly Ile Leu Lys Met Ala His Gly Arg Gly Met Thr Trp Ser Glu
    130                 135                 140

Ile Ala Phe Gly Leu Gly Leu Ala Thr Pro Gln Ala Ala Arg Gln Arg
145                 150                 155                 160

His Glu Arg Leu Ala Ser Arg Met Glu Ser Gly Ala Glu Lys Lys Ala
                165                 170                 175

Asp Gly


<210> SEQ ID NO 24
<211> LENGTH: 152
<212> TYPE: PRT
<213> ORGANISM: Streptomyces flaveolus (Streptomyces sp.(DSM 9954))

<400> SEQUENCE: 24

Val Gln Ala Ser Ser Gly Glu Thr Thr Pro Thr Thr Ser Arg Pro Gly
1               5                   10                  15

Arg Thr Pro Asn Trp Pro Ala Phe Ala Arg Ala Ser Glu Ala Glu Thr
            20                  25                  30

Arg Phe Ala Gly Asp Pro His Phe Pro Pro Ile Ala Asn Gly Leu Asp
        35                  40                  45

Tyr Leu Val Ser Val Val Glu Leu Leu Gln Arg Glu Lys Gly Ala Gly
    50                  55                  60

Ser Ala Arg Asp Leu Lys Tyr Ala Val Leu His Leu Ala Ala Gly Ala
65                  70                  75                  80

Glu Val Leu Pro Lys Ala Arg Leu Leu Met Glu His Trp Ser Leu Val
                85                  90                  95

Phe Thr Asp Pro Gly Ala Ala Thr Arg Thr Ala Leu Glu Asp Gly Ser
            100                 105                 110

Leu Ser Ser Cys Thr Pro Glu Arg Thr Arg Lys Arg Leu Asn Arg Arg
        115                 120                 125

Trp Thr Ser Ala Ser Pro Ala Arg Pro Ala Ser Met Thr Ser Arg Gly
    130                 135                 140

Ala Thr Ala Ala Glu Pro Tyr Ile
145                 150


<210> SEQ ID NO 25
<211> LENGTH: 144
<212> TYPE: PRT
<213> ORGANISM: Streptomyces flaveolus (Streptomyces sp.(DSM 9954))

<400> SEQUENCE: 25

Val Ser Leu Ile Glu Val Gly Pro Gly Gln Val Glu Leu Val Val Arg
1               5                   10                  15

Gly Pro Gly Val Leu Ala Thr Ser Val Arg Leu Phe Asp Trp Ser Arg
            20                  25                  30

Ala Asp Glu Tyr Glu Thr Val Phe Ala Val Glu Ala Ile Ala Asp Gly
        35                  40                  45

Val Arg Ala Arg Leu Glu Asn Val Thr Val Thr Val Trp Asp Asp Met
    50                  55                  60
```

```
Ser Ala Phe Phe Asp Gly Leu Ala Arg Asp Phe Arg Gly Trp Asp Gly
65                  70                  75                  80

Glu Arg Val Trp Ile Asn Asn His Leu Val Val Thr Ala Thr Phe Gly
                85                  90                  95

Ser Gly Gly His Val Tyr Val Asp Trp Thr Leu Gln Ser Gly Phe Phe
            100                 105                 110

Pro Gly Asp Trp Lys Cys Thr Val Thr Thr Val Ile Glu Ala Gly Glu
        115                 120                 125

Gly Met Thr Ala Val Ala Ala Asp Leu Arg Glu Phe Leu Arg Gln Glu
    130                 135                 140


<210> SEQ ID NO 26
<211> LENGTH: 32
<212> TYPE: DNA
<213> ORGANISM: Streptomyces flaveolus (Streptomyces sp.(DSM 9954))

<400> SEQUENCE: 26

aggaattcat ggcctcckcs rtsaactaca ay                                   32


<210> SEQ ID NO 27
<211> LENGTH: 32
<212> TYPE: DNA
<213> ORGANISM: Streptomyces flaveolus (Streptomyces sp.(DSM 9954))

<400> SEQUENCE: 27

tcggatccgc cgaagttsgt ctcrwabccc ca                                   32


<210> SEQ ID NO 28
<211> LENGTH: 31
<212> TYPE: DNA
<213> ORGANISM: Streptomyces flaveolus (Streptomyces sp.(DSM 9954))

<400> SEQUENCE: 28

aggaattcga catcgacats gtbwtcgagc a                                    31


<210> SEQ ID NO 29
<211> LENGTH: 32
<212> TYPE: DNA
<213> ORGANISM: Streptomyces flaveolus (Streptomyces sp.(DSM 9954))

<400> SEQUENCE: 29

tcggatccga tgatgcgctt swsbkdcatc ca                                   32


<210> SEQ ID NO 30
<211> LENGTH: 59
<212> TYPE: DNA
<213> ORGANISM: Streptomyces flaveolus (Streptomyces sp.(DSM 9954))

<400> SEQUENCE: 30

ctcgaccggt actgggccaa cgtggtggcc ggtgtcgaca ttccggggat ccgtcgacc      59


<210> SEQ ID NO 31
<211> LENGTH: 58
<212> TYPE: DNA
<213> ORGANISM: Streptomyces flaveolus (Streptomyces sp.(DSM 9954))

<400> SEQUENCE: 31

ggccagttcg cgcaggaagg cccgtacgcc gtcgtccggt gtaggctgga gctgcttc       58


<210> SEQ ID NO 32
<211> LENGTH: 59
```

<212> TYPE: DNA
<213> ORGANISM: Streptomyces flaveolus (Streptomyces sp.(DSM 9954))

<400> SEQUENCE: 32
gtggaaatcg gctcgggcgc gcccgaatta accgcgtcga ttccggggat ccgtcgacc 59

<210> SEQ ID NO 33
<211> LENGTH: 58
<212> TYPE: DNA
<213> ORGANISM: Streptomyces flaveolus (Streptomyces sp.(DSM 9954))

<400> SEQUENCE: 33
aatggatgta tcgtcgcagg acgcccagaa ttcacctgct gtaggctgga gctgcttc 58

<210> SEQ ID NO 34
<211> LENGTH: 59
<212> TYPE: DNA
<213> ORGANISM: Streptomyces flaveolus (Streptomyces sp.(DSM 9954))

<400> SEQUENCE: 34
gcgcagcaga gcccggaatc agaagtactg gacgtcacca ttccggggat ccgtcgacc 59

<210> SEQ ID NO 35
<211> LENGTH: 58
<212> TYPE: DNA
<213> ORGANISM: Streptomyces flaveolus (Streptomyces sp.(DSM 9954))

<400> SEQUENCE: 35
ggcgatctcg cccgcgcgga ccgccaccat ggacagcagt gtaggctgga gctgcttc 58

<210> SEQ ID NO 36
<211> LENGTH: 59
<212> TYPE: DNA
<213> ORGANISM: SStreptomyces flaveolus (Streptomyces sp.(DSM 9954))

<400> SEQUENCE: 36
gaggattgcg acggcgtcgt cctggcgttt ctgcgacaca ttccggggat ccgtcgacc 59

<210> SEQ ID NO 37
<211> LENGTH: 58
<212> TYPE: DNA
<213> ORGANISM: Streptomyces flaveolus (Streptomyces sp.(DSM 9954))

<400> SEQUENCE: 37
ctcctcgtcg gcttcggtga gtccgcggtc gcgcatcact gtaggctgga gctgcttc 58

<210> SEQ ID NO 38
<211> LENGTH: 59
<212> TYPE: DNA
<213> ORGANISM: Streptomyces flaveolus (Streptomyces sp.(DSM 9954))

<400> SEQUENCE: 38
gggccgcagg acaggtccgg cggcccggtg cgcggcgaga ttccggggat ccgtcgacc 59

<210> SEQ ID NO 39
<211> LENGTH: 58
<212> TYPE: DNA
<213> ORGANISM: Streptomyces flaveolus (Streptomyces sp.(DSM 9954))

<400> SEQUENCE: 39
cgcgccggag aacagcggga agtaggtgtc gaggtcgtct gtaggctgga gctgcttc 58

<210> SEQ ID NO 40

<211> LENGTH: 59
<212> TYPE: DNA
<213> ORGANISM: Streptomyces flaveolus (Streptomyces sp.(DSM 9954))

<400> SEQUENCE: 40
ggccggcccc ggagccctgg gcgccgccct gcgttcggga ttccggggat ccgtcgacc 59

<210> SEQ ID NO 41
<211> LENGTH: 58
<212> TYPE: DNA
<213> ORGANISM: Streptomyces flaveolus (Streptomyces sp.(DSM 9954))

<400> SEQUENCE: 41
gctctccacg gaggcgctca ccgcggcgac ggcggcctct gtaggctgga gctgcttc 58

<210> SEQ ID NO 42
<211> LENGTH: 59
<212> TYPE: DNA
<213> ORGANISM: Streptomyces flaveolus (Streptomyces sp.(DSM 9954))

<400> SEQUENCE: 42
gcggtcgtga ccggatcgtc ccgcggcatc ggcgcggcca ttccggggat ccgtcgacc 59

<210> SEQ ID NO 43
<211> LENGTH: 58
<212> TYPE: DNA
<213> ORGANISM: Streptomyces flaveolus (Streptomyces sp.(DSM 9954))

<400> SEQUENCE: 43
cacgccgtcg gcggtccagc cgccgtcgaa gcgcagggtt gtaggctgga gctgcttc 58

<210> SEQ ID NO 44
<211> LENGTH: 59
<212> TYPE: DNA
<213> ORGANISM: Streptomyces flaveolus (Streptomyces sp.(DSM 9954))

<400> SEQUENCE: 44
cttcggcgtc ctcgcgctcg cccacgccct cggcgatcca ttccggggat ccgtcgacc 59

<210> SEQ ID NO 45
<211> LENGTH: 58
<212> TYPE: DNA
<213> ORGANISM: Streptomyces flaveolus (Streptomyces sp.(DSM 9954))

<400> SEQUENCE: 45
gtgcatgccg atggacaggc ccgcgagcgc gaccacgtct gtaggctgga gctgcttc 58

<210> SEQ ID NO 46
<211> LENGTH: 59
<212> TYPE: DNA
<213> ORGANISM: Streptomyces flaveolus (Streptomyces sp.(DSM 9954))

<400> SEQUENCE: 46
gacgacctcg cgcggcaccg gtccgtcgtc caggcgatga ttccggggat ccgtcgacc 59

<210> SEQ ID NO 47
<211> LENGTH: 58
<212> TYPE: DNA
<213> ORGANISM: Streptomyces flaveolus (Streptomyces sp.(DSM 9954))

<400> SEQUENCE: 47
catctcgatg ccgccccggt cgtgcggcag gctgaagtct gtaggctgga gctgcttc 58

<210> SEQ ID NO 48
<211> LENGTH: 28
<212> TYPE: DNA
<213> ORGANISM: Streptomyces flaveolus (Streptomyces sp.(DSM 9954))

<400> SEQUENCE: 48
tttggatcct acaccggcca gggcgccc 28

<210> SEQ ID NO 49
<211> LENGTH: 40
<212> TYPE: DNA
<213> ORGANISM: Streptomyces flaveolus (Streptomyces sp.(DSM 9954))

<400> SEQUENCE: 49
tttggtaccg aggacgctag cgtcggccag ccaggggtgc 40

<210> SEQ ID NO 50
<211> LENGTH: 30
<212> TYPE: DNA
<213> ORGANISM: Streptomyces flaveolus (Streptomyces sp.(DSM 9954))

<400> SEQUENCE: 50
tttaagctta gcacccgtgc caccggtcac 30

<210> SEQ ID NO 51
<211> LENGTH: 36
<212> TYPE: DNA
<213> ORGANISM: Streptomyces flaveolus (Streptomyces sp.(DSM 9954))

<400> SEQUENCE: 51
gctagcgtcc tcggtacccc ggtgctcccc ggcacc 36

<210> SEQ ID NO 52
<211> LENGTH: 29
<212> TYPE: DNA
<213> ORGANISM: Streptomyces flaveolus (Streptomyces sp.(DSM 9954))

<400> SEQUENCE: 52
tttggatccg gtgttgtggg cggtgatgg 29

<210> SEQ ID NO 53
<211> LENGTH: 42
<212> TYPE: DNA
<213> ORGANISM: Streptomyces flaveolus (Streptomyces sp.(DSM 9954))

<400> SEQUENCE: 53
tttgaattcg gcgagtacta cggcatcggc cgtccaggcg gc 42

<210> SEQ ID NO 54
<211> LENGTH: 28
<212> TYPE: DNA
<213> ORGANISM: Streptomyces flaveolus (Streptomyces sp.(DSM 9954))

<400> SEQUENCE: 54
tttaagcttg cacgacgtgg ccgaagcg 28

<210> SEQ ID NO 55
<211> LENGTH: 42
<212> TYPE: DNA
<213> ORGANISM: Streptomyces flaveolus (Streptomyces sp.(DSM 9954))

<400> SEQUENCE: 55
tttgaattcg ccgtagtact cgccaccacc ctgctgcccg gc 42

<210> SEQ ID NO 56
<211> LENGTH: 30
<212> TYPE: DNA
<213> ORGANISM: Streptomyces flaveolus (Streptomyces sp.(DSM 9954))

<400> SEQUENCE: 56
tttgaattcg ggtggtccgg agctggatcg 30

<210> SEQ ID NO 57
<211> LENGTH: 30
<212> TYPE: DNA
<213> ORGANISM: Streptomyces flaveolus (Streptomyces sp.(DSM 9954))

<400> SEQUENCE: 57
cggcagcagg gcagggacta gtatggcggc 30

<210> SEQ ID NO 58
<211> LENGTH: 30
<212> TYPE: DNA
<213> ORGANISM: Streptomyces flaveolus (Streptomyces sp.(DSM 9954))

<400> SEQUENCE: 58
tttaagcttg gtgctcggac tgggcggagc 30

<210> SEQ ID NO 59
<211> LENGTH: 30
<212> TYPE: DNA
<213> ORGANISM: Streptomyces flaveolus (Streptomyces sp.(DSM 9954))

<400> SEQUENCE: 59
gccgccatac tagtccctgc cctgctgccg 30

<210> SEQ ID NO 60
<211> LENGTH: 29
<212> TYPE: DNA
<213> ORGANISM: Streptomyces flaveolus (Streptomyces sp.(DSM 9954))

<400> SEQUENCE: 60
tttgaattcc gacgacaccg gatacgggc 29

<210> SEQ ID NO 61
<211> LENGTH: 30
<212> TYPE: DNA
<213> ORGANISM: Streptomyces flaveolus (Streptomyces sp.(DSM 9954))

<400> SEQUENCE: 61
cggcagcagg acggtgacta gtacggtggc 30

<210> SEQ ID NO 62
<211> LENGTH: 29
<212> TYPE: DNA
<213> ORGANISM: Streptomyces flaveolus (Streptomyces sp.(DSM 9954))

<400> SEQUENCE: 62
tttaagcttc cacccatgtc tgcaccagg 29

<210> SEQ ID NO 63
<211> LENGTH: 20
<212> TYPE: DNA
<213> ORGANISM: Streptomyces flaveolus (Streptomyces sp.(DSM 9954))

<400> SEQUENCE: 63
gccaccgtac tagtcaccgt 20

-continued

```
<210> SEQ ID NO 64
<211> LENGTH: 31
<212> TYPE: DNA
<213> ORGANISM: Streptomyces flaveolus (Streptomyces sp.(DSM 9954))

<400> SEQUENCE: 64

atgaattcgt ggcggtcgtc ggcatggcct g                                  31


<210> SEQ ID NO 65
<211> LENGTH: 31
<212> TYPE: DNA
<213> ORGANISM: Streptomyces flaveolus (Streptomyces sp.(DSM 9954))

<400> SEQUENCE: 65

atggatcccc tcggtgccgc ggaacaggag c                                  31


<210> SEQ ID NO 66
<211> LENGTH: 32
<212> TYPE: DNA
<213> ORGANISM: Streptomyces flaveolus (Streptomyces sp.(DSM 9954))

<400> SEQUENCE: 66

atggatccgg cgatgaccga ctggctcgcc ac                                 32


<210> SEQ ID NO 67
<211> LENGTH: 31
<212> TYPE: DNA
<213> ORGANISM: Streptomyces flaveolus (Streptomyces sp.(DSM 9954))

<400> SEQUENCE: 67

ataagcttgg tccccgacgg tgagcagcac c                                  31
```

GENE CLUSTER

The present application is §371 application of PCT/CN2009/074178 filed Sep. 24, 2009, which claims priority to CN Application No. 200810200388.4, filed Sep. 24, 2008. The entire disclosure of each of the foregoing applications is incorporated by reference herein.

INTRODUCTION

The present invention relates to novel isolated DNA sequences which comprises a gene cluster encoding sanglifehrin synthase, processing and regulatory genes involved in the biosynthesis of a mixed non-ribosomal peptide/polyketide compound, or mutants having altered biosynthetic capability, polypeptides or mutants thereof encoded by DNA or the mutants, vectors containing the DNA or the mutants thereof, host cells transformed with the DNA, the mutants thereof, or the vector, and a method for producing sanglifehrin compounds. The present invention also provides compounds with cyclophilin inhibition activity useful as immunosuppressants, antivirals or cardiac protection agents.

FIELD OF THE INVENTION

The invention relates to the field of microorganism genetic resources and genetic engineering, and in particular relates to the cloning, sequence analysis, in vivo functional verification, and the use of the gene cluster for the biosynthesis of the immunosuppressant sanglifehrin A and related analogues.

BACKGROUND OF THE INVENTION

The immunosuppressant sanglifehrin A (SFA) is a mixed polyketide-peptide natural product from *Streptomyces* sp. A92-308110, also known as *Streptomyces flaveolus* or *Streptomyces* sp. DSM 9954—these titles are all used interchangeably in this and related documents (Sanglier et al., 1999; Fehr et al., 1999; WO 97/02285). Isolation of more than twenty structural analogues of sanglifehrin have been published to date, and SFA has one of the highest immunosuppressant activities among these analogues (Kallen et al., 2005; Sanglier et al., 1999). In SFA, the 22-membered macrolide backbone consists structurally of a polyketide carbon chain and a tripeptide chain. The peptide chain comprises one natural amino acid: valine, and two non-natural amino acids: (S)-m-tyrosine and (S)-piperazic acid, linked by an amide bond, and it is the β-nitrogen atom at position 1 of piperazic acid that is involved in amide bond formation, which stands in contrast to all other piperazic acid containing natural products isolated so far. In addition, a spirocyclic unit is linked to the macrolide by a polyketide long chain, forming a basket structure. The spirocyclic moiety contains nine chiral centers (SFA has seventeen in total) with a quaternary carbon center in the middle, which is unique in currently described natural products. A series of analogues have been directly isolated from fermentation broths of *Streptomyces* sp. A92-308110 (*S. flaveolus*), including sanglifehrin B, C, D, E, F, G, H, I, J, K and L (Fehr et al., 1999, Sanglier et al., 1999, WO98/07743). Sanglifehrin B (SFB), in particular, has been shown to possess higher immunosuppressive activity than SFA in MLR assays (Sanglier et al., 1999). Though the total synthesis of SFA and its macrocyclic analogues were achieved with heroic efforts (Sedrani et al., 2003; Nicolau et al., 1999; Paquette et al., 2002; Metternich et al., 1999), no specific in vivo and in vitro studies have been carried out on its biosynthetic pathway.

SFA has strong immunosuppressive activity (Powell and Zheng, 2006), inhibits HIV and HCV infection (Zander et al., 2003; Sokolskaja et al., 2004; Watashi et al., 2005) and prevents severe cardiac cell death caused by the pathological opening of mitochondrial membrane permeability transition pore (MPTP; Clarke et al., 2002). Compared with the immunosuppressants currently in clinical use, such as cyclosporin A (CsA), FK506 and rapamycin, SFA has a similar functional mechanism while having a different target effector site (Hartel et al 2006, Zhang & Liu., 2001; Zenke et al., 2001). CsA binds to cyclophilin A (CypA) (Handschumacher et al., 1984), whilst FK506 and rapamycin bind to FKBP, to form complexes (Schreiber, 1991); the CsA-CypA and FK506-FKBP complexes interact with the same target protein, calcineurin, thereby inhibiting the serine/threonine phosphatase activity of calcineurin, and blocking the production of cytokines, especially the transcription of interleukin 2 (IL-2), which finally lead to T cell arrest in $G_0$-$G_1$ stage (Liu et al., 1991). Rap-FKBP complexes interact with the protein kinase FRAP (also known as RAFT or mTOR) (Brown et al., 1994), and prevent phosphorylation of the IL-2 receptor on T cells, leading to arrest of the growing of T cells in G1-S stage. Whilst SFA has been shown to bind to cyclophilins such as Cyclophilin A and B, and inhibit their isomerase activities (Zenke et al 2001), currently the effector protein for SFA-CypA complex remains unknown.

Since the effector protein of the SFA-CypA complex has not yet been found, it was suggested that the immunosuppressive activity of SFA is not mediated directly via the the SFA-CypA complex. In the past 3 years, studies from many scientific groups have shown that SFA can competitively prevent NF-κB from binding the transcription site upstream of the P53 gene, to activate P53 and further inhibit the downstream Cyclin E-cdk2 phosphorylation of the signal pathway, thereby inhibiting the high phosphorylation of Rb in response to IL-2, and making cells insensitive to to IL-2, which forces them to remain in the G1-S stage (Zhang & Liu, 2001). Secondly, by an unknown mechanism, SFA inhibits production of IL-12$p^{70}$ while not affecting the growth of human dendritic cells (Steinschulte et al., 2003). IL-12$p^{70}$ plays a key role in regulating proliferation of Th1 and NK cells, and is the bridge linking innate immunity with adaptive immunity. In addition, the immunosuppressive drugs that are commercially available can lead to severe renal and central nervous system toxicity side effects (Paquette et al., 2002), thus their uses in some immune dysfunction diseases are hindered (for example, calcineurin is the underlying cause of both immunosuppressive and toxic effects of CsA and FK506). With the aim of developing an alternative immunosuppressant or immune modifier, other groups have carried out some development of SFA as a new generation of potent immunosuppressant with lower toxicity (WO 97/02285).

The study of structure-activity relationships between SFA macrocyclic fragments and CypA by X-ray diffraction showed that the tripeptide structure is embedded in the groove of CypA and is important for binding, while the side chain hydroxy group and carbonyl group respectively at positions 17 and 14 are not critical for binding; removal of the trans-diene from the saturated region C18-C22 reduces the binding constant 7 fold, suggesting the trans-diene stabilizes the conformation (Sedrani et al., 2003). A computer-modeling study shows that the spirocyclic unit of SFA may also contribute to the stability of the SFA-CypA binding (Pemberton et al., 2003). The crystal structure of the complete SFA-CypA complex shows that the binding regions in SFA-CypA are substantially the same as those in CsA-CypA, and both SFA and CsA mainly interact with residue W121, R55, H126, N102 and Q63; the C24-C32 chain between the macrocycle and the spirocyclic moiety make van der Waals contacts with residues I57, T119 and W121 of CypA; in addition, the presence of the long polyketide chain of SFA imposes a side-chain reorientation on W121, as compared with the crystal structure of CypA; within the spirocycle, only the methyl group C45 makes vdW contacts with side-chain atoms from I57 and F60 of CypA (Kallen et al., 2005).

The SFA-CypA complex can exist in a stable dimeric form, as shown by gel filtration chromatography. Based on crystal analysis, with the exception of the spirobicyclic and α-keto-butyrate moieties, all of the remaining parts of SFA are deeply buried in the dimer; the E,E-diene region C18-C22 is not involved in direct contacts with the CypA but instead forms vdW contacts with the meta-tyrosine of neighboring SFA within the dimer, which favors the dimeric association in the complex; the two SFA molecules make vdW contacts with each other in the region C18-C22; and a direct hydrogen bond links W121 of one CypA molecule and R148 of another CypA molecule in the dimer complex.

Using the streptomycete that is known to produce SFA, *Streptomyces* sp. A92-308110 (*S. flaveolus*), the inventors of the present invention cloned the biosynthetic gene cluster thereof, and further studied the biosynthesis of SFA by methods combining microbiology, molecular biology, biochemistry and organic chemistry. Through study of the biosynthesis, the enzymatic mechanism which generates distinctive chemical structures such as piperazic acid was revealed. Based on this, genetic modifications were made to the SFA biosynthetic pathway, and novel compounds were produced.

The present invention is particularly useful as it should enable the commercial application of recombinant DNA technology and biosynthetic engineering to increase the yield of sanglifehrins and generation of novel sanglifehrin analogues.

SUMMARY OF THE INVENTION

The present invention advantageously provides novel DNA sequences and proteins involved in the production of biosynthetic gene products, in particular biosynthesis of sanglifehrin. Specific embodiments of the genes and proteins are detailed in the accompanying sequence listing and the following description. SEQ ID No. 1 provides the nucleic acid responsible for the biosynthesis of sanglifehrin A.

Thus, the invention relates to the cloning, sequence analysis, functional verification, in vitro biochemical analysis and the use of the biosynthetic gene cluster of SFA, an immunosuppressive polyketide-nonribosomal peptide natural product produced by *Streptomyces* sp. A92-308110 (*S. flaveolus*) (available from the DSMZ, Braunschweig, Germany as *Streptomyces* sp. DSM 9954). In addition, targeted alterations were made to the genes encoding the biosynthetic pathway for generation of sanglifehrin, leading to microbial strains producing novel sanglifehrin analogues.

The invention allows direct manipulation of sanglifehrin A and related chemical structures via biosynthetic engineering of the genes and proteins involved in the biosynthesis of the sanglifehrin A. These chemical modifications may be either impossible or unfeasible to do by chemical methodologies due to the complexity of the structures.

The gene cluster isolated and characterized in this way enables targeted optimization of the production of sanglifehrin and sanglifehrin analogues, for example, by duplication of the gene cluster, or parts of the cluster, by overexpression of genes (in particular positive regulatory genes) using plasmid vectors and non-natural promoters, or by inactivation of negative regulators.

In addition, the sequenced and characterized cluster enables targeted biosynthetic preparation of sanglifehrin analogues, a number of examples of which are included in this document.

Examples include the following:

Inactivation of genes coding for proteins involved in individual biosynthetic steps, for example by gene disruption (see e.g. WO 2004/007709; WO 2004/058976).

Replacement of genes coding for proteins involved in individual biosynthetic steps, by gene replacement or by disruption followed by separate expression of genes from other biosynthetic pathways (see e.g. Gaisser et al., 2001; WO 01/79520; WO 2005/054266; WO2005/054265)

Exchange of individual modules or domains within the polyketide synthase ("PKS") or non-ribosomal peptide synthase ("NRPS") with modules or domains from other PKS or NRPS clusters, to enable generation of novel sanglifehrin analogues (for example as described in Oliynyk et al., 1996; WO 98/01546; WO 00/01827; Staunton and Wilkinson, 2001; Sheehan et al., 2006)

Use of the gene sequence to identify related biosynthetic clusters from other organisms, for example by use as a DNA probe (see e.g. Shen et al., 2002; Liu et al., 2002; Li et al., 2004; Huang et al., 2005; Jia et al., 2006; Fang et al., 2008).

Thus according to a first aspect of the invention there is provided an isolated nucleic molecule comprising:

(a) the sanglifehrin A biosynthesis gene cluster nucleic acid comprising SEQ ID No. 1;

(b) a nucleic acid having at least 80% sequence identity (e.g. at least 85 or 90 or 95 or 96 or 97 or 98 or 99% sequence identity) to the nucleic acid of (a) and which codes for polypeptides having the same enzymatic and regulatory activities for making a polyketide or a polyketide starter unit as those encoded by the nucleic acid of (a);

(c) a nucleic acid encoding one or more polypeptides having at least 80% amino acid sequence identity (e.g. at least 85 or 90 or 95 or 96 or 97 or 98 or 99% sequence identity) to one or more polypeptides encoded by the nucleic acid of (a) and which codes for one or more polypeptides having one or more of the necessary enzymatic or regulatory activities for making a polyketide or a polyketide starter unit or precursor;

(d) a nucleic acid portion of (a), (b) or (c) which codes for a polyketide synthase or a non-ribosomal peptide synthase polypeptide or an enzymatically active module of either, or a polyketide starter unit or precursor biosynthesis gene product or a polyketide biosynthesis regulatory polypeptide; or (e) a nucleic acid portion of (d) which encodes an enzymatically active domain of a polyketide synthase or a non-ribosomal peptide synthase polypeptide or an enzymatically active module of either, or a polyketide starter unit or precursor biosynthesis gene product or a polyketide biosynthesis regulatory polypeptide.

This and other aspects of the invention will be elaborated in the foregoing disclosure.

Definitions

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

As used herein the term "polyketide" refers to any molecule generated via biosynthesis involving a polyketide synthase (PKS). This may additionally include some elements from non-ribosomal peptide synthase (NRPS) domains and/or further biosynthetic modification, such as methylation or hydroxylation.

As used herein the term "hybrid polyketide" refers to any molecule generated via biosynthesis involving a polyketide synthase (PKS), where the gene cluster encoding this polyketide synthase has been altered by human intervention to lead to a different biosynthetic product. This may additionally include some elements from non-ribosomal peptide synthase domains and/or further biosynthetic modification, such as methylation or hydroxylation. The alterations themselves may include, but are not limited to, site directed mutagenesis of domains (eg acyltransferase domains), replacement of domains, modules or genes from the same or a heterologous PKS or NRPS cluster.

As used herein the term "high stringency conditions" means conditions where only very closely related or identical DNA sequences are hybridized. This is frequently done in Southern hybridisation by increasing the temperature of the wash buffer. For oligonucleotide probes the hybridization step can be performed at 5° C. above $T_m$ for perfectly matched sequences, where $T_m$ is calculated using a formula such as $T_m$=4×(number of GC base pairs)+2×(number of AT base pairs). An example of high stringency conditions is given in the section below entitled "Nucleic acid hybridization".

As used herein the term "heterologous host" in relation to a nucleic acid sequence, particularly a sanglifehrin biosynthetic cluster or part thereof, means a host that would not naturally contain such a nucleic acid sequence.

As used herein the term "heterologous" in connection with, for example a domain or module of a sanglifehrin PKS or NRPS, means a domain or module that would not naturally be present in that PKS or NRPS.

As used herein the term "non-native" means in connection with, for example, a domain or module of a sanglifehrin PKS or NRPS, a domain or module that would not naturally be present in that location in that PKS or NRPS; for instance it might be heterologous (i.e. from a different PKS or NRPS) or else it might be present in a different location in the same PKS or NRPS.

The pharmaceutically acceptable salts of compounds of the invention such as the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Hydrochloric acid salts are of particular interest. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts.

Alkyl, alkenyl and alkynyl groups may be straight chain or branched.

Examples of alkyl e.g. C1-C4 alkyl groups include methyl, ethyl, n-propyl, i-propyl and n-butyl.

DETAILED DESCRIPTION OF THE INVENTION

The whole gene cluster according to the invention comprises the nucleotide sequences or complementary sequences of 24 genes (SEQ ID NO: 1), including:

- one non-ribosomal peptide synthetase (NRPS) gene, sfaD, comprising altogether 3 modules, 10 functional domains, and responsible for the formation of the peptide moiety of the macrocyclic backbone;
- five linear polyketide synthase (PKS) genes, sfaE, sfaF, sfaG, sfaH, sfaI, responsible for the formation of the spirocycle, the polyketide long chain and the polyketide moiety of the macrocyclic backbone;
- one iterative polyketide synthase gene, sfaK, comprising 4 functional domains, and responsible for the biosynthesis of a special 6-carbon precursor en route for biosynthesis of the unusual 7-carbon extension unit;
- Three genes, sfaA, sfaB, sfaJ responsible for the biosynthesis of non-natural amino acid precursor building blocks;
- Seven genes sfaM, sfaN, sfaP, sfaQ, sfaL, sfaR, sfaO, responsible for biosynthesis of precursors, such as those for the starter unit;
- one regulatory gene, sfaC, associated with the fermentation yield of SFA;
- one MbtH protein encoding gene, sfaS, postulated to be associated with the regulation of the NRPS; and
- five genes with unknown function, sfaU1, sfaU2, sfaV1, sfaV2, sfaV3.

Thus the invention also provides an isolated nucleic molecule comprising one or more of (a) a linear PKS gene selected from sfaE, sfaF, sfaG, sfaH and sfaI, or (b) a NPRS gene sfaD, or (c) an iterative PKS gene sfaK, or (d) a starter unit or precursor biosynthesis gene selected from sfaA, sfaB, sfaJ, sfaM, sfaN, sfaP, sfaQ, sfaL, sfaO, or (e) a regulatory gene sfaC, or (f) a MtbH protein encoding gene sfaS, or (g) or a crotonyl-CoA reductase gene sfaR, or (h) a gene of unknown function selected from sfaU1, sfaU2, sfaV1, sfaV2, and sfaV3.

The aforementioned genes are typically defined by nucleic acids encoding for the proteins of SEQ ID Nos. 2-25.

In particular, the invention provides an isolated nucleic molecule comprising one or more of (a) a linear PKS gene selected from sfaE being residues 30707-37360 of SEQ ID No. 1, sfaF being residues 37394-50014 of SEQ ID No. 1, sfaG being residues 50017-60903 of SEQ ID No. 1, sfaH being residues 60918-85823 of SEQ ID No. 1 and sfaI being residues 85823-96040 of SEQ ID No. 1 or (b) a NRPS gene sfaD being residues 19885-30714 of SEQ ID No: 1 or (c) an iterative PKS gene sfaK being residues 97396-101943 of SEQ ID No. 1, or (d) a starter unit or precursor biosynthesis gene selected from sfaA being residues 17024-17854 of SEQ ID No. 1, sfaB being residues 17851-19191 of SEQ ID No. 1, sfaJ being residues 96225-97391 of SEQ ID No. 1, sfaM being residues 103210-103929 of SEQ ID No. 1, sfaN being residues 104001-105023 of SEQ ID No. 1, sfaP being residues 105366-107216 of SEQ ID No. 1, sfaQ being residues 107366-108145 of SEQ ID No. 1, sfaL being residues 101936-103213 of SEQ ID No. 1, sfaO being residues 105091-105345 of SEQ ID No. 1, or (e) a regulatory gene sfaC being residues 19193-19888 of SEQ ID No. 1, or (f) a MtbH protein encoding gene sfaS being residues 109583-109798 of SEQ ID No. 1, or (g) or a crotonyl-CoA reductase gene sfaR being residues 108150-109511 of SEQ ID No. 1, or (h) a gene of unknown function selected from sfaU1 being residues 14973-15413 of SEQ ID No. 1, sfaU2 being residues 15596-16063 of SEQ ID No. 1, sfaV1 being residues 109776-110312 of SEQ ID No. 1, sfaV2 being residues 111285-111743 of SEQ ID No. 1 and sfaV3 being residues 112218-112652 of SEQ ID No. 1; or comprising a nucleic acid sequence which encodes one or more of the same polypeptides as those encoded by the aforementioned genes but which differ only by virtue of the redundancy of the genetic code; or comprising a nucleic acid sequence capable of hybridizing to one or more of the above gene sequences under conditions of high stringency; or comprising a nucleic acid sequence having at least 70%, 75%, 80%, 85%, 90%, 95%, 96%, 97%, 98% or 99% identity to one or more of the above gene sequences and which encodes a polypeptide having the same function as the corresponding gene product; or comprising a nucleic acid sequence encoding one or more polypeptides having at least 80% amino acid sequence identity (e.g. at least 85 or 90 or 95 or 96 or 97 or 98 or 99% sequence identity) to one or more of the polypeptides encoded by the aforementioned genes and which have the same function; or fragments comprising at least 50, 100, 200, or 500 consecutive nucleotides of one or more of the aforementioned genes; or the complement of any of the aforementioned nucleic acid sequences.

There is also provided an isolated nucleic molecule comprising one or more of (a) a module or domain from a PKS gene selected from sfaE being residues 30707-37360 of SEQ ID No. 1, sfaF being residues 37394-50014 of SEQ ID No. 1, sfaG being residues 50017-60903 of SEQ ID No. 1, sfaH being residues 60918-85823 of SEQ ID No. 1 or sfaI being residues 85823-96040 of SEQ ID No. 1 or (b) a module or domain from the NRPS gene sfaD being residues 19885-30714 of SEQ ID No: 1, or (c) a domain from the iterative PKS gene sfaK being residues 97396-101943 of SEQ ID No. 1; or comprising a nucleic acid sequence which encodes one or more modules or domains of the same polypeptides as those encoded by the aforementioned genes but which differ only by virtue of the redundancy of the genetic code; or comprising a nucleic acid sequence capable of hybridizing to one or more of the above nucleic acid molecules under conditions of high stringency; or comprising a nucleic acid sequence having at least 70% identity to one or more of the above nucleic acid molecules and which encodes a polypeptide having the same function as a module or domain of the corresponding gene product; or comprising a nucleic acid sequence encoding one or more polypeptides having at least 80% amino acid sequence identity to one or more of the polypeptides encoded by a module or domain of the aforementioned genes and which have the same function; or fragments comprising at least 50 consecutive nucleotides of one or more of the modules or domains of the aforementioned genes; or the complement of any of the aforementioned nucleic acid sequences.

A module or domain of a gene is the portion of the gene that encodes a module or domain of the corresponding gene product.

There is also provided a hybrid polyketide producing gene cluster nucleic acid based on SEQ ID No. 1 in which one or more (e.g. one) domains, modules or genes have been deleted, mutated so as to make inactive or less active an enzymatic or regulatory function, mutated so as to have altered functionality, or replaced by an replacement, or in which one or more (e.g. one) non-native domains, modules or genes have been inserted, for example wherein one or more (e.g. one) domains, modules or genes have been replaced by (a) a domain, module or gene from elsewhere in the sanglifehrin A biosynthesis gene cluster or (b) a domain, module or gene which is heterologous to the sanglifehrin A biosynthesis gene cluster or wherein one or more (e.g. one) domains, modules or genes have been mutated to inactivate or make less active an enzymatic or regulatory function.

For example, there is provided a hybrid polyketide producing gene cluster nucleic acid wherein one or more PKS genes selected from sfaE, F, G, H and I have been modified whereby one or more domains or modules have been deleted, mutated so as to make inactive or less active an enzymatic function or so as have altered functionality or replaced by an replacement or whereby one or more non-native domains or modules have been inserted e.g. whereby one or more domains or modules from elsewhere in the SFA biosynthetic gene cluster or from a heterologous polyketide biosynthetic gene cluster have been inserted.

The modules of the PKS genes sfaE, F, G, H and I may be seen by reference to FIG. 7. Thus the modules may typically comprise KS-AT-ACP or KS-AT-DH-KR-ACP or KS-AT-KR-ACP or KS-AT-DH-ER-KR-ACP domains.

For example:

- an AT domain may be replaced with an AT domain from a heterologous PKS or from elsewhere within the SFA PKS which has a different substrate specificity; and/or
- a DH domain may be deleted or rendered inactive; and/or
- a DH domain from the SFA PKS or from a heterologous PKS may be inserted into a module;
- an ER domain may be deleted or rendered inactive; and/or
- an ER domain from the SFA PKS or from a heterologous PKS may be inserted into a module.
- the reductive loop of a given module (meaning the DH-KR or DH-ER-KR or the KR domains where present) may be replaced by a reductive loop having different elements.

In one embodiment, the AT domain of module 13 may be replaced with an AT domain from the SFA PKS or from a heterologous PKS which has a different substrate specificity e.g. one having specificity for methyl malonyl. This particular mutation leads to introduction of a methyl group at position 14.

In one embodiment the DH domain of one or more of modules 1, 3, 6, 7, 8, 10, 11 and 13 is deleted or rendered inactive. These particular mutations lead to introduction of one or more hydroxyl groups into the molecule, for example at positions 21 and/or 25.

There is also provided a hybrid polyketide producing gene cluster nucleic acid wherein the NRPS gene sfaD has been modified whereby one or more domains or modules have been deleted, mutated so as to make inactive or less active an enzymatic function or so as have altered functionality or replaced by an replacement or whereby one or more non-native domains or modules have been inserted.

There is also provided a hybrid polyketide producing gene cluster nucleic acid wherein regulatory gene sfaC has been modified so as to increase or decrease its activity, or deleted.

There is also provided a hybrid polyketide producing gene cluster nucleic acid wherein the iterative PKS gene sfaK has been modified whereby one or more domains have been deleted, mutated so as to make inactive or less active an enzymatic function or so as have altered functionality or replaced by an replacement or whereby one or more non-native domains have been inserted e.g. whereby one or more domains from elsewhere in the SFA biosynthetic gene cluster or from a heterologous polyketide biosynthetic cluster have been inserted.

The module of the iterative PKS gene sfaK may be seen by reference to FIG. 7. Thus the module comprises KS-AT-ACP-KR domains.

There is also provided a hybrid polyketide producing gene cluster nucleic acid wherein one or more starter unit or precursor biosynthesis genes selected from sfaA, B, J, M, N, P, Q, L and O have been deleted or modified so as to decrease their activity or modified or replaced so as to alter their substrate selectivity.

There is also provided a hybrid polyketide producing gene cluster nucleic acid wherein one or more starter unit or precursor biosynthesis genes or one or more operons containing one or more starter unit or precursor biosynthesis genes have been deleted or mutated so as to be inactive or less active at producing said starter unit or precursor than the native gene or operon.

More preferred embodiments of this aspect of the invention include isolated nucleic acid that encodes a domain of the PKS or NRPS of SEQ ID No. 1, residues 19885-30714, 30707-37360, 37394-50014, 50017-60903, 60918-85823, 85823-96040. These nucleic acids can be used, alone or in combination with nucleic acids encoding other PKS or NRPS domains or modules as intermediates, for example in the construction of recombinant vectors.

The present invention also provides for a method for identifying, isolating and cloning nucleic acid including any one of the DNA fragments described above. A preferred method comprises, for example, the following steps:

a) Setting up a genomic DNA bank (for example a cosmid library)
b) Screening this bank with the assistance of the DNA sequences of this invention
c) Isolating the clones identified as positive A general method for identifying the DNA fragments involved in the biosynthesis of sanglifehrins comprises, for example, the following steps:

a. Isolating DNA fragments with homology to the sanglifehrin gene cluster can be carried out by Southern blotting a cosmid library, probing with DNA fragments (for example of ~1 kb) from SEQ ID No. 1 to find cloned fragments with homology to the sanglifehrin cluster.
b. The cosmids which are seen to hybridise to the probe can then be removed, and the DNA sequenced.
c. Adjacent DNA regions can then be isolated by probing the cosmid library with the labeled cosmid isolated above, to cosmids containing overlapping DNA.

Other methods are described in Maniatis et al., 1998, Sambrook and Russell, 2001 and Kieser et al., 1999.

The invention further provides a nucleotide sequence, encoding a protein of unknown function. The amino acid sequence it codes for is as shown in SEQ ID NO: 2, and designated as sfaU1, and the corresponding nucleotide sequence is as shown in SEQ ID NO: 1, starting from base position 14973 to base position 15413.

The invention further provides a nucleotide sequence encoding another protein of unknown function. The amino acid sequence it codes for is as shown in SEQ ID NO: 3, and designated as sfaU2, and the corresponding nucleotide sequence is as shown in SEQ ID NO: 1, starting from base position 15596 to base position 16063.

The invention further provides a nucleotide sequence encoding a phenylalanine meta-hydroxylase. The amino acid sequence it codes for is as shown in SEQ ID NO: 4, and designated as sfaA, and the corresponding nucleotide sequence is as shown in SEQ ID NO: 1, starting from base position 17024 to base position 17854.

The invention further provides a nucleotide sequence encoding an ornithine N5-oxygenase. The amino acid sequence it codes for is as shown in SEQ ID NO: 5, and designated as sfaB, and the corresponding nucleotide sequence is as shown in SEQ ID NO: 1, starting from base position 17851 to base position 19191.

The invention further provides a nucleotide sequence encoding a transcription regulatory factor. The amino acid sequence it codes for is as shown in SEQ ID NO: 6, and designated as sfaC, and the corresponding nucleotide sequence is as shown in SEQ ID NO: 1, starting from base position 19193 to base position 19888.

The invention further provides a nucleotide sequence encoding a non-ribosomal peptide synthetase comprising the functional domains C, A, PCP, C, A, PCP, C, A, PCP, C, and responsible for biosynthesis of the peptide moiety of the macrocyclic backbone. The amino acid sequence it codes for is as shown in SEQ ID NO: 7, and designated as sfaD, and the corresponding nucleotide sequence is as shown in SEQ ID NO: 1, starting from base position 19885 to base position 30714.

The invention further provides a nucleotide sequence encoding a polyketide synthase comprising the functional domains ACP, KS, AT, DH, ER, KR, ACP, and responsible for biosynthesis of the precursor of the spirocyclic moiety. The amino acid sequence it codes for is as shown in SEQ ID NO: 8, and designated as sfaE, and the corresponding nucleotide sequence is as shown in SEQ ID NO: 1, starting from base position 30707 to base position 37360.

The invention further provides a loading domain specific for initiating PKS biosynthesis with a 2-ethylmalonamyl-S-thioester substrate, consisting of the first ACP from sfaE, the corresponding nucleotide sequence is as shown in SEQ ID NO: 1, starting from base position 30707 to base position 31082.

The invention further provides a nucleotide sequence encoding a polyketide synthase comprising the functional domains KS, AT, ACP, KS, AT, KR, ACP, KS, AT, KR, ACP, and responsible for biosynthesis of polyketide long chain. The amino acid sequence it codes for is as shown in SEQ ID NO: 9, designated as sfaF, and the corresponding nucleotide sequence is as shown in SEQ ID NO: 1, starting from base position 37394 to base position 50014.

The invention further provides a nucleotide sequence encoding a polyketide synthase comprising the functional domains KS, AT, KR, ACP, KS, AT, DH, ER, KR, ACP, and responsible for biosynthesis of much of the polyketide long chain. The amino acid sequence it codes for is as shown in SEQ ID NO: 10, designated as sfaG, and the corresponding nucleotide sequence is as shown in SEQ ID NO: 1, starting from base position 50017 to base position 60903.

The invention further provides a nucleotide sequence encoding a polyketide synthase comprising the functional domains KS, AT, DH, KR, ACP, KS, AT, DH, KR, ACP, KS, AT, KR, ACP, KS, AT, DH, KR, ACP, KS, AT, DH, KR, ACP, and responsible for biosynthesis of part of the polyketide moiety of the macrocyclic backbone. The amino acid sequence it codes for is as shown in SEQ ID NO: 11, designated as sfaH, and the corresponding nucleotide sequence is as shown in SEQ ID NO: 1, starting from base position 60918 to base position 85823.

The invention further provides a nucleotide sequence encoding a polyketide synthase comprising the functional domains KS, AT, KR, ACP, KS, AT, KR, ACP, and responsible for biosynthesis of part of the polyketide moiety of the macrocyclic backbone. The amino acid sequence it codes for is as shown in SEQ ID NO: 12, designated as sfaI, and the corresponding nucleotide sequence is as shown in SEQ ID NO: 1, starting from base position 85823 to base position 96040.

The invention further provides a nucleotide sequence encoding a zinc-finger dehydrogenase. The amino acid sequence it codes for is as shown in SEQ ID NO: 13, designated as sfaJ, and the corresponding nucleotide sequence is as shown in SEQ ID NO: 1, starting from base position 96225 to base position 97391.

The invention further provides a nucleotide sequence encoding an iterative polyketide synthase comprising the functional domains KS, AT, ACP, KR. The amino acid sequence it codes for is as shown in SEQ ID NO: 14, designated as sfaK, and the corresponding nucleotide sequence is as shown in SEQ ID NO: 1, starting from base position 97396 to base position 101943.

The invention further provides a nucleotide sequence encoding an acyltransferase. The amino acid sequence it codes for is as shown in SEQ ID NO: 15, designated as sfaL, and the corresponding nucleotide sequence is as shown in SEQ ID NO: 1, starting from base position 101936 to base position 103213.

The invention further provides a nucleotide sequence encoding a short chain dehydrogenase/reductase. The amino acid sequence it codes for is as shown in SEQ ID NO: 16, designated as sfaM, and the corresponding nucleotide sequence is as shown in SEQ ID NO: 1, starting from base position 103210 to base position 103929.

The invention further provides a nucleotide sequence encoding an acyl ketoacid synthase. The amino acid sequence it codes for is as shown in SEQ ID NO: 17, designated as sfaN, and the corresponding nucleotide sequence is as shown in SEQ ID NO: 1, starting from base position 104001 to base position 105023.

The invention further provides a nucleotide sequence encoding a free acyl carrier protein. The amino acid sequence it codes for is as shown in SEQ ID NO: 18, designated as sfaO, and the corresponding nucleotide sequence is as shown in SEQ ID NO: 1, starting from base position 105091 to base position 105345.

The invention further provides a nucleotide sequence encoding an asparagine synthase analogue. The amino acid sequence it codes for is as shown in SEQ ID NO: 19, designated as sfaP, and the corresponding nucleotide sequence is as shown in SEQ ID NO: 1, starting from base position 105366 to base position 107216.

The invention further provides a nucleotide sequence encoding a free thioesterase. The amino acid sequence it codes for is as shown in SEQ ID NO: 20, designated as sfaQ, and the corresponding nucleotide sequence is as shown in SEQ ID NO: 1, starting from base position 107366 to base position 108145.

The invention further provides a nucleotide sequence encoding a Crotonyl-coA reductase. The amino acid sequence it codes for is as shown in SEQ ID NO: 21, designated as sfaR, and the corresponding nucleotide sequence is as shown in SEQ ID NO: 1, starting from base position 108150 to base position 109511.

The invention further provides a nucleotide sequence encoding a MbtH-family protein, the amino acid sequence it codes for is as shown in SEQ ID NO: 22, designated as sfaS, and the corresponding nucleotide sequence is as shown in SEQ ID NO: 1, starting from base position 109583 to base position 109798.

The invention further provides a nucleotide sequence encoding a protein of unknown function. The amino acid sequence it codes for is as shown in SEQ ID NO: 23, designated as sfaV1, and the corresponding nucleotide sequence is as shown in SEQ ID NO: 1, starting from base position 109776 to base position 110312.

The invention further provides a nucleotide sequence encoding another protein of unknown function. The amino acid sequence it codes for is as shown in SEQ ID NO: 24, designated as sfaV2, and the corresponding nucleotide sequence is as shown in SEQ ID NO: 1, starting from base position 111285 to base position 111743.

The invention further provides a nucleotide sequence encoding another protein of unknown function. The amino acid sequence it codes for is as shown in SEQ ID NO: 25, designated as sfaV3, and the corresponding nucleotide sequence is as shown in SEQ ID NO: 1, starting from base position 112218 to position 112652.

The complementary sequence of SEQ ID NO: 1 may be obtained according to the principle of DNA base complementarity. The nucleotide sequence or part of the nucleotide sequence of SEQ ID NO: 1 may be obtained by polymerase chain reaction (PCR), or by suitable restriction enzyme digestion of corresponding DNA, or by other suitable techniques. The invention further provides a method to obtain a recombinant DNA plasmid comprising at least part of the DNA sequence in SEQ ID NO: 1.

The invention further provides a method to obtain a microorganism containing interrupted SFA biosynthetic genes, wherein at least one of the genes comprises the nucleotide sequence as shown in SEQ ID NO: 1.

The nucleotide sequence or part of the nucleotide sequence according to the invention may be obtained through a method based on polymerase chain reaction (PCR), or a gene similar to SFA biosynthetic gene can be obtained from other organisms by a Southern hybridization method or the like, using a DNA fragment comprising a sequence according to the invention as probe.

A cloned DNA comprising the nucleotide sequence or at least part of the nucleotide sequence according to the invention may be used to identify more library plasmids from the genomic library of *Streptomyces* sp. A92-308110 (*S. flaveolus*). These library plasmids comprise at least part of the sequence according to the invention, and comprise DNAs having not been cloned from the adjacent regions in the *Streptomyces* sp. A92-308110 (*S. flaveolus*) (*S. flaveolus*) genome as well.

Thus, for example, a nucleic acid or nucleotide sequence according to any aspect of the invention is a DNA.

The nucleotide sequence or at least part of the nucleotide sequence according to the invention may be modified or mutated. These methods includes insertion, replacement or deletion, polymerase chain reaction, error-prone polymerase chain reaction, site specific mutagenesis, re-ligation of different sequences, DNA shuffling with different parts of the sequence or with homologous sequences from other source, or mutagenesis by UV or chemical agent, etc.

The present invention also provides recombinant vectors such as DNA expression vectors comprising the above nucleic acids. Vectors typically comprise the aforementioned DNA together with one or more promoters or other regulatory elements. These vectors and methods of this invention enable one skilled in the art to generate recombinant host cells with the ability to produce polyketides. Thus the invention provides a method of preparing a polyketide, such as sanglifehrin A or a sanglifehrin A analogue, said method comprising culturing a transformed host cell, which host cell has been transformed with an expression vector comprising nucleic acids encoding all or part of the sanglifehrin gene cluster described in SEQ ID No. 1. A polyketide produceable by the aforemention method and which is not sanglifehrin A is also provided as an aspect of the invention. Desirably the vector comprises nucleic acid coding for a functional PKS which is able to generate sanglifehrin A or a sanglifehrin A analogue if cultured in an appropriate medium. In some embodiments the transformed host cell does naturally produce sanglifehrin A. In some embodiments the transformed host cell does not naturally produce sanglifehrin A. Such a transformed host cell is also provided as an aspect of the invention. A specific embodiment is a host cell transformed with a vector comprising nucleic acid encoding all or part of the sanglifehrin A biosynthesis gene cluster (e.g. it encodes the sanglifehrin A biosynthesis gene cluster exemplified by the nucleic acid of SEQ ID No. 1) which host cell does not naturally produce sanglifehrin A.

Thus, there are also provided:

- A polypeptide or plurality of polypeptides encoded by the any of the aforementioned nucleic acids;
- A polyketide synthase encoded by the aforementioned nucleic acid which encodes one or more polyketide biosynthesis proteins; and
- A hybrid protein encoded by a modular nucleic acid or gene cluster in which at least one domain or module or gene is not native to the sanglifehrin A biosynthesis gene cluster.

In another embodiment, the invention provides an isolated polypeptide comprising a sequence selected from the group consisting of SEQ ID Nos. 2-25; an isolated polypeptide consisting of at least 10, 50, 100, 200 or 500 consecutive amino acids of the polypeptides of SEQ ID Nos. 2-25; and an isolated polypeptide having at least 50%, 60%, 80%, 85%, 90%, 95%, 97% or 99% homology to the above sequences as determined by BLASTP (Altschul et al., 1990) with the default parameters.

The invention also provides a method of preparing a hybrid polyketide, said method comprising transforming a host cell with a recombinant vector comprising nucleic acids encoding all or part of the sanglifehrin gene cluster described in SEQ ID No. 1 in which at least one domain or module or gene is not native to the sanglifehrin A biosynthesis gene cluster, then culturing the transformed host cell.

The invention provides a polyketide produceable by the aforementioned process which is not sanglifehrin A.

The cloned gene comprising the nucleotide sequence or at least part of the nucleotide sequence according to the invention may by expressed in heterogeneous host by suitable expression system, to obtain corresponding or higher enzymatic or other biological activity or yield. These heterogeneous hosts include *Streptomyces, Pseudomonas, E. coli, Bacillus*, yeast, plants and animals, etc.

It is well known to those skilled in the art that polyketide gene clusters may be expressed in heterologous hosts (Pfeifer et al., 2001). Accordingly, the present invention includes the transfer of the sanglifehrin biosynthetic gene cluster with or without resistance and regulatory genes, either complete, engineered, containing mutations or containing deletions, for complementation in heterologous hosts. Methods and vectors for the transfer as defined above of such large pieces of DNA are well known in the art (Rawlings, 2001; Staunton and Weissman, 2001) or are provided herein in the methods disclosed.

In this context a preferred heterologous host cell strain is a prokaryote, more preferably an actinomycete or *Escherichia coli*, still more preferably include, but are not limited to *S. hygroscopicus, S. hygroscopicus* sp., *S. hygroscopicus* var. *ascomyceticus, Streptomyces tsukubaensis, Streptomyces coelicolor, Streptomyces lividans, Saccharopolyspora erythraea, Streptomyces fradiae, Streptomyces avermitilis, Streptomyces cinnamonensis, Streptomyces rimosus, Streptomyces albus, Streptomyces griseofuscus, Streptomyces longisporoflavus, Streptomyces venezuelae, Micromonospora griseorubida, Amycolatopsis mediterranei* or *Actinoplanes* sp. N902-109.

Thus, in a further aspect, the present invention provides novel strains wherein one or more of the genes coding for sanglifehrin biosynthesis are inactivated or deleted.

In a further aspect, the present invention provides novel strains where one or more modules or domains of the PKS genes sfaE, sfaF, sfaG, sfaH or sfaI are inactivated, deleted or replaced by non-native e.g. heterologous domains or modules. These strains may produce novel sanglifehrins. In particular there is provided an engineered strain based on an SFA producing strain wherein one or more PKS genes selected from sfaE, F, G, H and I have been modified whereby one or more domains or modules have been deleted, mutated so as to make inactive or less active an enzymatic function or so as have altered functionality or replaced by an replacement or whereby one or more non-native domains or modules have been inserted e.g. whereby one or more domains or modules from elsewhere in the SFA biosynthetis gene cluster or from a heterologous polyketide biosynthetic cluster have been inserted.

In a further aspect, the present invention provides novel strains where one or more modules or domains of the NRPS gene sfaD are inactivated, deleted or replaced by non-native e.g. heterologous domains or modules. These strains may produce novel sanglifehrins. In particular there is provided an engineered strain based on an SFA producing strain wherein NRPS gene sfaD has been modified whereby one or more domains or modules have been deleted, mutated so as to make inactive or less active an enzymatic function or so as have altered functionality or replaced by an replacement or whereby one or more non-native domains or modules have been inserted.

Further aspects of the invention include:

- An engineered strain based on an SFA producing strain wherein regulatory gene sfaC is modified so as to increase or decrease its activity, or deleted, or a regulatory element associated therewith (such as a promoter) that controls expression of sfaC is modified, replaced or deleted. For example a strain wherein regulatory gene sfaC or the control thereof is modified so as to increase its activity or expression level may produce SFA (or an SFA analogue) with greater yield. For example, sfaC may be overexpressed in the strain by using a promoter for overexpressing sfaC (such as permE) e.g. in a vector (such as those described in Kieser et al, 1999) and optionally together with a selectable marker (such as apramycin).

An engineered strain, not being a naturally SFA producing strain (i.e. a heterologous host) containing the SFA biosynthetic gene cluster under the control of one or more heterologous promoters. By use of powerful promoters such a strain may be used to produce SFA in high yields by means of a process involving culturing the strain and optionally isolating SFA.

A method for producing higher levels of sanglifehrins involving overexpressing sfaC.

An engineered strain based on an SFA producing strain wherein one or more starter unit or precursor biosynthesis genes selected from sfaA, B, J, M, N, P, Q, L and O have been deleted or modified so as to decrease their activity or modified or replaced so as to alter their substrate selectivity.

Aforementioned engineered strains based on an SFA producing strain may produce SFA or an SFA analogue if fed appropriately. Engineered strains may have any and all combinations of the above modifications and may have additional gene modifications.

The amino acid sequences according to the invention may be used to isolate a desired protein, and may be used for preparation of antibodies.

With certain amino acids deleted or substituted, polypeptides comprising the amino acid sequence or at least part of the sequence according to the invention may still have biological activity or even have new biological activity or desirable properties such as increased yield or optimized protein kinetics or others.

A gene or gene cluster comprising the nucleotide sequence or at least part of the nucleotide sequence according to the invention may be expressed in heterogeneous hosts, and their function in the host metabolic chain may be investigated by DNA Chip Technology.

A recombinant plasmid can be constructed by a genetic recombination from a gene or gene cluster comprising the nucleotide sequence or at least part of the nucleotide sequence according to the invention, to establish the biosynthetic pathway, or a method of insertion, replacement, deletion or inactivation can be used to establish the biosynthetic pathway.

A cloned gene or DNA fragment comprising nucleotide sequence or at least part of the nucleotide sequence according to the invention may be used to generate new structural analogues of SFA by interrupting one or several steps of SFA biosynthesis. The DNA fragment or gene may be used to increase the yield of SFA or derivatives thereof, the invention provides a method to increase yield in a genetically engineered microorganism. Examples of this include inactivation or deletion of negative regulators.

The non-ribosomal peptide synthetase according to the invention may be used to generate new peptide compounds, by deletion, insertion, alteration or inactivation of one or more domains, modules or genes of the non-ribosomal polypeptide synthetase from the same or a different non-ribosomal peptide synthetase system.

The polyketide synthase according to the invention may be used to generate new polyketides or hybrid polyketides, by deletion, insertion, alteration or inactivation of one or more domains, modules or genes of the polyketide synthase from the same or a different polyketide synthase system.

Fragments or genes comprising the nucleotide sequence or at least part of the nucleotide sequence according to the invention may be used to construct a library of nonribosomal peptide synthetases, or a library of derivatives of non-ribosomal polypeptide synthetases, or a combinatorial library.

Fragments or genes comprising the nucleotide sequence or at least part of the nucleotide sequence according to the invention may be used to construct a library of polyketide synthases, or a library of derivatives of polyketide synthases, or a combinatorial library.

In a word, all the gene and protein information associated with SFA biosynthesis provided herein can facilitate the understanding of biosynthesis mechanism of SFA natural products, and provides material and knowledge for further genetic engineering. The genes and their proteins provided herein may be used to search for and discover compounds, genes, or proteins that can be used in medicine, industry, or agriculture.

Additionally, in the present invention, specific changes have been made to the sanglifehrin biosynthetic gene cluster, with the original intention to understand the biosynthetic pathway, exemplify the inventions herein, and generate molecules for interrogation of the mechanism of immunosuppressant activity.

In general, sequence identity percentages may be determined by BLASTN (nucleic acid) or BLASTP (protein) (Altschul et al., 1990) with the default parameters.

Thus, in one aspect of the invention there is provided sanglifehrin analogue compounds of formula (I) or (II) or a pharmaceutically acceptable salt thereof:

Formula (I)

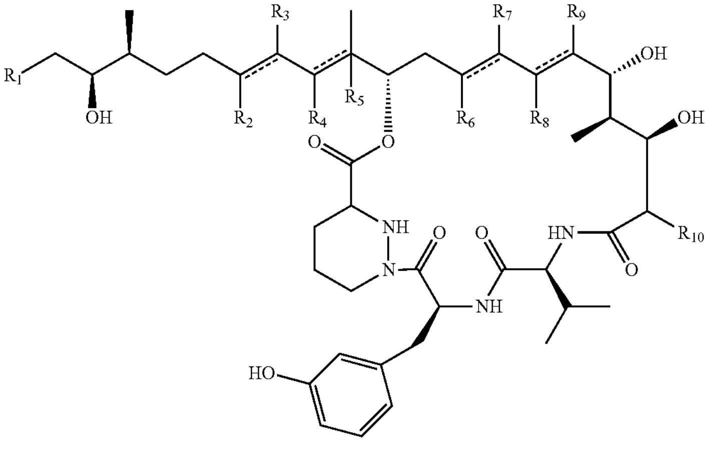

-continued

Formula (II)

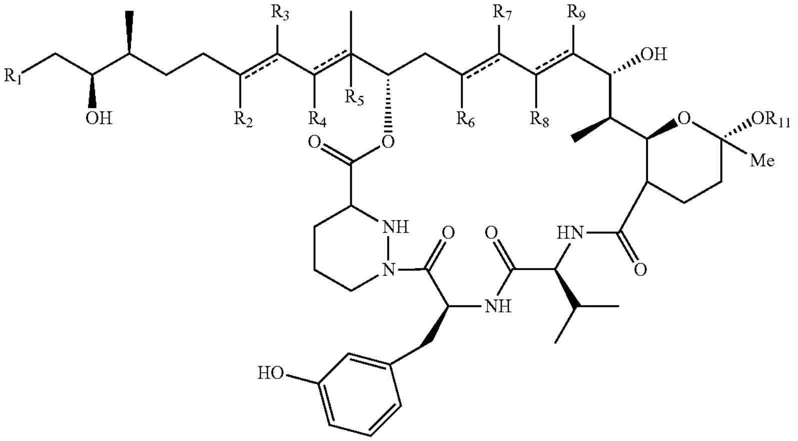

wherein:

$R_1$ represents one of moieties A, B or C:

A

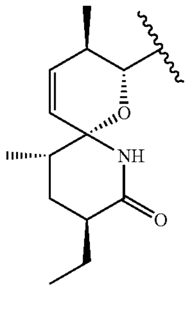

B

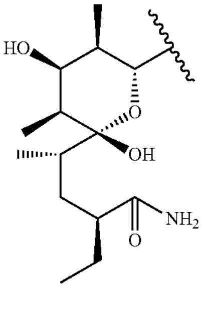

C

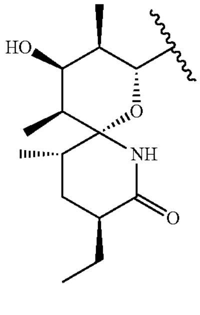

$R_2$ represents OH and $R_3$ represents H or $R_2$ and $R_3$ represent a bond;

$R_4$ represents OH and $R_5$ represents H or $R_4$ and $R_5$ represent a bond;

$R_6$ represents OH and $R_7$ represents H or $R_6$ and $R_7$ represent a bond;

$R_8$ represents OH and $R_9$ represents H or $R_8$ and $R_9$ represent a bond;

$R_{10}$ represents Me or $CH_2CH_2C(O)CH_3$;

$R_{11}$ represents H or Me;

with the proviso that when $R_{10}$ represents $CH_2CH_2C(O)CH_3$, then both $R_2$ and $R_4$ cannot represent OH and/or both $R_6$ and $R_8$ cannot represent OH, and with the proviso that when $R_{10}$ represents $CH_2CH_2C(O)CH_3$, then $R_2$ and $R_4$, and $R_6$ and $R_8$ cannot all represent bonds.

In one embodiment, $R_2$ represents OH, $R_3$ represents H and $R_4$ and $R_5$, $R_6$ and $R_7$ and $R_8$ and $R_9$ represent bonds and $R_{10}$ represents $CH_2CH_2C(O)CH_3$ In one embodiment, $R_5$ represents OH, $R_6$ represents H and $R_2$ and $R_3$, $R_6$ and $R_7$ and $R_8$ and $R_9$ represent bonds and $R_{10}$ represents $CH_2CH_2C(O)CH_3$ In one embodiment, $R_7$ represents OH, $R_8$ represents H and $R_4$ and $R_5$, $R_6$ and $R_2$ and $R_3$ and $R_9$ represent bonds and $R_{10}$ represents $CH_2CH_2C(O)CH_3$ In one embodiment, $R_8$ represents OH, $R_9$ represents H and $R_4$ and $R_5$, $R_6$ and $R_7$ and $R_2$ and $R_3$ represent bonds and $R_{10}$ represents $CH_2CH_2C(O)CH_3$ Preferably $R_1$ represents moiety C.

Preferably $R_{11}$ represents H;

Specific embodiments include the following:

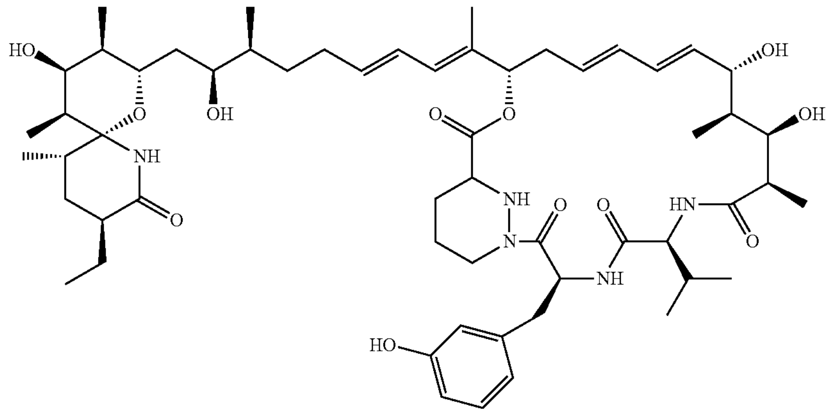

which may be expected to be produced by deletion/inactivation of sfaK optionally in conjunction with exchange of the AT of module 13 for an AT module which accepts methyl malonate in the SFA biosynthesis gene cluster;

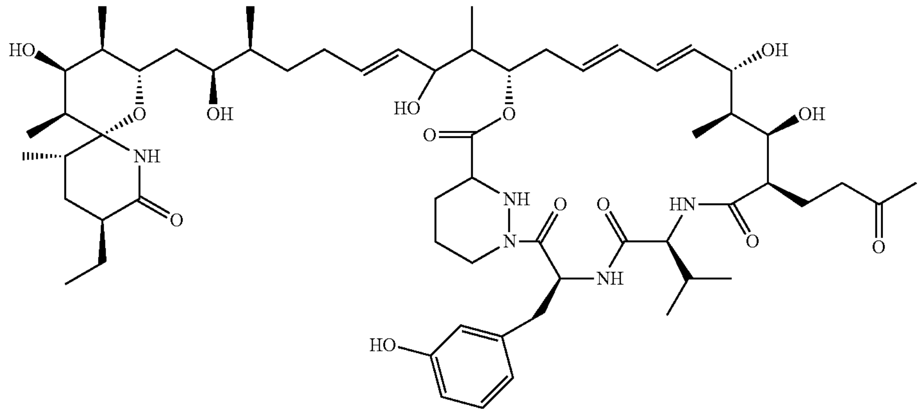 [SMILES: CC[C@H]1C[C@H](C)[C@@]2(NC1=O)O[C@@H](C[C@H](O)[C@@H](C)CC/C=C/C(O)C(C)[C@@H]1C/C=C/C=C/[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)[C@H](O)[C@@H]2C]

which may be expected to be produced by deletion/inactivation of the DH of module 8 in the SFA biosynthesis gene cluster;

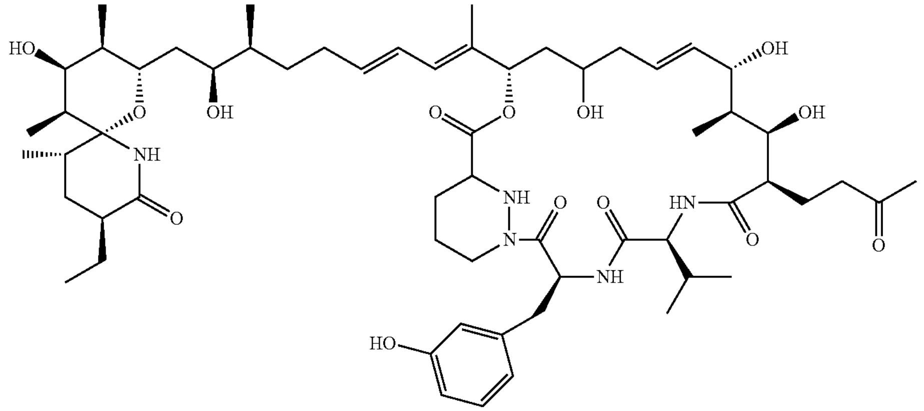 [SMILES: CC[C@H]1C[C@H](C)[C@@]2(NC1=O)O[C@@H](C[C@H](O)[C@@H](C)CC/C=C/C=C(\C)[C@@H]1CC(O)C/C=C/[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)[C@H](O)[C@@H]2C]

which may be expected to be produced by deletion/inactivation of the DH of module 10 in the SFA biosynthesis gene cluster;
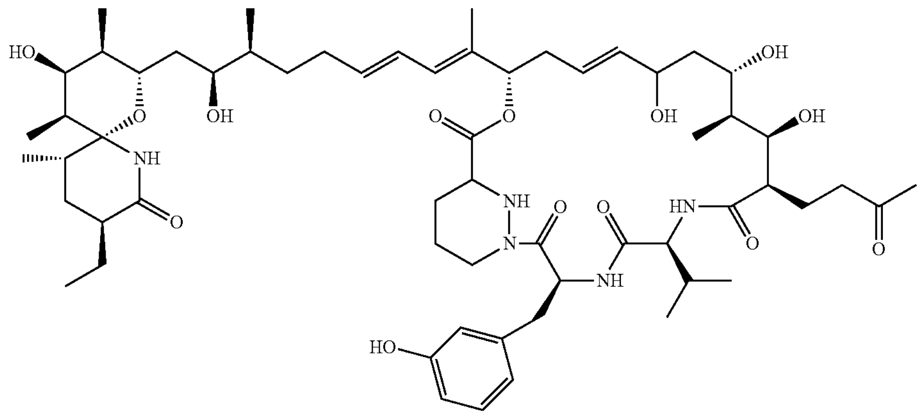 [SMILES: CC[C@H]1C[C@H](C)[C@@]2(NC1=O)O[C@@H](C[C@H](O)[C@@H](C)CC/C=C/C=C(\C)[C@@H]1C/C=C/C(O)C[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)[C@H](O)[C@@H]2C]
which may be expected to be produced by deletion/inactivation of the DH of module 11 in the SFA biosynthesis gene cluster;
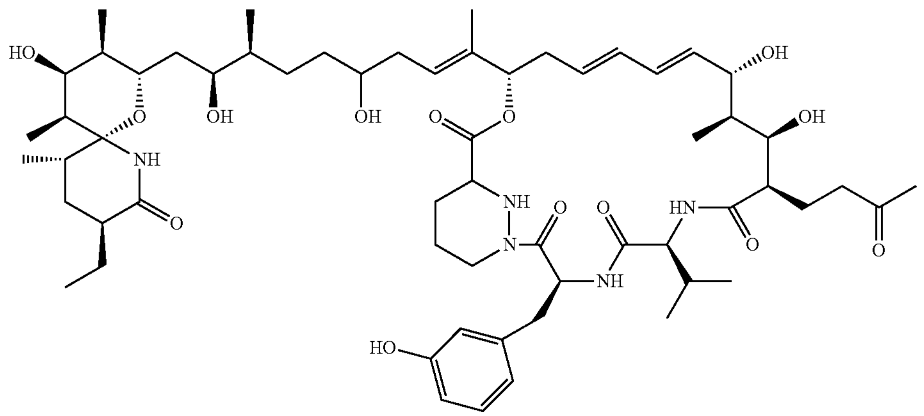 [SMILES: CC[C@H]1C[C@H](C)[C@@]2(NC1=O)O[C@@H](C[C@H](O)[C@@H](C)CCC(O)C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)[C@H](O)[C@@H]2C]
which may be expected to be produced by deletion/inactivation of the DH of module 7 in the SFA biosynthesis gene cluster;
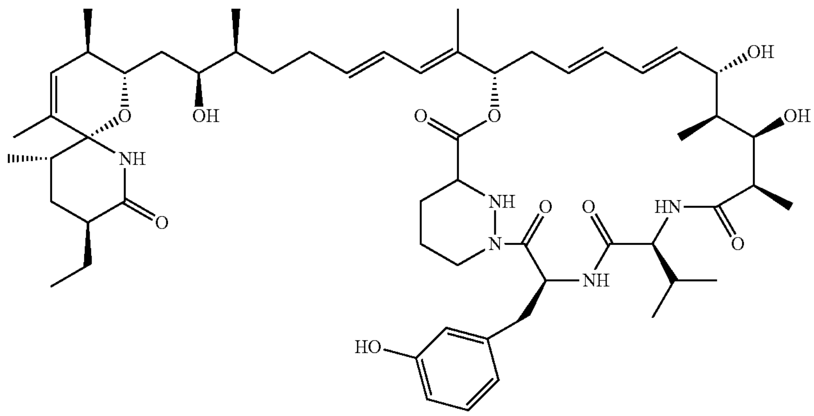

which may be expected to be produced by deletion/inactivation of sfaK optionally in conjunction with exchange of the AT of module 13 for an AT module which accepts methyl malonate in the SFA biosynthesis gene cluster;

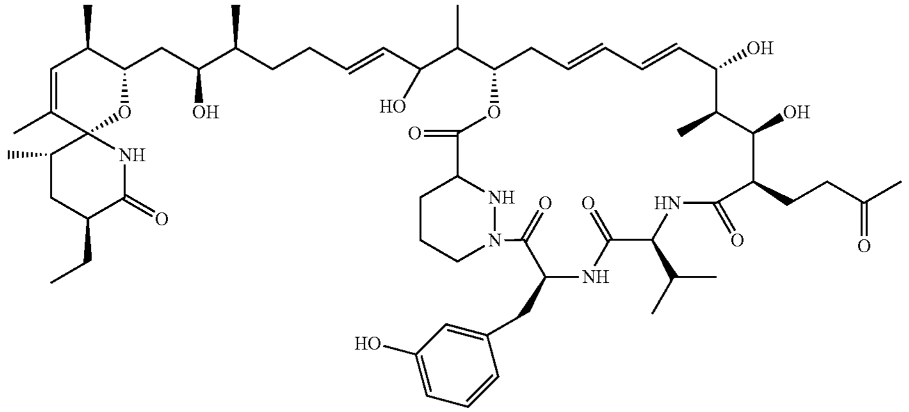 [SMILES: CC[C@H]1C[C@H](C)[C@@]2(NC1=O)O[C@@H](C[C@H](O)[C@@H](C)CC/C=C/C(O)C(C)[C@@H]1C/C=C/C=C/[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)C=C2C]

which may be expected to be produced by deletion/inactivation of the DH of module 8 in the SFA biosynthesis gene cluster;

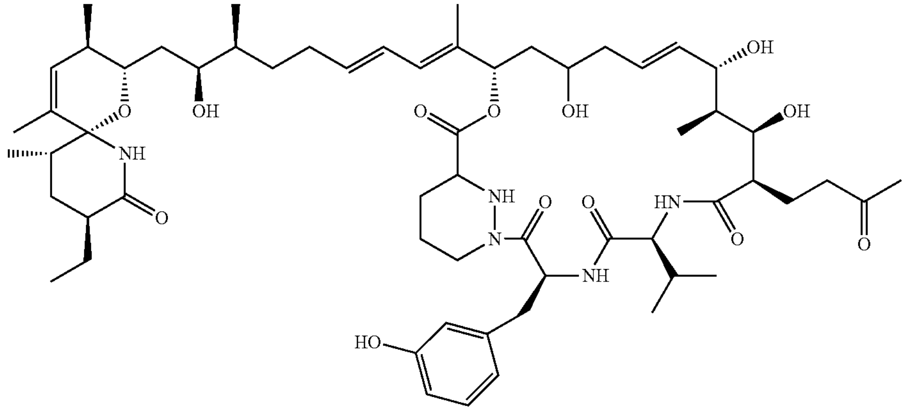 [SMILES: CC[C@H]1C[C@H](C)[C@@]2(NC1=O)O[C@@H](C[C@H](O)[C@@H](C)CC/C=C/C=C(\C)[C@@H]1CC(O)C/C=C/[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)C=C2C]

which may be expected to be produced by deletion/inactivation of the DH of module 10 in the SFA biosynthesis gene cluster;

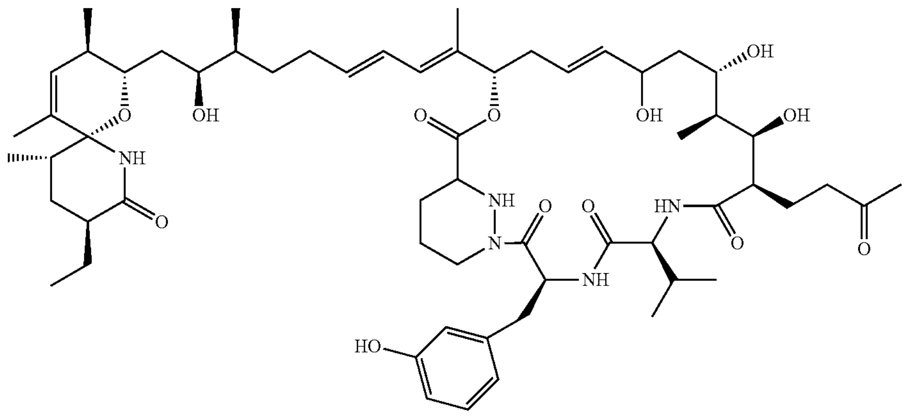 [SMILES: CC[C@H]1C[C@H](C)[C@@]2(NC1=O)O[C@@H](C[C@H](O)[C@@H](C)CC/C=C/C=C(\C)[C@@H]1C/C=C/C(O)C[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)C=C2C]

which may be expected to be produced by deletion/inactivation of the DH of module 11 in the SFA biosynthesis gene cluster;

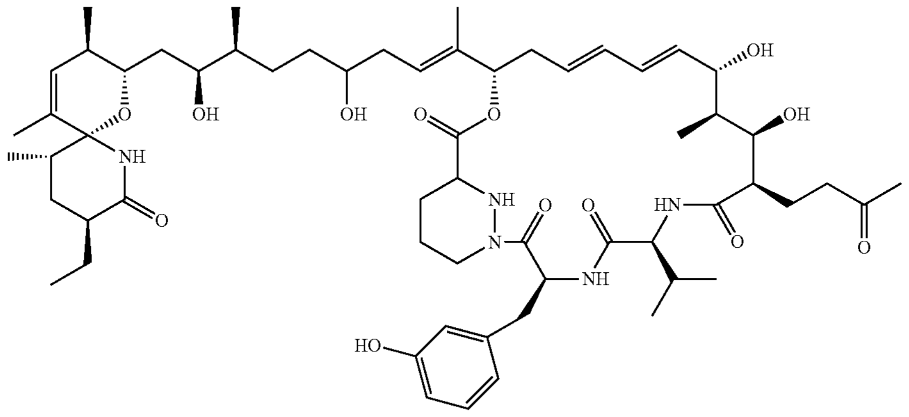 [SMILES: CC[C@H]1C[C@H](C)[C@@]2(NC1=O)O[C@@H](C[C@H](O)[C@@H](C)CCC(O)C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)C=C2C]

which may be expected to be produced by deletion/inactivation of the DH of module 7 in the SFA biosynthesis gene cluster;

and pharmaceutically acceptable salts thereof.

The above structures show a representative tautomer and the invention embraces all tautomers of the compounds of formulas (I) and (II) for example keto compounds where enol compounds are illustrated and vice versa.

The invention embraces all stereoisomers of the compounds defined by formulas (I) and (II) as shown above.

In a further aspect, the present invention provides processes for production of sanglifehrin analogues such as those defined by formulas (I) or (II) above by culturing a sanglifehrin analogue producing strain and optionally isolating the compounds produced.

In a further aspect, the present invention provides sanglifehrin analogues such as compounds of formula (I) and (II) or a pharmaceutically acceptable salt thereof, for use as a pharmaceutical.

The aforementioned compounds of formula (I) and (II) or a pharmaceutically acceptable salt thereof or a formulation thereof may be administered by any conventional method including topically (for example by inhalation, vaginally, intranasally, or by eye or ear drop), enterally (for example orally or rectally) or parenterally (for example by intravenous, intracavernosal, subcutaneous, intramuscular, intracardiac or intraperitoneal injection) or via a medical device (for example via a stent). The treatment may consist of a single dose or a plurality of doses over a period of time.

Whilst it is possible for sanglifehrin A or an analogue such as a compound of formula (I) and (II) or a pharmaceutically acceptable salt thereof to be administered alone, it is preferable to present it as a pharmaceutical composition, together with one or more pharmaceutically acceptable diluents or carriers. The diluents or carrier(s) must be “physiologically acceptable” in the sense of being compatible with the compound of the invention and not deleterious to the recipients thereof. In some cases, the diluent or carrier will be water or saline which will be sterile and pyrogen free.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the composition are prepared by uniformly and intimately bringing into association the active ingredient with liquid carriers or finely divided solid carriers or both, and then, if necessary, shaping the product.

Tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Compositions in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Aerosol compositions suitable for administering via inhalation can also be made using methods known in the art. Examples of this include administration of the compounds of the invention by inhalation in the form of a powder (e.g. micronized) or in the form of atomized solutions or suspensions. The aerosol composition may be placed in a suitable pressurized propellant, and may be used with additional equipment such as nebulizer or inhaler.

For applications to external tissues, for example the mouth and skin, the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base.

The compounds of the invention may also be administered using medical devices known in the art. For example, in one embodiment, a pharmaceutical composition of the invention can be administered with a needleless hypodermic injection device, such as the devices disclosed in U.S. Pat. No. 5,399,163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The compounds can be administered as the sole active agent, or in combination with other pharmaceutical agents.

In a further aspect, the present invention provides sanglifehrin analogues such as compounds of formula (I) and (II) or a pharmaceutically acceptable salt thereof, for use in the treatment or prevention of immune disorders, inflammatory disorders, cardiac diseases, viral diseases (such as HIV and HCV) and/or rejection of transplants.

In a further aspect, the present invention provides use of sanglifehrin analogues such as compounds of formula (I) and (II) or a pharmaceutically acceptable salt thereof, in the manufacture of a medicament for the treatment or prevention of immune disorders, inflammatory disorders, cardiac diseases, viral diseases (such as HIV and HCV) and/or rejection of transplants.

In a further aspect, the present invention provides a method for the treatment or prevention of immune disorders, inflammatory disorders, cardiac diseases, viral diseases (such as HIV and HCV) and/or rejection of transplants which comprises administering to a subject (especially a human subject) a therapeutically effective amount of a sanglifehrin analogue such as a compound of formula (I) and (II) or a pharmaceutically acceptable salt thereof.

For completeness, we provide the following further aspects of the invention:

A biosynthetic gene cluster of an immunosuppressant sanglifehrin A, characterized in that it comprises 24 genes responsible for sanglifehrin A biosynthesis, which are:

1) one non-ribosomal peptide backbone synthetase (NRPS) gene, sfaD, wherein:

sfaD locates in the nucleotide sequence of the gene cluster at bases 19885-30714, is 10830 base pairs in length, and encodes a non-ribosomal peptide synthetase of 3609 amino acids;

2) five type-I linear polyketide synthase (PKS) genes, sfaE, sfaF, sfaG, sfaH, sfaI, wherein:

sfaE locates in the nucleotide sequence of the gene cluster at bases 30707-37360, is 6654 base pairs in length, and encodes a polyketide synthase of 2217 amino acids;

sfaF locates in the nucleotide sequence of the gene cluster at bases 37394-50014, is 12621 base pairs in length, and encodes a polyketide synthase of 4206 amino acids;

sfaG locates in the nucleotide sequence of the gene cluster at bases 50017-60903, is 10887 base pairs in length, and encodes a polyketide synthase of 3628 amino acids;

sfaH locates in the nucleotide sequence of the gene cluster at bases 60918-85823, is 24906 base pairs in length, and encodes a polyketide synthase of 8301 amino acids;

sfaI locates in the nucleotide sequence of the gene cluster at bases 85823-96040, is 10218 base pairs in length, and encodes a polyketide synthase of 3405 amino acids;

3) one type-I iterative polyketide synthase gene, sfaK, wherein:

sfaK locates in the nucleotide sequence of the gene cluster at bases 97396-101943, is 4548 base pairs in length, and encodes a polyketide synthase of 1515 amino acids;

4) ten functional genes for precursor synthesis, sfaA, sfaB, sfaJ, sfaM, sfaN, sfaP, sfaQ, sfaR, sfaL, sfaO, wherein:

sfaA locates in the nucleotide sequence of the gene cluster at bases 17024-17854, is 831 base pairs in length, and encodes a phenylalanine meta-hydroxylase of 276 amino acids;

sfaB locates in the nucleotide sequence of the gene cluster at bases 17851-19191, is 1341 base pairs in length, and encodes a N5-ornithine oxygenase of 446 amino acids;

sfaJ locates in the nucleotide sequence of the gene cluster at bases 96225-97391, is 1167 base pairs in length, and encodes a zinc-finger dehydrogenase of 388 amino acids;

sfaM locates in the nucleotide sequence of the gene cluster at bases 103210-103929, is 720 base pairs in length, and encodes a short chain dehydratase/reductase of 239 amino acids;

sfaN locates in the nucleotide sequence of the gene cluster at bases 104001-105023, is 1023 base pairs in length, and encodes a ketosynthase of 340 amino acids;

sfaP locates in the nucleotide sequence of the gene cluster at bases 105366-107216, is 1851 base pairs in length, and encodes an asparagine synthase analogue of 616 amino acids;

sfaQ locates in the nucleotide sequence of the gene cluster at bases 107366-108145, is 780 base pairs in length, and encodes a thioesterase of 259 amino acids;

sfaR locates in the nucleotide sequence of the gene cluster at bases 108150-109511, is 1362 base pairs in length, and encodes a crotonyl-coA reductase of 453 amino acids;

sfaL locates in the nucleotide sequence of the gene cluster at bases 101936-103213, is 1278 base pairs in length, and encodes an acyltransferase of 425 amino acids highly homologous to the transacylation domain in polyketide synthase;

sfaO locates in the nucleotide sequence of the gene cluster at bases 105091-105345, is 255 base pairs in length, and encodes an acyl carrier protein of 84 amino acids;

5) two regulatory genes, sfaC and sfaS, wherein:

sfaC locates in the nucleotide sequence of the gene cluster at bases 19193-19888, is 696 base pairs in length, and encodes a transcription regulatory factor of 231 amino acids;

sfaS locates in the nucleotide sequence of the gene cluster at bases 109583-109798, is 216 base pairs in length, and encodes a MbtH factor of 71 amino acids;

6) five genes encoding functionally unknown proteins, sfaU1, sfaU2, sfaV1, sfaV2, sfaV3, wherein:

sfaU1 locates in the nucleotide sequence of the gene cluster at bases 14973-15413, is 441 base pairs in length, and encodes a functionally unknown protein of 146 amino acids;

sfaU2 locates in the nucleotide sequence of the gene cluster at bases 15596-16063, is 468 base pairs in length, and encodes a functionally unknown protein of 155 amino acids;

sfaV1 locates in the nucleotide sequence of the gene cluster at bases 109776-110312, is 537 base pairs in length, and encodes a functionally unknown protein of 178 amino acids;

sfaV2 locates in the nucleotide sequence of the gene cluster at bases 111285-111743, is 459 base pairs in length, and encodes a functionally unknown protein of 152 amino acids;

sfaV3 locates in the nucleotide sequence of the gene cluster at bases 112218-112652, is 435 base pairs in length, and encodes a functionally unknown protein of 144 amino acids.

The non-ribosomal peptide synthetase in the sanglifehrin A biosynthetic gene cluster, characterized in comprising the following modules or domains: peptidyl condensing-enzyme domain C, adenylation domain A, peptidyl carrier protein PCP, and a termination domain C for terminal group cyclization.

The polyketide synthase in the sanglifehrin A biosynthetic gene cluster, characterized in comprising the following modules or domains: keto condensing domain KS, transacylation domain AT, acyl carrier protein domain ACP, dehydration domain DH, keto reduction domain KR, and enol reduction domain ER.

A use of any protein encoded by the sanglifehrin A biosynthetic gene cluster, for the catalytic synthesis of the immunosuppressant sanglifehrin A and any corresponding analogues of its family.

A use of any protein encoded by the sanglifehrin A biosynthetic gene cluster, for the catalytic synthesis of the backbone of a hybrid polyketide-nonribosomal peptide.

The use of the sanglifehrin A biosynthetic gene cluster, wherein a genetic modification is made, and the biological fermentation of the mutant obtained produces non-natural analogues of sanglifehrin A, such as those hydroxylated at position 21 and 25.

The use of the sanglifehrin A biosynthetic gene cluster, wherein a genetic modification is made, and the biological fermentation of the mutant obtained produces compensatory products, non-natural analogues of sanglifehrin A which are substituted with methyl group at position 14.

Figure 1:
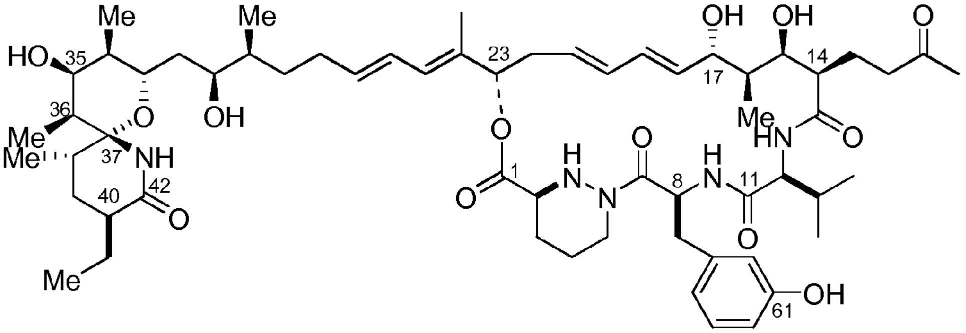
FIG. 1: Chemical structures of sanglifehrins (sanglifehrin A and analogues B, C and D).
Figure 1:
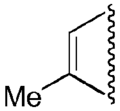
Figure 1:
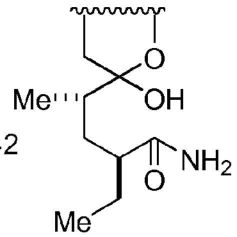
Figure 1:
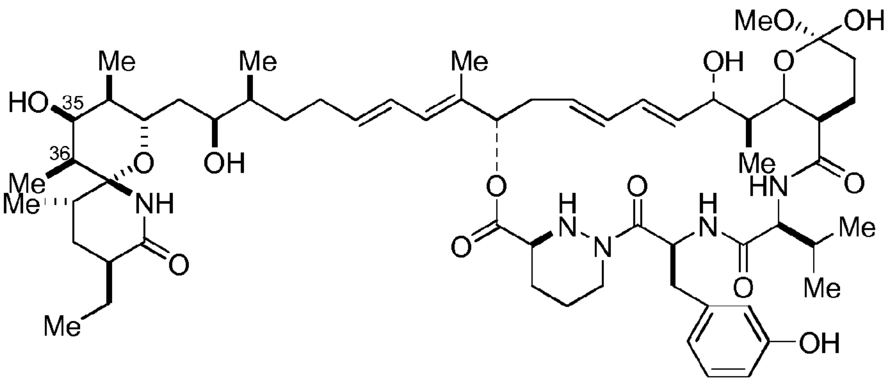
Figure 1:
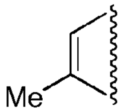
Figure 2:
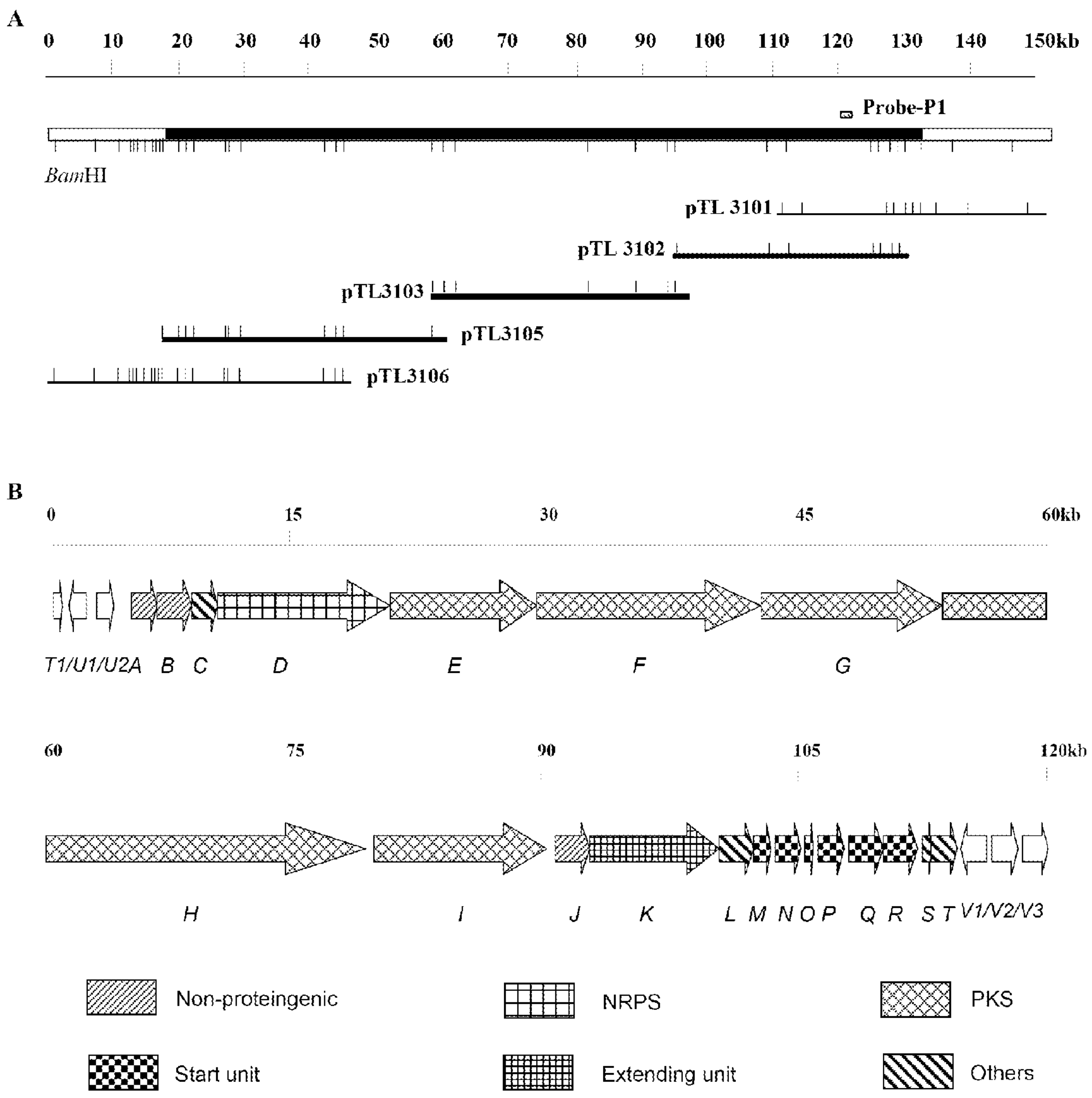
FIG. 2: Gene organization and restriction map of SFA biosynthetic gene cluster. (A) four overlapped cosmids representing the ~150 kb DNA region of the *Streptomyces* sp. A92-308110 (*S. flaveolus*) genome, B represents restriction enzyme BamHI, the solid line represents the parts that have already been DNA sequenced, Probe-P1 to P4 represent labeled probes; (B) the genetic organization of SFA biosynthetic gene cluster. Unknown: unknown gene; PKS: polyketide synthase gene; NRPS: non-ribosomal peptide synthetase gene; Beyond Cluster: gene outside boundary; Transposase: transposon; Modification: precursor synthesis gene
Figure 3:
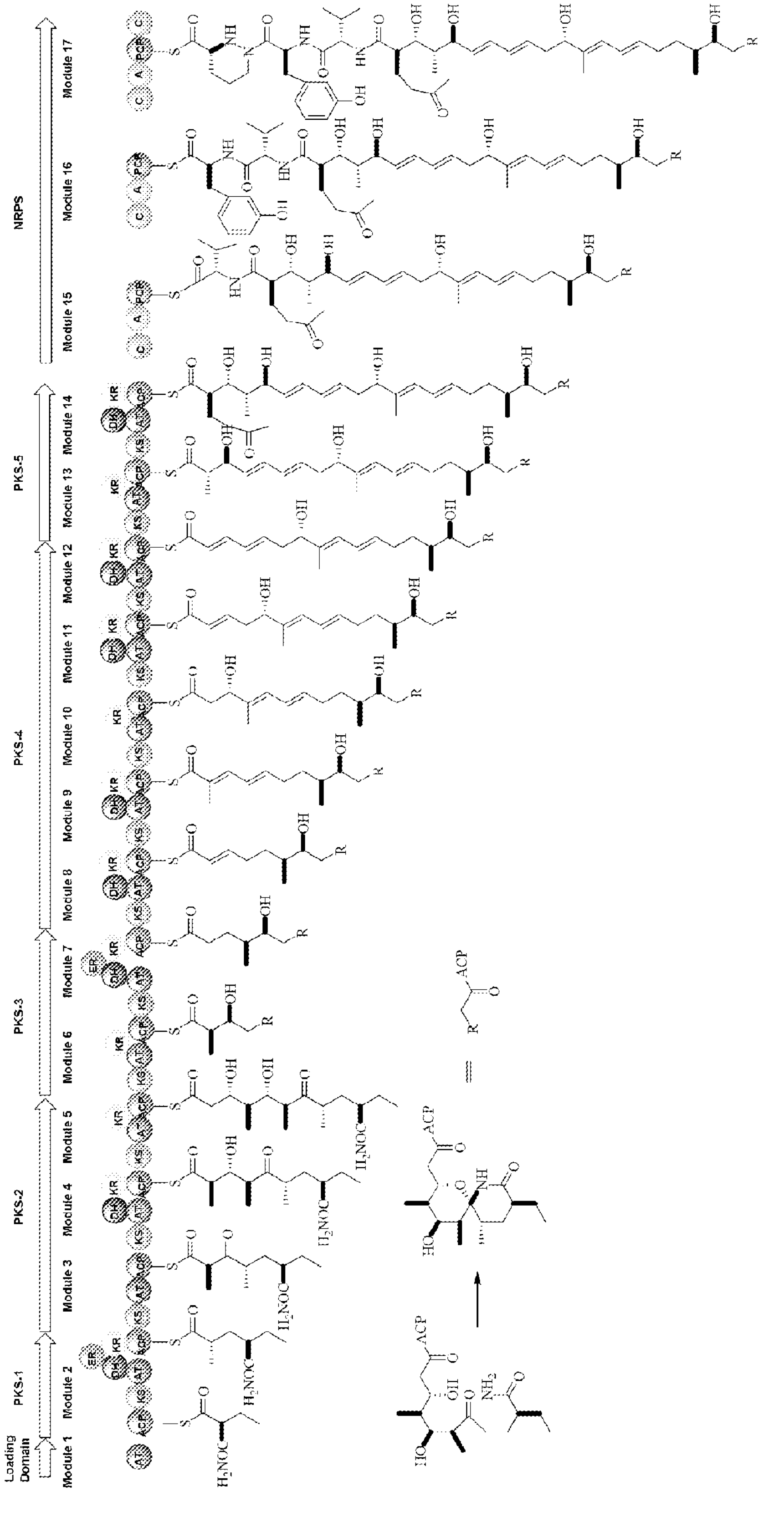
FIG. 3: Proposed biosynthetic pathways for each building block of SFA. (A) piperazic acid; (B) starter unit; (C) special extension unit. In steps marked with SfaX, X corresponds to the protein encoded by the respective gene in gene cluster as described herein; Marking a step with symbol "?" means that it is not yet clear whether the step is performed by an enzyme encoded by a gene of this gene cluster, or is performed in vivo by help of an enzyme involved in primary metabolism; A step without any mark means that it may be performed by help of a primary metabolism process.
Figure 4:
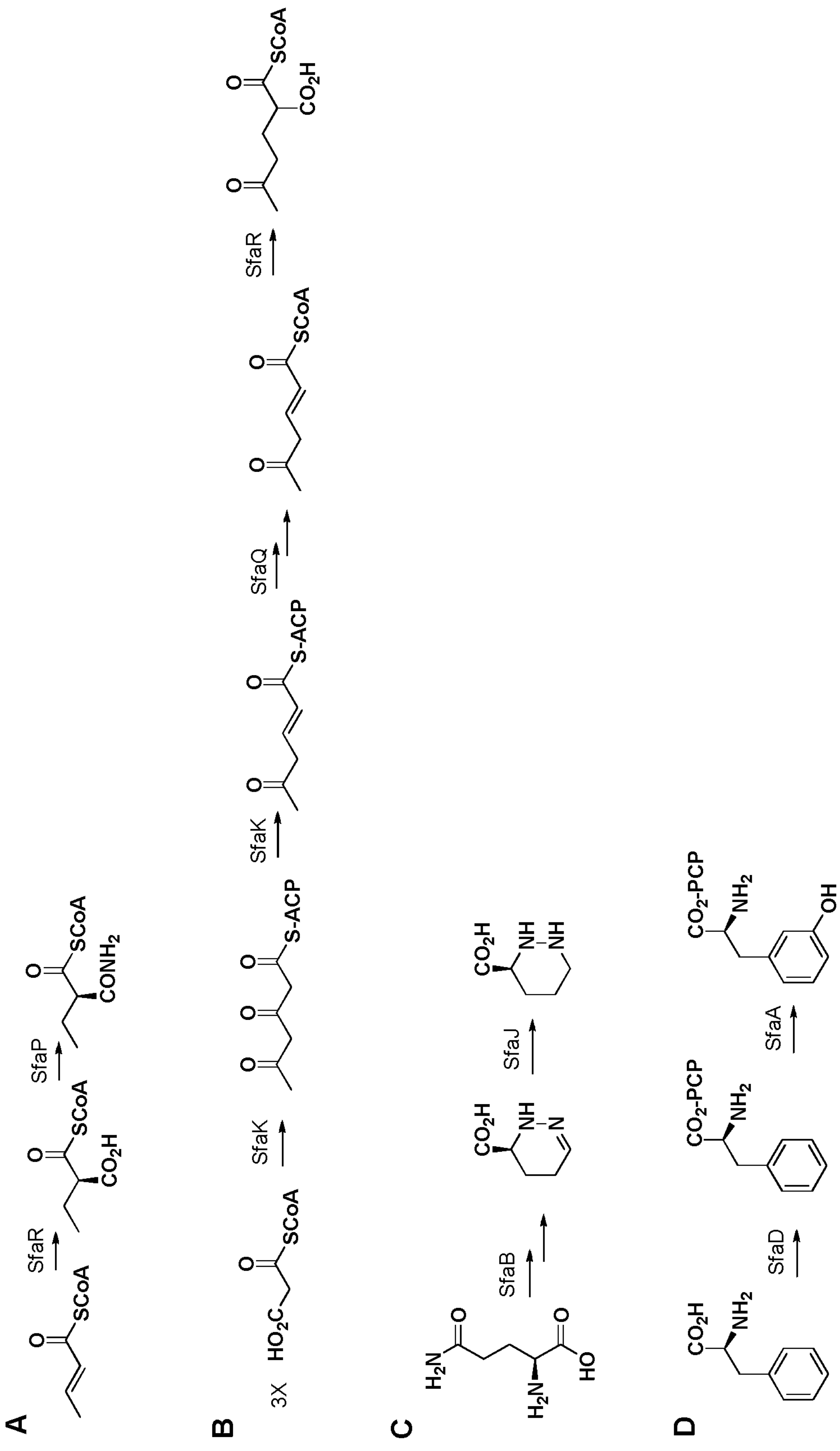
FIG. 4: Pathway for SFA backbone formation. PKS: polyketide synthase; NRPS: non-ribosomal peptide synthetase; KS: functional domain for keto synthesis; AT: functional domain for acyl transfer; KR: functional domain for keto reduction; ER: functional domain for enol reduction; DH: functional domain for dehydration; ACP: acyl carrier protein; C: functional domain for peptide condensation; A: functional domain for adenylation; PCP: peptidyl carrier protein.
Figure 5:
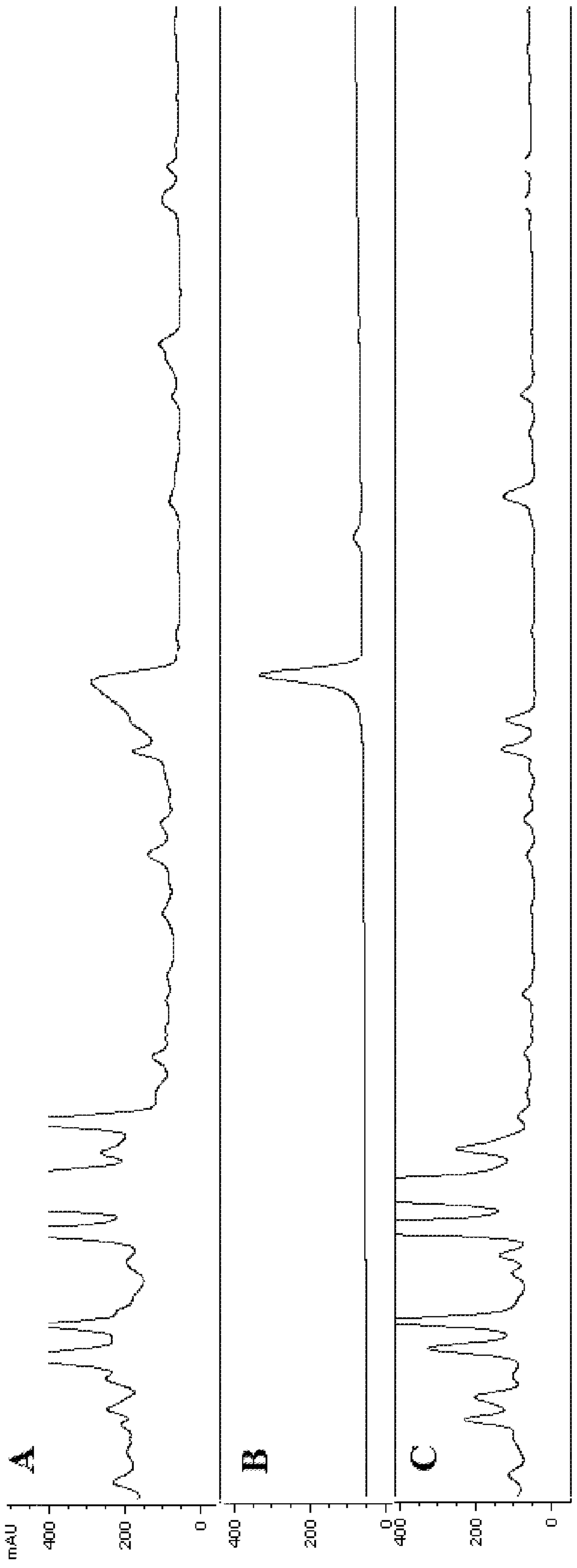
FIG. 5: High-performance liquid chromatography (HPLC) analysis of fermentation products derived from the interruption of the sequence of SFA biosynthetic gene cluster by cloned probe. WT: wild type; Standard: SFA standard; Mutant: mutant strain.
Figure 7:
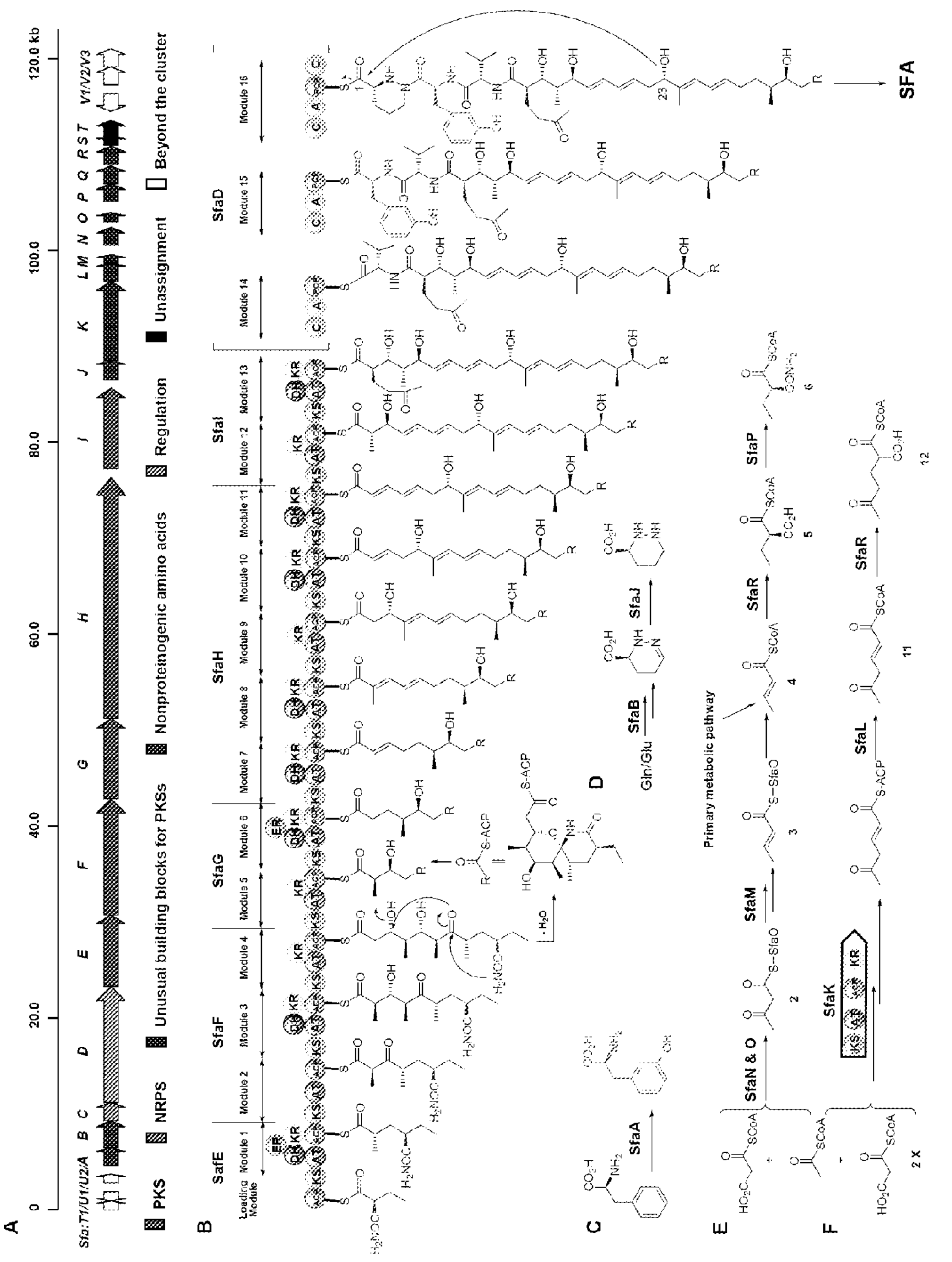
FIG. 7: Summary figure containing proposed biosynthetic pathway

The module numbering of FIG. 3 has been superceded by that of FIG. 7. Therefore when module numbers are referred herein the module numbers are those referred to in FIG. 7.

DESCRIPTION OF THE SEQUENCES OF THE SEQUENCE LISTING

SEQ ID No. 1: nucleic acid sequence of the SFA biosynthetic gene cluster

SEQ ID No. 2: amino acid sequence of SfaU1

SEQ ID No. 3: amino acid sequence of SfaU2
SEQ ID No. 4: amino acid sequence of SfaA
SEQ ID No. 5: amino acid sequence of SfaB
SEQ ID No. 6: amino acid sequence of SfaC
SEQ ID No. 7: amino acid sequence of SfaD
SEQ ID No. 8: amino acid sequence of SfaE
SEQ ID No. 9: amino acid sequence of SfaF
SEQ ID No. 10: amino acid sequence of SfaG
SEQ ID No. 11: amino acid sequence of SfaH
SEQ ID No. 12: amino acid sequence of SfaI
SEQ ID No. 13: amino acid sequence of SfaJ
SEQ ID No. 14: amino acid sequence of SfaK
SEQ ID No. 15: amino acid sequence of SfaL
SEQ ID No. 16: amino acid sequence of SfaM
SEQ ID No. 17: amino acid sequence of SfaN
SEQ ID No. 18: amino acid sequence of SfaO
SEQ ID No. 19: amino acid sequence of SfaP
SEQ ID No. 20: amino acid sequence of SfaQ
SEQ ID No. 21: amino acid sequence of SfaR
SEQ ID No. 22: amino acid sequence of SfaS
SEQ ID No. 23: amino acid sequence of SfaV1
SEQ ID No. 24: amino acid sequence of SfaV2
SEQ ID No. 25: amino acid sequence of SfaV3
SEQ ID Nos. 26-29: Primer sequences described in Example 1
SEQ ID Nos. 30 and 31: Primer sequences described in Example 11
SEQ ID Nos. 32-47: Primer sequences described in Example 12
SEQ ID Nos. 48-63: Primer sequences described in Example 14
SEQ ID Nos. 64-67: Primer sequences described in Example 16

General Methods

In general, methods were used as described in Maniatis et al., 1998, Sambrook and Russell, 2001 or in Kieser et al., 1999. Examples or alternative methods are detailed below.

Bacterial Strains and Plasmids

*Escherichia coli* DH10B (GibcoBRL) was grown in 2×TY medium as described by Sambrook and Russell (2001) and *E. coli* ET12567 (pUZ8002) as described in Paget et al. (1999) in 2×TY medium with kanamycin (25 mg/L) and chloramphenicol (12.5 mg/L). *E. coli* transformants were selected for with 100 mg/L ampicillin or 50 mg/L apramycin.

Most plasmids used are described in Kieser et al., 1999 and Sambrook et al., 2001. pTV1, also known as pBS3030, is described in Cheng et al., 2003, pIJ773 is described in GenBank accession no. AX657066.1. pANT841 is described in Genbank: AF438749

The sanglifehrin producer *Streptomyces* sp. A92-308110 (*S. flaveolus*) may be obtained from the DSMZ, Braunschweig, Germany as *Streptomyces* sp. DSM 9954.

Media Recipes

AS-1 Agar Medium:

| | g/100 mL |
|---|---|
| Yeast extract | 0.1 |
| L-Alanine | 0.02 |
| L-Arginine | 0.05 |
| Soluble starch | 0.5 |
| NaCl | 0.25 |
| $Na_2SO_4$ | 1.0 |
| Agar | 2.0 |

Distilled water to 100 ml
Medium is adjusted by NaOH to pH 7.5;

ISP4 Agar Medium:

| | g/L |
|---|---|
| Soluble starch | 10 |
| $K_2HPO_4$ | 1 |
| $MgSO_4•7H_2O$ | 1 |
| NaCl | 1 |
| $(NH4)_2SO_4$ | 2 |
| $CaCO_3$ | 2 |
| ISP trace salts solution | 1 mL |
| Agar | 20 |

Distilled water to 1000 ml, adjust to pH 7.2 prior to sterilisation

ISP Trace Salt Solution:

| | g/L |
|---|---|
| $FeSO_47H_2O$ | 1 |
| $MnCl_2•4H_2O$ | 1 |
| $ZnSO_4•7H_2O$ | 1 |

Distilled water to 1000 ml

IWL-4 Agar Medium:

IWL-4 agar medium was prepared by adding to each liter of ISP-4 medium 1 g tryptone and 0.5 g yeast extract, and adjusting the medium to pH 7.2 by NaOH Conjugation General Method Donor bacteria, *E. coli* S17-1 containing the plasmid of interest was inoculated into test tubes in 3-4 mL LB broth under supplemented with 50 μg/mL apramycin with shaking overnight. 500 μL was then inoculated into 50 mL LB supplemented with 50 μg/ml apramycin in 250 mL flasks at 37° C. and grown to an OD600 of 0.5. The cells were recovered in a 50 mL EP tube by centrifugation at 3800 rpm for 10 min. They were then re-suspended with 20 mL LB by vortexing and recovered again. This was repeated two times and the recovered cells re-suspended in 1 mL LB. Acceptor bacteria *Streptomyces* sp A92-309110 (*S. flaveolus*) were centrifuged at 12000 rpm 3 min to recover the spores and re-suspended with in 500 μL of 0.1 M TES twice, then heat shocked at 50° C. for 10 min and 500 μL TSB broth added. This was then The spores were then incubated at 37° C. for 4-5 h. The spores were recovered and resuspended in 1 mL LB. The bacteria were mixed in ratios from 1:99 to 99:1, with 1:1 generally yielding a successful transformation. The mixed bacteria were spread on MS agar and the plates dried in a laminar flow cabinet. The plates were then incubated at 30° C. for 14-16 h. The plates were spread again with 3-4 mL sterile water to remove most of the *E. coli* and the plates dried for 1 h in a laminar flow cabinet. The plates were then overlaid with 1 mL sterile water containing apramycin to at 1 mg/mL and nalidixic acid to at 1 mg/mL and incubated at 30° C. for 3-5 days. One or two or more single clones were selected and inoculated into 3 mL TSB broth with apramycin at 30 μg/mL with shaking at 30° C. for several days. 100 μL of fresh culture were spread onto ISP-4 agar and a double crossover allowed to occur by incubation for 2-3 days.

Total DNA Extraction from *Streptomyces* Sp A92-309110 (*S. Flaveolus*)

*Streptomyces* sp A92-309110 (*S. flaveolus*) spore suspensions stored at −80° C. were inoculated into 3 mL YEME medium. The culture was incubated for 12 h at 30° C., transferred into 1.5 mL EP tubes in two portions, centrifuged, and bacteria were recovered. Bacteria were resuspended in 500 μL STE solution; lysozyme was added to a final concentration of 4 mg/mL, and then incubated in a water bath at 37° C. for 30-45 min. After the bacteria had turned to are observed to become transparent and gel-like substance. Then, 250 μL of 2% SDS and 60 μL of 5 mol/L KAc were added, and well-mixed, frozen at −20° C. for 10 min, then centrifuged at 12000 rpm for 10 min. Supernatants were transferred into new EP 1.5 mL tubes. 500 μL 1:1 (v/v) phenol/chloroform mixture were added, and centrifuged at 10000 rpm for 3 min. This step was repeated several times until no more white denatured protein appeared at the interface. Then chloroform alone was used for another a final extraction. The supernatant was removed, well-mixed with an equal volume of isopropanol, left at room temperature for 30 min ro precipitate DNA, and centrifuged at 10000 rpm for 5 min. After washing with 70% alcohol and drying by suction filter, 200 μL TE buffer and 10 μL 10 mg/mL DNase-free RNase were added, and frozen at −20° C. for storage.

Fermentation of the SFA Producing Strain *Streptomyces* Sp A92-309110 (*S. Flaveolus*), and Related Strains, Product Isolation, Purification, and Identification a) Liquid Fermentation From a spore stock 50 μl (average concentration $1\times10^8$ per ml) was transferred into 3 mL TSB (Tryptic Soytone Broth, Sigma) under appropriate antibiotic pressure (apramycin 50 μg/ml or erythromycin 50 μg/ml depending on the resistant marker of the mutant) and was shaken (at 27° C., 250 rpm) for 30 h. From the primary culture 1 ml was transferred into 50 ml seed medium in 250 ml Erlenmeyer flask (diameter, 8.5 cm at bottom and 3.5 cm at mouth; height, 15 cm) and shaken (at 27° C., 250 rpm).

From the seed culture 5 mL was transferred into 90 ml production medium in 500 ml Erlenmeyer flask (diameter: 10.5 cm at bottom and 4 cm at mouth, height: 18 cm) and grown for 24 h at 25° C. (250 rpm), at which time 10 ml fresh production medium containing 4 g resin XAD-16 was added to the production culture (total 4 g XAD-16 in 100 mL production medium). The culture was incubated at the above conditions (25° C., 220 rpm), for further 3 days.

After fermentation was completed on day 4, the fermentation broth was passed through a paper filter aided by suction. The paper filter with the material remaining on it was transferred to a beaker, and frozen at −80° C. for 30 min, and freeze-dried overnight. 80-100 mL methanol was added to the dried material, stirred for 40 min, and filtered using suction. The filtered material was extracted with methanol for the second time, and filtered using suction. The resin was discarded, and the methanolic solutions were pooled, and dried under vacuum at 35-37° C. After evaporation to dryness, the material was transferred using two aliquots of 750 μL methanol. The two methanolic solutions were pooled and 1.5 mL aliquots were transferred to Ependurf tubes, and frozen at −20° C. for 1 h. The tubes were centrifuged at 12000 rpm, 4° C., for 10 min. The supernatant was transferred to new Eppendorf tubes, dried under vacuum until approximately 500 μL of liquid remained, which was then stored at 4° C.

Approximately 300 μL of the crude extract obtained as explained above was purified through flash column chromatography (RP-18), which was pre-rinsed with 40 mL of 40% acetonitrile in water. The column was then eluted with 40 mL of 50% acetonitrile in water, and 40-mL fractions were collected in separate tubes, and then concentrated. Pre-treated samples were further purified using LC-MS (using 80% acetonitrile in water containing 1% formic acid) for isolation and identification.

b) Solid Fermentation

For inoculation of several agar plates, 40 μL of spore stock was transferred to 3 mL TSB medium, and incubated overnight at 37° C. (while shaking at 250 rpm). From this overnight culture, 400-500 μL was transferred and spread evenly onto the surface of agar plates (150 mm) made either from R2YE, IWL-4, ISP-4, or AS-1 agar medium. Alternatively, aliquots (50 μL) of spore stock can be used to directly inoculate the agar plates. The inoculated agar plates were incubated at 30° C. for 6-7 days.

At the end of the incubation period, the culture on the agar medium was harvested into a 250 mL beaker and minced. 200 mL methanol was added to the material from one agar plate and the mixture was stirred for 2 h, then filtered through filter paper aided by suction. Solid materials were discarded, and the filtrate was dried in a rotary evaporator. In order to recover the fermentation product, two 500 μL aliquots of methanol were used to resuspend and transfer the dried material to 1.5 mL Eppendorf tubes. Purification of material from the methanolic concentrate followed a similar procedure as explained above for the liquid fermentation process. However, because there the content of water in solid media is low the freeze-drying step can be omitted. Samples were further purified using LC-MS (using 80% acetonitrile in water containing 1% formic acid) for isolation and identification.

Cloning SFA Biosynthetic Genes by PCR

The PCR system comprises: DMSO (8%, v/v), $MgCl_2$ (25 mM), dNTP (2.5 mM), degenerate primers (10 μM), Taq DNA polymerase (2.5 u), and a suitable amount of the total DNA of *Streptomyces* sp A92-309110 (*S. flaveolus*) as a template. First, 95° C., 3 min, 1 cycle; then, 94° C., 1 min, 68° C., 1 min, 72° C., 2 min, 5 cycles; 94° C., 1 min, 65° C., 1 min, 72° C., 2 min, 30 cycles; finally, 72° C., 10 min, 1 cycle. After PCR was finished, 1% Agarose Gel Electrophoresis was use to examine the results. DNA fragments of desired sizes were recovered from low melting point gel, and ligated with pGEM T Easy vector. *E. coli* DH5α competent cells were transformed, and spread on LB plate containing ampicillin, IPTG (Isopropyl-β-D-thiogalactopyranoside), and X-gal (5-Bromo-4-chloro-3-indolyl-β-D-galactoside) were used for blue-white selection. White bacterial colonies were picked for overnight culture, and plasmids were extracted. It was assessed by EcoRI digestion whether plasmids contained inserted DNA fragments of desired sizes. These plasmids were then sequenced.

Nucleic Acid Hybridization

Several microliters of mycelium or spores of the mutant strain to be assessed were inoculated into 3 mL TSB medium, shaken at 220 rpm, and cultured at 30° C. until the culture medium thickened. Then genomic DNA was extracted. Based on sequence analysis, a hybridization strategy was designed, probes were prepared, and suitable restriction enzyme sites were selected for genomic DNA digestion.

15 μL of probe (containing 0.5-3 μg DNA) was incubated in a boiling water bath for 10 min, then transferred immediately into a salt-ice bath to cool. 2 μL Hexanucleotide Mix (10×), 2 μL dNTP Labeled Mix, 1 μL Klenow Enzyme Labeled were sequentially added and well-mixed, then the mixture was incubated in a water bath at 37° C. for 16 h. 0.8 μL 0.8M EDTA (pH=8.0) was added to stop the reaction, and 2.5 μL 4M LiCl was added and well-mixed. 75 μL pre-chilled anhydrous alcohol was added for precipitation. The mixture was frozen at −80° C. for 40 min, and centrifuged at 12000 rpm, 4° C. for 20 min. DNA was collected, washed with 70% prechilled alcohol, vacuum dried and dissolved in 50 μL TE buffer and stored at 4° C. After electrophoresis, the agarose gel was soaked in 0.25M HCl for 20 min, rinsed with deionized water, and then soaked for another 20 min with gentle shaking after the basic buffer was added. After exchanging the buffer once, the gel was soaked for another 20 min. After washing several times with deionized water, DNA was transferred to a nylon membrane. Transfer apparatus (BioRad) was used for the transfer. Following the instructions of the apparatus, one piece of wet filter paper was placed on the bottom plate, then overlaid with a nylon membrane of suitable size. The membrane should be 1 cm larger than the gel on each side, then a plastic membrane was overlaid and the clamps are fixed. The agarose gel was treated as described above and then placed on the membrane pore. After the apparatus is connected with the vacuum pump, the pressure is adjusted to maintain at 5-8 mmHg. After making a vacuum-tight seal, around 1 L 10×SSC hybridization buffer is added, and the liquid surface should cover the agarose gel. The transfer is performed for 2 h. Fixing may then be performed by baking for 40 min in oven at 120° C., or alternatively by exposing to UV light (2 J/cm2). The membrane is then stored in a dark and cool place before use. The fixed nylon membrane was placed into hybridization tubes, and hybridization solution was added. Pre-hybridization was performed at 64° C. for 30 min, then probes were added, and hybridization was performed at the desired temperature for 16 h. The membrane was sequentially washed twice for 5 min with 2×SSC stringent washing buffer at room temperature; then washed twice for 15 min with 0.5×SSC stringent washing buffer at 64° C. After stringent washing, the nylon membrane was first equilibrated for 1-5 min with washing buffer, and then incubated with blocking solution for 30 min, then incubated with antibody solution for 30 min. After 1-2 washings with washing buffer, it was equilibrated for 2-5 min with detection buffer. Developing buffer was added, and the membrane was allowed to develop in the dark. When a suitable intensity was reached, the membrane was washed with deionized water to stop the reaction, and hybridization was completed.

EXAMPLES

Further description will be made to the invention with reference to the accompanying figures in the following context.

Example 1

Cloning the Crotonyl-CoA Reductase Gene Fragment from the SFA Gene Cluster

Hitherto, whilst the total synthesis of SFA has been successfully completed, its natural production pathway is barely known, particularly with respect to the mechanism of formation of the N—N bond of the piperazic acid unit, and the unusual polyketide extension unit that probably utilises an iterative polyketide synthase. For the past few years, isotope-labeled studies have shown that glutamic acid and glutamine may be the biosynthetic precursors of piperazic acid in certain systems that produce natural products comprising piperazic acid units (Umezawa et al., 2001; Miller et al., 2007). According to analysis of existing gene clusters and of other reported gene clusters for natural products comprising piperazic acid, the possibility of ornithine being a substrate is not excluded; moreover, the unusual extension unit, as a side substituent on the macrocyclic backbone, may be formed based on an unusual iterative polyketide synthase. The above-mentioned two units may play important roles in developing new drugs and studying structure-activity relationships. Thus, there is a need for analysis of the SFA biosynthetic gene cluster to elucidate the biosynthesis mechanism of SFA, and then to develop its potential pharmaceutical value.

Based on analysis of the hybrid PKS-NRPS structure for the macrocyclic backbone, the gene cluster was assumed to possess a long linear PKS-NRPS region, with no known homologues, leading to an increase in the difficulty of isolation and cloning of the biosynthetic gene cluster. Indeed, by probing with elements of PKS and NRPS genes, DNA from 11 PKS and 7 NRPS clusters was isolated, then used for gene inactivation studies. All of these led to no effect on sanglifehrin production. Eventually, the inventors managed to clone the gene cluster using other specific units as probes. By analysis of naturally occurring biosynthesis gene clusters for polyketide natural products which comprise ethyl group-based structures, the inventors noted that ethyl units were generally introduced by using ethylmalonyl-CoA as a building block. The inventors conceived that the SFA gene cluster may contain a CCR homologue. Therefore, degenerate CCR primers were designed to clone the sequence of the highly conserved region of the crotonyl-coA synthetase responsible for biosynthesis of ethyl unit, which we thought may be present in S. sp. A92-308110 (*S. flaveolus*) genome. The cloned sequence was then labeled as a probe to perform library screening. The sequences of degenerate primers were as follows:

```
CCR Long-For (SEQ ID: 26):
AGGAAT TCATGG CCTCCK CSRTSA ACTACA AY,

CCR Long-Rev (SEQ ID: 27):
TCGGAT CCGCCG AAGTTS GTCTCR WABCCC CA;

CCR Short-For (SEQ ID: 28):
AGGAAT TCGACA TCGACA TSGTBW TCGAG CA,

CCR Short-Rev (SEQ ID: 29)
TCGGAT CCGATG ATGCGC TTSWSB KDCATC CA.
```

Using these primers, two sequences of 900 bp and 300 bp were amplified from the *Streptomyces* sp A92-309110 (*S. flaveolus*) genome. The gel was cut, and the PCR fragments were recovered and digested by EcoRI and BamHI, and then cloned into pSP72 at EcoRI/BamHI site. The recombinant plasmids were identified by enzymatic digestion and sequencing. In total, three different sets of CCR gene fragments which were highly homologous to each other were cloned.

Example 2

Cloning, Sequence Analysis and Function Analysis of SFA Biosynthetic Gene Cluster Fragments cloned as described above in example 1 were labeled with digoxin, and library screening was performed. The resulting 3 sets of cosmids obtained were re-divided into groups, and their relative positions were established according to restriction mapping. The 6.4 kb BamHI end fragment of pTL3101 (cQXD03-126-6) was chosen as probe to perform chromosome walking, and cosmid pSL36 was obtained. Then 1.4 kb BamHI fragment was chosen to perform chromosome walking, and cosmids pTL3104 (cQXD04-49-1~50) were obtained. Then the BamHI fragment at the far left side was chosen to perform walking and cosmids pTL3106 (cQXD04-64-1~40) were obtained. After these three rounds of chromosome walking, a total of about 150 kb of chromosome DNA was cloned. Using PKS and NRPS degenerate primers respectively, PCR assays were performed on some cosmids, from some of which specific bands were amplified. This confirmed that the gene cluster comprises CCR and hybrid PKS-NRPS.

TABLE 1

| Sequence-based function analysis of the SFA biosynthetic gene cluster | | | | |
|---|---|---|---|---|
| gene | amino acid | similar protein | function of homologous protein | similarity/identity |
| sfaU1 | 150 | ZP_03193264 | unknown protein | 60/45 |
| sfaU2 | 112 | AAW49302 | resolvase/integrase | 81/75 |
| sfaA | 276 | YP_001509705 | Phenylalanine meta-hydroxylase | 70/57 |
| sfaB | 446 | YP_001852050 | ornithine N5-oxygenase | 73/61 |
| sfaC | 231 | YP_001852059 | transcription regulatory factor | 73/60 |
| sfaD | 3609 | YP_631823 | non-ribosomal peptide synthetase | 57/43 |
| sfaE | 2217 | ABC87510 | polyketide synthase | 65/52 |
| sfaF | 4206 | ABB88533 | polyketide synthase | 59/48 |
| sfaG | 3628 | NP_824075 | polyketide synthase | 63/54 |
| sfaH | 8301 | ZP_03174068 | polyketide synthase | 63/52 |
| sfaI | 3405 | DQ_450945 | polyketide synthase | 73/65 |
| sfaJ | 332 | YP_112153 | zinc-binding dehydrogenase | 67/51 |
| sfaK | 1515 | YP_001104567 | iterative linear polyketide synthase | 58/47 |
| sfaL | 425 | YP_480040 | acyltransferase | 54/42 |
| sfaM | 239 | YP_949278 | short chain dehydrogenase | 60/43 |
| sfaN | 340 | YP_001537010 | ketosynthase | 66/52 |
| sfaO | 84 | AAD_20269 | acyl carrier protein | 61/45 |
| sfaP | 616 | BAB12569 | asparagine synthase analogue | 77/68 |
| sfaQ | 259 | CAQ64680 | thioesterase | 70/58 |
| sfaR | 453 | YP_002204695 | Crotonyl-coA reductase | 91/86 |
| sfaS | 71 | YP_882427 | MbtH protein | 82/67 |
| sfaV1 | 178 | CAD18995 | unknown protein | 81/65 |
| sfaV2 | 152 | YP_002199237 | hypothetical protein | 63/53 |
| sfaV3 | 144 | YP_001159721 | hypothetical protein | 57/45 |

The three cosmids with the highest coverage were selected to undergo full-length sequencing, and the inventors obtained 118,372 bp of continuous nucleotide sequence. Bioinformatics analysis revealed that it comprised 44 open reading frames (ORFs), at least 19 ORFs of which were suggested to be related to SFA biosynthesis, including: 1 NRPS gene (sfaD) responsible for synthesis of macrocyclic tripeptide backbone; 5 PKS genes (sfaE-I) which complete synthesis of the macrocyclic polyketide backbone; 11 putative precursor synthesis genes (sfaA-B, sfaJ-R), responsible for synthesis of the starter unit and each condensation unit, and for backbone modification; 2 regulatory genes (sfaC and sfaS) involved in regulation of SFA biosynthesis. Results of function analysis of each gene were shown in the table above.

Example 3

Determination of the Boundaries of the SFA Biosynthetic Gene Cluster

According to sequence analysis, at about 40 kb from the upstream sequencing start point, there is an incomplete trace of transposition (upstream of sfaU1 and sfaU2); at about 20 kb from the downstream sequencing end point, there are obviously two transposase genes (i.e. sfaT2 and sfaT3), but part of the upstream transposition gene is missing. Using the two sequences described above as boundaries, all the ORFs may be divided into three sections:

The about 120 kb sequence in the middle is the core responsible for SFA backbone biosynthesis, as described above.

The upstream section comprises 16 genes that are putatively not relevant with SFA biosynthesis, including 9 functional genes (cytochrome p450 mono-oxygenase gene orf16, acyl carrier protein gene orf14, adenylase gene orf13, methyltransferases gene orf12, cytochrome p450 hydroxylase gene orf11, deoxy guanine kinase gene orf10, dehydrogenase gene orf9 and proteinase M23S gene orf6), 5 genes encoding unknown proteins (orf15, orf7, orf5, sfaJ1, and sfaJ2), 2 genes encoding regulatory factors (orf4 and orf8, which belong to TetR and LysR family respectively), and 1 glycosyl transfer coupled protein gene (orf3).

The downstream section comprises genes that are putatively not relevant with SFA biosynthesis, including 3 genes encoding unknown proteins (sfaV1, sfaV2, and sfaV3) and 2 transposase genes (sfaT2 and sfaT3). There is also 1 gene encoding TetR family regulatory factor (orf23), 1 gene encoding TetR-coupled membrane protein (orf24), 1 FAD mono-oxygenase gene (orf25), and 1 incomplete endonuclease gene (orf26).

Preliminary analysis of the gene cluster sequence helped the inventors to determine the putative boundaries of the SFA biosynthetic gene cluster. The left boundary is located just upstream of sfaA, including 2 functionally unknown genes (sfaU1 and sfaU2). The right boundary is located just downstream of the MbtH gene, including 3 functionally unknown genes and 2 transposase genes (sfaV1~3, orf21 and 22). As MbtH family proteins are often linked with NRPSs, the inventors presume that it is involved in the regulation of precursor biosynthesis. However, the activity of proteins of this family can be complemented by homologues elsewhere in the cluster; that is to say, all of the MbtH genes present in the whole genome would need to be knocked out, otherwise it will be complemented by its counterpart located at other site in the genome. As the total amount of MbtH in host bacteria was unknown, the downstream unknown protein and transposon were chosen for analysis. In addition, at 82 bp from the start of orf10, there is a 35 bp promoter sequence; and at 52 bp from where orf18 ends, there is a part of a ρ-independent terminator sequence. The whole gene cluster is located in the large transcriptional unit as described above. Based on the following analysis of the downstream transposases, it is presumed that this gene cluster comes from horizontal gene transfer.

3.1 Study of the Left Boundary

Study of the left boundary was focused on sfaU1 and sfaU2. sfaU1 has a full length of 453 bp, it encodes a functionally unknown protein of 150 amino acid residues, and shares 60% homology with an unknown protein in *Streptomyces sviceus*; sfaU2 has a full length of 468 bp, encodes a functionally unknown protein of 155 amino acid residues, which, upon analysis was seen to share 81% homology with a resolvase/integrase in *Streptomyces turgidiscabies*. A gene sfaU1 knockout was carried out and confirmed that it was not relevant to SFA biosynthesis. Meanwhile, the transposon sequences up- and down-stream of sfaU1 also imply the boundaries of the horizontal transfer of the gene cluster.

3.2 Study of the Right Boundary

Study of the right boundary was focused on sfaV1, sfaV2, sfaV3, and sfaT2. sfaV1 has a full length of 537 bp, it encodes an unknown protein of 178 amino acid residues, and shares 81% homology with an unknown protein in *Streptomyces cattleya*; sfaV2 has a full length of 459 bp, it encodes a functionally unknown protein of 152 amino acid residues, and shares 46% homology with an functionally unknown protein in *Streptomyces coelicolor*, sfaV3 has a full length of 435 bp, it encodes an unknown protein of 144 amino acid residues, shares 45% homology with an unknown protein in

*S. coelicolor*, and a certain homology with UDP-N-acetylglucosamine transferase in *Pseudomonas syringae* pv. tomato. SfaT2 has a full length of 534 bp, encodes a transposase of 177 amino acid residues, and is partly homologous to the IS-4 insertion sequence in *Burkholderia vietnamiensis*. Based on analysis of the transposon sequence, the downstream boundary was determined to locate adjacent to the transposon region.

Example 4

Proposal for Biosynthesis of the SFA Starter Unit

Endogenous acetoacetyl-CoA is reduced to hydroxy-butyryl CoA by the short chain dehydrogenase/reductases encoded by sfaM, then to Crotonyl-coA by an unknown primary metabolic dehydratase. Then, the crotonyl-coA is reductively carboxylated by crotonyl-coA reductase encoded by sfaR, and amidated by asparagine synthetase analogue encoded by sfaP. Afterwards, the extension by incorporation of the subsequent two-carbon unit is completed via the self-acylation of the starter acyl carrier protein (encoded by sfaE-ACP1). Meanwhile, a free acyltransferase having a modified function and encoded by sfaL is thought to be responsible for hydrolyzing other units which are erroneously added by self-acylation.

Example 5

Proposal for Biosynthesis of the m-Tyrosine in SFA

Traditional phenylalanine/tyrosine/tryptophan hydroxylation systems all rely on an electrophilic substitution reaction to realize hydroxylation in the electron-rich regions of aromatic systems. On the contrary, the meta-hydroxylation of phenylalanine occurs at the relatively electron-poor meta position of phenylalanine. Bioinformatics analysis of the second adenylation domain (A2) in the NRPS shows that its active fingerprint region shares no homology with the fingerprint regions of the adenylation domains which are responsible for recognizing phenylalanine in other systems, and it has no apparent association with tyrosine. The putative meta-hydroxylase, SfaA, was expressed in *E. coli* and isolated using standard methods. In vitro study of this protein in an AMP PPi assay (for methods see Garneau et al., 2005) showed that it had no activity on free phenylalanine, but did show activity to an acetylcysteamine (SNAC) thioester derivative. This suggests that phenylalanine is the optimal substrate for integration into the polypeptide backbone, i.e. after integration, in situ modification takes place to obtain the meta-tyrosine unit.

Example 6

Proposal for Biosynthesis of the SFA Piperazic Acid Unit

The third building block of the short peptide moiety in the SFA structure is a piperazic acid unit, which is involved in the integration of the peptide backbone in a 2,3-regioselective manner. The piperazic acid unit was initially presumed to be obtained from a proline precursor via dehydrogenation at 1,2-position, ammonolysis, $N^5$ oxidation to form cycle, and then reduction. However, previous labeled assays have showed that the real precursor of piperazic acid unit is glutamic acid (Umezawa et al., 2001, Miller et al., 2007). Therefore it is suggested that the piperazic acid unit is formed from a precursor molecule glutamic acid/glutamine via hydrogenation and dehydration, $N^5$ oxidation and then hydrogenation. Although no direct evidence of ornithine being the precursor has been obtained in other labeled assay systems, the inventors consider it possible that ornithine is involved in the piperazic acid formation in the system by direct $N^5$ oxidation to form the cycle, as seen in other systems (Fujimori et al., 2007).

Example 7

Proposal for Biosynthesis of the Unusual Extension Unit

Figure 6A:
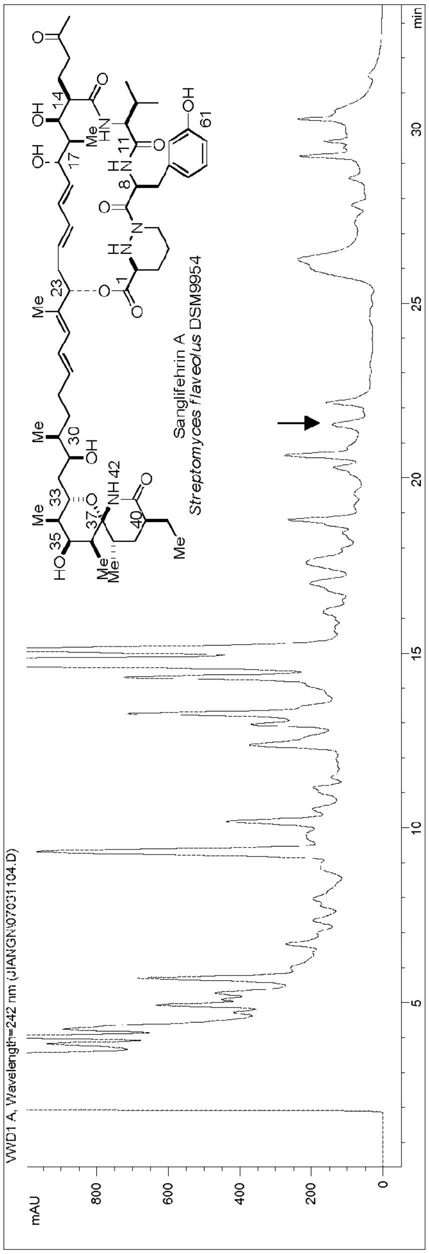
FIG. 6: High-performance liquid chromatography (HPLC) analysis of fermentation products of a mutant strain resulted from gene substitution. (A) wild type, (B) knock-out mutant of zinc binding dehydrogenase gene sfaJ, (C) knock-out mutant of iterative linear polyketide synthase gene sfaK, (D) knockout mutant of acyltransferase gene sfaL, (E) knockout mutant of short chain dehydrogenase gene sfaM, (F) knockout mutant of phenylalanine hydroxylase gene sfaA, (G) knockout mutant of ornithine oxygenase gene sfaB, (H) knockout mutant of fatty acid ketosynthase gene sfaN, (I) knockout mutant of asparagine synthase analogue gene sfaP, (J) knockout mutant of Crotonyl-coA reductase gene sfaR, (K) knockout mutant of left flanking unknown protein sfaU1, (L) knockout mutant of right flanking TetR regulatory factor, (M) DH domain of module 8 site-directed mutagenesis, (N) DH domain of module 10 site-directed mutagenesis. *Streptomyces* sp. A92-308110 (*S. flaveolus*); mv.: mutant strain (a mark used to distinguish from wild type); *tsekangensis*: T mutant (produces SFT); *hasangensis*: H mutant (produces SFH); *xuwengensis*: X mutant (produces SFX)
Figure 6B:
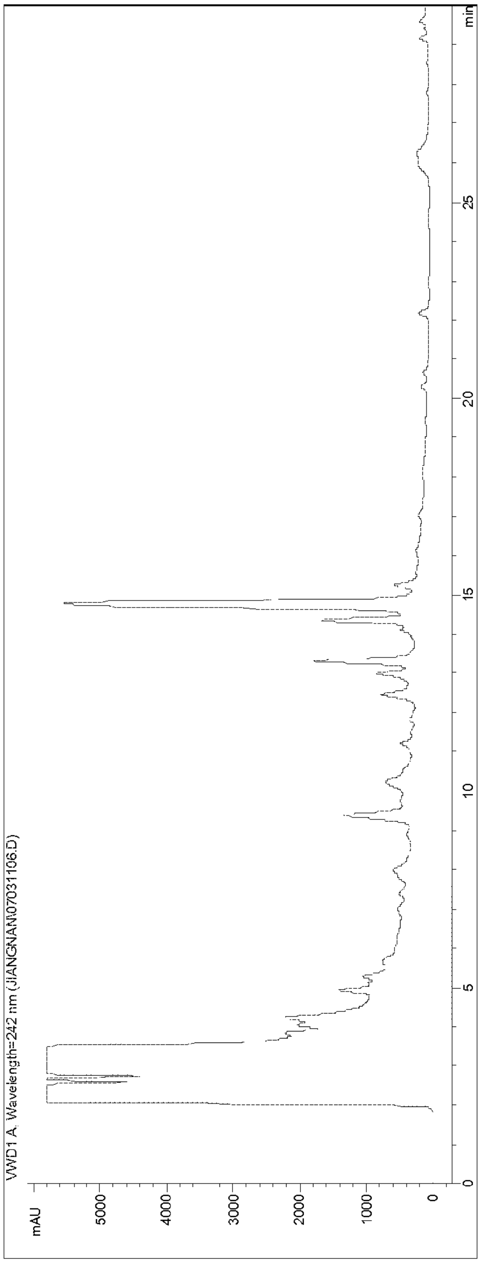
Figure 6C:
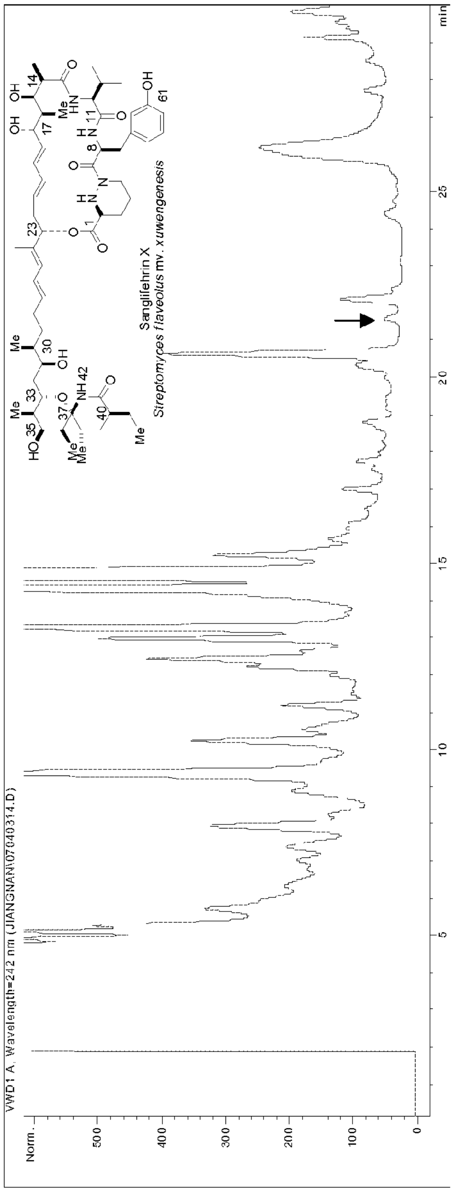
Figure 6D:
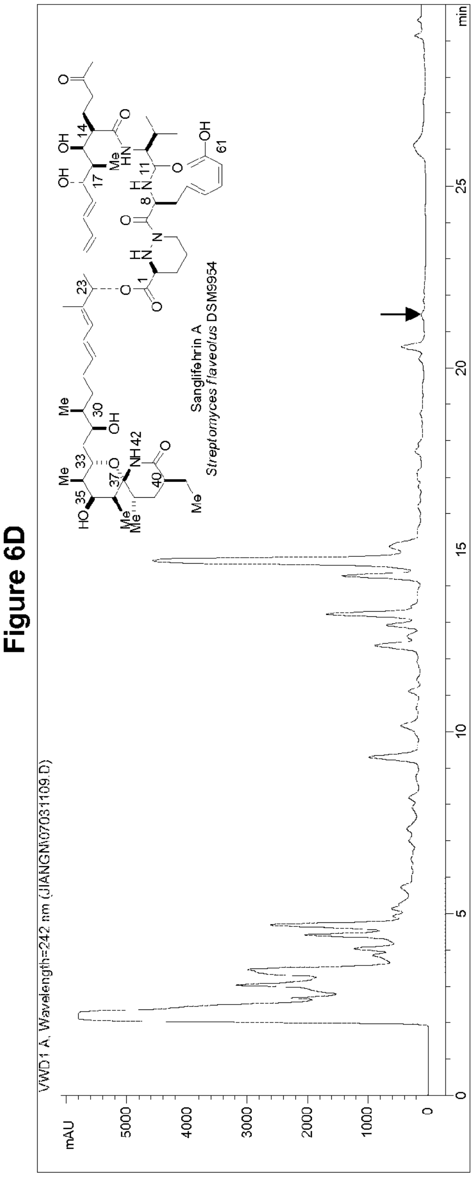
Figure 6E:
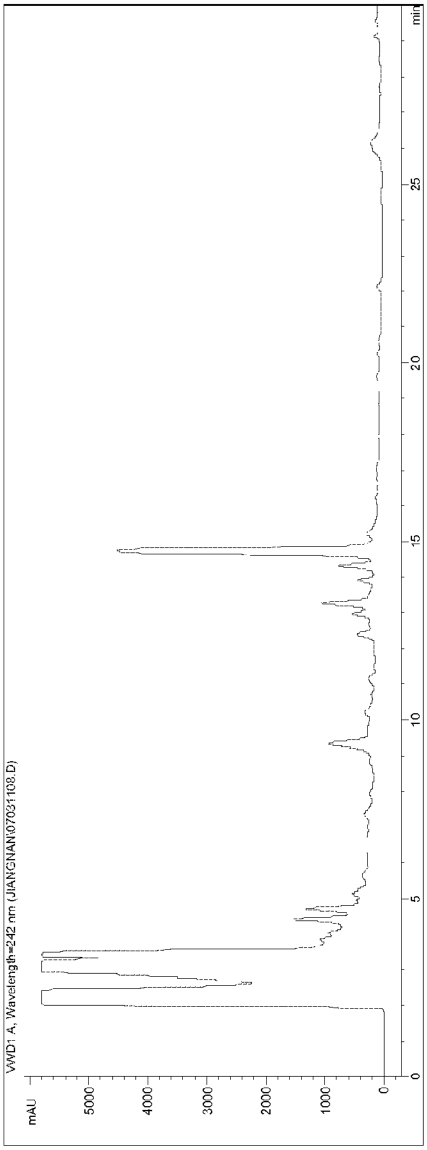
Figure 6F:
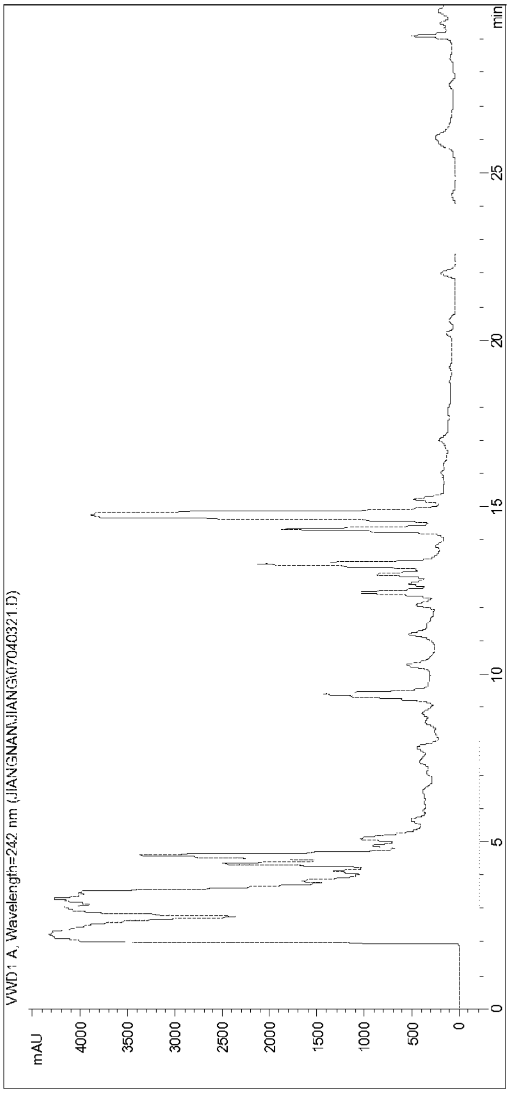
Figure 6G:
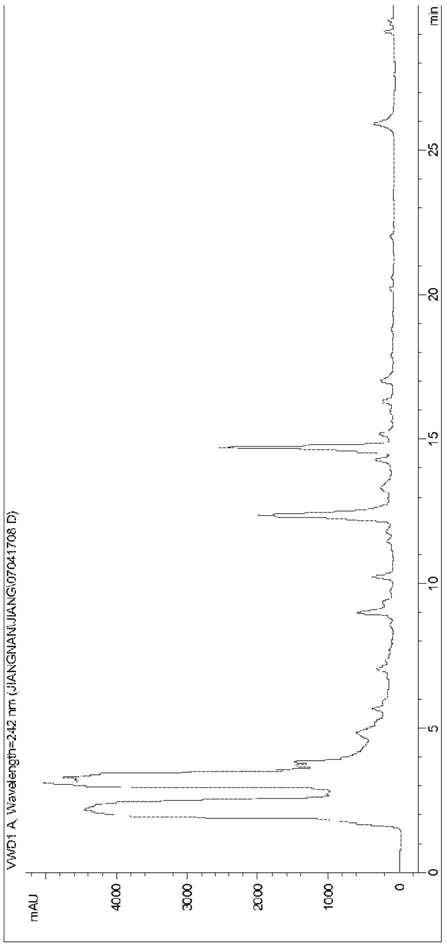
Figure 6H:
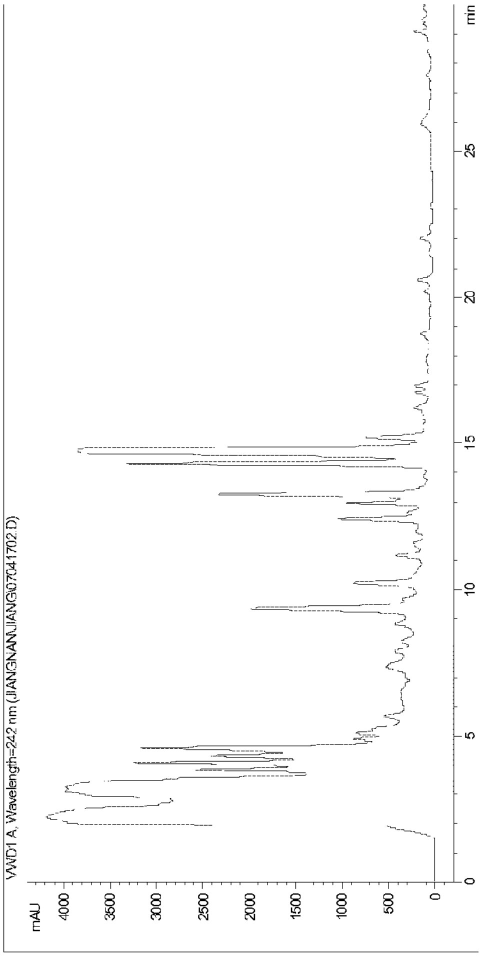
Figure 6I:
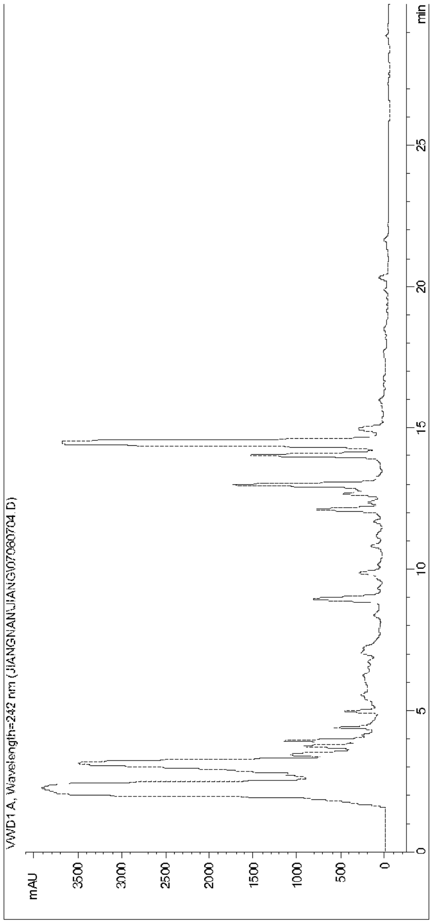
Figure 6J:
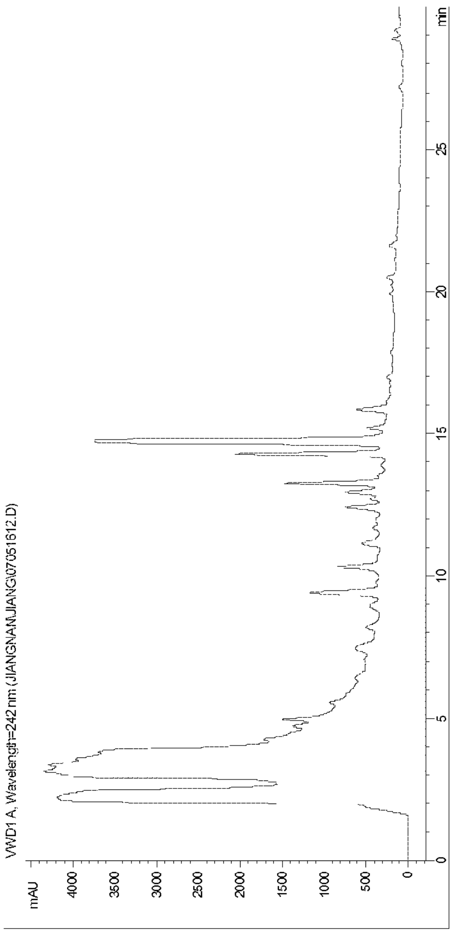
Figure 6K:
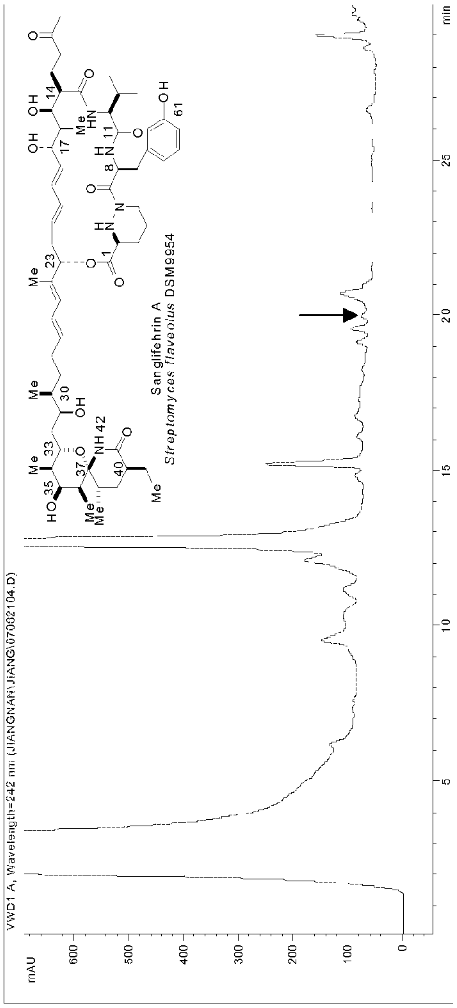
Figure 6L:
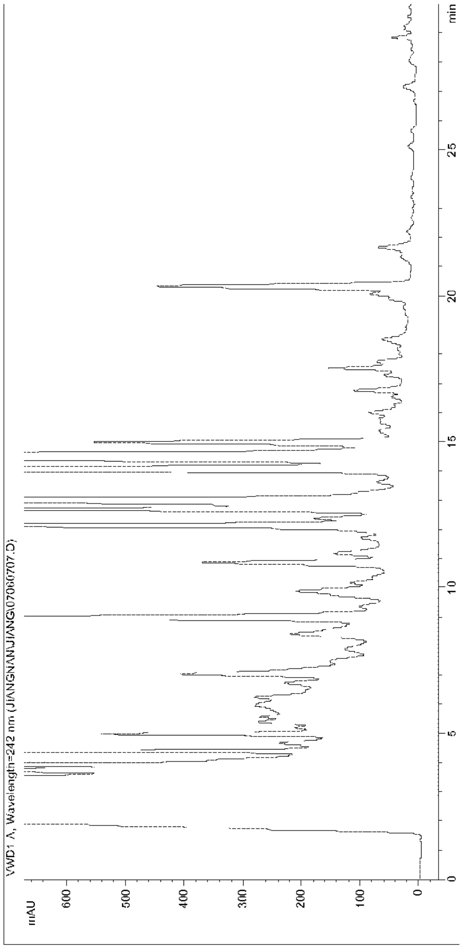
Figure 6M:
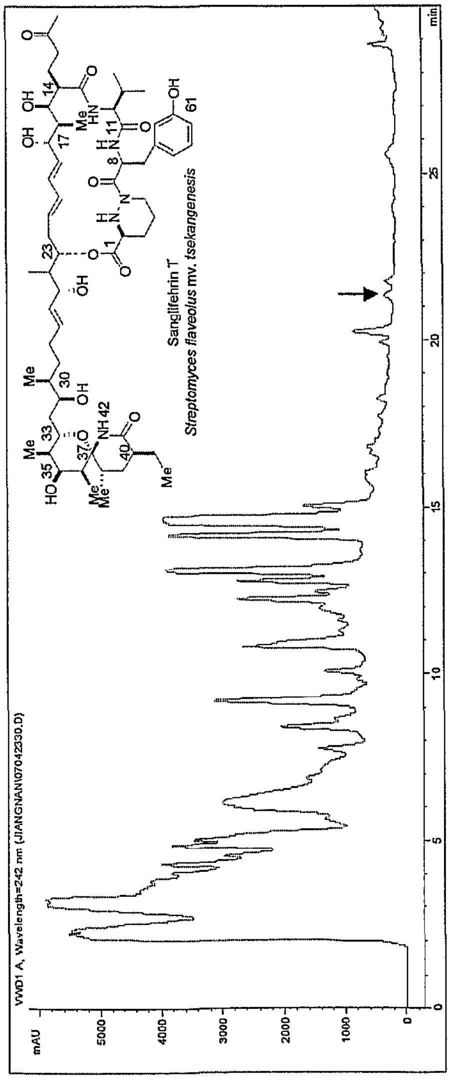
Figure 6N:
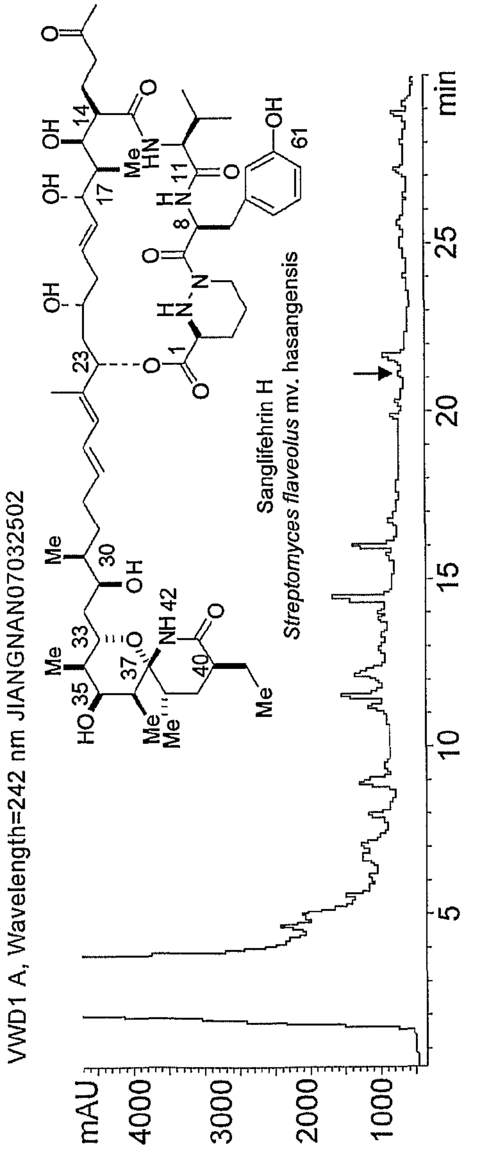

The iterative polyketide synthase encoded by sfaK is thought to be involved in biosynthesis of the 6-carbon unusual extender unit. Acetyl CoA or malonyl-CoA is used as a starter unit to go through two rounds of two-carbon extension, and triketo hexanoyl CoA is obtained. The keto group in the middle is then selectively reduced by the unusual oxidation-reduction domain at the terminal end of the said enzyme, and a partially reduced CoA derivative with a conjugated double bond is obtained. Then via reductive carboxylation by the crotonyl-coA reductase encoded by sfaR, it is activated to incorporate into the process of polyketide chain extension. In the identification of the fermentation product derived from the knockout mutant of sfaK, the inventors detected a signal of m/z 1033.4 (FIG. 6C). This supports the putative generation of a compensatory biosynthetic product, i.e. the special extension unit side chain is replaced by the substrate methylmalonyl-CoA which is nonoptimal in terms of the corresponding domain for transacylation in the PKS, so that a substitution product with a methyl side chain is obtained.

Example 8

Generation of Non-Natural Analogues of SFA by Genetic Means

The segments corresponding to various DH domains in the SFA biosynthetic gene cluster were inactivated by site-directed mutagenesis, so that a dehydratase lacking active-site residues is encoded. This dehydratase was used to act on an intermediate product which had been through the upstream AT recognition, transfer onto the ACP, condensation catalyzed by the KS, and reduction by the KR. Since the said dehydratase cannot exert its dehydration function to form a double bond, the SFA analogue with a hydroxy group is therefore obtained. The dehydratase domain (DH), is an enzymatic domain which catalyzes the dehydration of the hydroxy group derived from keto reduction, to form a double bond. The functional domain has a highly conserved motif LXXHXXXGXXXXP, wherein the histidine residue is the catalytic active center; leucine and glycine maintain normal folding; proline is sometimes not conserved and is functionally unknown. Thus, the histidine residue was chosen as the target for mutation. DH3/DH4/DH5/DH6 (the DH domains of modules 7, 8, 10 and 11) in SfaA4 (sfaH) (responsible respectively for the formation of the two sets of two double bonds inside and outside of the ester group of the macrolide) were chosen as target functional domains to be inactivated by site-directed mutagenesis. The polymerase chain reaction (PCR) was used to amplify 8 DNA fragments of around 1 kb flanking the motifs of the above-said functional domains, and these fragments were used as homologous arms. The histidine residue was changed into a nonpolar amino acid residue such as glycine/alanine or the like, to remove the dehydration function. Altered codons were introduced by primers, and two fragments carrying the mutation were ligated (restriction sites required for such ligation may be introduced by silent mutation). In this manner, homologous recombinant plasmids needed for site-directed mutagenesis were constructed. Corresponding mutants were fermented. Liquid chromatography/mass spectrometry detected M+18 signal peaks (LC-ESI-MS m/z1109.3, 1131.5), showing that the desired compounds were produced.

To facilitate the understanding of the present invention, Examples are further provided in the following, for illustrative purpose only and not limiting the scope of the invention.

Example 9

Construction of a Genetic Transfer System for the SFA Producing Strain *Streptomyces* sp A92-309110 (*S. Flaveolus*)

The target plasmid to be used in conjugative transfer was first transformed in *E. coli* S17-1. A single colony from a plate was picked and inoculated into tubes with 3 mL LB medium and corresponding antibiotic for selective pressure, and incubated overnight at 37° C. The culture was harvested the next day, 1 mL culture was pipetted and inoculated into a 250 mL shake flask containing 50 mL LB medium and corresponding antibiotic for selective pressure. Incubation was performed at 37° C. in a shaker until the $OD_{600}$ value reached around 0.5. The culture was transferred to 50 mL EP tubes, and centrifuged at 3800 rpm for 10 min at 16° C. Bacteria were recovered, and washed twice with 20 mL LB medium, then centrifuged under the same conditions. Bacteria were then recovered and resuspended in 1 mL LB before use.

One tube of cryopreserved spore suspension was taken and centrifuged at 12000 rpm for 3 min at room temperature. After the supernatant was removed, it was washed twice with 1 mL TES buffer, and resuspended in 500 μL TES buffer. Heat shock was performed in a water bath at 50° C. for 10 min, and then 500 μL TSB medium was added. The solution was well-mixed, incubated at 37° C. for 4-5 h, and then centrifuged to remove the supernatant entirely. The pellet was then resuspended with 1.5 mL LB before use.

The recipient bacteria and donor bacteria (each 100 μL) were spread on plates with MS medium (containing 10 mM $MgCl_2$), and cultured at 30° C. for 12-16 h. In addition, one plate, which was spread with recipient bacteria only, was used as negative control. After culturing, 4-5 mL sterile $ddH_2O$ was added to each plate, and the surface was gently scraped with a scraper. After the water was absorbed, the plate was dried for 1 h, then again coated with 1 mL sterile $ddH_2O$ (containing 12.5 μg/mL Am and 50 μg/mL NA) and cultured at 30° C. for 3-5 d.

A single well-grown colony which was successfully transformed was picked and inoculated into 3 mL TSB medium, containing antibiotic selection, if necessary. The culture was shaken at 30° C. After 1 d, around 1 μL of the culture was taken out and spread onto a 150 mm plate containing AmR ISP-4, then cultured for 2 d at 37° C. The plate was directly overlaid with solid plate medium containing kanamycin ISP-4, and cultured for 6-7 h at 37° C. Then the 2 pieces of culture medium were separated, and cultured for another 2 d at 37° C. respectively. Single colonies which had grown on AmR but not at the corresponding position on kanamycin plates were picked and inoculated into 3 mL TSB medium. The culture was shaken and ready for fermentation.

Example 10

Construction of a Gene Library of the SFA Producing Strain *Streptomyces* sp A92-309110 (*S. Flaveolus*)

10.1 Small-Scale Enzyme Digestion Assay

Firstly, the amount of Sau3Al to use was determined by a series of dilution experiments. A reaction system of 250 μl (containing genomic DNA (eg gDNAQXD01-82-1) 40 μl, BSA (100×) 2.5 μl) was first prepared, then the 250 μl reaction system was divided to 1×50 μl and 7×25 μl, and kept on ice. Then 2 μl of Sau3Al, which was previously diluted to 0.5 u/μl, was added to tube #1 containing the 50 μl reaction system, and well-mixed. Then 25 μl was transferred to the 25 μl in tube #2. These transfer steps were repeated 7 times. All systems were incubated in water bath at 37° C. for 15 min, then inactivated at 70° C. for 10 min. 0.4% agarose gel electrophoresis was run at 4° C. in a cold room, then stained with ethidium bromide. The quality of enzymatic digestion was examined under UV light or using a gel image system.

10.2 Large-Scale Enzyme Digestion Assay

According to the reaction conditions determined in preliminary experiments, 4 times the amount of the total DNA and the enzyme at corresponding concentration were used to prepare DNA fragments needed for constructing the library: The system was well-mixed on ice, divided evenly to 5 aliquots, and incubated in a water bath at 37° C. At 12, 14, 16, 18 and 20 min respectively, aliquots were taken out and inactivated at 70° C. for 10 min. 0.4% agarose gel electrophoresis was run at 4° C. in cold room, then stained with ethidium bromide. The quality of enzymatic digestion was examined under UV light or using a gel image system.

10.3 Dephosphorylation

Digested DNA fragments of suitable size were extracted sequentially with saturated phenol, and chloroform-isoamyl alcohol solution. 0.1 volume of 3M NaAc and 3 volumes of anhydrous alcohol were added to precipitate the DNA. Then the DNA pellet was washed with 70% alcohol, dried, and then resuspended in 200 μl water. 10 μl was removed as a control, and the remaining DNA was dephosphorylated. 10 μl SAP (Promega, 1 unit/μl) and 25 μl 10× buffer were added to 190 μl Sau3Al digested DNA, and then water was added to 250 μl. The system was incubated for 1 h at 37° C., supplemented with 7 μl SAP, and then well-mixed. After 1 h incubation, heat denaturation was performed at 70° C. to inactivate the enzyme. Extraction was performed sequentially with saturated phenol, chloroform:isoamyl alcohol solution. 0.1 volume of 3M NaAc and 3 volumes of anhydrous alcohol were added to precipitate DNA. Then the DNA was washed with 70% alcohol, dried, resuspended in 15 μl TE solution. Then it was examined to see whether dephosphorylation was complete. 0.3% Agarose Gel Electrophoresis was run at 4° C. in a cold room, and the gel was stained with ethidium bromide. The quality of enzyme digestion was examined under UV light or using a gel image system.

10.4 Preparation of SuperCos1 Vector

The single enzyme XbaI was used to linearize SuperCos1 between two cos sites, and then dephosphorylation was performed (to prevent self-ligation). Then, in order to insert partially digested fragments of genome DNA, digestion was performed with BamHI to obtain two arms of 1 kb and 7 kb. The prepared vector had the concentration of 1 μg/μl.

10.5 Ligation of Fragments Derived from Total DNA into SuperCos1 Vector

6 μl dephosphorylated DNA (around 2 μg/μl) and 4 μl prepared SuperCos1 ((around 1 μg/μl)) were mixed, and 1.2

μl was taken out as a control. To the remaining 8.8 μl of the mixture solution were added 1.2 μl T4 DNA ligase (NEB 400 u/μl) and 1.2 μl buffer, then well-mixed. Ligation was carried out for 16 h at 16° C. Agarose Gel Electrophoresis was run at 4° C. in a cold room. The gel was stained with ethidium bromide, and examined under UV light or using a gel image system.

10.6 Library Packaging

One Stratagene Gig Pack III XL packaging reagent was removed from the −80° C. freezer, and quick-thawed by hand. 4 μl ligation product was added, and gently pipetted 3 times. The mixture was incubated in a water bath at 22° C. for 2 hr, then removed and 500 μl SM buffer added, then inverted several times. 50 μl chloroform was added and the mixture inverted several times (now some protein-like precipitation should be visible). The mixture was then centrifuged for a few seconds. The supernatant was transferred by pipetting, and stored at 4° C.

10.7 Titration

Firstly, a single bacterial colony of *E. coli* VCS257 was picked from a plate and inoculated into LB to culture overnight. 500 μl of culture was taken and inoculated into 50 ml LB (10 mM $MgSO_4$, 0.2% maltose), and cultured at 37° C. with shaking. When the $OD_{600}$ of *E. coli* reached 0.84, 5 μl packaging solution was added to 45 μl SM buffer, then added into 50 μl of the *E. coli* VCS257. The tube was gently tapped to mix, then put into a water bath at 22° C. to incubate for 30 min. 400 μl LB was added, the tube inverted several times, then incubated in a water bath at 37° C. for 75 min (and inverted several times every 15 min). 250 μl was spread onto each LB plate (Amp100 μg/ml), and incubated overnight at 37° C.

10.8 Confirmation of Authenticity of Library

To prove that the bacterial colonies grown were not false-positive but really contained recombinant cosmids, 10 colonies were randomly picked, inoculated into LB (Amp100 μg/ml) and cultured. Cosmids were extracted according to the alkaline lysis method used for *E. coli* plasmid DNA mini-preps, then digested with BamHI and run on a 0.5% Agarose Gel.

10.9 Library Amplification

*E. coli* VCS257 was inoculated into 50 ml LB (containing 10 mM $MgSO_4$, 0.2% maltose) and cultured to $OD_{600}$=0.84, then transfection was immediately performed. Cell culture (100 μl) and packaging solution (100 μl) were gently mixed, incubated in a water bath at 22° C. for 30 min, then 800 μl LB was added to each of 5 microcentrifuge tubes, gently mixed, and incubated in a water bath at 37° C. for 75 min with gently mixing every 15 min. Whilst the incubation was being performed, 5 large plates (Amp concentration of 100 μg/ml) were placed at 37° C. in an incubator to prewarm. After incubation in the water bath was finished, plates were spread with the contents of one microcentrifuge tube for each plate, and incubated overnight at 37° C. After culturing for 18 hr (until bacterial colonies had grown well), 3~4 ml LB were added to each plate. Bacterial colonies were scraped with a scraper, and the culture solution was pipetted and transferred to a 50 ml centrifuge tube. Culture solutions from 5 large plates were pooled, and Ampicillin and sterile glycerol were added to final concentrations of 50 μg/ml and 18% (V/V). 250 μl/tube aliquots were stored at −80° C.

Example 11

Generation of an Engineered *Streptomyces* sp A92-309110 (*S. Flaveolus*) Strain Resulting in a Gene Replacement of the sfaK Gene by PCR-Targeting Generation of an engineered *Streptomyces* sp A92-309110 (*S. flaveolus*) strain with an in-frame deletion in the sfaK gene of the sanglifehrin biosynthetic cluster by PCR-targeting involves the majority of the sfaK coding region being replaced by an apramycin resistance marker and the oriT using the standard procedure of PCR-targeting (Gust et al 2002).

Primers 201-1L (SEQ ID NO: 30) and 201-1R (SEQ ID NO: 31) were designed according to the PCR-targeting procedure to amplify the apramycin resistance marker along with the oriT from the template pIJ773 (GenBank accession no. AX657066.1). The 5' region of each primer (not underlined) is identical to sfaK such that replacement of the sfaK sequence between the binding regions of the oligos with the replacement cassette from pIJ773, containing FRT, oriT, aac (3)IV and FRT will remove the activity of SfaK. The underlined 3' region of each oligo is identical to a sequence in pIJ773 for amplification of the replacement cassette. Within the replacement cassette, FRT is the FLP-recombinase recognition target sequence and the two FRT sequences flank the origin of transfer from RK2 (oriT) and the apramycin resistance gene (aac(3)IV), one skilled in the art will be familiar with this technique and it is described in detail in Gust et al 2002 and further supported by references within.

```
201-1L (SEQ ID NO: 30):
5'-CTCGACCGGTACTGGGCCAACGTGGTGGCCGGTGTCGACATTCCGG

GGATCCGTCGACC-3'

201-1R (SEQ ID NO: 31):
5'-GGCCAGTTCGCGCAGGAAGGCCCGTACGCCGTCGTCCGGTGTAGGC

TGGAGCTGCTTC-3'
```

Amplification of the ~1.4 kb PCR-targeting DNA cassette was achieved using the primers 201-1L (SEQ ID NO: 26) and 201-1R (SEQ ID NO: 27), pIJ773 as the template and Primer Star Polymerase (Takara Co. Ltd.) using standard conditions with an annealing temperature of 50° C. The cosmid pTL3102 covers an appropriate region of the sanglifehrin cluster and was first transformed into *E. coli* BW25113/pIJ790 to give the strain *E. coli* BW25113/pIJ790/3102. *E. coli* BW25113/pIJ790 is maintained at 30° C. in LB (Luria-Bertani medium; Sambrook et al., 1998) containing chloramphenicol (25 μg/mL). To make the gene replacement construct pTL3122 the steps outlined below were carried out. PCR-targeting was effected by transforming the gel purified DNA cassette into *E. coli* BW25113/3102 by electroporation, after electroporation the bacteria were incubated in LB at 37 degree centigrade for 1 h to induce recombination and express antibiotic resistance, then plated on LB agar containing 100 μg/mL apramycin for overnight incubation at same temperature. Apramycin resistant colonies were inoculated into LB supplemented with 100 μg/mL apramycin and incubate for overnight at 37° C. Cosmid DNA was isolated, and the presence of the resistance cassette confirmed by restriction enzyme digestion and DNA sequence analysis, the cosmid generated was named pTL3111. To facilitate transformation into *Streptomyces*, the cosmid size was reduced by cutting pTL3111 with BglII. The 13 kb BglII fragment containing the inactivated sfaK and acc(3)IV-containing resistance cassette was subcloned into pKC5201 to give the final replacement construct pTK3122. pKC5201 was derived from pKC1139 by replace the acc(3)IV with the neomycin resistance gene of supercos1. To generate the sfaK replacement mutant in *Streptomyces* sp A92-309110 (*S. flaveolus*), pTL3122 was transformed into *E. coli* S17-1 by electroporation to generate the *E. coli* donor strain for conjugation. *Streptomyces* sp A92-309110 (*S. flaveolus*) was transformed by conjugation with *E. coli* 517-1/pTL3122 as described in the general methods above. Apramycin resistant ex-conjugants were homogenized and streaked onto the ISP-4 agar supplemented with 50 μg/mL apramycin and cultured at 37° C. until well grown colonies were achieved. A series of single clones were used to inoculate 3 mL TSB broth supplemented with 30 μg/mL of apramycin shaking at 250 rpm, 37° C. for 4 days. 100 μL of each culture was spread onto ISP-4 agar an incubated at 37° C. for 2-3 days to induce the second crossover event. Single colonies were plated +/−neomycin to determine loss of the plasmid backbone. Neomycin sensitivity indicated loss of the plasmid sequence and colonies with that phenotype were analysed by PCR to confirm the replacement of sfaK with the DNA cassette had been achieved. One such colony was designated *Streptomyces flaveolus* mv. *xuwengensis*, with the alternative name *Streptomyces* sp. TL3011. Strains were then cultured according to the methods described, and the strains were seen to make Sanglifehrin X (see FIG. 6C).

Example 12

Generation of Engineered *Streptomyces* sp A92-309110 (*S. Flaveolus*) Strains Resulting in Gene Replacements of a Series of Sanglifehrin Biosynthesis Genes by PCR-Targeting Using similar methods to that described in example 11 above, replacement mutants of sfaA, sfaB, sfaC, sfaJ, sfaL, sfaM, sfaN and sfaP were constructed. In each case, majority of the coding region of the target gene was replaced by an apramycin resistance marker and the oriT using the standard procedure of PCR-targeting (Gust et al 2002). A pair of primers was designed for each target gene (Table 2) according to the PCR-targeting procedure to amplify the apramycin resistance marker along with the oriT from the template pIJ773 (GenBank accession no. AX657066.1). The 5' region of each primer (not underlined) is identical to the target gene such that replacement of the gene sequence between the binding regions of the oligos with the replacement cassette from pIJ773, containing FRT, oriT, aac(3)IV and FRT will remove the activity encoded by the gene. The underlined 3' region of each oligo is identical to a sequence in pIJ773 for amplification of the replacement cassette. Within the replacement cassette, FRT is the FLP-recombinase recognition target sequence and the two FRT sequences flank the origin of transfer from RK2 (oriT) and the apramycin resistance gene (aac(3)IV), one skilled in the art will be familiar with this technique and it is described in detail in Gust et al 2002 and further supported by references within.

Amplification of the ~1.4 kb PCR-targeting DNA cassette was achieved using the primers shown in table 2, pIJ773 as the template and Primer Star Polymerase (Takara Co. Ltd.) using standard conditions.

TABLE 2

Primers used for PCR-Targeting

| Primers | Primer sequences | Target gene |
|---|---|---|
| 201-2L SEQ ID NO: 32 | GTGGAAATCGGCTCGGGCGCGCCCGAATTAACCGCGTCGATTCCGGGGATCCGTCGACC | sfaA |
| 201-2R SEQ ID NO: 33 | AATGGATGTATCGTCGCAGGACGCCCAGAATTCACCTGCTGTAGGCTGGAGCTGCTTC | |

TABLE 2-continued

Primers used for PCR-Targeting

| Primers | Primer sequences | Target gene |
|---|---|---|
| 201-3L SEQ ID NO: 34 | GCGCAGCAGAGCCCGGAATCAGAAGTACTGGACGTCACCATTCCGGGGATCCGTCGACC | sfaB |
| 201-3R SEQ ID NO: 35 | GGCGATCTCGCCCGCGCGGACCGCCACCATGGACAGCAGTGTAGGCTGGAGCTGCTTC | |
| 201-4L SEQ ID NO: 36 | GAGGATTGCGACGGCGTCGTCCTGGCGTTTCTGCGACACATTCCGGGGATCCGTCGACC | sfaC |
| 201-4R SEQ ID NO: 37 | CTCCTCGTCGGCTTCGGTGAGTCCGCGGTCGCGCATCACTGTAGGCTGGAGCTGCTTC | |
| 201-5L SEQ ID NO: 38 | GGGCCGCAGGACAGGTCCGGCGGCCCGGTGCGCGGCGAGATTCCGGGGATCCGTCGACC | sfaJ |
| 201-5R SEQ ID NO: 39 | CGCGCCGGAGAACAGCGGGAAGTAGGTGTCGAGGTCGTCTGTAGGCTGGAGCTGCTTC | |
| 201-6L SEQ ID NO: 40 | GGCCGGCCCCGGAGCCCTGGGCGCCGCCCTGCGTTCGGGATTCCGGGGATCCGTCGACC | sfaL |
| 201-6R SEQ ID NO: 41 | GCTCTCCACGGAGGCGCTCACCGCGGCGACGGCGGCCTCTGTAGGCTGGAGCTGCTTC | |
| 201-7L SEQ ID NO: 42 | GCGGTCGTGACCGGATCGTCCCGCGGCATCGGCGCGGCCATTCCGGGGATCCGTCGACC | sfaM |
| 201-7R SEQ ID NO: 43 | CACGCCGTCGGCGGTCCAGCCGCCGTCGAAGCGCAGGGTTGTAGGCTGGAGCTGCTTC | |
| 201-8L SEQ ID NO: 44 | CTTCGGCGTCCTCGCGCTCGCCCACGCCCTCGGCGATCCATTCCGGGGATCCGTCGACC | sfaN |
| 201-8R SEQ ID NO: 45 | GTGCATGCCGATGGACAGGCCCGCGAGCGCGACCACGTCTGTAGGCTGGAGCTGCTTC | |
| 201-9L SEQ ID NO: 46 | GACGACCTCGCGCGGCACCGGTCCGTCGTCCAGGCGATGATTCCGGGGATCCGTCGACC | sfaP |
| 201-9R SEQ ID NO: 47 | CATCTCGATGCCGCCCCGGTCGTGCGGCAGGCTGAAGTCTGTAGGCTGGAGCTGCTTC | |

To make the gene replacement constructs, PCR-targeting is executed by transforming the gel purified cassette fragment into *E. coli* Bw25113/pIJ790/3106 (for sfaA, sfaB and sfaC as shown in table 3 or *E. coli* Bw25113/3102 (for sfaJ, sfaL, sfaM, sfaN and sfaP as shown in table 3) by electroporation. The strains are made in advance by transforming the cosmid pTL3106 or pTL3102 into *E. coli* Bw25113/pIJ709 by electroporation. After transformation, the bacteria was incubated in LB at 37° C. for 1 h to induce recombination and express antibiotic resistance, and then plated on LB agar containing 100 μg/mL of ampramycin for overnight incubation at 37° C. Apramycin resistant colonies were used to inoculate LB supplemented with 100 μg/mL ampramycin and incubated for overnight at 37° C. The recombinant cosmids are isolated by plasmid isolation Kit (Dingguo Co. Ltd.) and confirmed by restriction enzymes digestion and DNA sequence and given then names shown in table 3. Due to the low transformation efficiency for larger cosmid DNA into the recipient *Streptomyces* sp., direct transformation of the recombinant cosmids into *streptomyces* by conjugation were only successful for pTL3113 and pTL3114 which contained the cassettes for inactivation of sfaB and sfaC and resulted in the mutant strains TL3003 and TL3004 respectively. For the remainder, the inserts were shortened size by cutting the recombinant cosmids with restriction enzymes as shown in table 3. The resulting DNA fragments were subcloned into pKC5201 which is derived from pKC1139 by replace the acc(3)IV with the neomycin resistance gene of supercos1 to give the plasmids listed in table 3. These plasmids resulted in the incorporation of the desired mutations and the mutant strains were given the designated names shown in table 3; such that strain *Streptomyces* sp. TL3002 has sfaA replaced by the acc(3)IV-containing resistance cassette, *Streptomyces* sp. TL3005 has sfaJ replaced by the acc(3)IV-containing resistance cassette, *Streptomyces* sp. TL3006 has sfaL replaced by the acc(3)IV-containing resistance cassette, *Streptomyces* sp. TL3007 has sfaM replaced by the acc(3)IV-containing resistance cassette, *Streptomyces* sp. TL3008 has sfaN replaced by the acc(3)IV-containing resistance cassette and *Streptomyces* sp. TL3009 has sfaP replaced by the acc(3)IV-containing resistance cassette.

TABLE 3

The recombinant cosmids and plasmids

| Mutant generated | Target gene | Cosmid | Recombinant Cosmids | Enzymes to shorten the size | Fragments size after digestion (kb) | Plamid name |
|---|---|---|---|---|---|---|
| TL3002 | sfaA | pTL3106 | pTL3112 | Bg/II | 8 | pTL3123 |
| TL3003 | sfaB | pTL3106 | pTL3113 | N.A. | N.A. | N.A. |
| TL3004 | sfaC | pTL3106 | pTL3114 | N.A. | N.A. | N.A. |
| TL3005 | sfaJ | pTL3102 | pTL3115 | Bg/II/ EcoRI | 11 | pTL3124 |
| TL3006 | sfaL | pTL3102 | pTL3116 | EcoRI | 10 | pTL3125 |
| TL3007 | sfaM | pTL3102 | pTL3117 | EcoRI | 11 | pTL3126 |
| TL3008 | sfaN | pTL3102 | pTL3118 | EcoRI | 10.5 | pTL3127 |
| TL3009 | sfaP | pTL3102 | pTL3119 | EcoRI | 9.5 | pTL3128 |

Plasmids or cosmids for transformation of *Streptomyces* are first transformed into *E. coli* s17-1 and then conjugated into *Streptomyces* as described in example 9 above. The apramycin resistant conjugants are homogenised and streaked onto ISP-4 agar media supplemented with 50 μg/ml apramycin and cultured at 37° C. until well grown colonies were achieved. A series of single clones of each were used to inoculate 3 mL TSB broth supplemented with apramycin 30 μg/mL shaking at 250 rpm at 37° C. for four days. 100 μL of culture was spread onto ISP-4 agar at 37° C. for 2-3 days to induce the second crossover event. Single colonies were plated with and without neomycin to determine loss of the plasmid backbone. Neomycin sensitivity indicated loss of the plasmid sequence and colonies with that phenotype were analysed by PCR to confirm the replacement of the target gene with the DNA cassette had been achieved. The final mutant strains were given the strain names indicated in table 3.

Example 13

Generation of Engineered *Streptomyces* Sp A92-309110 (*S. Flaveolus*) Strains Resulting in Gene Deletion of sfaR Cosmid pTL3102 was digested with BglII and KpnI. The resulting 4.7 kbp DNA fragment was and cloned into BglII/KpnI-digested pSP72 to create pTL3132. An internal 674 bp DNA fragment of pTL3132 was removed by Eco72I digestion and the vector self-ligated to create pTL3133. The BglII and HindIII fragment of pTL3133 was cloned into the BamHI/HindIII-digested pKC1139 to make pTL3129, which was used to engineer gene deletion of sfaR.

The generation of the desired double recombinant strain was carried out using similar procedures to those described above. *E. coli* 517-1/pTL3129 was used to transform *Streptomyces* sp A92-309110 (*S. flaveolus*) by conjugation. The apramycin resistant conjugants were homogenised and streaked onto ISP-4 agar media supplemented with 50 μg/mL ampramycin and cultured at 37° C. until well grown colonies were achieved. A series of single clones of each were used to inoculate 3 mL TSB broth supplemented with apramycin 30 μg/mL shaking at 250 rpm at 37° C. for four days. 100 μL of culture was spread onto ISP-4 agar at 37° C. for 2-3 days to induce the second crossover event. After inducing the double crossover recombination at 37° C. colonies with negative apramycin phenotype are picked out for genotype conformation by PCR. The desired PCR product is about 700 bp different from the 1.4 kbp wild-type pattern. The final strain which was deleted in sfaR was designated *Streptomyces* sp. TL3010.

Example 14

Generation of DH Mutants in Each of the 4 DH Domains of sfaH

The four DH domains of sfaH are contained within PKS modules 7, 8, 10 and 11. As described in the patent text above, the activity of a DH domain can be removed by site-directed mutagenesis to alter the active site histidine to a nonpolar amino acid. This was carried out for the four DH domains of modules 7, 8, 10 and 11 by amplifying 2 arms for each DH using the primers outlined in table 4 below.

TABLE 4

| | primers | SEQ ID NO | sequence |
|---|---|---|---|
| DH (module 7) left arm | 105A-2 | SEQ ID NO: 48 | TTT**GGATCC**TACACCGGCCAGGGCGCCC |
| | 105C-2 | SEQ ID NO: 49 | TTT**GGTACC**GAGGACGCT**AGC**GTCGGCCAGCCAGGGGTGC |
| DH (module 7) right arm | 105B-2 | SEQ ID NO: 50 | TTT**AAGCTT**AGCACCCGTGCCACCGGTCAC |
| | 105D-2 | SEQ ID NO: 51 | **GCT**AGCGTCCTC**GGTACC**CCGGTGCTCCCCGGCACC |
| DH (module 8) left arm | 106A-2 | SEQ ID NO: 52 | TTT**GGATCC**GGTGTTGTGGGCGGTGATGG |
| | 106C-2 | SEQ ID NO: 53 | TTT**GAATTCGGC**G**AGTACT**AC**GGC**ATCGGCCGTCCAGGCGGC |
| DH (module 8) right arm | 106B-2 | SEQ ID NO: 54 | TTT**AAGCTT**GCACGACGTGGCCGAAGCG |

TABLE 4-continued

| | primers | SEQ ID NO | sequence |
|---|---|---|---|
| | 106D-2 | SEQ ID NO:55 | TTTGAATTCGCCGTAGTACTCGCCACCACCCTGCTGCCCGGC |
| DHmod10 left arm | 107A | SEQ ID NO: 56 | TTTGAATTCGGGTGGTCCGGAGCTGGATCG |
| | 107C | SEQ ID NO: 57 | CGGCAGCAGGGCAGGGACTAGTATGGCGGC |
| DH (module 10) right arm | 107B | SEQ ID NO: 58 | TTTAAGCTTGGTGCTCGGACTGGGCGGAGC |
| | 107D | SEQ ID NO: 59 | GCCGCCATACTAGTCCCTGCCCTGCTGCCG |
| DH (module 11) left arm | 108A | SEQ ID NO: 60 | TTTGAATTCCGACGACACCGGATACGGGC |
| | 108C | SEQ ID NO: 61 | CGGCAGCAGGACGGTGACTAGTACGGTGGC |
| DH (module 11) right arm | 108B | SEQ ID NO: 62 | TTTAAGCTTCCACCCATGTCTGCACCAGG |
| | 108D | SEQ ID NO: 63 | GCCACCGTACTAGTCACCGT |

Therefore, in order to generate the appropriate sequence to mutate the DH of module 7, the left arm was amplified with primers 105A-2 and 105C-2 and the resulting 1.2 kbp DNA fragment cloned into pANT841 to give 01-44-1 and the right arm was amplified with primers 105B-2 and 105D-2 and the resulting 1.2 kbp DNA fragment cloned into pANT841 (Genbank: AF438749) to give 01-44-2.

In order to generate the appropriate sequence to mutate the DH of module 8, the left arm was amplified with primers 106A-2 and 106C-2 and the resulting 1 kbp DNA fragment cloned into pANT841 to give 01-44-3 and the right arm was amplified with primers 106B-2 and 106D-2 and the resulting 1 kbp DNA fragment cloned into pANT841 to give 01-44-4.

In order to generate the appropriate sequence to mutate the DH of module 10, the left arm was amplified with primers 107A and 107C and the resulting 1 kbp DNA fragment cloned into pTLV1 to give 01-28-1 and the right arm was amplified with primers 107B and 107D and the resulting 1 kbp DNA fragment cloned into pTLV1 to give 01-28-2.

In order to generate the appropriate sequence to mutate the DH of module 11, the left arm was amplified with primers 108A and 108C and the resulting 1 kbp DNA fragment cloned into pTLV1 to give 01-28-3 and the right arm was amplified with primers 108B and 108D and the resulting 1 kbp DNA fragment cloned into pTLV1 to give 01-28-4.

Construction of the final plasmid for each target mutation, entails three-fragment ligation. The plasmids containing the PCR fragments that carry the target left and right regions of homology were digested with appropriate restriction enzymes and ligated into appropriately digested vector pKC1139 (BamHI/KpnI for 105AC, KpnI/HindIII for 105BD, BamHI/EcoRI for 106AC, EcoRI/HindIII for 106BD, EcoRI/SpeI for 107AC, HindIII/SpeI for 107BD, EcoRI/SpeI for 108AC, HindIII/SpeI for 108BD). Ligation reactions were used to transform *E. coli* DH5α. Plasmid DNA was analysed by restriction digestions. Final plasmids to effect the double cross-over events for transformation of *Streptomyces* are first transformed into *E. coli* s17-1 and then conjugated into *Streptomyces* as described in Example 9 above The apramycin resistant conjugants were homogenised and streaked onto ISP-4 agar media supplemented with 50 μg/ml ampramycin and cultured at 37° C. until well grown colonies were achieved. A series of single clones of each were used to inoculate 3 mL TSB broth supplemented with apramycin 30 μg/mL shaking at 250 rpm at 37° C. for four days. 100 μL of culture was spread onto ISP-4 agar at 37° C. for 2-3 days to induce the second crossover event. Single colonies were plated +/−apramycin to determine loss of the plasmid backbone. Apramycin sensitivity indicated loss of the plasmid sequence and colonies with that phenotype were analysed by PCR followed by restriction enzyme digestion of the amplified fragment in each case to confirm the mutation of DH domains. Restriction enzyme digestion of the PCR products of these DH mutants gives two fragments due to the restriction site that is introduced along with the mutation, which is contrary to that of the wild type. Strains were grown under standard fermentation conditions described above, and seen to produce the desired products (See FIG. 6).

Example 15

Characterization of SfaR as a Pathway-Specific Reductase/Carboxylase

To validate the central role of SfaR for unusual building block supply in the proposed pathway, we first inactivated sfaR by in-frame deletion. The resultant mutant completely lost the ability to produce SFA, suggesting that it functions as a pathway-specific ccr homolog essential to the SFA biosynthesis (see example 16). Secondly, we heterologously expressed and purified the N-terminal 6× His-tagged SfaR to near homogeneity for in vitro studies. As expected, in the presence of NADPH and bicarbonate, crotonyl-S-CoA (FIG. 7, 4) was efficiently converted by SfaR to the major product ethylmalonyl-S-CoA (FIG. 7, 5) along with the shunt product butyryl-S-CoA (FIG. 7, 7). Omitting bicarbonate in the reaction mixture, crotonyl-S-CoA was accordingly reduced to butyryl-S-CoA. For crotonyl-S-CoA, $K_m$=8.4×10−4 M, $K_{cat}$=6.8×10−3/min, and $K_m/K_{cat}$=1.2×10−1 M·min. To exclude the possibility that the reaction directly occurs on the ACP, SfaO was expressed and purified as a N-terminal 6×His-tagged derivative. Attempts with crotonyl-S-SfaO as the substrate failed to detect any activity of SfaR, providing the evidence that SfaR carries the activities on the CoA-based crotonyl-S-CoA rather than the ACP-based crotonyl-S-SfaO (FIG. 7, 3). Thirdly, to detect the substrate flexibility of SfaR, we synthesized the 5-carbon substrate pentenyl-S-CoA. Intriguingly, under the conditions with and without bicarbonate, SfaR performed the reduction and reductive carboxylation on pentenyl-S-CoA (FIG. 7, 8) rapidly to generate pentanoyl-S-CoA and propylmalonyl-CoA (FIG. 7, 10), respectively, showing the efficiencies comparable to the activities on the 4-carbon substrate, crotonyl-S-CoA. Under the conditions used, the reductive carboxylation took place too fast to be measured for kinetics analysis; and for pentenyl-S-CoA in reductively producing pentanoyl-S-CoA, $K_m$, $K_{cat}$ and $K_m/K_{cat}$ values were 1.4×10−3 M, 4.2×10−2/min and =3.4×10−2 M·min, respectively.

Example 16

Generation of Engineered *Streptomyces* sp A92-309110 (*S. Flaveolus*) Strains Resulting in Gene Deletion of sfaK and Production of Novel Compounds PCR is carried out using genomic DNA or cosmid DNA as a template, and the primer pairs sfaK-L-for (SEQ ID: 64) and sfaK-L-rev (SEQ ID: 65) to generate one PCR product (designated SfaK-L), and sfaK-R-for (SEQ ID: 66) and SfaK-R-rev (SEQ ID: 67) to generate the other (designated sfaK-R). These PCR products are isolated, and then digested with restriction enzymes (sfaK-L with EcoRI and BamHI, and sfaK-R with BamHI and HindIII), then ligated into pKC1139 previously digested with EcoRI and HindIII. The plasmid psfaKKO is isolated.

The generation of the desired double recombinant strain is carried out using similar procedures to those described in previous examples. *E. coli* S17-1/psfaKKO is used to transform *Streptomyces* sp A92-309110 (*S. flaveolus*) by conjugation. The apramycin resistant conjugants are homogenised and streaked onto ISP-4 agar media supplemented with 50 μg/mL ampramycin and cultured at 37° C. until well grown colonies are achieved. A series of single clones of each are used to inoculate 3 mL TSB broth supplemented with apramycin 30 μg/mL shaking at 250 rpm at 37° C. for four days. 100 μL of culture is spread onto ISP-4 agar at 37° C. for 2-3 days to induce the second crossover event. After inducing the double crossover recombination at 37° C. colonies with negative apramycin phenotype are picked out for genotype confirmation by PCR. The desired PCR product is about 1700 bp different from the wild-type pattern. The final strain which is deleted in sfaK is designated *Streptomyces* sp. sfaKKO.

*Streptomyces* sp. sfaKKO is grown under standard fermentation conditions described above. The fermentation broth is seen to contain a new peak corresponding to a sanglifehrin of molecular weight 1034.3, presumed to be the product sanglifehrin X. Products are isolated using standard methods.

REFERENCES

Altschul, S. F., W. Gish, et al. (1990). “Basic local alignment search tool.” *J Mol Biol* 215(3): 403-10.

Banteli, R., J. Wagner, et al. (2001). “Synthesis of derivatives of the novel cyclophilin-binding immunosuppressant sanglifehrin A with reduced numbers of polar functions.” *Bioorg Med Chem Lett* 11(12): 1609-12.

Brown, E. J., M. W. Albers, et al. (1994). “A mammalian protein targeted by G1-arresting rapamycin-receptor complex.” *Nature* 369(6483): 756-758.

Cheng, Y. Q., G. L. Tang, et al. (2003). “Type I polyketide synthase requiring a discrete acyltransferase for polyketide biosynthesis.” *Proc Natl Acad Sci USA* 100(6): 3149-54.

Clarke, S. J., G. P. McStay, et al. (2002). “Sanglifehrin A acts as a potent inhibitor of the mitochondrial permeability transition and reperfusion injury of the heart by binding to cyclophilin-D at a different site from cyclosporin A.” *J Biol Chem* 277(38): 34793-9.

Fang, J., Y. Zhang, et al. (2008). “Cloning and characterization of the tetrocarcin A gene cluster from *Micromonospora chalcea* NRRL 11289 reveals a highly conserved strategy for tetronate biosynthesis in spirotetronate antibiotics.” *J Bacteriol* 190(17): 6014-25.

Fehr, T., J. Kallen, et al. (1999). “Sanglifehrins A, B, C and D, novel cyclophilin-binding compounds isolated from *Streptomyces* sp. A92-308110. II. Structure elucidation, stereochemistry and physico-chemical properties.” *J Antibiot (Tokyo)* 52(5): 474-9.

Fujimori, D. G., S. Hrvatin, et al. (2007). “Cloning and characterization of the biosynthetic gene cluster for kutznerides.” *Proc Natl Acad Sci USA* 104(42): 16498-503.

Fujimori, D. G., S. Hrvatin, et al. (2007). “Cloning and characterization of the biosynthetic gene cluster for kutznerides.” *Proc Natl Acad Sci USA* 104(42): 16498-503.

Gaisser, S., R. Lill, et al. (2001). “New erythromycin derivatives from *Saccharopolyspora erythraea* using sugar O-methyltransferases from the spinosyn biosynthetic gene cluster.” *Molecular Microbiology* 41(5): 1223-1231.

Garneau, S., P. C. Dorrestein, et al. (2005). “Characterization of the formation of the pyrrole moiety during clorobiocin and coumermycin A1 biosynthesis.” *Biochemistry* 44(8): 2770-80.

Handschumacher, R. E., M. W. Harding, et al. (1984). “Cyclophilin: a specific cytosolic binding protein for cyclosporin A.” *Science* 226(4674): 544-7.

Hartel, C., P. Iblher, et al. (2006). “Immunosuppressive activity of the immunophilin-binding drug Sanglifehrin A in human whole blood: potent inhibition of interleukin-6 produced by lymphocytes and monocytes.” *Scand J Immunol* 63(1): 26-34.

Huang, F., S. F. Haydock, et al. (2005). “The neomycin biosynthetic gene cluster of *Streptomyces fradiae* NCIMB 8233: characterisation of an aminotransferase involved in the formation of 2-deoxystreptamine.” *Org Biomol Chem* 3(8): 1410-8.

Jia, X. Y., Z. H. Tian, et al. (2006). “Genetic characterization of the chlorothricin gene cluster as a model for spirotetronate antibiotic biosynthesis.” *Chem Biol* 13(6): 575-85.

Kallen, J., R. Sedrani, et al. (2005). “Structure of human cyclophilin A in complex with the novel immunosuppressant sanglifehrin A at 1.6 A resolution.” *J Biol Chem* 280 (23): 21965-71.

Kazuo Umezawa, Y. I., Osamu Kawase, Hiroshi Naganawa and Shinichi Kondo (2001). “Biosynthesis of polyoxypeptin A: novel amino acid 3-hydroxy-3-methylproline derived from isoleucine.” *J. Chem. Soc., Perkin Trans.* 1: 1550-1553.

Kieser, T., M. J. Bibb, et al., Eds. (1999). *Practical Streptomyces Genetics*, John Innes Foundation.

Li, T. L., F. Huang, et al. (2004). “Biosynthetic gene cluster of the glycopeptide antibiotic teicoplanin: characterization of two glycosyltransferases and the key acyltransferase.” *Chem Biol* 11(1): 107-19.

Liu, J., F. J D., et al. (1991). “Calcineurin is a common target of cyclophilin-cyclosporin A and FKBP-FK506 complexes.” *Cell* 66(4): 807-815.

Liu, W., S. D. Christenson, et al. (2002). “Biosynthesis of the enediyne antitumor antibiotic C-1027.” *Science* 297(5584): 1170-3.

Maniatis, T., E. F. Fritsch, et al., Eds. (1998). *Molecular Cloning. A Laboratory manual*, Cold Spring Harbor Laboratory.

Metternich, R., Denni, D., Thai, B, Sedrani, R. (1999). “Toward a Total Synthesis of the Immunosuppressant Sanglifehrin A. Preparation of Two Relay Compounds by Degradation and Their Use in the Reassembly of the Natural Product.” *J. Org. Chem.* 64: 9632-9639.

Miller, E. D., C. A. Kauffman, et al. (2007). *J Org Chem* 72: 323-330.

Oliynyk, M., M. J. B. Brown, et al. (1996). “A hybrid modular polyketide synthase obtained by domain swapping.” *Chemistry & Biology* 3(10): 833-839.

Paquette, L. A., M. Duan, et al. (2002). “A convergent three-component total synthesis of the powerful immunosuppressant (−)-sanglifehrin a.” *J Am Chem Soc* 124(16): 4257-70.

Pemberton, T. J. and J. E. Kay (2003). “Cyclophilin sensitivity to sanglifehrin A can be correlated to the same specific tryptophan residue as cyclosporin A.” *FEBS Lett* 555(2): 335-40.

Pfeifer, B. A. and C. Khosla (2001). “Biosynthesis of polyketides in heterologous hosts.” *Microbiology and Molecular Biology Reviews* 65(1): 106-118.

Powell, J. D. and Y. Zheng (2006). "Dissecting the mechanism of T-cell anergy with immunophilin ligands." *Curr Opin Investig Drugs* 7(11): 1002-7.

Rawlings, B. J. (2001). "Type I polyketide biosynthesis in bacteria (Part A-erythromycin biosynthesis)." *Nat Prod Rep* 18(2): 190-227.

Rawlings, B. J. (2001). "Type I polyketide biosynthesis in bacteria (Part B)." *Natural Product Reports* 18(3): 231-281.

Sambrook, J. and D. Russel, Eds. (2001). *Molecular Cloning: A laboratory manual* (*third edition*), Cold Spring Harbor Laboratory Press.

Sanglier, J. J., V. Quesniaux, et al. (1999). "Sanglifehrins A, B, C and D, novel cyclophilin-binding compounds isolated from *Streptomyces* sp. A92-308110. I. Taxonomy, fermentation, isolation and biological activity." *J Antibiot* (*Tokyo*) 52(5): 466-73.

Schreiber, S. (1991). "Chemistry and biology of the immunophilins and their immunosuppressive ligands." *Science* 251(4991): 283-287.

Sedrani, R., J. Kallen, et al. (2003). "Sanglifehrin-cyclophilin interaction: degradation work, synthetic macrocyclic analogues, X-ray crystal structure, and binding data." *J Am Chem Soc* 125(13): 3849-59.

Sheehan, L. S., R. E. Lill, et al. (2006). "Engineering of the Spinosyn PKS: Directing Starter Unit Incorporation." *J Nat Prod* 69(12): 1702-10.

Sokolskaja, E., D. M. Sayah, et al. (2004). "Target cell cyclophilin A modulates human immunodeficiency virus type 1 infectivity." *J Virol* 78(23): 12800-8.

Staunton, J. and K. J. Weissman (2001). "Polyketide biosynthesis: a millennium review." *Natural Product Reports* 18(4): 380-416.

Staunton, J. and B. Wilkinson (2001). "Combinatorial biosynthesis of polyketides and nonribosomal peptides." *Current Opinion in Chemical Biology* 5(2): 159-164.

Steinschulte, C., T. Taner, et al. (2003). "Cutting edge: sanglifehrin A, a novel cyclophilin-binding immunosuppressant blocks bioactive IL-12 production by human dendritic cells." *J Immunol* 171(2): 542-6.

Umezawa, K., Y. Ikeda, et al. (2001). *J Chem Soc Perkin Trans* 1: 1550-1553.

Watashi, K., N. Ishii, et al. (2005). "Cyclophilin B is a functional regulator of hepatitis C virus RNA polymerase." *Mol Cell* 19(1): 111-22.

Zander, K., M. P. Sherman, et al. (2003). "Cyclophilin A interacts with HIV-1 Vpr and is required for its functional expression." *J Biol Chem* 278(44): 43202-13.

Zenke, G., U. Strittmatter, et al. (2001). "Sanglifehrin A, a novel cyclophilin-binding compound showing immunosuppressive activity with a new mechanism of action." *J Immunol* 166(12): 7165-71.

Zhang, L. H. and J. O. Liu (2001). "Sanglifehrin A, a novel cyclophilin-binding immunosuppressant, inhibits IL-2-dependent T cell proliferation at the G1 phase of the cell cycle." *J Immunol* 166(9): 5611-8.

Zhang, L. H., H. D. Youn, et al. (2001). "Inhibition of cell cycle progression by the novel cyclophilin ligand sanglifehrin A is mediated through the NFkappa B-dependent activation of p53." *J Biol Chem* 276(47): 43534-40.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and suitable and more suitable groups and embodiments of groups recited above.

The invention claimed is:

1. An isolated nucleic acid molecule comprising the sanglifehrin A biosynthesis gene cluster of SEQ ID NO: 1, wherein:

(i) sfaK (residues 97396-101943 of SEQ ID NO: 1), encoding a polypeptide of SEQ ID NO: 14, has been deleted or inactivated, whereby the linear polyketide synthase gene sfaK is knocked out; and/or (ii) sfaA (residues 17024-17854 of SEQ ID NO: 1), encoding a polypeptide of SEQ ID NO: 4, has been deleted or inactivated, whereby the phenylalanine hydroxylase gene sfaA is knocked out.

2. An isolated nucleic acid comprising a hybrid polyketide producing gene cluster based on the sanglifehrin A biosynthesis gene cluster of SEQ ID NO: 1 in which one or more genes have been deleted, mutated so as to make inactive or less active an enzymatic or regulatory function, wherein the genes that have been deleted, mutated so as to make inactive or less active an enzymatic or regulatory function is (i) sfaK (residues 97396-101943 of SEQ ID NO: 1), encoding a polypeptide of SEQ ID NO: 14, whereby the linear polyketide synthase gene sfaK is knocked out; and/or (ii) sfaA (residues 17024-17854 of SEQ ID NO: 1), encoding a polypeptide of SEQ ID NO: 4, whereby the phenylalanine hydroxylase gene sfaA is knocked out.

3. A hybrid polyketide producing gene cluster nucleic acid according to claim 2 wherein one or more genes have been replaced by (a) a domain, module or gene from elsewhere in the sanglifehrin A biosynthesis gene cluster or (b) a domain, module or gene which is heterologous to the sanglifehrin A biosynthesis gene cluster.

4. A hybrid polyketide producing gene cluster nucleic acid according to claim 2 wherein one or more domains, modules or genes have been mutated to inactivate or make less active an enzymatic or regulatory function.

5. An isolated nucleic acid according to claim 2 which is a DNA.

6. A vector comprising a DNA according to claim 5 together with one or more promoters or other regulatory elements.

7. A host cell transformed with a vector according to claim 6.

8. A host cell according to claim 7 transformed with a vector comprising nucleic acid encoding all or part of the sanglifehrin A biosynthesis gene cluster which host cell does not naturally produce sanglifehrin A.

9. A method for producing a polyketide which comprises culturing a transformed host cell according to claim 8.

* * * * *